(12) United States Patent
Brys et al.

(10) Patent No.: US 8,637,257 B2
(45) Date of Patent: Jan. 28, 2014

(54) MOLECULAR TARGETS AND COMPOUNDS, AND METHODS TO IDENTIFY THE SAME, USEFUL IN THE TREATMENT OF BONE AND JOINT DEGENERATIVE DISEASES

(75) Inventors: Reginald Christophe Xavier Brys, Mechelen (BE); Nick Ernest René Vandeghinste, Mechelen (BE)

(73) Assignee: Galapagos NV, Mechelen (BE)

( * ) Notice: Subject to any disclaimer, the term of this patent is extended or adjusted under 35 U.S.C. 154(b) by 693 days.

(21) Appl. No.: 12/214,787

(22) Filed: Jun. 19, 2008

(65) Prior Publication Data

US 2009/0117107 A1 May 7, 2009

Related U.S. Application Data

(60) Provisional application No. 60/936,569, filed on Jun. 20, 2007.

(51) Int. Cl.
*G01N 33/53* (2006.01)
*C12Q 1/00* (2006.01)
*C07H 21/00* (2006.01)

(52) U.S. Cl.
USPC ........... 435/7.1; 435/6.1; 435/6.19; 435/7.21; 435/7.91; 435/7.92; 536/23.1

(58) Field of Classification Search
None
See application file for complete search history.

(56) References Cited

U.S. PATENT DOCUMENTS

| | | | |
|---|---|---|---|
| 5,449,753 | A | 9/1995 | Stracke et al. |
| 5,731,167 | A | 3/1998 | Stracke et al. |
| 6,048,693 | A | 4/2000 | Bitter |
| 6,080,779 | A | 6/2000 | Gasper et al. |
| 6,084,069 | A | 7/2000 | Stracke et al. |
| 6,277,981 | B1 | 8/2001 | Tu et al. |
| 6,416,951 | B1 | 7/2002 | Schmidt et al. |
| 6,417,338 | B1 | 7/2002 | Stracke et al. |
| 6,500,615 | B1 | 12/2002 | Schmidt et al. |
| 2003/0180258 | A1 | 9/2003 | van Es et al. |
| 2003/0198627 | A1 | 10/2003 | Arts et al. |
| 2004/0071660 | A1 | 4/2004 | Havenga et al. |
| 2007/0184444 | A1 | 8/2007 | Abbas et al. |

FOREIGN PATENT DOCUMENTS

| | | |
|---|---|---|
| WO | WO 9314202 | 7/1993 |
| WO | WO 9532221 | 11/1995 |
| WO | WO 9846751 | 10/1998 |
| WO | WO 9964582 | 12/1999 |
| WO | WO 02067858 | 9/2002 |
| WO | WO 02070744 | 9/2002 |
| WO | WO 03020931 | 3/2003 |
| WO | WO 03054166 A2 * | 7/2003 |
| WO | WO 2004094636 | 11/2004 |
| WO | WO 2005063976 | 7/2005 |
| WO | WO 2005121778 | 12/2005 |
| WO | WO 2005124342 | 12/2005 |
| WO | WO 2006040357 | 4/2006 |

OTHER PUBLICATIONS

Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495 (1994).*
Qureshi et al. Implant Design Affects Markers of Bone Resorption and Formation in Total Hip Replacement. Journal of Bone and Mineral Research vol. 17/No. 5, pp. 800-807 (2002).*
Bucay, N. et al (1998) Osteoprotegerin-deficient mice develop early onset osteoporosis and arterial calcification Genes Dev 12(9):1260-1268.
Choy, EH and Panayi, GS (2001) Cytokine pathways and joint inflammation in rheumatoid arthritis N Engl J Med. 344(12):907-916.
Ferry, G et al (2003) Autotaxin is released from adipocytes, catalyzes lysophosphatidic acid synthesis, and activates preadipocyte proliferation. Up-regulated expression with adipocyte differentiation and obesity J Biol Chem 278(20):18162-18169.
Firestein, GS (2003) Evolving concepts of rheumatoid arthritis Nature 423(6937):356-61.
Gravallese, EM (2002) Bone Destruction in Arthritis Ann Rheum Dis 61 Suppl 2:ii84-86.
Ho, SP et al (1996) Potent antisense oligonucleotides to the human multidrug resistance-1 mRNA are rationally selected by mapping RNA-accessible sites with oligonucleotide libraries Nucl Acids Res 24:1901-1907.
Ho, SP et al (1998) Mapping of RNA accessible sites for antisense experiments with oligonucleotide libraries Nature Biotechnology 16:59-63.
Inui, T et al (1997) Cathepsin K antisense oligodeoxynucleotide inhibits osteoclastic bone resorption J Biol Chem 272(13):8109-8112.
Kawagoe, H et al (1995) Molecular cloning and chromosomal assignment of the human brain-type phosphodiesterase I/nucleotide pyrophosphatase gene (PDNP2) Genomics 30(2):380-384.
Kim, N (2000) Diverse Roles of the Tumor Necrosis Factor Family Member TRANCE in Skeletal Physiology Revealed by TRANCE Deficiency and Partial Rescue by a Lymphocyte-Expressed TRANCE Transgene Proc Natl Sci 97(20):10905-10910.
Mishra, RK et al (1994) In vitro selection of antisense oligonucleotides targeted to a hairpin structure Life Sciences 317(11):977-982.

(Continued)

*Primary Examiner* — Elizabeth C Kemmerer
*Assistant Examiner* — Regina M Deberry
(74) *Attorney, Agent, or Firm* — Klauber & Jackson, LLC

(57) ABSTRACT

The present invention relates to methods for identifying agents capable of inhibiting the expression or activity of proteins involved in the processes modulating osteoclastogenesis, which inhibition is useful in the prevention and/or treatment of bone and joint degenerative diseases and diseases involving aberrant activity or differentiation of osteoclasts. In particular, the present invention provides methods for identifying agents for use in the prevention and/or treatment of rheumatoid arthritis.

14 Claims, 15 Drawing Sheets

(56) References Cited

OTHER PUBLICATIONS

Navarette Santos, A (1998) Detection of autotaxin mRNA injoint pannus of patients suffering from rheumatoid arthritis Eur J Cell Biol 75(Suppl 48): 83, Abstract.

Onyia, JE et al (2004) Novel and Selective Small Molecule Stimulators of Osteoprotegerin Expression Inhibit Bone Resorption J Pharmacol Exp Ther 309(1):369-379.

Pettit, AR et al (2001) TRANCE/RANKL Knockout Mice are Protected from Bone Erosion in a Serum Transfer Model of Arthritis Am J Pathol 159(5):1689-1699.

Pettit, AR et al (2006) RANKL Protein is Expressed at the Pannus-Bone Interface at Sites of Articular Bone Erosion in Rheumatoid Arthritis Rheumatology 45(9):1068-1076.

Redlich, K. et al (2004) Repair of Local Bone Erosions and Reversal of Systemic Bone Loss upon Therapy with Anti-Tumor Necrosis Factor in Combination wit Osteoprotegerin or Parathyroid Hormone in Tumor Necrosis Factor-Mediated Arthritis Am J Pathol 164(2):543-555.

Roodman, GD (2004) Mechanisms of Bone Metastasis N Engl J Med 350(16):1655-1664.

Smolen, JS and Steiner, G (2003) Therapeutic strategies for rheumatoid arthritis Nat Rev Drug Discov. 2(6):473-488.

Stull, RA et al (1992) Predicting antisense oligonucleotide inhibitory efficacy: a computational approach using histograms and thermodynamic indices Nucl Acids Res 20(13):3501-3508.

Tani-Ishii, N et al (1997) Osteopontin antisense deoxyoligonucleotides inhibit bone resorption by mouse osteoclasts in vitro J Peridonal Res 32(6):480-486.

Valleala, H. et al (2003) Two Year Randomized Controlled Trial of Etidronate in Rheumatoid Arthritis: Changes in Serum Aminoterminal Telopeptides Correlate with Radiographic Progression of Disease J Rheumatol 30(3):468-473.

Ferguson, CG et al (2006) A Fluorogenic Phospholipid Substrate to Detect Lysophospholipase D/Autotaxin Activity Org Lett 8(10):2023-2026.

Umezu-Goto, M et al (2002) Autotaxin has Lysophospholipase D Activity Leading to Tumor Cell Growth and Motility by Lysophosphatidic Acid Production Journal of Cell Biol 158(2):227-233.

* cited by examiner

Schematic view of a normal joint and its changes in rheumatoid arthritis (From Smolen and Steiner, 2003).

Figure 4

General Layout of control plate

|   | 1 | 2 | 3 | 4 | 5 | 6 | 7 | 8 | 9 | 10 | 11 | 12 | 13-24 |
|---|---|---|---|---|---|---|---|---|---|----|----|----|----|
| A | P1 | P1 | N1 | N1 | P2 | P2 | N2 | N2 | P3 | P3 | N3 | N3 | |
| B | P1 | Bl | N1 | Bl | P2 | Bl | N2 | Bl | P3 | Bl | N3 | Bl | |
| C | N1 | N1 | P2 | P2 | N2 | N2 | P3 | P3 | N3 | N3 | P1 | P1 | |
| D | N1 | Bl | P2 | Bl | N2 | Bl | P3 | Bl | N3 | Bl | P1 | Bl | |
| E | P2 | P2 | N2 | N2 | P3 | P3 | N3 | N3 | P1 | P1 | N1 | N1 | |
| F | P2 | Bl | N2 | Bl | P3 | Bl | N3 | Bl | P1 | Bl | N1 | Bl | |
| G | N2 | N2 | P3 | P3 | N3 | N3 | P1 | P1 | N1 | N1 | P2 | P2 | |
| H | N2 | Bl | P3 | Bl | N3 | Bl | P1 | Bl | N1 | Bl | P2 | Bl | |
| I | P3 | P3 | N3 | N3 | P1 | P1 | N1 | N1 | P2 | P2 | N2 | N2 | |
| J | P3 | Bl | N3 | Bl | P1 | Bl | N1 | Bl | P2 | Bl | N2 | Bl | |
| K | N3 | N3 | P1 | P1 | N1 | N1 | P2 | P2 | N2 | N2 | P3 | P3 | |
| L | N3 | Bl | P1 | Bl | N1 | Bl | P2 | Bl | N2 | Bl | P3 | Bl | |
| M | P1 | P1 | N1 | N1 | P2 | P2 | N2 | N2 | P3 | P3 | N3 | N3 | |
| N | P1 | Bl | N1 | Bl | P2 | Bl | N2 | Bl | P3 | Bl | N3 | Bl | |
| O | N1 | N1 | P2 | P2 | N2 | N2 | P3 | P3 | N3 | N3 | P1 | P1 | |
| P | N1 | Bl | P2 | Bl | N2 | Bl | P3 | Bl | N3 | Bl | P1 | Bl | |

Performance of control plate

|   | 1 | 2 | 3 | 4 | 5 | 6 | 7 | 8 | 9 | 10 | 11 | 12 |
|---|---|---|---|---|---|---|---|---|---|----|----|----|
| A | 2998 | 2895 | 831 | 908.4 | 3096 | 3010 | 706.7 | 788.2 | 3058 | 3135 | 710.1 | 655.8 |
| B | 2353 | 814.2 | 509.1 | 812.1 | 2448 | 800.3 | 478.3 | 646.5 | 2627 | 871.6 | 611.8 | 633.3 |
| C | 923 | 838.5 | 2777 | 2790 | 617.4 | 694.5 | 2935 | 2892 | 745.1 | 780.1 | 3176 | 2880 |
| D | 844 | 641.4 | 2745 | 683.5 | 492.9 | 647.2 | 2667 | 778.2 | 623 | 752.9 | 2703 | 898.2 |
| E | 3390 | 2873 | 620.4 | 577.3 | 2665 | 3116 | 767.3 | 786.1 | 2963 | 2876 | 780.9 | 687.5 |
| F | 2849 | 868.2 | 489.6 | 610.9 | 2612 | 1009 | 579.3 | 717.5 | 2634 | 813.9 | 587 | 608 |
| G | 680.9 | 641.4 | 3358 | 2881 | 674.9 | 857.7 | 3205 | 3190 | 597.7 | 681.8 | 3191 | 3103 |
| H | 565.2 | 632.9 | 2387 | 802 | 493.1 | 573.2 | 2929 | 856.4 | 459.5 | 779.7 | 2967 | 864.7 |
| I | 2760 | 2849 | 792.3 | 814.5 | 3098 | 2996 | 730.5 | 796 | 3162 | 3089 | 498.6 | 587.4 |
| J | 2861 | 810.4 | 531.2 | 627.1 | 2478 | 842.5 | 633.5 | 783.9 | 2691 | 870.4 | 555.1 | 658.4 |
| K | 812.9 | 841.7 | 3178 | 3050 | 823.5 | 829.5 | 3211 | 2902 | 674.3 | 667.2 | 3053 | 2889 |
| L | 723.2 | 711.8 | 2768 | 935.4 | 635.5 | 750.7 | 2709 | 906.6 | 602.1 | 855.7 | 2879 | 967.7 |
| M | 3388 | 3085 | 749.8 | 731.4 | 3144 | 2815 | 671.3 | 647.4 | 3084 | 2941 | 694.9 | 660.9 |
| N | 2968 | 791.7 | 622.6 | 623.8 | 2826 | 876.2 | 554 | 714 | 2773 | 1006 | 630.6 | 583.4 |
| O | 918.1 | 911.8 | 3167 | 3100 | 637.8 | 656.5 | 3066 | 2977 | 709.1 | 705.7 | 3049 | 2937 |
| P | 897.6 | 931.4 | 2928 | 848.2 | 615.8 | 941.9 | 3090 | 1093 | 660.6 | 698.7 | 2915 | 1243 |

| | AVERAGE | Standard deviation | % Positive |
|---|---|---|---|
| P1 | 2946 | 235 | 100 |
| P2 | 2958 | 215.3 | 100 |
| P3 | 2898 | 212.4 | 100 |
| N1 | 747 | 134.1 | 0 |
| N2 | 613.3 | 77.3 | 0 |
| N3 | 702.6 | 95.64 | 0 |
| Blanco | 795.6 | 141.4 | 8.3 |
| All positives | 2934 | 219.5 | |
| All negatives | 687.6 | 117.7 | | hit calling value 993.7

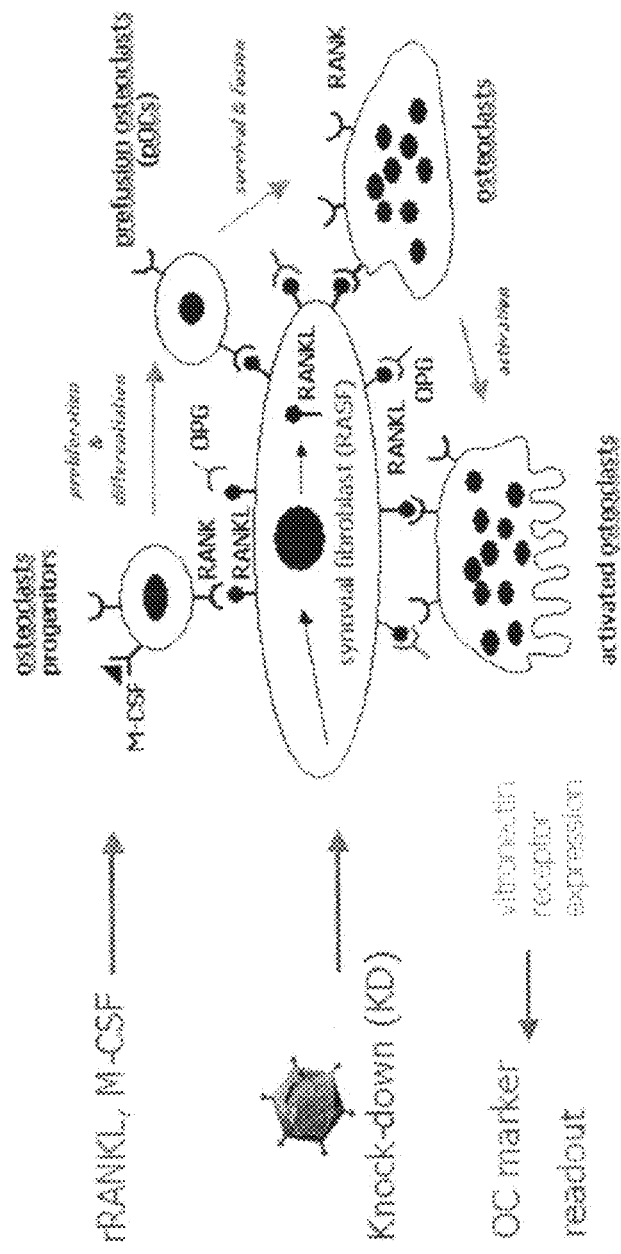

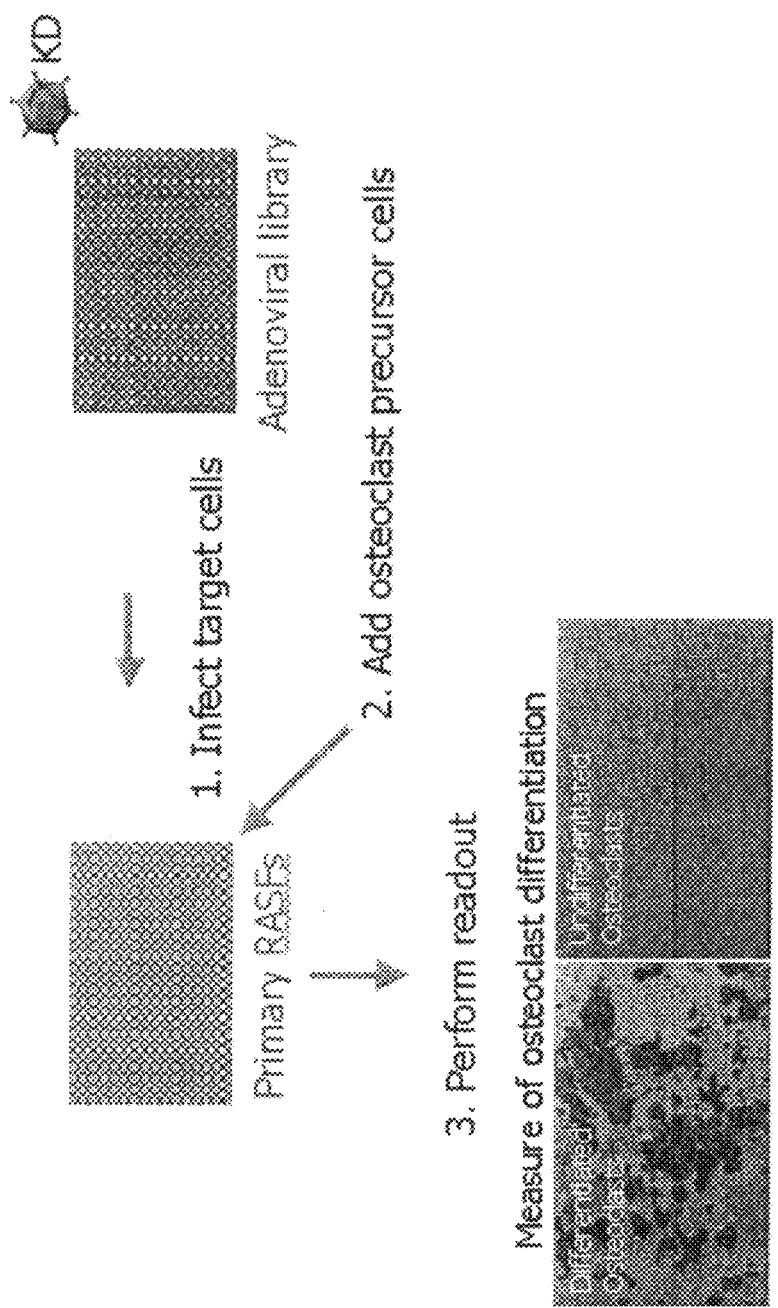

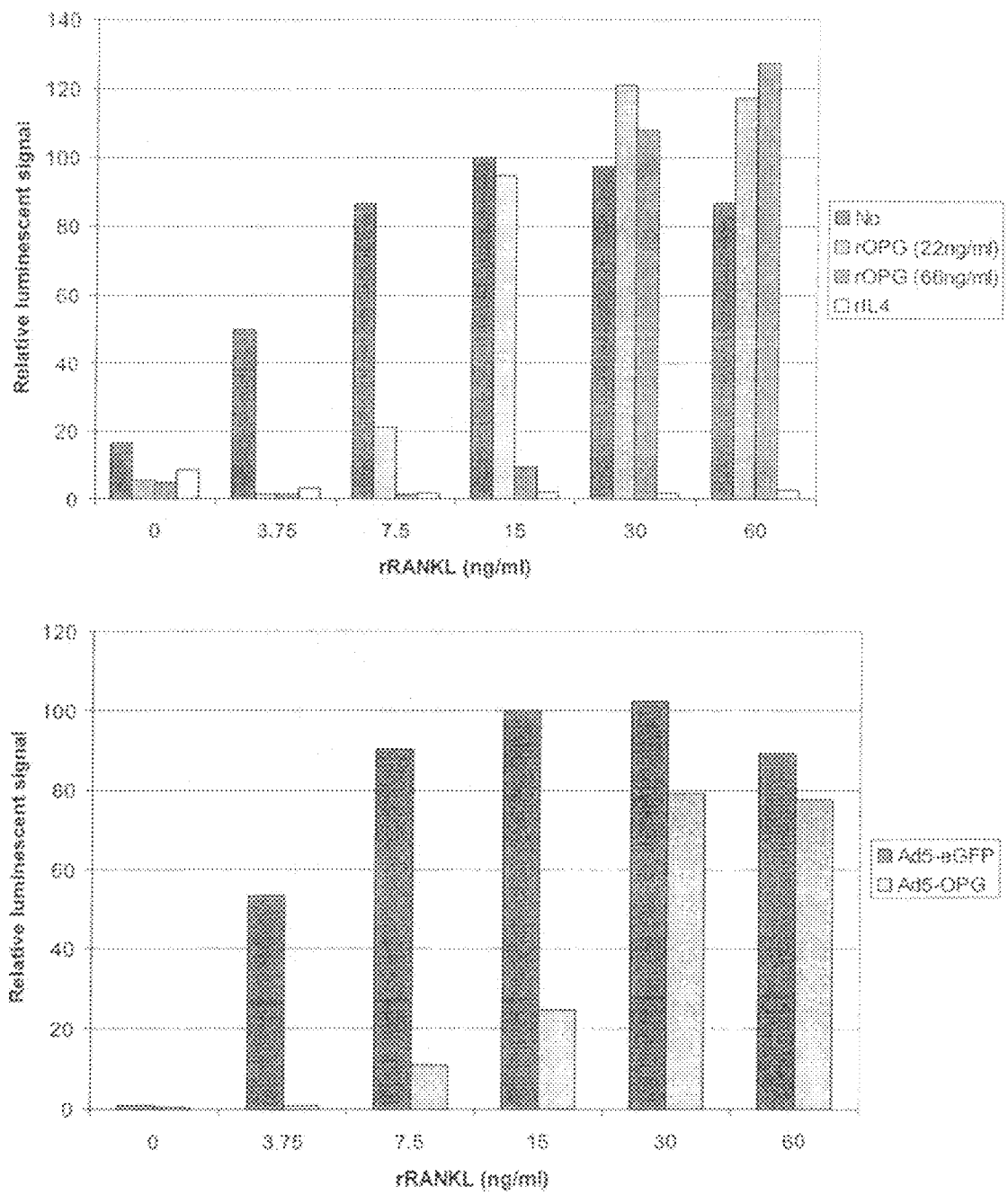

SCREEN B

3 MOI rescreening of OPG

| HIT REF | SYMBOL | RUN A | | | RUN B | | | RUN A score @ # MOIs | RUN B score @ # MOIs | OPG confirmed |
|---|---|---|---|---|---|---|---|---|---|---|
| | | 4 µL cutoff = 2.3 | 2 µL cutoff = 2.0 | 1 µL cutoff = 2.0 | 4 µL cutoff = 2.2 | 2 µL cutoff = 2.4 | 1 µL cutoff = 2.3 | | | |
| H51-122 | ENPP2 | 7.84 | 4.82 | 3.39 | 5.05 | 4.80 | 5.64 | 3 | 3 | Hit |
| H51-137 | MRAS | 3.85 | 3.68 | 4.06 | 4.79 | 4.39 | 3.76 | 3 | 3 | 1 |
| H51-240 | PTK6 | 8.35 | 5.40 | 5.56 | 0.09 | 2.25 | 5.87 | 3 | 2 | 1 |

3 MOI screening in OC assay

| HIT REF | SYMBOL | RUN A | | | RUN B | | | RUN C | | | RUN A score @ # MOIs | RUN B score @ # MOIs | RUN C score @ # MOIs | OC confirmed hit |
|---|---|---|---|---|---|---|---|---|---|---|---|---|---|---|
| | | 4 µL cutoff = -1.8 | 2 µL cutoff = -1.8 | 1 µL cutoff = -1.8 | 4 µL cutoff = -1.8 | 2 µL cutoff = -1.8 | 1 µL cutoff = -1.8 | 4 µL cutoff = -1 | 2 µL cutoff = 1.9 | 1 µL cutoff = 1.4 | | | | |
| H51-122 | ENPP2 | 2.82 | 3.20 | 4.09 | -4.26 | 1.29 | 3.73 | 5.85 | 4.64 | 8.47 | 7.58 | NA | NA | NA | 3 | 2 | NA | 1 |
| H51-137 | MRAS | 3.18 | 3.12 | 3.47 | 2.03 | -2.88 | 2.90 | 3.59 | 2.08 | 1.76 | 1.32 | 2.46 | NA | NA | NA | 3 | 1 | NA | 1 |
| H51-240 | PTK6 | 0.35 | 3.10 | 3.48 | 3.75 | -4.12 | 3.23 | 5.18 | 5.22 | 4.60 | 6.90 | 5.91 | NA | NA | NA | 2 | 3 | NA | 1 |

Figure 10

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   | Ad5-MMP1-KD | Ad5-Luc-KD_v13 | Ad5-eGFP-KD_v5 | Ad5-M6PR-KD_v1 | Ad5-MMP1-KD | Ad5-Luc-KD_v13 | Ad5-eGFP-KD_v5 | Ad5-M6PR-KD_v1 | Ad5-Luc-KD_v13 | Ad5-Luc-KD_v13 |   |
| C |   | Ad5-Hit-KD | Ad5-Hit-KD | Ad5-Hit-KD | Ad5-Hit-KD | Ad5-Hit-KD | Ad5-Hit-KD | Ad5-Hit-KD | Ad5-Hit-KD | Ad5-Hit-KD | Ad5-Hit-KD |   |
| D |   | Ad5-Hit-KD | Ad5-Hit-KD | Ad5-Hit-KD | Ad5-Hit-KD | Ad5-Hit-KD | Ad5-Hit-KD | Ad5-Hit-KD | Ad5-Hit-KD | Ad5-Hit-KD | Ad5-Hit-KD |   |
| E |   | Ad5-Hit-KD | Ad5-Hit-KD | Ad5-Hit-KD | Ad5-Hit-KD | Ad5-Hit-KD | Ad5-Hit-KD | Ad5-Hit-KD | Ad5-Hit-KD | Ad5-Hit-KD | Ad5-Hit-KD |   |
| F |   | Ad5-Hit-KD | Ad5-Hit-KD | Ad5-Hit-KD | Ad5-Hit-KD | Ad5-Hit-KD | Ad5-Hit-KD | Ad5-Hit-KD | Ad5-Hit-KD | Ad5-Hit-KD | Ad5-Hit-KD |   |
| G |   | Ad5-MMP1-KD | Ad5-Luc-KD_v13 | Ad5-eGFP-KD_v5 | Ad5-M6PR-KD_v1 | Ad5-MMP1-KD | Ad5-Luc-KD_v13 | Ad5-eGFP-KD_v5 | Ad5-M6PR-KD_v1 | Ad5-Luc-KD_v13 | Ad5-Luc-KD_v13 |   |
| H |   |   |   |   |   |   |   |   |   |    |    |    |

SEQUENCE LISTING

<160> NUMBER OF SEQ ID NOS: 108

<210> SEQ ID NO 1
<211> LENGTH: 5608
<212> TYPE: DNA
<213> ORGANISM: Homo sapiens

<400> SEQUENCE: 1

```
aagacggatt ctcagacaag gcttgcaaat gccccgcagc catcatttaa ctgcacccgc    60
agaatagtta cggtttgtca cccgaccctc ccggatcgcc taatttgtcc ctagtgagac   120
cccgaggctc tgcccgcgcc tggcttcttc gtagctggat gcatatcgtg ctccgggcag   180
cgcgggcgca gggcacgcgt tcgcgcacac cctagcacac atgaacacgc gcaagagctg   240
aaccaagcac ggtttccatt tcaaaagggg agacagcctc taccgcgatt gtagaagaga   300
ctgtggtgtg aattagggac cgggaggcgt cgaacggagg aacggttcat cttagagact   360
aattttctgg agtttctgcc cctgctctgc gtcagccctc acgtcacttc gccagcagta   420
gcagaggcgg cggcggcggc tcccggaatt gggttggagc aggagcctcg ctggctgctt   480
cgctcgcgct ctacgcgctc agtccccggc ggtagcagga gcctggaccc aggcgccgcc   540
ggcgggcgtg aggcgccgga gcccggcctc gaggtgcata ccggaccccc attcgcatct   600
aacaaggaat ctgcgcccca gagagtcccg ggagcgccgc cggtcggtgc ccggcgcgcc   660
gggccatgca gcgacggccg ccgcggagct ccgagcagcg gtagcgcccc cctgtaaagc   720
ggttcgctat gccggggcca ctgtgaaccc tgccgcctgc cggaacactc ttcgctccgg   780
accagctcag cctctgataa gctggactcg gcacgcccgc aacaagcacc gaggagttaa   840
gagagccgca agcgcaggga aggcctcccc gcacgggtgg gggaaagcgg ccggtgcagc   900
gcggggacag gcactcgggc tggcactggc tgctagggat gtcgtcctgg ataaggtggc   960
atggacccgc catggcgcgg ctctggggct tctgctggct ggttgtgggc ttctggaggg  1020
ccgctttcgc ctgtcccacg tcctgcaaat gcagtgcctc tcggatctgg tgcagcgacc  1080
cttctcctgg catcgtggca tttccgagat tggagcctaa cagtgtagat cctgagaaca  1140
tcaccgaaat tttcatcgca aaccagaaaa ggttagaaat catcaacgaa gatgatgttg  1200
aagcttatgt gggactgaga aatctgacaa ttgtggattc tggattaaaa tttgtggctc  1260
ataaagcatt tctgaaaaac agcaacctgc agcacatcaa ttttacccga aacaaactga  1320
cgagtttgtc taggaaacat ttccgtcacc ttgacttgtc tgaactgatc ctggtgggca  1380
atccatttac atgctcctgt gacattatgt ggatcaagac tctccaagag gctaaatcca  1440
gtccagacac tcaggatttg tactgcctga atgaaagcag caagaatatt cccctggcaa  1500
acctgcagat acccaattgt ggtttgccat ctgcaaatct ggccgcacct aacctcactg  1560
tggaggaagg aaagtctatc acattatcct gtagtgtggc aggtgatccg gttcctaata  1620
tgtattggga tgttggtaac ctggtttcca acatatgaa tgaaacaagc cacacacagg  1680
gctccttaag gataactaac atttcatccg atgacagtgg gaagcagatc tcttgtgtgg  1740
cggaaaatct tgtaggagaa gatcaagatt ctgtcaacct cactgtgcat tttgcaccaa  1800
ctatcacatt tctcgaatct ccaacctcag accaccactg gtgcattcca ttcactgtga  1860
aaggcaaccc caaaccagcg cttcagtggt tctataacgg ggcaatattg aatgagtcca  1920
aatacatctg tactaaaata catgttacca atcacacgga gtaccacggc tgcctccagc  1980
tggataatcc cactcacatg aacaatgggg actacactct aatagccaag aatgagtatg  2040
gaaggatgaa gaaacagatt tctgctcact tcatgggctg gcctggaatt gacgatggtg  2100
caaacccaaa ttatcctgat gtaatttatg aagattatgg aactgcagcg aatgacatcg  2160
gggacaccac gaacagaagt aatgaaatcc cttccacaga cgtcactgat aaaaccggtc  2220
gggaacatct ctcggtctat gctgtggtgg tgattgcgtc tgtggtggga ttttgccttt  2280
tggtaatgct gtttctgctt aagttggcaa gacactccaa gtttggcatg aaagatttct  2340
catggtttgg atttgggaaa gtaaaatcaa gacaaggtgt tggcccagcc tccgttatca  2400
```

```
gcaatgatga tgactctgcc agcccactcc atcacatctc caatgggagt aacactccat    2460
cttcttcgga aggtggccca gatgctgtca ttattggaat gaccaagatc cctgtcattg    2520
aaaatcccca gtactttggc atcaccaaca gtcagctcaa gccagacaca tttgttcagc    2580
acatcaagcg acataacatt gttctgaaaa gggagctagg cgaaggagcc tttggaaaag    2640
tgttcctagc tgaatgctat aacctctgtc ctgagcagga caagatcttg gtggcagtga    2700
agaccctgaa ggatgccagt gacaatgcac gcaaggactt ccaccgtgag gccgagctcc    2760
tgaccaacct ccagcatgag cacatcgtca agttctatgg cgtctgcgtg gagggcgacc    2820
ccctcatcat ggtctttgag tacatgaagc atggggacct caacaagttc ctcagggcac    2880
acggccctga tgccgtgctg atggctgagg gcaacccgcc cacggaactg acgcagtcgc    2940
agatgctgca tatagcccag cagatcgccg cgggcatggt ctacctggcg tcccagcact    3000
tcgtgcaccg cgatttggcc accaggaact gcctggtcgg ggagaacttg ctggtgaaaa    3060
tcggggactt ggggatgtcc cgggacgtgt acagcactga ctactacagg gtcggtggcc    3120
acacaatgct gcccattcgc tggatgcctc cagagagcat catgtacagg aaattcacga    3180
cggaaagcga cgtctggagc ctgggggtcg tgttgtggga gattttcacc tatggcaaac    3240
agccctggta ccagctgtca aacaatgagg tgatagagtg tatcactcag ggccgagtcc    3300
tgcagcgacc ccgcacgtgc ccccaggagg tgtatgagct gatgctgggg tgctggcagc    3360
gagagcccca catgaggaag aacatcaagg gcatccatac cctccttcag aacttggcca    3420
aggcatctcc ggtctacctg gacattctag gctagggccc ttttccccag accgatcctt    3480
cccaacgtac tcctcagacg ggctgagagg atgaacatct tttaactgcc gctggaggcc    3540
accaagctgc tctccttcac tctgacagta ttaacatcaa agactccgag aagctctcga    3600
gggaagcagt gtgtacttct tcatccatag acacagtatt gacttctttt tggcattatc    3660
tctttctctc tttccatctc ccttggttgt tccttttttct ttttttaaat tttcttttc    3720 tttttttttt cgtcttccct gcttcacgat tcttacccct tcttttgaat caatctggct    3780
tctgcattac tattaactct gcatagacaa aggccttaac aaacgtaatt tgttatatca    3840
gcagacactc cagtttgccc accacaacta acaatgcctt gttgtattcc tgcctttgat    3900
gtggatgaaa aaagggaaa acaaatattt cacttaaact ttgtcacttc tgctgtacag    3960
atatcgagag tttctatgga ttcacttcta tttatttatt attattactg ttcttattgt    4020
ttttggatgg cttaagcctg tgtataaaaa agaaacttg tgttcaatct gtgaagcctt    4080
tatctatggg agattaaaac cagagagaaa gaagatttat tatgaaccgc aatatgggag    4140
gaacaaagac aaccactggg atcagctggt gtcagtccct acttaggaaa tactcagcaa    4200
ctgttagctg ggaagaatgt attcggcacc ttcccctgag gacctttctg aggagtaaaa    4260
agactactgg cctctgtgcc atggatgatt cttttcccat caccagaaat gatagcgtgc    4320
agtagagagc aaagatggct tccgtgagac acaagatggc gcatagtgtg ctcggacaca    4380
gttttgtctt cgtaggttgt gatgatagca ctggtttgtt tctcaagcgc tatccacaga    4440 accttttgtca acttcagttg aaaagaggtg gattcatgtc cagagctcat ttcgggtca    4500 ggtgggaaag ccaagaactt ggaaaagata agacaagcta taaattcgga ggcaagtttc    4560
ttttacaatg aacttttcag atctcacttc cctccgaccc ctaacttcca tgcccacccg    4620
tccttttaac tgtgcaagca aaattgtgca tggtcttcgt cgattaatac cttgtgtgca    4680
gacactactg ctccagacgt cgtttccctg ataggtagag cagatccata aaaaggtatg    4740
acttatacaa ttaggggaag ctaatggagt ttattagctg agtatcaatg tctctgcgtt    4800
```

```
gtacggtggt gatgggtttt aatgaatatg gaccctgaag cctggaaatc ctcatccacg   4860
tcgaacccac aggactgtgg gaagggcaga atcaatccct aagggaaagg aaacctcacc   4920
ctgagggcat cacatgcact catgttcagt gtacacaggt caagtcccct gctctgggct   4980
ctagttggga gagtggtttc attccaagtg tactccattg tcagtatgct gttttttgttt  5040 ccttcactcc attcaaaaag tcaaaataca aaatttggca cagcatgcca acgggaggct   5100
gtgcccagac caagcactgg aagtgtgctt ctaggcatag tcattggttt tgcaaaaaga   5160
gggctcaaat ttaaatagaa atttacagct atttgaatgg tcagatatac aagaaagaa    5220 aaatatttct gttcctcaag aaaacttgct accctctgtg aggggaattt tgctaaactt   5280
gacatcttta taacatgagc cagattgaaa gggagtgatt ttcattcatc ttaggtcatg   5340
ttatttcata tttgtttctg aaggtgcgat agctctgttt taggttttgc ttgcgcctgt   5400
taattactgg aacaccttat ttttcattaa aggctttgaa agccaattct caaaaattca   5460
aaagtgcaaa ttaacagaac aaaaggaaat ccagtagcaa ctgcagtcaa gcagggagt   5520 tgacaagata aaccttacgt ccattcaagt tatatgctgg cctatgagag atgagagttg   5580
ggtcgtttgt tctctttgtt gatgattt                                     5608

<210> SEQ ID NO 2
<211> LENGTH: 7111
<212> TYPE: DNA
<213> ORGANISM: Homo sapiens

<400> SEQUENCE: 2
gcgtcagccc tcacgtcact tcgccagcag tagcagaggc ggcggcggcg gctcccggaa     60
ttgggttgga gcaggagcct cgctggctgc ttcgctcgcg ctctacgcgc tcagtccccg    120
gcggtagcag gagcctggac ccaggcgccg ccggcgggcg tgaggcgccg gagcccggcc    180
tcgaggtgca taccggaccc ccattcgcat ctaacaagga atctgcgccc cagagagtcc    240
cgggagcgcc gccggtcggt gcccggcgcg ccgggccatg cagcgacggc cgccgcggag    300
ctccgagcag cggtagcgcc cccctgtaaa gcggttcgct atgccggggc cactgtgaac    360
cctgccgcct gccggaacac tcttcgctcc ggaccagctc agcctctgat aagctggact    420
cggcacgccc gcaacaagca ccgaggagtt aagagagccg caagcgcagg gaaggcctcc    480
ccgcacgggt gggggaaagc ggccggtgca gcgcggggac aggcactcgg gctggcactg    540
gctgctaggg atgtcgtcct ggataaggtg gcatggaccc gccatggcgc ggctctgggg    600
cttctgctgg ctggttgtgg gcttctggag ggccgctttc gcctgtccca cgtcctgcaa    660
atgcagtgcc tctcggatct ggtgcagcga cccttctcct ggcatcgtgg catttccgag    720
attggagcct aacagtgtag atcctgagaa catcaccgaa attttcatcg caaaccagaa    780
aaggttagaa atcatcaacg aagatgatgt tgaagcttat gtgggactga aaatctgac    840 aattgtggat tctggattaa aatttgtggc tcataaagca tttctgaaaa acagcaacct    900
gcagcacatc aatttttaccc gaaacaaact gacgagtttg tctaggaaac atttccgtca    960
ccttgacttg tctgaactga tcctggtggg caatccattt acatgctcct gtgacattat   1020
gtggatcaag actctccaag aggctaaatc cagtccagac actcaggatt tgtactgcct   1080
gaatgaaagc agcaagaata ttccccctgg caaacctgcag ataccccaatt gtggtttgcc   1140 atctgcaaat ctggccgcac ctaacctcac tgtggaggaa ggaaagtcta tcacattatc   1200
ctgtagtgtg gcaggtgatc cggttcctaa tatgtattgg gatgttggta acctggtttc   1260
caaacatatg aatgaaacaa gccacacaca gggctcctta aggataacta acatttcatc   1320
```

```
cgatgacagt gggaagcaga tctcttgtgt ggcggaaaat cttgtaggag aagatcaaga    1380
ttctgtcaac ctcactgtgc attttgcacc aactatcaca tttctcgaat ctccaacctc    1440
agaccaccac tggtgcattc cattcactgt gaaaggcaac cccaaaccag cgcttcagtg    1500
gttctataac ggggcaatat tgaatgagtc caaatacatc tgtactaaaa tacatgttac    1560
caatcacacg gagtaccacg gctgcctcca gctggataat cccactcaca tgaacaatgg    1620
ggactacact ctaatagcca agaatgagta tgggaaggat gagaaacaga tttctgctca    1680
cttcatgggc tggcctggaa ttgacgatgg tgcaaaccca aattatcctg atgtaattta    1740
tgaagattat ggaactgcag cgaatgacat cggggacacc acgaacagaa gtaatgaaat    1800
cccttccaca gacgtcactg ataaaaccgg tcgggaacat ctctcggtct atgctgtggt    1860
ggtgattgcg tctgtggtgg gattttgcct tttggtaatg ctgtttctgc ttaagttggc    1920
aagacactcc aagtttggca tgaaaggttt tgttttgttt cataagatcc cactggatgg    1980
gtagctgaaa taaaggaaaa gacagagaaa ggggctgtgg tgcttgttgg ttgatgctgc    2040
catgtaagct ggactcctgg gactgctgtt ggcttatccc gggaagtgct gcttatctgg    2100
ggttttctgg tagatgtggg cggtgtttgg aggctgtact atatgaagcc tgcatatact    2160
gtgagctgtg attggggaac accaatgcag aggtaactct caggcagcta agcagcacct    2220
caagaaaaca tgttaaatta atgcttctct tcttacagta gttcaaatac aaaactgaaa    2280
tgaaatccca ttggattgta cttctcttct gaaaagtgtg cttttgacc ctactggaca    2340 tttattgact taattgcttc tgtttattaa aattgacctg caaagttaaa aaaaaattaa    2400
agttgagaac aggtataagt gcacactgaa tagtctaatc tacatgtaac acatatttta    2460
gtgtgatttt ctatactcta atcagcactg aattcagagg gtttgacttt ttcatctata    2520
acacagtgac taaagagtt aagggtatat ataccatcac tttgggactt ggtagtatta    2580
ttaaaaggtt atttccttca ctgtcaataa aagtccaaat gtttagctta ggtctgagag    2640
tcaaacaatg ttaaggattg tcttaaagtt ccttagccag caaaacaaaa caaaacaaaa    2700
caaacaaatg aaaaacgttt aaaaagaaga agaagaaaaa aaacaagaac aagcagcaac    2760
agctgttttg ttgggctat agatttaagt taggcatagt caatttcaga ataactaaga    2820
gtggaatata tgcatatggt gaaattataa ccttgccctt ttttatttgc cctctgcgat    2880
ccacctgctt tttagaagtc tgccgagtga gaaggccaca gtatctcatg ctgtttgcat    2940
tacagaactg cagcttttct actctgaaaa ggcctgggag cagaatggct ggcctgctgt    3000
gagcaggaga ggagattcta agaaggatag tccccctac aacatactgt catactgctg    3060
ggttttcatg ggtaggaaag cttgtcctga ccccagcagc aaagaggtgg caggtcgcta    3120
atgaatatat gctttataat gtccttcttc attgctgaga gggcagcctt agagctgtgg    3180
atttctgcat cccccctgag tctgacccat ggacacctgt tcattcact ttagcatcac    3240 agtgaccttt gtatgctctg ttcagtctgt gtcaggcagt atgcttgtcc tgaagagagg    3300
tttggctatc cccaccccac cccaccccac cctgttcctt ttttatcagg aggacttcag    3360
agccaggcct gcagcatttt gtttgaaaac acaatcagct ctgacagtta gacatgcaca    3420
cagacgccat agctggattg gaaacattga tgttttaaaa atttattttt tttggaaata    3480
gttgcacaaa tgctgcaatt tagctttaag gttctataga ttttaacta gtccaacaca    3540 gtcagaaaca ttgttttgaa tcctctgtaa accaaggcat taatcttaat aaaccaggat    3600
ccatttaggt accacttgat ataaaaagga tatccataat gaatatttta tactgcatcc    3660
tttacattag ccactaaata cgttattgct tgatgaagac ctttcacaga atcctatgga    3720
```

```
ttgcagcatt tcacttggct acttcatacc catgccttaa agaggggcag tttctcaaaa    3780
gcagaaacat gccgccagtt ctcaagtttt cctcctaact ccatttgaat gtaagggcag    3840
ctggccccca atgtggggag gtccgaacat tttctgaatt cccatttttct tgttcgcggc    3900
taaatgacag tttctgtcat tacttagatt ccgatctttc ccaaaggtgt tgatttacaa    3960
agaggccagc taatagcaga aatcatgacc ctgaaagaga gatgaaattc aagctgtgag    4020
ccaggcagga gctcagtatg gcaaaggttc ttgagaatca gccatttggt acaaaaaaga    4080
ttttttaaagc ttttatgtta taccatggag ccatagaaag gctatggatt gtttaagaac    4140
tattttaaag tgttccagac ccaaaaagga aaaataaaaa aaaaggaata tttgtaccca    4200
acagctagaa ggattgcaag gtagattttt gttttaaaat ggagagaagt ggacagataa    4260
ggccatttaa tatatcaaag atcagttgac atctcctagg gaatgatgaa acagcaggc    4320
tattagaaaa ttatttcata tagttctcgt gttcttttct tttttttaat ccctgaaggg    4380
atgatcagta acatagcttc tcttttctgt actctagacc accccttttc atcattttgc    4440
tttttatgtc tcccataaga aatgtgcttt ttagagcttc ctaatgcatg tgttgcatta    4500
ttgcagcatt agaaaaggag aggtagcatt tttgctgaaa tcgggcctgt cactctccaa    4560
taaaggttct ggcacttcaa tgccaggcag gtctcctaaa tgaacagaat gatctgtgtg    4620
agccgatgcc tgcccttcca gaggggccac tgtcccagc cgcagccaac tgtgtcccac    4680
aggaatggga gcctaggttt ccaaatcttg tgattcttta ggagaaacat gaaacctgga    4740
tttcgtgtga aatgtcccga ttgttaaaaa gttggctcaa ttattttaa acatttgt    4800
aagccaacaa aagtctgtgg gctgccagtt tattacttt gtcttaaaac atgatcattg    4860
ttctctcacg gtatccttct gtcttcccgt tgcaaattca cttttctttc ttcctgacat    4920
tgccattgag ggctttgtta ccacaagcta agaaactgag tttaacagcc cagttatctg    4980
caacatgtca attacctttg ctcctctcct gtgattccca ccatgctgtg accctcagct    5040
gtctcccttt gctgggaatt ctgcaccaat gtctcccctc aacccattcc ctggttggtc    5100
ctactcccgt gtggccagag acatcctagc aaatccttcc tcctattata tctgacacta    5160
atttctttt aacagcgctc atgtctcttg gcccagtcag gtgctgccag gtttagatag    5220
gaaagtacat gtcccatttt catgggtgcc cttaatgtgg tccacgtcct atatcttatt    5280
atatttactc atggctcaat gggggcctcc agagaccctc tcaggctgct gagctagact    5340
aaggaatgca tccaccgtca tcacatgaga cactgactct gtgacgacaa aagtacaaac    5400
agtctgaggc taagaaaggt tcatctcaca acaggaaaaa caaatctcaa cacacattag    5460
agataattga ttcaggggtt ttctctccca gtctcccagc agggactgat ttcatttctg    5520
acccactagg ttttcttttcc agaaataggt agcaaggaca agaactaaac aatcccagcc    5580
ccacccagca acacagaaca caggagtttg cttttggctt ctcactctcc aagtaaccct    5640
gaattaggcc cagaatggct gaggcttgga gcatctcctc agacagagca gaggcgacac    5700
ctcttcaggg gtgtgtggag taaatagctc gaagagctga agacagaaaa ccagtttcac    5760
gccaggtgcg agagagagca taatggaggg aagcccgctt tctctctcct cttctttct    5820
ctttatttct ttagagcact tgactttttt ttctctctct ctctagtatt ctaaactgac    5880
cccatgacca actgagaatt tattttttgtt tcattggttg tttcacagaa ttagaacaca    5940
cacgactttt tattcctcca ttgcaaaatg gaatcaagat actacacaag acctgtgctt    6000
tcttcctttg catgatttac acctccgcct gttttggtgc tagctgtcta gaacttctct    6060
cttggtttga atctgattcc ttcacactac actagaagtt tatttcatct tgttttgtct    6120
```

| | |
|---|---|
| agactccaga tacagaggga cagctggact gaggacaagc aattccatct agcatagggt | 6180 |
| ctctcagggt tggtgcatcc agccacatgg gcagggccag tcacatctag tctatgtccc | 6240 |
| cagagccctt ggagttgcgc agcttagctg acttgactcc aaggaaatta gtacagaagt | 6300 |
| aaccactcta ttaagtgtgt tctgctatgt tcacatgcct gtagtacctg caaaccatgc | 6360 |
| caggttcatc taaagacata ggggaagatt aaggactctt ttggacagac catgaattga | 6420 |
| atttgctgcc aggtgctgcc agactgaatt tggctgacag aactcccagc ccaggaaagt | 6480 |
| tccatgacaa tgactgtcgc agaaggaaat ttcccactaa agtcagtcca ttttcaagtt | 6540 |
| ttggtcttca gagacaaaag aacgtcccag ccacctgatt ttgatggtga ggtaactcta | 6600 |
| agttgaattc aggctagtgt tgcagtatag ctttggcatg ttcatgagtg agcacccaga | 6660 |
| atgtgttgaa ccaaccccca cccctaacta ctgactatga ctgcagtggg tttttatggg | 6720 |
| gaaaaaagt gtgaaaagca aaagaaagg aacagagatt ttttatcacc tttattgtaa | 6780 |
| gacagtccat ttatgaattg agtataaaca catacaaagt aacaagagat tcctaagaaa | 6840 |
| cgcaaatcct tgagtttcac gcacttcatg ttcaaccatt tgctgtaatc cagaggcagc | 6900 |
| ctgtgaatca ttctcatgcc ctgttttttt tttttttttc ctataatgtt ctgggtttaa | 6960 |
| aagccatctt ttccacattt tctgtaaata atggataatc attttaaaaa tttttatttt | 7020 |
| tagtgctgtt ttaacaatgt agatagatca taaatgtact tgctgaattc aatcattttt | 7080 |
| aacaagccaa taaagtttga taattcatct c | 7111 |

<210> SEQ ID NO 3
<211> LENGTH: 5560
<212> TYPE: DNA
<213> ORGANISM: Homo sapiens

<400> SEQUENCE: 3

| | |
|---|---|
| aagacggatt ctcagacaag gcttgcaaat gccccgcagc catcatttaa ctgcacccgc | 60 |
| agaatagtta cggtttgtca cccgaccctc ccggatcgcc taatttgtcc ctagtgagac | 120 |
| cccgaggctc tgcccgcgcc tggcttcttc gtagctggat gcatatcgtg ctccgggcag | 180 |
| cgcgggcgca gggcacgcgt tcgcgcacac cctagcacac atgaacacgc gcaagagctg | 240 |
| aaccaagcac ggtttccatt tcaaaaaggg agacagcctc taccgcgatt gtagaagaga | 300 |
| ctgtggtgtg aattagggac cgggaggcgt cgaacggagg aacggttcat cttagagact | 360 |
| aattttctgg agtttctgcc cctgctctgc gtcagccctc acgtcacttc gccagcagta | 420 |
| gcagaggcgg cggcggcggc tcccggaatt gggttggagc aggagcctcg ctggctgctt | 480 |
| cgctcgcgct ctacgcgctc agtccccggc ggtagcagga gcctggaccc aggcgccgcc | 540 |
| ggcgggcgtg aggcgccgga gcccggcctc gaggtgcata ccggaccccc attcgcatct | 600 |
| aacaaggaat ctgcgcccca gagagtcccg ggagcgccgc cggtcggtgc cggcgcgcc | 660 |
| gggccatgca gcgacggccg ccgcggagct ccgagcagcg gtagcgcccc cctgtaaagc | 720 |
| ggttcgctat gccggggcca ctgtgaaccc tgccgcctgc cggaacactc ttcgctccgg | 780 |
| accagctcag cctctgataa gctggactcg gcacgcccgc aacaagcacc gaggagttaa | 840 |
| gagagccgca agcgcaggga aggcctcccc gcacgggtgg gggaaagcgg ccggtgcagc | 900 |
| gcggggacag gcactcgggc tggcactggc tgctagggat gtcgtcctgg ataaggtggc | 960 |
| atggacccgc catggcgcgg ctctggggct tctgctggct ggttgtgggc ttctggaggg | 1020 |
| ccgctttcgc ctgtcccacg tcctgcaaat gcagtgcctc tcggatctgg tgcagcgacc | 1080 |
| cttctcctgg catcgtggca tttccgagat tggagcctaa cagtgtagat cctgagaaca | 1140 |

```
tcaccgaaat tttcatcgca aaccagaaaa ggttagaaat catcaacgaa gatgatgttg    1200
aagcttatgt gggactgaga aatctgacaa ttgtggattc tggattaaaa tttgtggctc    1260
ataaagcatt tctgaaaaac agcaacctgc agcacatcaa ttttacccga aacaaactga    1320
cgagtttgtc taggaaacat ttccgtcacc ttgacttgtc tgaactgatc ctggtgggca    1380
atccatttac atgctcctgt gacattatgt ggatcaagac tctccaagag gctaaatcca    1440
gtccagacac tcaggatttg tactgcctga atgaaagcag caagaatatt ccctggcaa    1500 acctgcagat acccaattgt ggtttgccat ctgcaaatct ggccgcacct aacctcactg    1560
tggaggaagg aaagtctatc acattatcct gtagtgtggc aggtgatccg gttcctaata    1620
tgtattggga tgttggtaac ctggtttcca acatatgaa tgaaacaagc cacacacagg    1680
gctccttaag gataactaac atttcatccg atgacagtgg gaagcagatc tcttgtgtgg    1740
cggaaaatct tgtaggagaa gatcaagatt ctgtcaacct cactgtgcat tttgcaccaa    1800
ctatcacatt tctcgaatct ccaacctcag accaccactg gtgcattcca ttcactgtga    1860
aaggcaaccc caaaccagcg cttcagtggt tctataacgg ggcaatattg aatgagtcca    1920
aatacatctg tactaaaata catgttacca atcacacgga gtaccacggc tgcctccagc    1980
tggataatcc cactcacatg aacaatgggg actacactct aatagccaag aatgagtatg    2040
ggaaggatga gaaacagatt tctgctcact tcatgggctg gcctggaatt gacgatggtg    2100
caaacccaaa ttatcctgat gtaatttatg aagattatgg aactgcagcg aatgacatcg    2160
gggacaccac gaacagaagt aatgaaatcc cttccacaga cgtcactgat aaaaccggtc    2220
gggaacatct ctcggtctat gctgtggtgg tgattgcgtc tgtggtggga ttttgccttt    2280
tggtaatgct gtttctgctt aagttggcaa gacactccaa gttttggcatg aaaggcccag    2340 cctccgttat cagcaatgat gatgactctg ccagcccact ccatcacatc tccaatggga    2400
gtaacactcc atcttcttcg gaaggtggcc cagatgctgt cattattgga atgaccaaga    2460
tccctgtcat tgaaaatccc cagtactttg gcatcaccaa cagtcagctc aagccagaca    2520
catttgttca gcacatcaag cgacataaca ttgttctgaa aagggagcta ggcgaaggag    2580
cctttggaaa agtgttccta gctgaatgct ataacctctg tcctgagcag gacaagatct    2640
tggtggcagt gaagaccctg aaggatgcca gtgacaatgc acgcaaggac ttccaccgtg    2700
aggccgagct cctgaccaac ctccagcatg agcacatcgt caagttctat ggcgtctgcg    2760
tggagggcga ccccctcatc atggtctttg agtacatgaa gcatgggac ctcaacaagt    2820 tcctcagggc acacgcccct gatgccgtgc tgatggctga gggcaacccg cccacggaac    2880
tgacgcagtc gcagatgctg catatagccc agcagatcgc cgcgggcatg gtctacctgg    2940
cgtcccagca cttcgtgcac cgcgatttgg ccaccaggaa ctgcctggtc ggggagaact    3000
tgctggtgaa aatcggggac tttgggatgt cccgggacgt gtacagcact gactactaca    3060
gggtcggtgg ccacacaatg ctgcccattc gctggatgcc tccagagagc atcatgtaca    3120
ggaaattcac gacggaaagc gacgtctgga gcctgggggt cgtgttgtgg gagattttca    3180
cctatggcaa acagccctgg taccagctgt caaacaatga ggtgatagag tgtatcactc    3240
agggccgagt cctgcagcga ccccgcacgt gccccaggaa ggtgtatgag ctgatgctgg    3300
ggtgctggca gcgagagccc cacatgagga gaaacatcaa gggcatccat accctccttc    3360
agaacttggc caaggcatct ccggtctacc tggacattct aggctagggc cttttcccc    3420 agaccgatcc ttcccaacgt actcctcaga cgggctgaga ggatgaacat ctttttaactg    3480 ccgctggagg ccaccaagct gctctccttc actctgacag tattaacatc aaagactccg    3540
```

| | |
|---|---|
| agaagctctc gagggaagca gtgtgtactt cttcatccat agacacagta ttgacttctt | 3600 |
| tttggcatta tctctttctc tctttccatc tcccttggtt gttcctttt ctttttttaa | 3660 |
| attttctttt tcttttttt ttcgtcttcc ctgcttcacg attcttaccc tttctttga | 3720 |
| atcaatctgg cttctgcatt actattaact ctgcatagac aaaggcctta acaaacgtaa | 3780 |
| tttgttatat cagcagacac tccagtttgc ccaccacaac taacaatgcc ttgttgtatt | 3840 |
| cctgcctttg atgtggatga aaaaaaggga aaacaaatat ttcacttaaa ctttgtcact | 3900 |
| tctgctgtac agatatcgag agtttctatg gattcacttc tatttattta ttattattac | 3960 |
| tgttcttatt gtttttggat ggcttaagcc tgtgtataaa aaagaaaact tgtgttcaat | 4020 |
| ctgtgaagcc tttatctatg ggagattaaa accagagaga aagaagattt attatgaacc | 4080 |
| gcaatatggg aggaacaaag acaaccactg ggatcagctg gtgtcagtcc ctacttagga | 4140 |
| aatactcagc aactgttagc tgggaagaat gtattcggca ccttccctg aggacctttc | 4200 |
| tgaggagtaa aaagactact ggcctctgtg ccatggatga ttcttttccc atcaccagaa | 4260 |
| atgatagcgt gcagtagaga gcaaagatgg cttccgtgag acacaagatg gcgcatagtg | 4320 |
| tgctcggaca cagttttgtc ttcgtaggtt gtgatgatag cactggtttg ttctcaagc | 4380 |
| gctatccaca gaacctttgt caacttcagt tgaaaagagg tggattcatg tccagagctc | 4440 |
| atttcggggt caggtgggaa agccaagaac ttggaaaaga taagacaagc tataaattcg | 4500 |
| gaggcaagtt tcttttacaa tgaacttttc agatctcact tccctccgac ccctaacttc | 4560 |
| catgcccacc cgtcctttta actgtgcaag caaaattgtg catggtcttc gtcgattaat | 4620 |
| accttgtgtg cagacactac tgctccagac gtcgtttccc tgataggtag agcagatcca | 4680 |
| taaaaaggta tgacttatac aattagggga agctaatgga gtttattagc tgagtatcaa | 4740 |
| tgtctctgcg ttgtacggtg gtgatgggtt ttaatgaata tggaccctga agcctggaaa | 4800 |
| tcctcatcca cgtcgaaccc acaggactgt gggaagggca gaatcaatcc ctaagggaaa | 4860 |
| ggaaacctca ccctgagggc atcacatgca ctcatgttca gtgtacacag gtcaagtccc | 4920 |
| ttgctctggg ctctagttgg gagagtggtt tcattccaag tgtactccat tgtcagtatg | 4980 |
| ctgtttttgt ttccttcact ccattcaaaa agtcaaaata caaatttgg cacagcatgc | 5040 |
| caacgggagg ctgtgcccag accaagcact ggaagtgtgc ttctaggcat agtcattggt | 5100 |
| tttgcaaaaa gagggctcaa atttaaatag aaatttacag ctatttgaat ggtcagatat | 5160 |
| accaagaaag aaaaatattt ctgttcctca agaaacttg ctaccctctg tgagggaat | 5220 |
| tttgctaaac ttgacatctt tataacatga gccagattga aagggagtga ttttcattca | 5280 |
| tcttaggtca tgttatttca tatttgtttc tgaaggtgcg atagctctgt tttaggtttt | 5340 |
| gcttgcgcct gttaattact ggaacacctt atttttcatt aaaggctttg aaagccaatt | 5400 |
| ctcaaaaatt caaaagtgca aattaacaga acaaaaggaa atccagtagc aactgcagtc | 5460 |
| aagcgaggga gttgacaaga taaaccttac gtccattcaa gttatatgct ggcctatgag | 5520 |
| agatgagagt tgggtcgttt gttctctttg ttgatgattt | 5560 |

<210> SEQ ID NO 4
<211> LENGTH: 8696
<212> TYPE: DNA
<213> ORGANISM: Homo sapiens

<400> SEQUENCE: 4

| | |
|---|---|
| aagacggatt ctcagacaag gcttgcaaat gccccgcagc catcatttaa ctgcacccgc | 60 |
| agaatagtta cggtttgtca cccgacccto ccggatcgcc taatttgtcc ctagtgagac | 120 |

```
cccgaggctc tgcccgcgcc tggcttcttc gtagctggat gcatatcgtg ctccgggcag    180
cgcgggcgca gggcacgcgt tcgcgcacac cctagcacac atgaacacgc gcaagagctg    240
aaccaagcac ggtttccatt tcaaaaaggg agacagcctc taccgcgatt gtagaagaga    300
ctgtggtgtg aattagggac cgggaggcgt cgaacggagg aacggttcat cttagagact    360
aattttctgg agtttctgcc cctgctctgc gtcagccctc acgtcacttc gccagcagta    420
gcagaggcgg cggcggcggc tcccggaatt gggttggagc aggagcctcg ctggctgctt    480
cgctcgcgct ctacgcgctc agtccccggc ggtagcagga gcctggaccc aggcgccgcc    540
ggcgggcgtg aggcgccgga gcccggcctc gaggtgcata ccggaccccc attcgcatct    600
aacaaggaat ctgcgcccca gagagtcccg ggagcgccgc cggtcggtgc ccggcgcgcc    660
gggccatgca gcgacggccg ccgcggagct ccgagcagcg gtagcgcccc cctgtaaagc    720
ggttcgctat gccggggcca ctgtgaaccc tgccgcctgc cggaacactc ttcgctccgg    780
accagctcag cctctgataa gctggactcg gcacgcccgc aacaagcacc gaggagttaa    840
gagagccgca agcgcaggga aggcctcccc gcacgggtgg gggaaagcgg ccggtgcagc    900
gcggggacag gcactcgggc tggcactggc tgctagggat gtcgtcctgg ataaggtggc    960
atggacccgc catggcgcgg ctctggggct tctgctggct ggttgtgggc ttctggaggg   1020
ccgctttcgc ctgtcccacg tcctgcaaat gcagtgcctc tcggatctgg tgcagcgacc   1080
cttctcctgg catcgtggca tttccgagat tggagcctaa cagtgtagat cctgagaaca   1140
tcaccgaaat tttcatcgca aaccagaaaa ggttagaaat catcaacgaa gatgatgttg   1200
aagcttatgt gggactgaga aatctgacaa ttgtggattc tggattaaaa tttgtggctc   1260
ataaagcatt tctgaaaaac agcaacctgc agcacatcaa ttttacccga acaaaactga   1320
cgagtttgtc taggaaacat ttccgtcacc ttgacttgtc tgaactgatc ctggtgggca   1380
atccatttac atgctcctgt gacattatgt ggatcaagac tctccaagag gctaaatcca   1440
gtccagacac tcaggatttg tactgcctga atgaaagcag caagaatatt cccctggcaa   1500
acctgcagat acccaattgt ggtttgccat ctgcaaatct ggccgcacct aacctcactg   1560
tggaggaagg aaagtctatc acattatcct gtagtgtggc aggtgatccg gttcctaata   1620
tgtattggga tgttggtaac ctggtttcca acatatgaa tgaaacaagc cacacacagg   1680
gctccttaag gataactaac atttcatccg atgacagtgg gaagcagatc tcttgtgtgg   1740
cggaaaatct tgtaggagaa gatcaagatt ctgtcaacct cactgtgcat tttgcaccaa   1800
ctatcacatt tctcgaatct ccaacctcag accaccactg gtgcattcca ttcactgtga   1860
aaggcaaccc caaaccagcg cttcagtggt tctataacgg ggcaatattg aatgagtcca   1920
aatacatctg tactaaaata catgttacca atcacacgga gtaccacggc tgcctccagc   1980
tggataatcc cactcacatg aacaatgggg actacactct aatagccaag aatgagtatg   2040 gaaggatga gaaacagatt tctgctcact tcatgggctg gcctggaatt gacgatggtg   2100
caaacccaaa ttatcctgat gtaatttatg aagattatgg aactgcagcg aatgacatcg   2160
gggacaccac gaacagaagt aatgaaatcc cttccacaga cgtcactgat aaaaccggtc   2220
gggaacatct ctcggtctat gctgtggtgg tgattgcgtc tgtggtggga ttttgccttt   2280
tggtaatgct gttcctgctt aagttggcaa gacactccaa gttggcatg aaagatttct   2340 catggtttgg atttgggaaa gtaaaatcaa gacaaggtgt tggcccagcc tccgttatca   2400
gcaatgatga tgactctgcc agcccactcc atcacatctc caatgggagt aacactccat   2460
cttcttcgga aggtggccca gatgctgtca ttattggaat gaccaagatc cctgtcattg   2520
```

```
aaaatcccca gtactttggc atcaccaaca gtcagctcaa gccagacaca tggcccagag    2580
gttcccccaa gaccgcctga taataatttg gtatttggag gctcctgtgt cactgcagga    2640
actaaaggag gctaaatcca tgcctgatgg aggagaagag ttctatggtt atctgcaaat    2700
tctggccaga caacatcttg acgtcactcc ttagcttcca taacctagcc aagcaagaag    2760 ttgccttttcc aagacaaagc agtgtgctct aatgactaac ccctcaaagt actatgccac    2820
tttaactata gacccatctc ctcgatcaat caggatggca agatggagct gaggagctca    2880
gcaacatcaa gtctggagtt ggtctttaac tcaactagct cgtttagacg tgtctgaaca    2940
ccacatcacc tgacagcacg gggtggtttc ccagtaaaat ttacaaactc agctcaaggg    3000
cagctgtgtt gctttccttt ccttgactgc tgagaaactt tttgacaggg aacaatggaa    3060
acacaccttc tgagctgaaa caaacaaaca gaaacaaaac atactaacca gcaaaatccc    3120
caaatcatca atcttgggtt ctcttgaagg gcaggagtgt gttttatctt ctcccgtcgg    3180
agcaaacact atagatgtcc tccctaaaat tctgtcttcc ctagagcagc cttgtaaatt    3240
agctagggtc ctagggttga ggcctaaatc aacttaaaat tgtctctaaa tatgtacctg    3300
gatgtgtttg tacttgcaga gcatgccctc ttcatgtgcc tagggctagt aactccctgt    3360
ggcagaggca tgtaaagtat tctgactttt ttttttttcaa cttaattcca tttccaatga    3420
aatggatttt taaaaatttt ctccagagtg tgccatactt ctccagctat tatagttaat    3480
gtgtgtgtat ccttgtgtat atgtgtgttt gtgtgtgcat atgtgttttc ctagtggtta    3540
catgcttact aggcaattat gtaaataagc acagattcat aggccagcta ggcctgagga    3600
aagaagacat tataaaggga gggagtattt taacattagc taaagctatc acacaaggca    3660
cccattctgc tcccctcaac agccacagcc cacttcgtcc ttgtcttacc aataagggga    3720
aaggctggag gtgatatttt tcacagaacc gcagaggttt tgaacatatt tgcaacatta    3780
ctttgagtac acatgagcaa aaattctgaa ttacatccag gaccccagaa gctcattaga    3840
tcaaagagtg cggggcccct cagagttacc agagattatc tgcagacttc agtgcaatcg    3900
aatgaccatg gtccattttg atggtcagag gtaggactga aaaacgggta gaaacaattg    3960
ctttagcgct tccttctgta ctttgcctat taatgttttg tctttcaaaa atatattttc    4020
tcctaattgt ttaattggcc aaataatggc tgctttggga gttgtttgta tgccttggaa    4080
ggccatggcc tgcactttaa aaataagcta agtccattct gcccagcacg agcattagga    4140
cagagaatgc acttatttta ggatccttaa aaattgcttc ttttatggca cactgggttg    4200
acgactcatc tcgtgggagc cttcatggca cattgctgct gttctgcagg tcccaataca    4260
attccttccc cctctcagtg ccacggcccc cccattgcta gctacacaat ttgatatcat    4320 attcccttttt caactccaaa ggagatgata agaagctatc aaataatgct ttaaaaaagc    4380
aacttgagtt tcttaaaaga aaggaaatga atacatgctg cataattaca tttaaaatgt    4440
aagccatgtt attataagcc gcactgagat gaagatttgt tagcaaacca gtttcaagca    4500
cactcacagt gaagtaaaat catgttttta gcatctgacc attgggtaat attattcttt    4560
gttatcaaaa gagaaatatc acccaagtat agtatactta gacctcctag aggaaacact    4620
ccagtcctaa gcttggtgtc tgaaaagaaa aacaaaaata aagattatgg atttaggtca    4680
gggagacaga gtgatattct gaagactgtg tttactccct catcatcggc caaccaagat    4740
ggagttctgc atcctgcaca tatcagacat ttcagtccaa tttcaccaaa gcatcagtga    4800
tgttctagaa gcatcccagc agatggagga tcctaatgta tttgttctgg gtatttccca    4860
aggcccagcc tgactggagt gtgtgtacca acaggatgaa tccaatcaag ctacgccccc    4920
```

```
attttggttt cggattggcc actcttgcat gtgctagtag attgtggacc aggaccagct    4980
gagcaaacac agttgcagag tagcctccta tgttgctaag aagctcctgc tacccaggtg    5040
ctttgaacaa ttgagtgctc cctctggtta agtagagatg gcaccaccgg agttttcctt    5100
ggatgtgagg ctcaatcctt tacggcagct attataacaa agtgaaggtt ttctccctgg    5160
gaaatgcagc ttttctctgt ctttactaat tctgccagcc tgtgagagta accaccgtag    5220
ctgggcttct tctcagatta attgtcatgc caggtctcct tcctggggag ctgtgatgct    5280
gctctgaggt tgattgctga ggttgtagtg ggttttttgtt tgtttttgtt tagttttttct  5340 tgattgttct tctttctctt gaatggcaag agaagaaaca ctttctctaa cccacggcca    5400
ggaaggaaat ggggagagag ctacttctta gttcaacctg gttgccacat aaaggaatct    5460
ctctccttgg actcagcccc taactggaag caagagccac tgccctctga gactgagaga    5520
gcagcccgag gaggagatga atccattctg ccctttgttt gggtttgctt cctgtcagtg    5580
agagaatgct gaggcagttc ctgttatgtg aaactttcat ttttaaaacc aggacagtcc    5640
taaacagact ggaatgagtt ggtcaatccc agttggtata ggcccaatga ttttgctag     5700 taagatagga ttgtcttcct cacccaaaat gccttcaagt gccctaaaat gggtattta     5760 aaataagaat aaataatgta gatttagtag aaaacctgga aaacataaga aacaaagatg    5820
aaacgaaaag tcccatgtaa ttccaccagt tagagttaac cactgatatc gtttggatat    5880
atggctttct agtcttgtgg atatcctttt aatctcttgt aatataaagt ctgaccatat    5940
gtgtccttgc atttgtttgt actggactct gttaatattt ctatagtaat ggctcacttt    6000
ggggagattg tgctgcacag tgtgtaggaa gcacattggg tgtattattc ccagttttgt    6060
attttgtatt tccttggaga tgtgcagggg ttaagagcgg gggtctggcc atagctggcc    6120
acgtcagact ctcatatggt aagtatcaca gagcacatga ggcctgtgtt atgcgctgga    6180
aagactcagg aaatgagagg ctctcttgtt ctgacaaggc aggctgagag ctctcattta    6240
gggtcatcac tccagataac tccaaatgca gtttattgct caactgaagc agatgatcac    6300
tttttgcctc caagttcttc accctagcta gctcctttca aagagccgag tatgctggat    6360
cttaaagggc caaactagtt acatctcata catttcctga tgtttaggga tgccttcact    6420
tccatcaagg ataccttggc tgtgcaagga cctctgatag ctggagtctc cttttggtca    6480
ctcccagctt tgcttaaact tgatggagtt tgctgtccag tgatccccgg atctttcatc    6540
atgaaagcct tccttcctct cctgatgtct caggcctcta gacctagact ggggttctgg    6600
caaggaggcc tctatcaata gtatgacatc caataatatg ttagtgttga tattttgcac    6660
agtaatatta agtttaagag attataaaaa tgagttcaaa tgaataagtt cctgtgatgt    6720
aagagattag atatgtgtga tttcagaacc aaagccaggg gggaatccca gaaagaaaac    6780
aataatataa tcctagtttc tatatattat ttttattcat tactgtatat gggtagagat    6840
caatattctt tcttatgctg ttactattaa ttaacacatt ttttaaccat gccattgaac    6900
ttttgggtgc attaaagtgg aacccaagct cctcattaga taataatggc atttggactg    6960
agtgccatat tcctaaattt ccaataaagt ggttgatata gagaggacag gataaagccc    7020
tatagtgtgc agttatatca aaacagctag tctccacttt agggaatgcc tttactagag    7080
attacatgaa atgtctgctt ataaaataag cagagatggc accactaagc agccacctga    7140
attgttttcc tacaggaatg attacttttc agatccattt atgttttcat gctcaatact    7200 tactccccctt ccctgcaaca cccaaagagt ttacttttgc aagtcatttg gtcttcagtc   7260
tactactgag gaatagagag gcactaactg ctttacccag gatcagaact catgttctta    7320
```

```
ccttctatta atagagtact tgagccagat ggactaactg gtctcacatt ttctctatct    7380
tggttttact tccataaaca tcaatatctt tacccacatg atttttccat cctcccattt    7440
ttttccatat gtattagggt tcaggaacta tgatgctaat gatcacattt cttcctagtt    7500
cctaatttca ttagtgccat ttcctgatat ctacagaaac aattatcaat acatgtagct    7560
gcttgagcct tatttagaag gctagccttt cttttccaag tgctgtcaga atgtatacat    7620
ttagtctgtc ttttccctt ttaggagtct ttgttctggg ttgatggcaa aattcctctt     7680
tttacatgtg agattttga tttcactgaa ttctacctag attttatgg acattggatt     7740
ttaaagagga aaacactcat tttcttagta agatattggt gatacatagc tatgccattg    7800
atttccatac tcctgagctt tggggaggga gacagtggcc aagtagcagg cagaataaga    7860
tcatcactca tgtcctgaat caatcacact ttccttctcg gattgtgtat atgctctgcc    7920
acttcctaca tattacatcc tgagtttta agtaaagtgg atcttagcca gatttgagtc     7980
taatggctga ttcatcggca tagttcttgg cgttaacatc tcagtgtcct ctttagttct    8040
ctttgaggat tcatgtcatt gagggccttt gtgcctccac ttgtctcagt atgaggaaga    8100
actttggtgt gagggcggag ctatgtgaag ggttgctggg ttgggggatt agttcatatg    8160
gtccccatgc catctattta cttttggaga gagggggactt tgagtgggtg gtatggata    8220
gatgttcctc aaggaaaccc tgctggctaa tgggcactac atctgtgtat tactgtgatt    8280
ctctctgtaa gctccccatg tggccaagga ccccctcct accagggcac ttcctgccac     8340
ctcattgcac tggtctcaac cattcagcct gctgctgctg caccatgttg ggctgcggta    8400
ggataggaa ggggttctgt tgattgctaa atgttgccta actttatttc cctctcccac     8460
atttcatgca agggagcgga cctaacacat gacttgcatt ctcttcctat gttcagaaac    8520
tccagggctt gcccacgtgt atgtatgagt gaccaatgga gcttggaatt ctttatctat    8580
atgatctgtc cgaaaatgag atcttttgta ctggaatttg tgatgtagtt gatcattcag    8640
agccaaacgc atataccaat aaagacaaga ctgtcatata aaaaaaaaaa aaaaaa        8696

<210> SEQ ID NO 5
<211> LENGTH: 8648
<212> TYPE: DNA
<213> ORGANISM: Homo sapiens

<400> SEQUENCE: 5
aagacggatt ctcagacaag gcttgcaaat gccccgcagc catcatttaa ctgcacccgc      60
agaatagtta cggtttgtca cccgaccctc ccggatcgcc taatttgtcc ctagtgagac     120
cccgaggctc tgcccgcgcc tggcttcttc gtagctggat gcatatcgtg ctccgggcag    180
cgcgggcgca gggcacgcgt tcgcgcacac cctagcacac atgaacacgc gcaagagctg    240
aaccaagcac ggtttccatt tcaaaaaggg agacagcctc taccgcgatt gtagaagaga    300
ctgtggtgtg aattagggac cgggaggcgt cgaacggagg aacggttcat cttagagact    360
aattttctgg agtttctgcc cctgctctgc gtcagccctc acgtcacttc gccagcagta    420
gcagaggcgg cggcggcggc tcccggaatt gggttggagc aggagcctcg ctggctgctt    480
cgctcgcgct ctacgcgctc agtccccggc ggtagcagga gcctggaccc aggcgccgcc    540
ggcgggcgtg aggcgccgga gccggcctc gaggtgcata ccggaccccc attcgcatct    600
aacaaggaat ctgcgcccca gagagtcccg ggagcgccgc cggtcggtgc ccggcgcgcc    660
gggccatgca gcgacggccg ccgcggagct ccgagcagcg gtagcgcccc cctgtaaagc    720
ggttcgctat gccggggcca ctgtgaaccc tgccgcctgc cggaacactc ttcgctccgg    780
```

-continued

| | |
|---|---|
| accagctcag cctctgataa gctggactcg gcacgcccgc aacaagcacc gaggagttaa | 840 |
| gagagccgca agcgcaggga aggcctcccc gcacgggtgg gggaaagcgg ccggtgcagc | 900 |
| gcggggacag gcactcgggc tggcactggc tgctagggat gtcgtcctgg ataaggtggc | 960 |
| atggacccgc catggcgcgg ctctgggggct tctgctggct ggttgtgggc ttctggaggg | 1020 |
| ccgctttcgc ctgtcccacg tcctgcaaat gcagtgcctc tcggatctgg tgcagcgacc | 1080 |
| cttctcctgg catcgtggca tttccgagat tggagcctaa cagtgtagat cctgagaaca | 1140 |
| tcaccgaaat tttcatcgca aaccagaaaa ggttagaaat catcaacgaa gatgatgttg | 1200 |
| aagcttatgt gggactgaga aatctgacaa ttgtggattc tggattaaaa tttgtggctc | 1260 |
| ataaagcatt tctgaaaaac agcaacctgc agcacatcaa ttttacccga aacaaactga | 1320 |
| cgagtttgtc taggaaacat ttccgtcacc ttgacttgtc tgaactgatc ctggtgggca | 1380 |
| atccatttac atgctcctgt gacattatgt ggatcaagac tctccaagag gctaaatcca | 1440 |
| gtccagacac tcaggatttg tactgcctga atgaaagcag caagaatatt cccctggcaa | 1500 |
| acctgcagat acccaattgt ggtttgccat ctgcaaatct ggccgcacct aacctcactg | 1560 |
| tggaggaagg aaagtctatc acattatcct gtagtgtggc aggtgatccg gttcctaata | 1620 |
| tgtattggga tgttggtaac ctggtttcca aacatatgaa tgaaacaagc cacacacagg | 1680 |
| gctccttaag gataactaac atttcatccg atgacagtgg gaagcagatc tcttgtgtgg | 1740 |
| cggaaaatct tgtaggagaa gatcaagatt ctgtcaacct cactgtgcat tttgcaccaa | 1800 |
| ctatcacatt tctcgaatct ccaacctcag accaccactg gtgcattcca ttcactgtga | 1860 |
| aaggcaaccc caaaccagcg cttcagtggt tctataacgg ggcaatattg aatgagtcca | 1920 |
| aatacatctg tactaaaata catgttacca atcacacgga gtaccacggc tgcctccagc | 1980 |
| tggataatcc cactcacatg aacaatgggg actacactct aatagccaag aatgagtatg | 2040 |
| ggaaggatga gaaacagatt tctgctcact tcatgggctg gcctggaatt gacgatggtg | 2100 |
| caaacccaaa ttatcctgat gtaatttatg aagattatgg aactgcagcg aatgacatcg | 2160 |
| gggacaccac gaacagaagt aatgaaatcc cttccacaga cgtcactgat aaaaccggtc | 2220 |
| gggaacatct ctcggtctat gctgtggtgg tgattgcgtc tgtggtggga ttttgccttt | 2280 |
| tggtaatgct gtttctgctt aagttggcaa gacactccaa gtttggcatg aaaggcccag | 2340 |
| cctccgttat cagcaatgat gatgactctg ccagcccact ccatcacatc tccaatggga | 2400 |
| gtaacactcc atcttcttcg gaaggtggcc cagatgctgt cattattgga atgaccaaga | 2460 |
| tccctgtcat tgaaaatccc cagtactttg gcatcaccaa cagtcagctc aagccagaca | 2520 |
| catggcccag aggttccccc aagaccgcct gataataatt tggtatttgg aggctcctgt | 2580 |
| gtcactgcag gaactaaagg aggctaaatc catgcctgat ggaggagaag agttctatgg | 2640 |
| ttatctgcaa attctggcca gacaacatct tgacgtcact ccttagcttc cataacctag | 2700 |
| ccaagcaaga agttgccttt ccaagacaaa gcagtgtgct ctaatgacta accccctcaaa | 2760 |
| gtactatgcc actttaacta tagacccatc tcctcgatca atcaggatgg caagatggag | 2820 |
| ctgaggagct cagcaacatc aagtctggag ttggtcttta actcaactag ctcgtttaga | 2880 |
| cgtgtctgaa caccacatca cctgacagca cggggtggtt tcccagtaaa atttacaaac | 2940 |
| tcagctcaag ggcagctgtg ttgctttcct tccttgact gctgagaaac ttttgacag | 3000 |
| ggaacaatgg aaacacacct tctgagctga aacaaacaaa cagaaacaaa acatactaac | 3060 |
| cagcaaaatc cccaaatcat caatcttggg ttctcttgaa gggcaggagt gtgttttatc | 3120 |
| ttctcccgtc ggagcaaaca ctatagatgt cctccctaaa attctgtctt ccctagagca | 3180 |

```
gccttgtaaa ttagctaggg tcctagggtt gaggcctaaa tcaacttaaa attgtctcta   3240
aatatgtacc tggatgtgtt tgtacttgca gagcatgccc tcttcatgtg cctagggcta   3300
gtaactccct gtggcagagg catgtaaagt attctgactt ttttttttttc aacttaattc   3360 catttccaat gaaatggatt tttaaaaatt ttctccagag tgtgccatac ttctccagct   3420
attatagtta atgtgtgtgt atccttgtgt atatgtgtgt ttgtgtgtgc atatgtgttt   3480
tcctagtggt tacatgctta ctaggcaatt atgtaaataa gcacagattc ataggccagc   3540
taggcctgag gaaagaagac attataaagg gagggagtat tttaacatta gctaaagcta   3600
tcacacaagg cacccattct gctcccctca acagccacag cccacttcgt ccttgtctta   3660
ccaataaggg gaaaggctgg aggtgatatt tttcacagaa ccgcagaggt tttgaacata   3720
tttgcaacat tactttgagt acacatgagc aaaaattctg aattacatcc aggacccag   3780 aagctcatta gatcaaagag tgcggggccc ctcagagtta ccagagatta tctgcagact   3840
tcagtgcaat cgaatgacca tggtccattt tgatggtcag aggtaggact gaaaaacggg   3900
tagaaacaat tgctttagcg cttccttctg tactttgcct attaatgttt tgtctttcaa   3960
aaatatattt tctcctaatt gtttaattgg ccaaataatg gctgctttgg gagttgtttg   4020
tatgccttgg aaggccatgg cctgcacttt aaaaataagc taagtccatt ctgcccagca   4080
cgagcattag gacagagaat gcacttattt taggatcctt aaaaattgct tcttttatgg   4140
cacactgggt tgacgactca tctcgtggga gccttcatgg cacattgctg ctgttctgca   4200
ggtcccaata caattccttc cccctctcag tgccacggcc ccccattgc tagctacaca   4260 atttgatatc atattccctt tcaactccaa aaggagatga taagaagcta tcaaataatg   4320
cttaaaaaaa gcaacttgag tttcttaaaa gaaaggaaat gaatacatgc tgcataatta   4380
catttaaaat gtaagccatg ttattataag ccgcactgag atgaagattt gttagcaaac   4440
cagtttcaag cacactcaca gtgaagtaaa atcatgtttt tagcatctga ccattgggta   4500
atattattct ttgttatcaa aagagaaata tcacccaagt atagtatact tagacctcct   4560
agaggaaaca ctccagtcct aagcttggtg tctgaaaaga aaacaaaaa taaagattat   4620 ggatttaggt cagggagaca gagtgatatt ctgaagactg tgtttactcc ctcatcatcg   4680
gccaaccaag atggagttct gcatcctgca catatcagac atttcagtcc aatttcacca   4740
aagcatcagt gatgttctag aagcatccca gcagatggag gatcctaatg tatttgttct   4800
gggtatttcc caaggcccag cctgactgga gtgtgtgtac caacaggatg aatccaatca   4860
agctacgccc ccatttttggt ttcggattgg ccactcttgc atgtgctagt agattgtgga   4920
ccaggaccag ctgagcaaac acagttgcag agtagcctcc tatgttgcta agaagctcct   4980
gctacccagg tgctttgaac aattgagtgc tccctctggt taagtagaga tggcaccacc   5040
ggagtttttc ttggatgtga ggctcaatcc tttacggcag ctattataac aaagtgaagg   5100
ttttctccct gggaaatgca gcttttctct gtctttacta attctgccag cctgtgagag   5160
taaccaccgt agctgggctt cttctcagat taattgtcat gccaggtctc cttcctgggg   5220
agctgtgatc tgctctgagg ttgattgct gaggttgtag tgggttttg tttgttttg   5280 tttagttttt cttgattgtt cttctttctc ttgaatggca agagaagaaa cactttctct   5340
aacccacggc caggaaggaa atggggagag agctacttct tagttcaacc tggttgccac   5400
ataaaggaat ctctctcctt ggactcagcc cctaactgga agcaagagcc actgccctct   5460
gagactgaga gagcagcccg aggaggagat gaatccattc tgcccctttgt ttgggtttgc   5520 ttcctgtcag tgagagaatg ctgaggcagt tcctgttatg tgaaactttc attttaaaa   5580
```

```
ccaggacagt cctaaacaga ctggaatgag ttggtcaatc ccagttggta taggcccaat    5640
gatttttgct agtaagatag gattgtcttc ctcacccaaa atgccttcaa gtgccctaaa    5700
atgggtattt taaaataaga ataaataatg tagatttagt agaaaacctg gaaaacataa    5760
gaaacaaaga tgaaacgaaa agtcccatgt aattccacca gttagagtta accactgata    5820
tcgtttggat atatggcttt ctagtcttgt ggatatcctt ttaatctctt gtaatataaa    5880
gtctgaccat atgtgtcctt gcatttgttt gtactggact ctgttaatat ttctatagta    5940
atggctcact ttggggagat tgtgctgcac agtgtgtagg aagcacattg ggtgtattat    6000
tcccagtttt gtattttgta tttccttgga gatgtgcagg ggttaagagc gggggtctgg    6060
ccatagctgg ccacgtcaga ctctcatatg gtaagtatca cagagcacat gaggcctgtg    6120
ttatgcgctg gaaagactca ggaaatgaga ggctctcttg ttctgacaag gcaggctgag    6180
agctctcatt tagggtcatc actccagata actccaaatg cagtttattg ctcaactgaa    6240
gcagatgatc acttttttgcc tccaagttct tcaccctagc tagctccttt caaagagccg    6300
agtatgctgg atcttaaagg gccaaactag ttacatctca tacatttcct gatgtttagg    6360
gatgccttca cttccatcaa ggatacettg gctgtgcaag gacctctgat agctggagtc    6420
tccttttggt cactcccagc tttgcttaaa cttgatggag tttgctgtcc agtgatcccc    6480
ggatctttca tcatgaaagc cttccttcct ctcctgatgt ctcaggcctc tagacctaga    6540
ctggggttct ggcaaggagg cctctatcaa tagtatgaca tccaataata tgttagtgtt    6600
gatattttgc acagtaatat taagtttaag agattataaa aatgagttca atgaataag    6660 ttcctgtgat gtaagagatt agatatgtgt gatttcagaa ccaaagccag gggggaatcc    6720
cagaaagaaa acaataatat aatcctagtt tctatatatt attttttattc attactgtat    6780 atgggtagag atcaatattc tttcttatgc tgttactatt aattaacaca ttttttaacc    6840
atgccattga acttttgggt gcattaaagt ggaacccaag ctcctcatta gataataatg    6900
gcatttggac tgagtgccat attcctaaat ttccaataaa gtggttgata tagagaggac    6960
aggataaagc cctatagtgt gcagttatat caaaacagct agtctccact ttagggaatg    7020
cctttactag agattacatg aaatgtctgc ttataaaata agcagagatg gcaccactaa    7080
gcagccacct gaattgtttt cctacaggaa tgattacttt tcagatccat ttatgttttc    7140
atgctcaata cttactcccc ttccctgcaa cacccaaaga gtttacttt gcaagtcatt    7200 tggtcttcag tctactactg aggaatagag aggcactaac tgctttaccc aggatcagaa    7260
ctcatgttct taccttctat taatagagta cttgagccag atggactaac tggtctcaca    7320
ttttctctat cttggtttta cttccataaa catcaatatc tttacccaca tgatttttcc    7380
atcctcccat ttttttccat atgtattagg gttcaggaac tatgatgcta atgatcacat    7440
ttcttcctag ttcctaattt cattagtgcc atttcctgat atctacagaa acaattatca    7500
atacatgtag ctgcttgagc cttatttaga aggctagcct ttcttttcca agtgctgtca    7560
gaatgtatac atttagtctg tcttttttccc ttttaggagt cttttgttctg ggttgatggc    7620 aaaattcctc tttttacatg tgagattttt gatttcactg aattctacct agattttat    7680 ggacattgga ttttaaagag gaaaacactc atttttcttag taagatattg gtgatacata    7740
gctatgccat tgatttccat actccctgagc tttggggagg gagacagtgg ccaagtagca    7800
ggcagaataa gatcatcact catgtcctga atcaatcaca cttttccttct cggattgtgt    7860 atatgctctg ccacttccta catattacat cctgagtttt taagtaaagt ggatcttagc    7920
cagatttgag tctaatggct gattcatcgg catagttctt ggcgttaaca tctcagtgtc    7980
```

-continued

| | |
|---|---|
| ctctttagtt ctctttgagg attcatgtca ttgagggcct tgtgcctcc acttgtctca | 8040 |
| gtatgaggaa gaactttggt gtgagggcgg agctatgtga agggttgctg ggttggggga | 8100 |
| ttagttcata tggtccccat gccatctatt tacttttgga gagagggac tttgagtggg | 8160 |
| tgggtatgga tagatgttcc tcaaggaaac cctgctggct aatgggcact acatctgtgt | 8220 |
| attactgtga ttctctctgt aagctcccca tgtggccaag gaccccctc ctaccagggc | 8280 |
| acttcctgcc acctcattgc actggtctca accattcagc ctgctgctgc tgcaccatgt | 8340 |
| tgggctgcgg taggataggg aaggggttct gttgattgct aaatgttgcc taactttatt | 8400 |
| tccctctccc acatttcatg caagggagcg gacctaacac atgacttgca ttctcttcct | 8460 |
| atgttcagaa actccagggc ttgcccacgt gtatgtatga gtgaccaatg gagcttggaa | 8520 |
| ttctttatct atatgatctg tccgaaaatg agatctttg tactggaatt tgtgatgtag | 8580 |
| ttgatcattc agagccaaac gcatatacca ataaagacaa gactgtcata taaaaaaaaa | 8640 |
| aaaaaaaa | 8648 |

<210> SEQ ID NO 6
<211> LENGTH: 7033
<212> TYPE: DNA
<213> ORGANISM: Homo sapiens

<400> SEQUENCE: 6

| | |
|---|---|
| cacagagcga cagagacatt tattgttatt tgttttttgg tggcaaaaag ggaaaatggc | 60 |
| gaacgactcc cctgcaaaaa gtctggtgga catcgacctc tcctccctgc gggatcctgc | 120 |
| tgggattttt gagctggtgg aagtggttgg aaatggcacc tatggacaag tctataaggg | 180 |
| tcgacatgtt aaaacgggtc agttggcagc catcaaagtt atggatgtca ctgaggatga | 240 |
| agaggaagaa atcaaactgg atataaatat gctaaagaaa tactctcatc acagaaacat | 300 |
| tgcaacatat tatggtgctt tcatcaaaaa gagccctcca ggacatgatg accaactctg | 360 |
| gcttgttatg gagttctgtg gggctgggtc cattacagac cttgtgaaga caccaaagg | 420 |
| gaacacactc aaagaagact ggatcgctta catctccaga gaaatcctga ggggactggc | 480 |
| acatcttcac attcatcatg tgattcaccg ggatatcaag ggccagaatg tgttgctgac | 540 |
| tgagaatgca gaggtgaaac ttgttgactt tggtgtgagt gctcagctgg acaggactgt | 600 |
| ggggcggaga aatacgttca taggcactcc ctactggatg gctcctgagg tcatcgcctg | 660 |
| tgatgagaac ccagatgcca cctatgatta cagaagtgat ctttggtctt gtggcattac | 720 |
| agccattgag atggcagaag gtgctccccc tctctgtgac atgcatccaa tgagagcact | 780 |
| gtttctcatt cccagaaacc ctcctcccg gctgaagtca aaaaaatggt cgaagaagtt | 840 |
| ttttagtttt atagaagggt gcctggtgaa gaattacatg cagcggccct ctacagagca | 900 |
| gcttttgaaa catcctttta aagggatca gccaaatgaa aggcaagtta gaatccagct | 960 |
| taaggatcat atagatcgta ccaggaagaa gagaggcgaa aagatgaaa ctgagtatga | 1020 |
| gtacagtggg agtgaggaag aagaggagga agtgcctgaa caggaaggag agccaagttc | 1080 |
| cattgtgaac gtgcctggtg agtctactct tcgccgagat tcctgagac tgcagcagga | 1140 |
| gaacaaggaa cgttccgagg ctcttcggag acaacagtta ctacaggagc aacagctccg | 1200 |
| ggagcaggaa gaatataaaa ggcaactgct ggcagagaga cagaagcgga ttgagcagca | 1260 |
| gaaagaacag aggcgacggc tagaagagca acaaggaga gagcgggaag ctagaaggca | 1320 |
| gcaggaacgt gaacagcgaa ggagagaaca agaagaaaag aggcgtcag aggagttgga | 1380 |
| gagaaggcgc aaagaagaag aggagaggag acgggcagaa gaagaaaga ggagagttga | 1440 |

| | |
|---|---|
| aagagaacag gagtatatca ggcgacagct agaagaggag cagcggcact tggaagtcct | 1500 |
| tcagcagcag ctgctccagg agcaggccat gttactgcat gaccatagga ggccgcaccc | 1560 |
| gcagcactcg cagcagccgc caccaccgca gcaggaaagg agcaagccaa gcttccatgc | 1620 |
| tcccgagccc aaagcccact acgagcctgc tgaccgagcg cgagaggttc ctgtgagaac | 1680 |
| aacatctcgc tcccctgttc tgtcccgtcg agattcccca ctgcagggca gtgggcagca | 1740 |
| gaatagccag gcaggacaga gaaactccac cagcagtatt gagcccaggc ttctgtggga | 1800 |
| gagagtggag aagctggtgc ccagacctgg cagtggcagc tcctcagggt ccagcaactc | 1860 |
| aggatcccag cccgggtctc accctgggtc tcagagtggc tccggggaac gcttcagagt | 1920 |
| gagatcatca tccaagtctg aaggctctcc atctcagcgc ctggaaaatg cagtgaaaaa | 1980 |
| acctgaagat aaaaaggaag ttttcagacc cctcaagcct gctggcgaag tggatctgac | 2040 |
| cgcactggcc aaagagcttc gagcagtgga agatgtacgg ccacctcaca agtaacgga | 2100 |
| ctactcctca tccagtgagg agtcggggac gacggatgag gaggacgacg atgtggagca | 2160 |
| ggaaggggct gacgagtcca cctcaggacc agaggacacc agagcagcgt catctctgaa | 2220 |
| tttgagcaat ggtgaaacgg aatctgtgaa accatgatt gtccatgatg atgtagaaag | 2280 |
| tgagccggcc atgaccccat ccaaggaggg cactctaatc gtccgccaga ctcagtccgc | 2340 |
| tagtagcaca ctccagaaac acaaatcttc ctcctccttt acacctttta tagaccccag | 2400 |
| attactacag atttctccat ctagcggaac aacagtgaca tctgtggtgg gattttcctg | 2460 |
| tgatgggatg agaccagaag ccataaggca agatcctacc cggaaaggct cagtggtcaa | 2520 |
| tgtgaatcct accaacacta ggccacagag tgacaccccg gagattcgta aatacaagaa | 2580 |
| gaggtttaac tctgagattc tgtgtgctgc cttatgggga gtgaatttgc tagtgggtac | 2640 |
| agagagtggc ctgatgctgc tggacagaag tggccaaggg aaggtctatc ctcttatcaa | 2700 |
| ccgaagacga tttcaacaaa tggacgtact tgagggcttg aatgtcttgg tgacaatatc | 2760 |
| tggcaaaaag gataagttac gtgtctacta tttgtcctgg ttaagaaata aaatacttca | 2820 |
| caatgatcca gaagttgaga agaagcaggg atggacaacc gtaggggatt tggaaggatg | 2880 |
| tgtacattat aaagttgtaa aatatgaaag aatcaaattt ctggtgattg ctttgaagag | 2940 |
| ttctgtggaa gtctatgcgt gggcaccaaa gccatatcac aaatttatgg cctttaagtc | 3000 |
| atttggagaa ttggtacata agccattact ggtggatctc actgttgagg aaggccagag | 3060 |
| gttgaaagtg atctatggat cctgtgctgg attccatgct gttgatgtgg attcaggatc | 3120 |
| agtctatgac atttatctac caacacatgt aagaaagaac ccacactcta tgatccagtg | 3180 |
| tagcatcaaa ccccatgcaa tcatcatcct ccccaataca gatggaatgg agcttctggt | 3240 |
| gtgctatgaa gatgagggg tttatgtaaa cacatatgga aggatcacca aggatgtagt | 3300 |
| tctacagtgg ggagagatgc ctacatcagt agcatatatt cgatccaatc agacaatggg | 3360 |
| ctggggagag aaggccatag agatccgatc tgtggaaact ggtcacttgg atggtgtgtt | 3420 |
| catgcacaaa agggctcaaa gactaaaatt cttgtgtgaa cgcaatgaca aggtgttctt | 3480 |
| tgcctctgtt cggtctggtg gcagcagtca ggtttatttc atgaccttag gcaggacttc | 3540 |
| tcttctgagc tggtagaagc agtgtgatcc agggattact ggcctccaga gtcttcaaga | 3600 |
| tcctgagaac ttggaattcc ttgtaactgg agctcggagc tgcaccgagg caaccagga | 3660 |
| cagctgtgtg tgcagacctc atgtgttggg ttctctcccc tccttcctgt tcctcttata | 3720 |
| taccagttta tccccattct tttttttttt cttactccaa aataaatcaa ggctgcaatg | 3780 |
| cagctggtgc tgttcagatt ctaccatcag gtgctataag tgtttgggat tgagcatcat | 3840 |

```
actggaaagc aaacacctttt cctccagctc cagaattcct tgtctctgaa tgactctgtc    3900
ttgtgggtgt ctgacagtgg cgacgatgaa catgccgttg gttttattgg cagtgggcac    3960
aaggaggtga gaagtggtgg taaaaggagc ggagtgctga agcagagagc agatttaata    4020
tagtaacatt aacagtgtat ttaattgaca tttcttttt gtaatgtgac gatatgtgga    4080
caaagaagaa gatgcaggtt taagaagtta atatttataa aatgtgaaag acacagttac    4140
taggataact tttttgtggg tggggcttgg gagatgggt ggggtgggtt aagggggtccc    4200 attttgtttc tttggatttg ggtgggggt cctggccaag aactcagtca tttttctgtg    4260
taccaggttg cctaaatcat gtgcagatgg ttctaaaaaa aaaaaaaaaa aaaaaaaaaa    4320
aaggaaaaaa aaaagaaaa agaaaacgtg tgcattttgt ataatggcca gaactttgtc    4380
gtgtgacagt attagcactg cctcagttaa aggtttaatt tttgtttaaa cctagacgtg    4440
caacaaaagt tttaccacag tctgcacttg cagaagaaag aaaaaaattc aaaccacatg    4500 tttattttt ttttgcctac ctcattgttc ttaatgcatt gagaggtgat ttagttata    4560 tgttttgga agaaaccatt aatgtttaat ttaatcttaa taccaaaacg accagattga    4620
agtttgactt ttattgtcac aaatcagcag gcacaagaac tgtccatgaa gatgggaaat    4680
agccttaagg ctgatgcagt ttacttacaa gtttagaaac cagaatgctt tgtttttacc    4740
agattcacca ttagaggttg atggggcaac tgcagcccat gacacaagat ctcattgttc    4800
tcgatgtaga ggggttggta gcagacaggt ggttacatta gaatagtcac acaaactgtt    4860
cagtgttgca ggaaccttt cttggggtg ggggagtttc ccttttctaa aaatgcaatg    4920
cactaaaact attttaagaa tgtagttaat tctgcttatt cataaagtgg gcatcttctg    4980
tgttttaggt gtaatatcga agtcctggct tttctcgttt tctcacttgc tctcttgttc    5040
tctgtttttt taaaccaatt ttactttatg aatatattca tgacatttgt aataaatgtc    5100
ttgagaaaga atttgtttca tggcttcatg gtcatcactc aagctcccgt aaggatatta    5160
ccgtctcagg aaaggatcag gactccatgt cacagtcctg ccatcttact ttcctcttgt    5220
cgagttctga gtggaaataa ctgcattatg gctgctttaa cctcagtcat caaaagaaac    5280
ttgctgtttt ttaggcttga tctttttcct ttgtggttaa ttttcctgta tattgtgaaa    5340
atgggggatt ttccctctgc tcccacccac ctaaacacag cagccatttg tacctgtttg    5400
cttcccatcc cacttggcac ccactctgac ctcttgtcag tttcctgttc ctggttccat    5460 cttttttgaaa aaggccctcc tttgagctac aaacatctgg taagacaagt acatccactc    5520
atgaatgcag acacagcagc tggtggtttt gtgtatacct gtaaagacaa gctgagaagc    5580 ttacttttg gggaagtaaa agaagatgga aatggatgtt tcatttgtat gagtttggag    5640
cagtgctgaa ggccaaagcc gcctactggt ttgtagttaa cctagagaag gttgaaaaat    5700
taatcctacc tttaaaggga tttgaggtag gctggattcc atcgccacag gactttagtt    5760
agaattaaat tcctgcttgt aatttatatc catgtttagg cttttcataa gatgaaacat    5820
gccacagtga acacactcgt gtacatatca agagaagaag gaaaggcaca ggtggagaac    5880
agtaaaaggt gggcagatgt ctttgaagaa atgctcaatg tctgatgcta agtgggagaa    5940
ggcagagaac aaaggatgtg gcataatggt cttaacatta tccaaagact tgaagctcca    6000
tgtctgtaag tcaaatgtta cacaaaaaaa aatgcaaatg gtgtttcatt ggaattacca    6060
agtgcttaga acttgctggc tttcccatag gtggtaaagg ggtctgagct cacaccgagt    6120
tgtgcttggc ttgcttgtgc agctccaggc accggtggg cactctggtg gtgtttgtgg    6180
tgaactgaat tgaatccatt gttgggctta agttactgaa attggaacac cctttgtcct    6240
```

-continued

```
tctcggcggg ggcttcctgg tctgtgcttt acttggcttt tttccttccc gtcttagcct    6300
cacccccttg tcaaccagat tgagttgcta tagcttgatg cagggaccca gtgaagtttc    6360
tccgttaaag attgggagtc gtcgaaatgt ttagattctt ttaggaaagg aattattttc    6420
ccccctttta cagggtagta acttctccac agaagtgcca atatggcaaa attacacaag    6480
aaaacagtat tgcaatgaca ccattacata aggaacattg aactgttaga ggagtgctct    6540
tccaaacaaa acaaaaatgt ctctaggttt agtcagagct ttcacaagta ataacctttc    6600
tgtattaaaa tcagagtaac cctttctgta ttgagtgcag tgttttttac tcttttctca    6660
tgcacatgtt acgttggaga aaatgtttac aaaaatggtt ttgttacact aatgcgcacc    6720
acatatttat ggtttatttt aagtgacttt ttatgggtta tttaggtttt cgtcttagtt    6780
gtagcacact taccctaatt ttgccaatta ttaatttgct aaatagtaat acaaatgaca    6840
aactgcatta aatttactaa ttataaaagc tgcaaagcag actggtggca agtacacagc    6900
ccttttttt gcagtgctaa cttgtctact gtgtattatg aaaattactg ttgtcccccc    6960
acccttttt ccttaaataa agtaaaaatg acacctaaaa aaaaaaaaa aaaaaaaaa    7020
aaaaaaaaaa aaa    7033

<210> SEQ ID NO 7
<211> LENGTH: 7495
<212> TYPE: DNA
<213> ORGANISM: Homo sapiens

<400> SEQUENCE: 7
cacagagcga cagagacatt tattgttatt tgttttttgg tggcaaaaag ggaaaatggc      60
gaacgactcc cctgcaaaaa gtctggtgga catcgacctc tcctccctgc gggatcctgc     120
tgggattttt gagctggtgg aagtggttgg aaatggcacc tatggacaag tctataaggg     180
tcgacatgtt aaaacgggtc agttggcagc catcaaagtt atggatgtca ctgaggatga     240
agaggaagaa atcaaactgg agataaatat gctaaagaaa tactctcatc acagaaacat     300
tgcaacatat tatggtgctt tcatcaaaaa gagccctcca ggacatgatg accaactctg     360
gcttgttatg gagttctgtg gggctgggtc cattacagac cttgtgaaga acaccaaagg     420
gaacacactc aaagaagact ggatcgctta catctccaga gaaatcctga ggggactggc     480
acatcttcac attcatcatg tgattcaccg ggatatcaag ggccagaatg tgttgctgac     540
tgagaatgca gaggtgaaac ttgttgactt tggtgtgagt gctcagctgg acaggactgt     600
ggggcggaga aatacgttca taggcactcc ctactggatg gctcctgagg tcatcgcctg     660
tgatgagaac ccagatgcca cctatgatta cagaagtgat cttttggtctt gtggcattac     720
agccattgag atggcagaag gtgctccccc tctctgtgac atgcatccaa tgagagcact     780
gtttctcatt cccagaaacc ctcctccccg gctgaagtca aaaaaatggt cgaagaagtt     840
ttttagtttt atagaagggt gcctggtgaa gaattacatg cagcggccct ctacagagca     900
gcttttgaaa catccttta aagggatca gccaaatgaa aggcaagtta gaatccagct     960
taaggatcat atagatcgta ccaggaagaa gagaggcgag aaagatgaaa ctgagtatga    1020
gtacagtggg agtgaggaag aagaggagga agtgcctgaa caggaaggag agccaagttc    1080
cattgtgaac gtgcctggtg agtctactct tcgccgagat ttcctgagac tgcagcagga    1140
gaacaaggaa cgttccgagg ctcttcggag acaacagtta ctacaggagc aacagctccg    1200
ggagcaggaa gaatataaaa ggcaactgct ggcagagaga cagaagcgga ttgagcagca    1260
gaaagaacag aggcgacggc tagaagagca acaaaggaga gagcgggaag ctagaaggca    1320
```

```
gcaggaacgt gaacagcgaa ggagagaaca agaagaaaag aggcgtctag aggagttgga    1380
gagaaggcgc aaagaagaag aggagaggag acgggcagaa gaagaaaaga ggagagttga    1440
aagagaacag gagtatatca ggcgacagct agaagaggag cagcggcact tggaagtcct    1500
tcagcagcag ctgctccagg agcaggccat gttactggag tgccgatggc gggagatgga    1560
ggagcaccgg caggcagaga ggctccagag gcagttgcaa caagaacaag catatctcct    1620
gtctctacag catgaccata ggaggccgca cccgcagcac tcgcagcagc cgccaccacc    1680
gcagcaggaa aggagcaagc caagcttcca tgctcccgag cccaaagccc actacgagcc    1740
tgctgaccga gcgcgagagg tggaagatag atttaggaaa actaaccaca gctcccctga    1800
agcccagtct aagcagacag gcagagtatt ggagccacca gtgccttccc gatcagagtc    1860 ttttccaat ggcaactccg agtctgtgca tcccgccctg cagagaccag cggagccaca    1920
ggtacagtgg tcccacctgg catctctcaa gaacaatgtt tcccctgtct cgcgatccca    1980
ttccttcagt gacccttctc ccaaatttgc acaccaccat cttcgttctc aggacccatg    2040
tccaccttcc cgcagtgagg tgctcagtca gagctctgac tctaagtcag aggcgcctga    2100
ccctacccaa aaggcttggt ctagatcaga cagtgacgag gtgcctccaa gggttcctgt    2160
gagaacaaca tctcgctccc ctgttctgtc ccgtcgagat tccccactgc agggcagtgg    2220
gcagcagaat agccaggcag gacagagaaa ctccaccagc agtattgagc ccaggcttct    2280
gtgggagaga gtggagaagc tggtgcccag acctggcagt ggcagctcct cagggtccag    2340
caactcagga tccagcccg gtctcacccc tgggtctcag agtggctccg gggaacgctt    2400
cagagtgaga tcatcatcca agtctgaagg ctctccatct cagcgcctgg aaaatgcagt    2460 gaaaaacct gaagataaaa aggaagtttt cagaccctc aagcctgctg gcgaagtgga    2520
tctgaccgca ctggccaaag agcttcgagc agtggaagat gtacggccac ctcacaaagt    2580
aacggactac tcctcatcca gtgaggagtc ggggacgacg gatgaggagg acgacgatgt    2640
ggagcaggaa ggggctgacg agtccacctc aggaccagag gacaccagag cagcgtcatc    2700
tctgaatttg agcaatggtg aaacggaatc tgtgaaaacc atgattgtcc atgatgatgt    2760
agaaagtgag ccggccatga ccccatccaa ggagggcact ctaatcgtcc gccagactca    2820
gtccgctagt agcacactcc agaaacacaa atcttcctcc tcctttacac cttttataga    2880
ccccagatta ctacagattt ctccatctag cggaacaaca gtgacatctg tggtgggatt    2940
ttcctgtgat gggatgagac cagaagccat aaggcaagat cctacccgga aaggctcagt    3000
ggtcaatgtg aatcctacca acactaggcc acagagtgac accccggaga ttcgtaaata    3060
caagaagagg tttaactctg agattctgtg tgctgcctta tggggagtga atttgctagt    3120
gggtacagag agtggcctga tgctgctgga cagaagtggc caaggaagg tctatcctct    3180 tatcaaccga agacgatttc aacaaatgga cgtacttgag ggcttgaatg tcttggtgac    3240
aatatctggc aaaaggata agttacgtgt ctactatttg tcctggttaa gaaataaaat    3300
acttcacaat gatccagaag ttgagaagaa gcagggatgg acaaccgtag gggatttgga    3360
aggatgtgta cattataaag ttgtaaaata tgaaagaatc aaatttctgg tgattgctt    3420 gaagagttct gtggaagtct atgcgtgggc accaaagcca tatcacaaat ttatggcctt    3480
taagtcattt ggagaattgg tacataagcc attactggtg gatctcactg ttgaggaagg    3540
ccagaggttg aaagtgatct atggatcctg tgctggattc catgctgttg atgtggattc    3600
aggatcagtc tatgacattt atctaccaac acatatccag tgtagcatca acccccatgc    3660
aatcatcatc ctccccaata cagatggaat ggagcttctg gtgtgctatg aagatgaggg    3720
```

```
ggtttatgta aacacatatg gaaggatcac caaggatgta gttctacagt ggggagagat   3780
gcctacatca gtagcatata ttcgatccaa tcagacaatg gctggggag agaaggccat    3840 agagatccga tctgtggaaa ctggtcactt ggatggtgtg ttcatgcaca aaagggctca   3900
aagactaaaa ttcttgtgtg aacgcaatga caaggtgttc tttgcctctg ttcggtctgg   3960
tggcagcagt caggtttatt tcatgacctt aggcaggact tctcttctga gctggtagaa   4020
gcagtgtgat ccagggatta ctggcctcca gagtcttcaa gatcctgaga acttggaatt   4080
ccttgtaact ggagctcgga gctgcaccga gggcaaccag gacagctgtg tgtgcagacc   4140
tcatgtgttg ggttctctcc cctccttcct gttcctctta tataccagtt tatccccatt   4200
cttttttttt ttcttactcc aaaataaatc aaggctgcaa tgcagctggt gctgttcaga   4260
ttctaccatc aggtgctata agtgtttggg attgagcatc atactggaaa gcaaacacct   4320
ttcctccagc tccagaattc cttgtctctg aatgactctg tcttgtgggt gtctgacagt   4380
ggcgacgatg aacatgccgt tggttttatt ggcagtgggc acaaggaggt gagaagtggt   4440
ggtaaaagga gcggagtgct gaagcagaga gcagatttaa tatagtaaca ttaacagtgt   4500
atttaattga catttctttt ttgtaatgtg acgatatgtg gacaaagaag aagatgcagg   4560
tttaagaagt taatatttat aaaatgtgaa agacacagtt actaggataa ctttttttgtg   4620 ggtgggctt gggagatggg gtggggtggg ttaaggggtc ccatttttgtt tctttggatt    4680 tggggtgggg gtcctggcca agaactcagt cattttctg tgtaccaggt tgcctaaatc     4740
atgtgcagat ggttctaaaa aaaaaaaaa aaaaaaaaa aaaggaaaaa aaaaaaagaa      4800
aaagaaaacg tgtgcatttt gtataatggc cagaactttg tcgtgtgaca gtattagcac   4860
tgcctcagtt aaaggtttaa ttttttgttta aacctagacg tgcaacaaaa gttttaccac   4920
agtctgcact tgcagaagaa agaaaaaaat tcaaaccaca tgtttatttt tttttttgcct   4980 acctcattgt tcttaatgca ttgagaggtg atttagttta tatgttttg gaagaaacca     5040 ttaatgttta atttaatctt aataccaaaa cgaccagatt gaagtttgac tttttattgtc   5100 acaaatcagc aggcacaaga actgtccatg aagatgggaa atagccttaa ggctgatgca    5160
gtttacttac aagtttagaa accagaatgc tttgttttta ccagattcac cattagaggt    5220
tgatggggca actgcagccc atgacacaag atctcattgt tctcgatgta gaggggttgg    5280
tagcagacag gtggttacat tagaatagtc acacaaactg ttcagtgttg caggaacctt    5340
ttcttggggg tgggggagtt tcccttttct aaaaatgcaa tgcactaaaa ctattttaag    5400
aatgtagtta attctgctta ttcataaagt gggcatcttc tgtgttttag gtgtaatatc    5460
gaagtcctgg cttttctcgt tttctcactt gctctcttgt tctctgtttt tttaaaccaa    5520 ttttactttta tgaatatatt catgacattt gtaataaatg tcttgagaaa gaatttgttt   5580
catggcttca tggtcatcac tcaagctccc gtaaggatat taccgtctca ggaaaggatc    5640
aggactccat gtcacagtcc tgccatctta ctttcctctt gtcgagttct gagtggaaat    5700
aactgcatta tggctgcttt aacctcagtc atcaaaagaa acttgctgtt ttttaggctt    5760
gatctttttc ctttgtggtt aatttttcctg tatattgtga aaatggggga ttttccctct   5820
gctcccaccc acctaaacac agcagccatt tgtacctgtt tgcttcccat cccacttggc    5880
acccactctg acctcttgtc agtttcctgt tcctggttcc atctttttga aaaaggccct    5940
cctttgagct acaaacatct ggtaagacaa gtacatccac tcatgaatgc agacacagca   6000
gctggtggtt ttgtgtatac ctgtaaagac aagctgagaa gcttactttt tgggggaagta  6060 aaagaagatg gaaatggatg tttcatttgt atgagtttgg agcagtgctg aaggccaaag   6120
```

```
                                  -continued
ccgcctactg gtttgtagtt aacctagaga aggttgaaaa attaatccta cctttaaagg      6180
gatttgaggt aggctggatt ccatcgccac aggactttag ttagaattaa attcctgctt      6240
gtaatttata tccatgttta ggcttttcat aagatgaaac atgccacagt gaacacactc      6300
gtgtacatat caagagaaga aggaaaggca caggtggaga acagtaaaag gtgggcagat      6360
gtctttgaag aaatgctcaa tgtctgatgc taagtgggag aaggcagaga acaaaggatg      6420
tggcataatg gtcttaacat tatccaaaga cttgaagctc catgtctgta agtcaaatgt      6480
tacacaaaaa aaaatgcaaa tggtgtttca ttggaattac caagtgctta gaacttgctg      6540
gctttcccat aggtggtaaa ggggtctgag ctcacaccga gttgtgcttg gcttgcttgt      6600
gcagctccag gcacccggtg ggcactctgg tggtgtttgt ggtgaactga attgaatcca      6660
ttgttgggct taagttactg aaattggaac accctttgtc cttctcggcg ggggcttcct      6720
ggtctgtgct ttacttggct ttttccttc ccgtcttagc ctcaccccct tgtcaaccag       6780
attgagttgc tatagcttga tgcagggacc cagtgaagtt tctccgttaa agattgggag      6840
tcgtcgaaat gtttagattc ttttaggaaa ggaattattt tccccccttt tacagggtag      6900
taacttctcc acagaagtgc caatatggca aaattacaca agaaaacagt attgcaatga      6960
caccattaca taaggaacat tgaactgtta gaggagtgct cttccaaaca aaacaaaaat      7020
gtctctaggt ttagtcagag cttctcacaag taataacctt tctgtattaa aatcagagta     7080 acccttctg tattgagtgc agtgttttt actcttttct catgcacatg ttacgttgga        7140
gaaaatgttt acaaaatgg ttttgttaca ctaatgcgca ccacatattt atggtttatt       7200
ttaagtgact ttttatgggt tatttaggtt ttcgtcttag ttgtagcaca cttaccctaa      7260
ttttgccaat tattaatttg ctaaatagta atacaaatga caaactgcat taaatttact     7320
aattataaaa gctgcaaagc agactggtgg caagtacaca gccctttttt ttgcagtgct     7380
aacttgtcta ctgtgtatta tgaaaattac tgttgtcccc ccaccctttt ttccttaaat     7440
aaagtaaaaa tgacacctaa aaaaaaaaaa aaaaaaaaaa aaaaaaaaaa aaaaa           7495

<210> SEQ ID NO 8
<211> LENGTH: 7171
<212> TYPE: DNA
<213> ORGANISM: Homo sapiens

<400> SEQUENCE: 8
cacagagcga cagagacatt tattgttatt tgttttttgg tggcaaaaag ggaaaatggc        60
gaacgactcc cctgcaaaaa gtctggtgga catcgacctc tcctccctgc gggatcctgc       120
tgggattttt gagctggtgg aagtggttgg aaatggcacc tatggacaag tctataaggg       180
tcgacatgtt aaaacgggtc agttggcagc catcaaagtt atggatgtca ctgaggatga       240
agaggaagaa atcaaactgg agataaaatat gctaaagaaa tactctcatc acagaaacat      300
tgcaacatat tatggtgctt tcatcaaaaa gagccctcca ggacatgatg accaactctg       360
gcttgttatg gagttctgtg gggctgggtc cattacagac cttgtgaaga acaccaaagg       420
gaacacactc aaagaagact ggatcgctta catctccaga gaaatcctga gggactggc        480 acatcttcac attcatcatg tgattcaccg ggatatcaag gccagaatgt gttgctgac        540 tgagaatgca gaggtgaaac ttgttgactt tggtgtgagt gctcagctgg acaggactgt       600
ggggcggaga aatacgttca taggcactcc ctactggatg ctcctgagg tcatcgcctg       660 tgatgagaac ccagatgcca cctatgatta cagaagtgat ctttggtctt gtggcattac       720
agccattgag atggcagaag gtgctccccc tctctgtgac atgcatccaa tgagagcact       780
```

```
gtttctcatt cccagaaacc ctcctccccg gctgaagtca aaaaaatggt cgaagaagtt        840
ttttagtttt atagaagggt gcctggtgaa gaattacatg cagcggccct ctacagagca        900
gcttttgaaa catcctttta taagggatca gccaaatgaa aggcaagtta gaatccagct        960
taaggatcat atagatcgta ccaggaagaa gagaggcgag aaagatgaaa ctgagtatga       1020
gtacagtggg agtgaggaag aagaggagga agtgcctgaa caggaaggag agccaagttc       1080
cattgtgaac gtgcctggtg agtctactct tcgccgagat ttcctgagac tgcagcagga       1140
gaacaaggaa cgttccgagg ctcttcggag acaacagtta ctacaggagc aacagctccg       1200
ggagcaggaa gaatataaaa ggcaactgct ggcagagaga cagaagcgga ttgagcagca       1260
gaaagaacag aggcgacggc tagaagagca acaaggaga gagcgggaag ctagaaggca       1320
gcaggaacgt gaacagcgaa ggagagaaca agaagaaaag aggcgtctag aggagttgga       1380
gagaaggcgc aaagaagaag aggagaggag acgggcagaa gaagaaaaga ggagagttga       1440
aagagaacag gagtatatca ggcgacagct agaagaggag cagcggcact tggaagtcct       1500
tcagcagcag ctgctccagg agcaggccat gttactgcat gaccatagga ggccgcaccc       1560
gcagcactcg cagcagccgc caccaccgca gcaggaaagg agcaagccaa gcttccatgc       1620
tcccgagccc aaagcccact acgagcctgc tgaccgagcg cgagaggtgg aagatagatt       1680
taggaaaact aaccacagct cccctgaagc ccagtctaag cagacaggca gagtattgga       1740
gccaccagtg ccttcccgat cagagtcttt ttccaatggc aactccgagt ctgtgcatcc       1800
cgccctgcag agaccagcgg agccacaggt tcctgtgaga caacatctc gctcccctgt       1860
tctgtcccgt cgagattccc cactgcaggg cagtgggcag cagaatagcc aggcaggaca       1920
gagaaactcc accagcagta ttgagcccag gcttctgtgg gagagagtgg agaagctggt       1980
gcccagacct ggcagtggca gctcctcagg gtccagcaac tcaggatccc agcccgggtc       2040
tcaccctggg tctcagagtg gctccgggga acgcttcaga gtgagatcat catccaagtc       2100
tgaaggctct ccatctcagc gcctggaaaa tgcagtgaaa aaacctgaag ataaaaagga       2160
agttttcaga cccctcaagc ctgctggcga agtggatctg accgcactgg ccaaagagct       2220
tcgagcagtg gaagatgtac ggccacctca caaagtaacg gactactcct catccagtga       2280
ggagtcgggg acgacggatg aggaggacga cgatgtggag caggaagggg ctgacgagtc       2340
cacctcagga ccagaggaca ccagagcagc gtcatctctg aatttgagca atggtgaaac       2400
ggaatctgtg aaaaccatga ttgtccatga tgatgtagaa agtgagccgg ccatgacccc       2460
atccaaggag ggcactctaa tcgtccgcca gactcagtcc gctagtagca cactccagaa       2520
acacaaatct tcctcctcct ttacacccttt tatagacccc agattactac agatttctcc       2580
atctagcgga caacagtga catctgtggt gggattttcc tgtgatggga tgagaccaga       2640
agccataagg caagatccta cccggaaagg ctcagtggtc aatgtgaatc ctaccaacac       2700
taggccacag agtgacaccc cggagattcg taaatacaag aagaggttta actctgagat       2760
tctgtgtgct gccttatggg gagtgaattt gctagtgggt acagagagtg gcctgatgct       2820
gctggacaga agtggccaag ggaaggtcta tcctcttatc aaccgaagac gatttcaaca       2880
aatggacgta cttgagggct tgaatgtctt ggtgacaata tctggcaaaa aggataagtt       2940
acgtgtctac tatttgtcct ggttaagaaa taaaatactt cacaatgatc cagaagttga       3000
gaagaagcag ggatggacaa ccgtagggga tttggaagga tgtgtacatt ataaagttgt       3060
aaaatatgaa agaatcaaat ttctggtgat tgctttgaag agttctgtgg aagtctatgc       3120
gtgggcacca aagccatatc acaaatttat ggcctttaag tcatttggag aattggtaca       3180
```

```
taagccatta ctggtggatc tcactgttga ggaaggccag aggttgaaag tgatctatgg    3240
atcctgtgct ggattccatg ctgttgatgt ggattcagga tcagtctatg acatttatct    3300
accaacacat atccagtgta gcatcaaacc ccatgcaatc atcatcctcc ccaatacaga    3360
tggaatggag cttctggtgt gctatgaaga tgagggggtt tatgtaaaca catatggaag    3420
gatcaccaag gatgtagttc tacagtgggg agagatgcct acatcagtag catatattcg    3480
atccaatcag acaatgggct ggggagagaa ggccatagag atccgatctg tggaaactgg    3540
tcacttggat ggtgtgttca tgcacaaaag ggctcaaaga ctaaaattct tgtgtgaacg    3600
caatgacaag gtgttctttg cctctgttcg gtctggtggc agcagtcagg tttatttcat    3660
gaccttaggc aggacttctc ttctgagctg gtagaagcag tgtgatccag ggattactgg    3720
cctccagagt cttcaagatc ctgagaactt ggaattcctt gtaactggag ctcggagctg    3780
caccgagggc aaccaggaca gctgtgtgtg cagacctcat gtgttgggtt ctctcccctc    3840
cttcctgttc ctcttatata ccagtttatc cccattcttt ttttttttct tactccaaaa    3900
taaatcaagg ctgcaatgca gctggtgctg ttcagattct accatcaggt gctataagtg    3960
tttgggattg agcatcatac tggaaagcaa acacctttcc tccagctcca gaattccttg    4020
tctctgaatg actctgtctt gtgggtgtct gacagtggcg acgatgaaca tgccgttggt    4080
tttattggca gtgggcacaa ggaggtgaga agtggtggta aaaggagcgg agtgctgaag    4140
cagagagcag atttaatata gtaacattaa cagtgtattt aattgacatt tcttttttgt    4200
aatgtgacga tatgtggaca agaagaagaa tgcaggttta agaagttaat atttataaaa    4260
tgtgaaagac acagttacta ggataacttt tttgtgggtg gggcttggga gatggggtgg    4320
ggtgggttaa ggggtcccat tttgtttctt tggatttggg gtgggggtcc tggccaagaa    4380
ctcagtcatt tttctgtgta ccaggttgcc taaatcatgt gcagatggtt ctaaaaaaaa    4440
aaaaaaaaaa aaaaaaaaaa ggaaaaaaaa aagaaaaag aaaacgtgtg cattttgtat    4500
aatggccaga actttgtcgt gtgacagtat tagcactgcc tcagttaaag gtttaatttt    4560
tgtttaaacc tagacgtgca acaaaagttt taccacagtc tgcacttgca gaagaaagaa    4620
aaaaattcaa accacatgtt tattttttt ttgcctacct cattgttctt aatgcattga    4680
gaggtgattt agtttatatg tttttggaag aaaccattaa tgtttaattt aatcttaata    4740
ccaaaacgac cagattgaag tttgactttt attgtcacaa atcagcaggc acaagaactg    4800
tccatgaaga tgggaaatag ccttaaggct gatgcagttt acttacaagt ttagaaacca    4860
gaatgctttg tttttaccag attcaccatt agaggttgat ggggcaactg cagcccatga    4920
cacaagatct cattgttctc gatgtagagg ggttggtagc agacaggtgg ttacattaga    4980
atagtcacac aaactgttca gtgttgcagg aaccttttct tgggggtggg ggagtttccc    5040
ttttctaaaa atgcaatgca ctaaaactat tttaagaatg tagttaattc tgcttattca    5100
taaagtgggc atcttctgtg ttttaggtgt aatatcgaag tcctggcttt tctcgttttc    5160
tcacttgctc tcttgttctc tgtttttta accaatttt actttatgaa tatattcatg    5220
acatttgtaa taaatgtctt gagaaagaat ttgtttcatg gcttcatggt catcactcaa    5280
gctcccgtaa ggatattacc gtctcaggaa aggatcagga ctccatgtca cagtcctgcc    5340
atcttacttt cctcttgtcg agttctgagt ggaaataact gcattatggc tgctttaacc    5400
tcagtcatca aaagaaactt gctgtttttt aggcttgatc ttttccttt gtggttaatt    5460 ttcctgtata ttgtgaaaat gggggatttt ccctctgctc ccaccccacct aaacacagca    5520 gccatttgta cctgtttgct tcccatccca cttggcaccc actctgacct cttgtcagtt    5580
```

-continued

| | |
|---|---|
| tcctgttcct ggttccatct ttttgaaaaa ggccctcctt tgagctacaa acatctggta | 5640 |
| agacaagtac atccactcat gaatgcagac acagcagctg gtggttttgt gtatacctgt | 5700 |
| aaagacaagc tgagaagctt acttttgggg gaagtaaaag aagatggaaa tggatgtttc | 5760 |
| atttgtatga gtttggagca gtgctgaagg ccaaagccgc ctactggttt gtagttaacc | 5820 |
| tagagaaggt tgaaaaatta atcctacctt taaagggatt tgaggtaggc tggattccat | 5880 |
| cgccacagga ctttagttag aattaaattc ctgcttgtaa tttatatcca tgtttaggct | 5940 |
| tttcataaga tgaaacatgc cacagtgaac acactcgtgt acatatcaag agaagaagga | 6000 |
| aaggcacagg tggagaacag taaaaggtgg gcagatgtct tgaagaaat gctcaatgtc | 6060 |
| tgatgctaag tgggagaagg cagagaacaa aggatgtggc ataatggtct taacattatc | 6120 |
| caaagacttg aagctccatg tctgtaagtc aaatgttaca caaaaaaaaa tgcaaatggt | 6180 |
| gtttcattgg aattaccaag tgcttagaac ttgctggctt tcccataggt ggtaaagggg | 6240 |
| tctgagctca caccgagttg tgcttggctt gcttgtgcag ctccaggcac ccggtgggca | 6300 |
| ctctggtggt gtttgtggtg aactgaattg aatccattgt tgggcttaag ttactgaaat | 6360 |
| tggaacaccc tttgtccttc tcggcggggg cttcctggtc tgtgctttac ttggcttttt | 6420 |
| tccttcccgt cttagcctca cccccttgtc aaccagattg agttgctata gcttgatgca | 6480 |
| gggacccagt gaagtttctc cgttaaagat tgggagtcgt cgaaatgttt agattctttt | 6540 |
| aggaaaggaa ttattttccc ccctttaca gggtagtaac ttctccacag aagtgccaat | 6600 |
| atggcaaaat tacacaagaa aacagtattg caatgacacc attacataag gaacattgaa | 6660 |
| ctgttagagg agtgctcttc caaacaaaac aaaaatgtct ctaggtttag tcagagcttt | 6720 |
| cacaagtaat aacctttctg tattaaaatc agagtaaccc tttctgtatt gagtgcagtg | 6780 |
| ttttttactc ttttctcatg cacatgttac gttggagaaa atgttacaa aaatggtttt | 6840 |
| gttacactaa tgcgcaccac atatttatgg tttattttaa gtgacttttt atgggttatt | 6900 |
| taggttttcg tcttagttgt agcacactta ccctaatttt gccaattatt aatttgctaa | 6960 |
| atagtaatac aaatgacaaa ctgcattaaa tttactaatt ataaaagctg caaagcagac | 7020 |
| tggtggcaag tacacagccc ttttttttgc agtgctaact tgtctactgt gtattatgaa | 7080 |
| aattactgtt gtcccccccac ccttttttcc ttaaataaag taaaaatgac acctaaaaaa | 7140 |
| aaaaaaaaaa aaaaaaaaa aaaaaaaaaa a | 7171 |

<210> SEQ ID NO 9
<211> LENGTH: 4837
<212> TYPE: DNA
<213> ORGANISM: Homo sapiens

<400> SEQUENCE: 9

| | |
|---|---|
| cgaggagagt accgggccgg cccggctgcc gcgcgaggag cgcggtcggc ggcctggtct | 60 |
| gcggctgaga tacacagagc gacagagaca tttattgtta tttgtttttt ggtggcaaaa | 120 |
| agggaaaatg gcgaacgact cccctgcaaa aagtctggtg gacatcgacc tctcctccct | 180 |
| gcgggatcct gctgggattt ttgagctggt ggaagtggtt ggaaatggca cctatggaca | 240 |
| agtctataag ggtcgacatg ttaaaacggg tcagttggca gccatcaaag ttatggatgt | 300 |
| cactgaggat gaagaggaag aaatcaaact ggagataaat atgctaaaga atactctca | 360 |
| tcacagaaac attgcaacat attatggtgc tttcatcaaa aagagccctc aggacatga | 420 |
| tgaccaactc tggcttgtta tggagttctg tggggctggg tccattacag accttgtgaa | 480 |
| gaacaccaaa gggaacacac tcaaagaaga ctggatcgct tacatctcca gagaaatcct | 540 |

```
gaggggactg gcacatcttc acattcatca tgtgattcac cgggatatca agggccagaa    600
tgtgttgctg actgagaatg cagaggtgaa acttgttgac tttggtgtga gtgctcagct    660
ggacaggact gtggggcgga gaaatacgtt cataggcact ccctactgga tggctcctga    720
ggtcatcgcc tgtgatgaga acccagatgc cacctatgat tacagaagtg atctttggtc    780
ttgtggcatt acagccattg agatggcaga aggtgctccc cctctctgtg acatgcatcc    840
aatgagagca ctgtttctca ttcccagaaa ccctcctccc cggctgaagt caaaaaaatg    900
gtcgaagaag ttttttagtt ttatagaagg gtgcctggtg aagaattaca tgcagcggcc    960
ctctacagag cagcttttga acatcctttt tataagggat cagccaaatg aaaggcaagt   1020
tagaatccag cttaaggatc atatagatcg taccaggaag aagagaggcg agaaagatga   1080
aactgagtat gagtacagtg ggagtgagga agaagaggag gaagtgcctg aacaggaagg   1140
agagccaagt tccattgtga acgtgcctgg tgagtctact cttcgccgag atttcctgag   1200
actgcagcag gagaacaagg aacgttccga ggctcttcgg agacaacagt tactacagga   1260
gcaacagctc cgggagcagg aagaatataa aaggcaactg ctggcagaga gacagaagcg   1320
gattgagcag cagaaagaac agaggcgacg gctagaagag caacaaagga gagagcggga   1380
agctagaagg cagcaggaac gtgaacagcg aaggagagaa caagaagaaa agaggcgtct   1440
agaggagttg gagagaaggc gcaaagaaga agaggagagg agacgggcag aagaagaaaa   1500
gaggagagtt gaaagagaac aggagtatat caggcgacag ctagaagagg agcagcggca   1560
cttggaagtc cttcagcagc agctgctcca ggagcaggcc atgttactgg agtgccgatg   1620
gcgggagatg gaggagcacc ggcaggcaga gaggctccag aggcagttgc aacaagaaca   1680
agcatatctc ctgtctctac agcatgacca taggaggccg cacccgcagc actcgcagca   1740
gccgccacca ccgcagcagg aaaggagcaa gccaagcttc catgctcccg agcccaaagc   1800
ccactacgag cctgctgacc gagcgcgaga ggtggaagat agatttagga aaactaacca   1860
cagctcccct gaagcccagt ctaagcagac aggcagagta ttggagccac cagtgccttc   1920
ccgatcagag tcttttttcca atggcaactc cgagtctgtg catcccgccc tgcagagacc   1980
agcggagcca caggtacagt ggtcccacct ggcatctctc aagaacaatg tttcccctgt   2040
ctcgcgatcc cattccttca gtgacccttc tcccaaattt gcacaccacc atcttcgttc   2100
tcaggaccca tgtccacctt cccgcagtga ggtgctcagt cagagctctg actctaagtc   2160
agaggcgcct gaccctaccc aaaaggcttg gtctagatca gacagtgacg aggtgcctcc   2220
aagggttcct gtgagaacaa catctcgctc ccctgttctg tcccgtcgag attcccact    2280
gcagggcagt gggcagcaga atagccaggc aggacagaga aactccacca gcagtattga   2340
gcccaggctt ctgtgggaga gagtggagaa gctggtgccc agacctggca gtggcagctc   2400
ctcagggtcc agcaactcag gatcccagcc cgggtctcac cctgggtctc agagtggctc   2460
cggggaacgc ttcagagtga gatcatcatc caagtctgaa ggctctccat ctcagcgcct   2520
ggaaaatgca gtgaaaaaac ctgaagataa aaaggaagtt ttcagacccc tcaagcctgc   2580
tggcgaagtg gatctgaccg cactggccaa agagcttcga gcagtggaag atgtacggcc   2640
acctcacaaa gtaacggact actcctcatc cagtgaggag tcggggacga cggatgagga   2700
ggacgacgat gtggagcagg aaggggctga cgagtccacc tcaggaccag aggacaccag   2760
agcagcgtca tctctgaatt tgagcaatgg tgaaacggaa tctgtgaaaa ccatgattgt   2820
ccatgatgat gtgaaaagtg agccggccat gaccccatcc aaggagggca ctctaatcgt   2880
ccgccagagt acagttgacc aaaagcgtgc cagccatcat gagagcaatg gctttgccgg   2940
```

-continued

| | |
|---|---|
| tcgcattcac ctcttgccag atctcttaca gcaaagccat tcctcctcca cttcctccac | 3000 |
| ctcctcctcc ccatcctcca gccagccgac acccaccatg tccccacaga caccccagga | 3060 |
| caagctcact gctaatgaga ctcagtccgc tagtagcaca ctccagaaac acaaatcttc | 3120 |
| ctcctccttt acaccttta tagaccccag attactacag atttctccat ctagcggaac | 3180 |
| aacagtgaca tctgtggtgg gattttcctg tgatgggatg agaccagaag ccataaggca | 3240 |
| agatcctacc cggaaaggct cagtggtcaa tgtgaatcct accaacacta ggccacagag | 3300 |
| tgacaccccg gagattcgta atacaagaa gaggtttaac tctgagattc tgtgtgctgc | 3360 |
| cttatgggga gtgaatttgc tagtgggtac agagagtggc ctgatgctgc tggacagaag | 3420 |
| tggccaaggg aaggtctatc ctcttatcaa ccgaagacga tttcaacaaa tggacgtact | 3480 |
| tgagggcttg aatgtcttgg tgacaatatc tggcaaaaag gataagttac gtgtctacta | 3540 |
| tttgtcctgg ttaagaaata aaatacttca caatgatcca gaagttgaga agaagcaggg | 3600 |
| atggacaacc gtaggggatt tggaaggatg tgtacattat aaagttgtaa atatgaaag | 3660 |
| aatcaaattt ctggtgattg cttttgaagag ttctgtggaa gtctatgcgt gggcaccaaa | 3720 |
| gccatatcac aaatttatgg cctttaagtc atttggagaa ttggtacata agccattact | 3780 |
| ggtggatctc actgttgagg aaggccagag gttgaaagtg atctatggat cctgtgctgg | 3840 |
| attccatgct gttgatgtgg attcaggatc agtctatgac atttatctac caacacatgt | 3900 |
| aagaaagaac ccacactcta tgatccagtg tagcatcaaa ccccatgcaa tcatcatcct | 3960 |
| ccccaataca gatggaatgg agcttctggt gtgctatgaa gatgagggg tttatgtaaa | 4020 |
| cacatatgga aggatcacca aggatgtagt tctacagtgg ggagagatgc ctacatcagt | 4080 |
| agcatatatt cgatccaatc agacaatggg ctggggagag aaggccatag agatccgatc | 4140 |
| tgtggaaact ggtcacttgg atggtgtgtt catgcacaaa agggctcaaa gactaaaatt | 4200 |
| cttgtgtgaa cgcaatgaca aggtgttctt tgcctctgtt cggtctggtg gcagcagtca | 4260 |
| ggtttatttc atgaccttag gcaggacttc tcttctgagc tggtagaagc agtgtgatcc | 4320 |
| agggattact ggcctccaga gtcttcaaga tcctgagaac ttggaattcc ttgtaactgg | 4380 |
| agctcggagc tgcaccgagg gcaaccagga cagctgtgtg tgcagacctc atgtgttggg | 4440 |
| ttctctcccc tccttcctgt tcctcttata taccagttta tccccattct tttttttttt | 4500 |
| cttactccaa aataaatcaa ggctgcaatg cagctggtgc tgttcagatt ctaccatcag | 4560 |
| gtgctataag tgtttgggat tgagcatcat actggaaagc aaacacctt cctccagctc | 4620 |
| cagaattcct tgtctctgaa tgactctgtc ttgtgggtgt ctgacagtgg cgacgatgaa | 4680 |
| catgccgttg gttttattgg cagtgggcac aaggaggtga gaagtggtgg taaaagaagc | 4740 |
| agagtgctga agcagagagc agatttaata tagtaacatt aacagtgtat ttaattgaca | 4800 |
| tttctttttt gtaaacctga cgagatgtgg acaaaga | 4837 |

<210> SEQ ID NO 10
<211> LENGTH: 2429
<212> TYPE: DNA
<213> ORGANISM: Homo sapiens

<400> SEQUENCE: 10

| | |
|---|---|
| ccggcggggg cgccgcggag agcggagggc gccgggctgc ggaacgcgaa gcggagggcg | 60 |
| cgggaccctg cacgccgccc gcgggcccat gtgagcgcca tgcggcgccg cgcagcccgg | 120 |
| ggacccggcc cgccgccccc agggcccgga ctctcgcgc tgccgctgcc gctgctgctg | 180 |
| ctgctggcgc tggggacccg cggggctgc gccgcgcccg cacccgcgcc gcgcgccgag | 240 |

-continued

```
gacctcagcc tgggagtgga gtggctaagc aggttcggtt acctgccccc ggctgacccc      300
acaacagggc agctgcagac gcaagaggag ctgtctaagg ccatcacagc catgcagcag      360
tttggtggcc tggaggccac cggcatcctg gacgaggcca ccctggccct gatgaaaacc      420
ccacgctgct ccctgccaga cctccctgtc ctgacccagg ctcgcaggag acgccaggct      480
ccagccccca ccaagtggaa caagaggaac ctgtcgtgga gggtccggac gttcccacgg      540
gactcaccac tggggcacga cacggtgcgt gcactcatgt actacgccct caaggtctgg      600
agcgacattg cgccctgaa cttccacgag gtggcgggca gcgccgccga catccagatc       660
gacttctcca aggccgacca taacgacggc taccccttcg acggcccggg cggcaccgtg      720
gcccacgcct tcttccccgg ccaccaccac accgccgggg acacccactt tgacgatgac      780
gaggcctgga ccttccgctc ctcggatgcc cacgggatgg acctgttttgc agtggctgtc     840 cacgagtttg ccacgccat  tgggttaagc catgtggccg ctgcacactc catcatgcgg      900
ccgtactacc agggcccggt gggtgacccg ctgcgctacg ggctccccta cgaggacaag      960
gtgcgcgtct ggcagctgta cggtgtgcgg gagtctgtgt ctcccacggc gcagcccgag     1020
gagcctcccc tgctgccgga gccccctgac aaccggtcca cgcgccccgcc caggaaggac    1080 gtgccccaca gatgcagcac tcactttgac gcggtggccc agatccgggg tgaagctttc     1140
ttcttcaaag gcaagtactt ctggcggctg acgcgggacc ggcacctggt gtccctgcag     1200
ccggcacaga tgcaccgctt ctggcggggc ctgccgctgc acctggacag cgtggacgcc     1260
gtgtacgagc gcaccagcga ccacaagatc gtcttcttta aggagacag gtactgggtg     1320 ttcaaggaca ataacgtaga ggaaggatac ccgcgccccg tctccgactt cagcctcccg     1380
cctggcggca tcgacgctgc cttctcctgg gcccacaatg acaggactta tttcttttaag    1440 gaccagctgt actggcgcta cgatgaccac acgaggcaca tggaccccgg ctaccccgcc     1500
cagagccccc tgtggagggg tgtccccagc acgctgacg acgccatgcg ctggtccgac     1560
ggtgcctcct acttcttccg tgccaggag tactggaaag tgctggatgg cgagctggag     1620
gtggcacccg gtacccaca gtccacggcc cgggactggc tggtgtgtgg agactcacag      1680
gccgatggat ctgtggctgc gggcgtggac gcggcagagg ggccccgcgc ccctccagga     1740
caacatgacc agagccgctc ggaggacggt tacgaggtct gctcatgcac ctctggggca     1800
tcctctcccc cggggcccc aggcccactg gtggctgcca ccatgctgct gctgctgccg      1860
ccactgtcac caggcgccct gtggacagcg gcccaggccc tgacgctatg acacacagcg     1920
cgagcccatg agaggacaga ggcggtggga cagcctggcc acagagggca aggactgtgc     1980
cggagtccct gggggaggtg ctggcgcggg atgaggacgg gccaccctgg caccggaagg     2040
ccagcagagg gcactgcccg ccagggctgg gcaggctcag gtggcaagga cggagctgtc     2100
ccctagtgag ggactgtgtt gactgacgag ccgaggggtg gccgctccag aagggtgccc     2160
agtcaggccg caccgccgcc agcctcctcc ggccctggag ggagcatctc gggctggggg    2220
cccacccctc tctgtgccgg cgccaccaac cccacccaca ctgctgcctg gtgctcccgc     2280
cggcccacag gcctccgtc  cccaggtccc cagtggggca gccctcccca cagacgagcc     2340
ccccacatgg tgccgcggca cgtcccccct gtgacgcgtt ccagaccaac atgacctctc     2400
cctgctttgt aaaaaaaaaa aaaaaaaaa                                       2429
```

<210> SEQ ID NO 11
<211> LENGTH: 1699
<212> TYPE: DNA
<213> ORGANISM: Homo sapiens

```
<400> SEQUENCE: 11
gctggcccag gtgagcgggc gcgctggtcc aggtgagcgg gcgcgtcccc gcgacggcgc      60
tgcctgcccg aggcggttca cgtaaagaca gcgagatcct gagggccagc cgggaaggag     120
gcgtggatat ggagctggct gctgccaagt ccggggcccg cgccgctgcc tagcgcgtcc     180
tggggactct gtggggacgc gccccgcgcc gcggctcggg gacccgtaga gcccggcgct     240
gcgcgcatgg ccctgctctc gcgccccgcg ctcaccctcc tgctcctcct catggccgct     300
gttgtcaggt gccaggagca ggcccagacc accgactgga gagccaccct gaagaccatc     360
cggaacggcg ttcataagat agacacgtac ctgaacgccg ccttggacct cctgggaggc     420
gaggacggtc tctgccagta taaatgcagt gacggatcta agcctttccc acgttatggt     480
tataaaccct ccccaccgaa tggatgtggc tctccactgt ttggtgttca tcttaacatt     540
ggtatccctt ccctgacaaa gtgttgcaac caacacgaca ggtgctatga gacctgtggc     600
aaaagcaaga atgactgtga tgaagaattc cagtattgcc tctccaagat ctgccgagat     660
gtacagaaaa cactaggact aactcagcat gttcaggcat gtgaaacaac agtggagctc     720
ttgtttgaca gtgttataca tttaggttgt aaaccatatc tggacagcca acgagccgca     780
tgcaggtgtc attatgaaga aaaaactgat ctttaaagga gatgccgaca gctagtgaca     840
gatgaagatg gaagaacata cctttgcaaa taactaatg ttttttacaac ataaaactgt     900 cttattttg tgaaaggatt attttgagac cttaaaataa tttatatctt gatgttaaaa     960
cctcaaagca aaaaagtga gggagatagt gaggggaggg cacgcttgtc ttctcaggta    1020
tcttccccag cattgctccc ttacttagta tgccaaatgt cttgaccaat atcaaaaaca    1080
agtgcttgtt tagcggagaa ttttgaaaag aggaatatat aactcatttt cacaaccaca    1140
tttaccaaaa aaagagatca aatataaaat tcatcataat gtctgttcaa cattatctta    1200
tttgaaaaat ggggaaatta tcacttacaa gtatttgttt actatgaaat tttaaataca    1260
catttatgcc tagaaggaac ggactttttt ttttctattt taattacaca taatatgtaa    1320
ttaaagtaca acataatatg ttgtttctct gtagcccgtt gagcatatga gtaagtcaca    1380
tttctattag gactacttac aaggacaagg tttccatttt tccagttgta aaattggaac    1440
catcagctga taacctcgta gggagcaacc ccaggatagc taagtgttat gtaatatgcc    1500
tagaaggtga tgtgaatgcg attcagaagc atagccactc ccattttatg agctactcac    1560
atgacaaatg tcatcttttg ctataacctt tgccaagtta gagaaaagat ggatttaatg    1620
agataaatga aaagatattt aacctaatat atcaaggcaa aaaaaaaaa aaaaaaaaa    1680 aaaaaaaaaa aaaaaaaa                                                 1699

<210> SEQ ID NO 12
<211> LENGTH: 4617
<212> TYPE: DNA
<213> ORGANISM: Homo sapiens

<400> SEQUENCE: 12
ctccatcttt ctagtcccca ccttcccccgg tgcagacacc cggcgaagcc cacccggttt      60
tcccagcggc atttccgatg acagcttcgg ggctacgtgt cctgtgctgt cggagacgca     120
caggaagcaa agtttgtgag aagccttggg ggcgactttg ccttgggcac ccgcatttgt     180
gcgtctgcga ggtgcctcgg tgtgcgcgga gctagtttcc cagtttcccg ggccccctccc     240 ttctccgagc ccctctagcg atttgtttag gaaaagtgat gacatgaact agtagtggag     300
aatcgcagcg ccgctcccccg ccctggggag ggaggggagc cccggagagc ctgccggtgg     360
```

```
gagctggaag caggctcccg gctgagcgcc ccagcccgaa aggcagggtc tgggtgcggg    420
aagagggctc ggagctgcct tcctgctgcc ttggggccgc ccagatgagg gaacagcccg    480
atttgcctgg ttctgattct ccaggctgtc gtggttgtgg aatgcaaacg ccagcacata    540
atggaaacag gacctgaaga cccttccagc atgccagagg aaagttcccc caggcggacc    600
ccgcagagca ttccctacca ggacctccct cacctggtca atgcagacgg acagtacctc    660
ttctgcaggt actggaaacc cacaggcaca cccaaggccc tcatctttgt gtcccatgga    720
gccggagagc acagtggccg ctatgaagag ctggctcgga tgctgatggg gctggacctg    780
ctggtgttcg cccacgacca tgttggccac ggacagagcg aaggggagag gatggtagtg    840
tctgacttcc acgttttcgt cagggatgtg ttgcagcatg tggattccat gcagaaagac    900
taccctgggc ttcctgtctt ccttctgggc cactccatgg gaggcgccat cgccatcctc    960
acggccgcag agaggccggg ccacttcgcc ggcatggtac tcatttcgcc tctggttctt   1020
gccaatcctg aatctgcaac aactttcaag gtccttgctg cgaaagtgct caaccttgtg   1080
ctgccaaact tgtccctcgg gcccatcgac tccagcgtgc tctctcggaa taagacagag   1140
gtcgacattt ataactcaga cccctgatc tgccgggcag ggctgaaggt gtgcttcggc   1200
atccaactgc tgaatgccgt ctcacgggtg gagcgcgccc tccccaagct gactgtgccc   1260
ttcctgctgc tccagggctc tgccgatcgc ctatgtgaca gcaaggggc ctacctgctc   1320 atggagttag ccaagagcca ggacaagact ctcaagattt atgaaggtgc ctaccatgtt   1380
ctccacaagg agcttcctga agtcaccaac tccgtcttcc atgaaataaa catgtgggtc   1440
tctcaaagga cagccacggc aggaactgcg tccccaccct gaatgcattg gccggtgccc   1500
ggctcatggt ctgggggatg caggcagggg aagggcagag atggcttctc agatatggct   1560
tgccaaaaaa aaaaaaaaa aaaaatcaga aattggagaa atccttagca caattttcta   1620
aaaaataaca gacattttg ttatacatta gactatcaga cactggacct accttaatgg   1680
ttagacactt tatgcaaaaa aagagaaagg tcccaggtga ttttccacaa agaatgtgct   1740
aaaatgtcca ctgaaaacaa agccaagcct ctgccctgcc tctcccagct cccacaaggg   1800
ttccaggaat tcctggtgtt cccaggacac cagactgcaa taactggagg cgcctccttc   1860
ctgcccaccc ttcgctcacg ccccagcgcc ctctctgacc agcctccgct tggtggcctt   1920
cctctggccg tgtgatgagg tggttgctgt ctccataggg gccagctccc cagggcagac   1980
tcacgtgccc ctctgaggct cagaaaatgc ccagcccttc ctcaaaatga gcagccaccc   2040
atgactttgt gggctccttg ttagcctgag accaggcttt gcagagggggc gggggggtgag   2100 gcttagccca gaaggagaac tgagcaggaa accaaggctc ttctctgtcc cctgcccttc   2160
ccctcctgcc aggggaggc tcaggttggt ccccgagtgc cgcctgtact cacaaaggct   2220
gcctttcctc tagagtcact aattttacct gatgctatga gagaatcata ttgaagatga   2280
aatgtctaat atataatgta tattttaaag cagagactat tttggtggat aggtgggagg   2340
gagcaagggg agtttgaggg aatcagagct tgatgctact gtacagaact ggacaggttg   2400
ggccggcagt ggtggggcca gagggctctg tgctctagga gctaagccag cagccccga   2460 gagggacttt ggctgggcct ttcctatggg caaggcccag tgctcttcct gcccaccagg   2520
gaccatggag cagtggcacc ctatgggct atgatcccta ggcctgggcc tgggcctgcc   2580 tatgcccag agctaccctg ggagtgtcag tgctagcagc acagctacct ctggtggcag   2640
gagaagagag gccagcacac gcagcaggcc aggccttcct gtccaggtct gcatggagca   2700
ctcggtgacc cagagcaggg actggaggca ccccagcccc tgcccaggc cacagcagga   2760
```

```
caggccggga caggcctcac ccaaggccaa ggctggcatc agccaatcat tcagagctga    2820
ggccctgggc ctagcctgcc cttctcaggt gccaatacca ccccagccct gcccttggcc    2880 tcacttttc ccagcaataa gtggggttca ccaccgcct cgggaatact ttcccttct      2940 aaatgggact tgctgttacc tcaggaggct ccttagtgca aatatgaccc tggtcagggc    3000
tttgccaccg ttgaagccct gcagaaggtg caatgtaggg gttctggggc cacagaggag    3060
aggccacttc ccaccaggac ccccaacatg aagtctaggc ctcagggct cccgcccttc    3120 ttcctccagc agcgggaact gccactgctc tcccaggccc tgttctggag gctaaccttg    3180
gttcctggag agtgtgcccc tccacccctcc ctccagcagc cctgatcaca ccatgagagc    3240
caggaacggg tcaccctgct gaagatcact ctgtgccctg ggggaggagc caagccctca    3300
ccccacaagg ggcaggtggg ggcttggttg ctgacccggc ccaagtcccc acagagcacc    3360
ttctgtagct ccagcttgtc tccctggctt ctctttgaag gagaaaaatg taaaatatgc    3420
actgagaaag ccagccccgc ctgcttagtc agccccggca gcagggcagc catgggaact    3480
caggaaaagc aggaaccctt tccaaaagcc cagagatgcc ctgggctcag atctgtaatt    3540
ctcccaggag ctgtgataga gcaggccaca caaagtccct acgcctccct gctgcctccc    3600
ccagatgcat gtggtggcat caccattccc caaattgaat atcagcatgc ggcctgacca    3660
gggactcttt agatgcatga atttatttat atgaaggctc tcacagagac acacacagca    3720
cttcagtagc atttgcattc ctggttaaag aatcaccaat atttaaaata aaactttcc    3780 tgaaattggg actgtcatgt tatccagaag ggctggtaca tccgcccacc atgtcccct    3840 gctgggtcag gagccaacac aggaccctgc gtgtgagcgt gcctgacatc tcacgcacgg    3900
ccactccaga gccggtccct gtccttggaa agctgtgaag ccttgcgttg agttccttct    3960
cgatactgac ggctccgtgc tgacattctg agctctggag tcacaccagc gcaggggcgt    4020
ggaggaactg aggtttggaa ggaatgccag gtctcgcaca gcttggcctc gagaaggtga    4080
gaggaaggca aaggccaggg aggggaccca gagaggcctg gcacacaagg cccaagcacc    4140
accgtcaaca cagcccagtc catacagaaa tgggtttcat gcctgaaaag cttttttacag    4200 aaagatgccg cctgtagcca gtgacagccg caacccctaca ggcctcagtt ccttgcagag    4260
gtgaggggta gagagtcagc ctccctccct tccagcagcg acccagcttc cctccacttc    4320
caggtggtgc tgggctcacc gagggagcac tggtgggtgc tctgaaaacc cacaggatcc    4380
cacctccagg cccacctggg tcccatctca ctctcttctt ctttcaccaa ttgctaacat    4440
agaccttgtt gggatcacga tggcttcaca agccagctgt tgggtttgct atgtcactgt    4500
ggctcagtca catccctgcg tgtatactgt ctgcggggca catatgtatc catttagagc    4560
taaaggaatc agtgtacact acagctaatc ctaataaatc cgatgttttc ggaaaaa      4617

<210> SEQ ID NO 13
<211> LENGTH: 4192
<212> TYPE: DNA
<213> ORGANISM: Homo sapiens

<400> SEQUENCE: 13
tggcggcgca gacgccgcac cctgtcgccg cgaagccggt cgcgcgcagc tcgtcccggc      60
cctggcccgc cgcaaacgag gatccgctgc gctcggggaa cgcgacagcg gcgctcgtgg    120
ccccggacct gaagacccctt ccagcatgcc agaggaaagt tccccccagc ggaccccgca    180
gagcattccc taccaggacc tccctcacct ggtcaatgca gacggacagt acctcttctg    240
caggtactgg aaacccacag gcacacccaa ggccctcatc tttgtgtccc atggagccgg    300
```

```
agagcacagt ggccgctatg aagagctggc tcggatgctg atggggctgg acctgctggt    360
gttcgcccac gaccatgttg gccacggaca gagcgaaggg gagaggatgg tagtgtctga    420
cttccacgtt ttcgtcaggg atgtgttgca gcatgtggat tccatgcaga aagactaccc    480
tgggcttcct gtcttccttc tgggccactc catgggaggc gccatcgcca tcctcacggc    540
cgcagagagg ccgggccact tcgccggcat ggtactcatt tcgcctctgg ttcttgccaa    600
tcctgaatct gcaacaactt tcaaggtcct tgctgcgaaa gtgctcaacc ttgtgctgcc    660
aaacttgtcc ctcgggccca tcgactccag cgtgctctct cggaataaga cagaggtcga    720
catttataac tcagaccccc tgatctgccg ggcagggctg aaggtgtgct cggcatcca    780 actgctgaat gccgtctcac gggtggagcg cgccctcccc aagctgactg tgcccttcct    840
gctgctccag ggctctgccg atcgcctatg tgacagcaaa ggggcctacc tgctcatgga    900
gttagccaag agccaggaca agactctcaa gatttatgaa ggtgcctacc atgttctcca    960
caaggagctt cctgaagtca ccaactccgt cttccatgaa ataaacatgt gggtctctca   1020
aaggacagcc acggcaggaa ctgcgtcccc accctgaatg cattggccgg tgcccggctc   1080
atggtctggg ggatgcaggc aggggaaggg cagagatggc ttctcagata tggcttgcca   1140
aaaaaaaaaa aaaaaaaaaa tcagaaattg gagaaatcct tagcacaatt ttctaaaaaa   1200
taacagacat ttttgttata cattagacta tcagacactg gacctacctt aatggttaga   1260
cactttatgc aaaaaaagag aaaggtccca ggtgattttc cacaaagaat gtgctaaaat   1320
gtccactgaa aacaaagcca agcctctgcc ctgcctctcc cagctcccac aagggttcca   1380
ggaattcctg gtgttcccag acaccagac tgcaataact ggaggcgcct ccttcctgcc   1440 caccctttcgc tcacgcccca gcgccctctc tgaccagcct ccgcttggtg gccttcctct   1500
ggccgtgtga tgaggtggtt gctgtctcca taggggccag ctccccaggg cagactcacg   1560
tgcccctctg aggctcagaa aatgcccagc ccttcctcaa aatgagcagc cacccatgac   1620
tttgtgggct ccttgttagc ctgagaccag gctttgcaga ggggcggggg gtgaggctta   1680
gcccagaagg agaactgagc aggaaaccaa ggctcttctc tgtcccctgc ccttccctc    1740 ctgccagggg gaggctcagg ttggtccccg agtgccgcct gtactcacaa aggctgcctt   1800
tcctctagag tcactaattt tacctgatgc tatgagagaa tcatattgaa gatgaaatgt   1860
ctaatatata atgtatattt taaagcagag actattttgg tggataggtg ggagggagca   1920 agggagttt gagggaatca gagcttgatg ctactgtaca gaactggaca ggttgggccg    1980
gcagtggtgg ggccagaggg ctctgtgctc taggagctaa gccagcagcc cccgagaggg   2040
gacttggctg ggccttttcct atgggcaagg cccagtgctc ttcctgccca ccagggacca   2100
tggagcagtg gcaccctatg gggctatgat ccctaggcct gggcctgggc ctgcctatgg   2160
cccagagcta ccctgggagt gtcagtgcta gcagcacagc tacctctggt ggcaggagaa   2220
gagaggccca gcacagcagc aggccaggcc ttcctgtcca ggtctgcatg gagcactcgg   2280
tgacccagag cagggactgg aggcaccccc agccctgccc caggccacag caggacaggc   2340
cgggacaggc ctcacccaag gccaaggctg gcatcagcca atcattcaga gctgaggccc   2400
tgggcctagc ctgcccttct caggtgccaa taccacccca gccctgccct tggcctcact   2460 tttcccagc aataagtggg gttcaccacc cgcctcggga atactttccc cttctaaatg    2520
ggacttgctg ttacctcagg aggctcctta gtgcaaatat gaccctggtc agggctttgc   2580
caccgttgaa gccctgcaga aggtgcaatg taggggttct ggggcacag aggagaggcc    2640 acttcccacc aggaccccca acatgaagtc taggcctcag gggctcccgc ccttcttcct   2700
```

| | |
|---|---|
| ccagcagcgg gaactgccac tgctctccca ggccctgttc tggaggctaa ccttggttcc | 2760 |
| tggagagtgt gccccctccac cctccctcca gcagccctga tcacaccatg agagccagga | 2820 |
| acgggtcacc ctgctgaaga tcactctgtg ccctggggga ggagccaagc cctcaccccca | 2880 |
| caaggggcag gtgggggctt ggttgctgac ccggcccaag tccccacaga gcaccttctg | 2940 |
| tagctccagc ttgtctccct ggcttctctt tgaaggagaa aaatgtaaaa tatgcactga | 3000 |
| gaaagccagc ccgcctgct tagtcagccc cggcagcagg gcagccatgg gaactcagga | 3060 |
| aaagcaggaa ccctttccaa aagcccagag atgccctggg ctcagatctg taattctccc | 3120 |
| aggagctgtg atagagcagg ccacacaaag tccctacgcc tccctgctgc ctcccccaga | 3180 |
| tgcatgtggt ggcatcacca ttccccaaat tgaatatcag catgcggcct gaccagggac | 3240 |
| tctttagatg catgaattta tttatatgaa ggctctcaca gagacacaca cagcacttca | 3300 |
| gtagcatttg cattcctggt taaagaatca ccaatattta aaataaaaac tttcctgaaa | 3360 |
| ttgggactgt catgttatcc agaagggctg gtacatccgc ccaccatgtc ccctgctgg | 3420 |
| gtcaggagcc aacacaggac cctgcgtgtg agcgtgcctg acatctcacg cacggccact | 3480 |
| ccagagccgg tccctgtcct tggaaagctg tgaagccttg cgttgagttc cttctcgata | 3540 |
| ctgacggctc cgtgctgaca ttctgagctc tggagtcaca ccagcgcagg ggcgtggagg | 3600 |
| aactgaggtt tggaaggaat gccaggtctc gcacagcttg gcctcgagaa ggtgagagga | 3660 |
| aggcaaaggc cagggagggg acccagagag gcctggcaca caaggcccaa gcaccaccgt | 3720 |
| caacacagcc cagtccatac agaaatgggt ttcatgcctg aaaagctttt tacagaaaga | 3780 |
| tgccgcctgt agccagtgac agccgcaacc ctacaggcct cagttccttg cagaggtgag | 3840 |
| gggtagagag tcagcctccc tcccttccag cagcgaccca gcttccctcc acttccaggt | 3900 |
| ggtgctgggc tcaccgaggg agcactgtg ggtgctctga aaacccacag gatcccacct | 3960 |
| ccaggcccac ctgggtccca tctcactctc ttcttctttc accaattgct aacatagacc | 4020 |
| ttgttgggat cacgatggct tcacaagcca gctgttgggt ttgctatgtc actgtggctc | 4080 |
| agtcacatcc ctgcgtgtat actgtctgcg gggcacatat gtatccattt agagctaaag | 4140 |
| gaatcagtgt acactacagc taatcctaat aaatccgatg ttttcggaaa aa | 4192 |

<210> SEQ ID NO 14
<211> LENGTH: 2910
<212> TYPE: DNA
<213> ORGANISM: Homo sapiens

<400> SEQUENCE: 14

| | |
|---|---|
| cagcctccct ctcccacctc tgtctgcccg ctgcctcttg tctagctgct gtcaggagct | 60 |
| gactgcctcc agggctggaa tcctgtgctc cctctgtgcc cagagcccca cgatgtcggc | 120 |
| caacgccaca ctgaagccac tctgccccat cctggagcag atgagccgtc tccagagcca | 180 |
| cagcaacacc agcatccgct acatcgacca cgcggccgtg ctgctgcacg ggctggcctc | 240 |
| gctgctgggc ctggtggaga tggagtcat cctcttcgtg gtgggctgcc gcatgcgcca | 300 |
| gaccgtggtc accacctggg tgctgcacct ggcgctgtcc gacctgttgg cctctgcttc | 360 |
| cctgccttc ttcacctact tcttggccgt gggccactcg tgggagctgg gcaccacctt | 420 |
| ctgcaaactg cactcctcca tcttcttct caacatgttc gccagcggct tcctgctcag | 480 |
| cgccatcagc ctggaccgct gcctgcaggt ggtgcggccg gtgtgggcgc agaaccaccg | 540 |
| caccgtggcc gcggcgcaca agtctgcctt ggtgctttgg gcactagcgg tgctcaacac | 600 |
| ggtgccctat ttcgtgttcc gggacaccat ctcgcggctg gacgggcgca ttatgtgcta | 660 |

```
ctacaatgtg ctgctcctga acccggggcc tgaccgcgat gccacgtgca actcgcggca    720
ggtggccctg gccgtcagca agttcctgct ggccttcctg gtgccgctgg cgatcatcgc    780
ctcgagccac gcggccgtga gcctgcggtt gcagcaccgc ggccgccggc ggccaggccg    840
cttcgtgcgc ctggtggcgg ccgtcgtggc cgccttcgcg ctctgctggg ggccctacca    900
cgtgttcagc ctgctggagg cgcgggcgca cgcaaacccg gggctgcggc cgctcgtgtg    960
gcgcgggctc cccttcgtca ccagcctggc cttcttcaac agcgtggcca acccggtgct   1020
ctacgtgctc acctgccccg acatgctgcg caagctgcgg cgctcgctgc gcacggtgct   1080
ggagagcgtg ctggtggacg acagcgagct gggtggcgcg ggaagcagcc gccgccgccg   1140
cacctcctcc accgcccgct cggcctcccc tttagctctc tgcagccgcc cggaggaacc   1200
gcggggcccc gcgcgtctcc tcggctggct gctgggcagc tgcgcagcgt ccccgcagac   1260 gggcccctg aaccgggcgc tgagcagcac ctcgagttag aacccggccc acgtagggcg   1320
gcactcacac gcgaaagtat caccagggtg ccgcggttca attcgatatc cggactcctg   1380
ccgcagtgat caaagtccga ggggcgggac ccaggcacct gcattttaaa gcgccccggg   1440
agactctgaa tcttttttcag aaacagtgag ttaaagcagt gcttctcaaa ccttgatgtg   1500
cctgtgaatc acctaggggt cttgttaagt gcagtctgat ccaggaggcc ggggccgggt   1560
actgagagtc tgcacttaac aagctcccag gccgagaagc cagtgcggca ggttcacagg   1620
cgaggcctgg agtaacacaa agtgaaactc ataatagact tcccactcta gggcagtgga   1680
gtcggaaggg cacacggggt gcgtctcccc ggagttcagt tttaccagat gatgggggag   1740
gggggaagga gttttatgtt aaaccatcca tgtattttg gagaagagag aggaaaggtt    1800
tgagaagcac tgttccagcc tgccctcttc atttagccaa tgcttactgc gctagacgct   1860
tcatcccaca atcttaaggg gcagcttcta ttagccagtc tttacagctg agcacattct   1920
ggctcaggga ggttaagtga cttgcccagt tcagggcta acgaccacag ggtctgcact   1980
ctaaccctag gcatcacatg ctcaatgact ctctggtgag cgaggacatt ctctgaccta   2040
ctcgagggac ttaagatgct accttgtgac ccagcactgc ccaaagtgct tccaaggcag   2100
aagcagcagg ggatggcgtg gtcaagcact cgggaaacct ggggctaatc aaatccaatg   2160
ggggaaatga ctaaaagtct tcggtcgtta gaagttgaat gggcacagca actctaagac   2220
tacagcacac gtcatttctt agctaagcgg accagcctcc ctgtcggcct ggtgttctgt   2280
gggatccctc tgggcactgg taatcccaag atctgtgcag ccccgcctcc aggccacatg   2340
gggctgggca gctaccattt cccttttgcg gatgggaggg gtaacttgca cctctgacct   2400
atcacttcca ctgcaccccg tctcattcct ccacctgccg tggacttggg gtcagagact   2460
gctgtgtttg agctctgcag cccagggacc gaaaagttgg tgtcaatgaa ttttgcttgg   2520
tggatgaaat gtcagtggaa gaagcagatg agaaactctt gagatcttgg tcctgtgttt   2580
tttctgccac caaaggccag ggtcactgaa ggcctggccc acagcaggtg ctgagcaaag   2640
ggaacagtga ggtgcccagc tagctgcaga gccaccctgt gttgacacct cgcccctgct   2700
ccctcccatc ccttccccct ttactcatag cacttccccc attggacacg tggtgcattt   2760
tgcttgttta ttatgttttc tctccatcag aatgaaagct cctcgagggc agggactttg   2820
gtctattgtc tgtatttgcc ggtgcctagg attgtgcctg tatgcaacag gcactcaata   2880 aatattttg ctgtagactg gacaggcatg                                     2910

<210> SEQ ID NO 15
<211> LENGTH: 2960
<212> TYPE: DNA
```

<213> ORGANISM: Homo sapiens

<400> SEQUENCE: 15

```
actccctctc tggatgtgtc tgctgccgcc attgtgcggc gctggtcccc tcagagggtt      60
cctgctgctg ccggtgcctt ggaccctccc cctcgcttct cgttctactg ccccaggagc     120
ccggcgggtc cgggactccc gtccgtgccg gtgcgggcgc cggcatgtgg ctgtgggagg     180
accagggcgg cctcctgggc cctttctcct tcctgctgct agtgctgctg ctggtgacgc     240
ggagcccggt caatgcctgc ctcctcaccg gcagcctctt cgttctactg cgcgtcttca     300
gctttgagcc ggtgccctct tgcagggccc tgcaggtgct caagccccgg gaccgcattt     360
ctgccatcgc ccaccgtggc ggcagccacg acgcgcccga aacacgctg gcggccattc      420
ggcaggcagc taagaatgga gcaacaggcg tggagttgga cattgagttt acttctgacg     480
ggattcctgt cttaatgcac gataacacag tagataggac gactgatggg actgggcgat     540
tgtgtgattt gacatttgaa caaattagga agctgaatcc tgcagcaaac cacagactca     600
ggaatgattt ccctgatgaa aagatcccta ccctaaggga agctgttgca gagtgcctaa     660
accataacct cacaatcttc tttgatgtca aaggccatgc acacaaggct actgaggctc     720
taaagaaaat gtatatggaa tttcctcaac tgtataataa tagtgtggtc tgttctttct     780
tgccagaagt tatctacaag atgagacaaa cagatcggga tgtaataaca gcattaactc     840
acagaccttg gagcctaagc catacaggag atgggaaacc acgctatgat actttctgga     900
aacattttat atttgttatg atggacattt tgctcgattg gagcatgcat aatatcttgt     960
ggtacctgtg tggaatttca gctttcctca tgcaaaagga ttttgtatcc ccggcctact    1020
tgaagaagtg gtcagctaaa ggaatccagg ttgttggttg gactgttaat acctttgatg    1080
aaaagagtta ctacgaatcc catcttggtt ccagctatat cactgacagc atggtagaag    1140
actgcgaacc tcacttctag actttcacgg tgggacgaaa cgggttcaga aactgccagg    1200
ggcctcatac agggatatca aaataccctt tgtgctagcc caggccctgg ggaatcaggt    1260
gactcacaca aatgcaatag ttggtcactg catttttacc tgaaccaaag ctaaacccgg    1320
tgttgccacc atgcaccatg gcatgccaga gttcaacact gttgctcttg aaaatctggg    1380
tctgaaaaaa cgcacaagag cccctgccct gccctagctg aggcacacag ggagacccag    1440
tgaggataag cacagattga attgtacagt ttgcagatgc agatgtaaat gcatgggaca    1500
tgcatgataa ctcagagttg acattttaaa acttgccaca cttatttcaa atatttgtac    1560
tcagctatgt taacatgtac tgtagacatc aaacttgtgg ccatactaat aaaattatta    1620
aaaggagcac taaaggaaaa ctgtgtgcca agcatcatat cctaaggcat acggaatttg    1680
gggaagccac catgcaatcc agtgaggctt cagtgtacag caaccaaaat ggtagggagg    1740
tcttgaagcc aatgagggat ttatagcatc ttgaatagag agctgcaaac caccaggggg    1800
cagagttgca ttttttccagg ctttttagga agctctgcaa cagatgtgat ctgatcatag    1860
gcaattagaa ctggaagaaa cttccaaaaa tatctaggtt tgtcctcatt ttacaaatga    1920
ggaaactaaa ctctgtggaa gggaaggggt tgcctcaaaa gtcacagctt agctgggcac    1980
agtggctcat gccgataatc ccagcaattc agaaagctga ggcaggagga ttacttgagg    2040
ccagactggg caatatagca agaccccatc tctaaaaaat taggcatggt ggtgcatgcc    2100
tgtattccca gctactcagg aggttgaggt gggaggatca cttgagccca gaagttcaag    2160
gctgcaatga gccatgatta caccacggca ctacaacctt ggtggcacag tgagaacctg    2220
actcttaaaa aaaaaaaaaa aaaaaaaaa aaaaagataa ctagaacttc tagaacatct    2280
```

```
tgtttacagt tagccagaaa ctatacaagt ggtttaacat gcattatctt actcaatcca    2340
tacaaaagtc ttatggaggt gttagcactc tttctactga tgaagaactg aggtacttca    2400
taaaaccact tacccaaggt gtcttgagtc tggtacaact ggcattcaaa tctaggtcag    2460 tctgcccccca gagccactac ccttacccct cactgaatct gcctttatat tgttgagccc    2520
atgaccccaa actgctcttt ccaatttgaa cttccaggga ttttattgtg aacttacata    2580
gcaacattaa aatgaagttg aattgttttt aatggcaacg ccgtctgtct cctctagctt    2640
accgcttctc acctttcaac cccatctgtg gcctttgtcc aggcccacag cttagccatg    2700
gcttccctcc tgcatccctg ccgtgggttg ctggcctcac acttgcagca gctggacagt    2760
gattttagaa ggccaccagt ccccatagct atgtgacaat gagaagcaaa ctttttttgtg    2820 acagattgta ttggcatagg catgatagat ggggattggt acgttttgaa tcagcatttg    2880
caaaaaaatt gtcttgaatt ttaaaataaa caacaaagat ttgttcattg agtgcaaaaa    2940
aaaaaaaaaa aaaaaaaaaa                                                2960

<210> SEQ ID NO 16
<211> LENGTH: 2519
<212> TYPE: DNA
<213> ORGANISM: Homo sapiens

<400> SEQUENCE: 16
gctgggccac agcctggtcc tgccgctgcg cccgcccgcc atggtgtccc gggaccaggc      60
tcacctgggc cccaagtatg tgggcctctg ggacttcaag tcccggacgg acgaggagct     120
gagcttccgc gcggggacg tcttccacgt ggccaggaag gaggagcagt ggtggtgggc     180
cacgctgctg gacgaggcgg gtggggccgt ggcccagggc tatgtgcccc acaactacct     240
ggccgagagg gagacggtgg agtcggaacc gtggttcttt ggctgcatct cccgctcgga     300
agctgtgcgt cggctgcagg ccgagggcaa cgccacgggc gccttcctga tcagggtcag     360
cgagaagccg agtgccgact acgtcctgtc ggtgcgggac acgcaggctg tgcggcacta     420
caagatctgg cggcgtgccg ggggccggct gcacctgaac gaggcggtgt ccttcctcag     480
cctgcccgag cttgtgaact accacagggc ccagagcctg tcccacgcc tgcggctggc     540 cgcgccctgc cggaagcacg agcctgagcc cctgccccat gggatgact gggagaggcc     600 gagggaggag ttcacgctct gcaggaagct ggggtccggc tactttgggg aggtcttcga     660
ggggctctgg aaagaccggg tccaggtggc cattaaggtg atttctcgag acaacctcct     720
gcaccagcag atgctgcagt cggagatcca ggccatgaag aagctgcggc acaaacacat     780
cctggcgctg tacgccgtgg tgtccgtggg ggaccccgtg tacatcatca cggagctcat     840
ggccaagggc agcctgctgg agctgctccg cgactctgat gagaaagtcc tgcccgtttc     900
ggagctgctg gacatcgcct ggcaggtggc tgagggcatg tgttacctgg agtcgcagaa     960
ttacatccac cgggacctgg ccgccaggaa catcctcgtc ggggaaaaca ccctctgcaa    1020
agttggggac ttcgggttag ccaggcttat caaggaggac gtctacctct cccatgacca    1080
caatatcccc tacaagtgga cggccccctga agcgctctcc cgaggccatt actccaccaa    1140
atccgacgtc tggtcctttg ggattctcct gcatgagatg ttcagcaggg gtcaggtgcc    1200
ctacccaggc atgtccaacc atgaggcctt cctgagggtg acgcggct accgcatgcc    1260 ctgccctctg gagtgcccgc ccagcgtgca caagctgatg ctgacatgct ggtgcaggga    1320
ccccgagcag agaccctgct tcaaggccct gcgggagagg ctctccagct tcaccagcta    1380
cgagaacccg acctgagctg ctgtggagcg ggcatggccg ggccctgctg aggagggcc    1440
```

-continued

| | |
|---|---|
| tgggcagagg gcctggacct gggatcaagg cccacgcgct tccctggggt ttactgaggt | 1500 |
| gatgggtgca ggaaaggttc acaaatgtgg agtgtctgcg tccaatacac gcgtgtgctc | 1560 |
| ctctccttac tccatcgtgt gtgccttggg tctcagctgc tgacacgcag cctgctctgg | 1620 |
| agcctgcaga tgagatccgg gagactgaca cgaagccagc agaggtcaga ggggactctg | 1680 |
| accacagccc gctctctggc tgtctgtctg cagtgcccgg ctgagggtgg gaggcaaaca | 1740 |
| cgccttgttc ctgctcttcc cagttcagct tggtgggaga aagtcattcg cgtggctcgg | 1800 |
| gacgctcatg taaatttggt tttggtgctc aagggttctt tcctcccagg ggcaggtgtt | 1860 |
| tctttcctgt ttgtcttgtg tcttgagagc ttggccttat gaccagtgag aactctctcc | 1920 |
| ctggtctctg ccagcccaag catcactgcc cgaggcgcca gctcagtttc accgtccacg | 1980 |
| tccacaaggg gcttttccca ccttcacctt tgtcgctggg tcagtgctgg aaagcgcccc | 2040 |
| tcactcctgc gctgacaagg gcccttctct actgtctgtg gggtggttcc gggctggggg | 2100 |
| ggctgcctcc tttgcacctg attttgaagg tgtctctttc atccatggtt aagtcataaa | 2160 |
| aagcttattg gttttggttt tgactcacct gaaagttttt ttggtttaaa agaagaatag | 2220 |
| gcggggcacg gtggctcatg cctgtaatcc cagcactttg ggaggctgag gcaggtggat | 2280 |
| cacgaggtca ggagatcgac accatcctgg ctaacacggt gaaacccgt ctctactaaa | 2340 |
| aaatacaaaa aattagctgg gtgtggtggt ggggtgggc gcctgtagtc ccagctacgt | 2400 |
| gggaggctga ggcagcagac tggtgtgaac ccgggaggtg gagcttgcag tgagccgaga | 2460 |
| tcgcgccact gcactccagc ctgggcgaca gagcgagact ccatctcaaa aaaaaaaaa | 2519 |

<210> SEQ ID NO 17
<211> LENGTH: 4454
<212> TYPE: DNA
<213> ORGANISM: Homo sapiens

<400> SEQUENCE: 17

| | |
|---|---|
| gggtttcacc atgttgccta ggctggtctt gaactcctga cctcaggcga ttcacccgcc | 60 |
| tcggcctccc aaagtgttag gattacaggc gtgagccacc gcgcccggct tgaattgtac | 120 |
| acttcaaaag gtggaatttt atggtgttga attatatctt tatttttta acggggggaa | 180 |
| aatgacgccg ctggagagga gttagcggaa ctgaaacaat gaaatggtgc gcgagtgtcg | 240 |
| cctgtccccg tcgcatccat cccaacgaag tttgggccct ggaacggtgc acccagaagg | 300 |
| cctgcgggga gagacgctgg ggcatgatct ggaagaaaga cgtctcagga ttcgaaggga | 360 |
| atgcagctaa ggtggcggcg gaggttcgcc taggactggg gaggcgtccc taggctcaga | 420 |
| agttggcccg gccggagcgg agatttaaag gttggagcgc agaggctctt aaagaggccg | 480 |
| agtcgaattc ccactcggcg tccaccttaa agccagctcc ccggcaccac ggatctgacc | 540 |
| cgggtctgac ctacgagaaa catggcaacc agcgccgtcc ccagtgacaa cctccccaca | 600 |
| tacaagctgg tggtggtggg ggatgggggt gtggcaaaa gtgccctcac catccagttt | 660 |
| ttccagaaga tctttgtgcc tgactatgac cccaccattg aagactccta cctgaaacat | 720 |
| acggagatta caatcaatg ggccatcttg gacgttctgg acacagctgg gcaggaggaa | 780 |
| ttcagcgcca tgcgggagca atacatgcgc acggggatg gcttcctcat cgtctactcc | 840 |
| gtcactgaca aggccagctt tgagcacgtg gaccgcttcc accagcttat cctgcgcgtc | 900 |
| aaagacaggg agtcattccc gatgatcctc gtggccaaca aggtcgattt gatgcacttg | 960 |
| aggaagatca ccagggagca aggaaaagaa atggcgacca acacaatat tccgtacata | 1020 |
| gaaaccagtg ccaaggaccc acctctcaat gtcgacaaag ccttccatga cctcgttaga | 1080 |

```
gtaattaggc aacagattcc ggaaaaaagc cagaagaaga agaagaaaac caaatggcgg    1140
ggagaccggg ccacaggcac ccacaaactg caatgtgtga tcttgtgaca ggcctgaggc    1200
cctgggcaca gtgacggtgg cctggccagc cctcgggacc cctccccacc taactgcact    1260
gaaaccattt ctaaccacaa cccttggccc aaggacttgg tacaggaagg gagaagggca    1320
ggtgggcagg gagcagacag ggtctggctt tgcccagagg gcacgggctt tcccacctct    1380
caaagagaca aggaagccac ctgtaagcag aagcagcatc caagtgcccc tggccccccc    1440
atgtgttgat tcaacccggt tcctcccccct ctctcggtgg gtgtgttgtt tattgtaact    1500
acatagtgtt ggtttgatgt ggaagtgttt atccacatac aaagtacaaa acaagccatg    1560
aacaagcttc tttcccttac cccccatcca caatgtctga gcttggatgt cttttataga    1620
tttttaaatt attttagtga ttattatttt attaaagggg tctgggctca ctgcctggtg    1680
aagtttcaag tgttcagcag acctctctgg taacatatct ggaatattgt tgttgttttt    1740
taaccgagtt ttcccatcag tgccaaaact caactcaatc tgaaagtaga gtgtctgaga    1800
ggacagaagg taatgggaac tgtagctgga ggcctcaggc catgggtcaa acctgggagg    1860
gaaagagacc ctacacatgg cctagaaatg agagaagaga gaggtattta cccagaggat    1920
tttcctatgg ttggggatgc aaatattaga aaacagattg tattttgctg aggggagtgg    1980
ctgtcatgag catgtcagtt ctaaaagggg ttttcattat cctggaaatg tataaactaa    2040
agtaagctga ttggctttgc aaacatgttc atttgttttt cagacagtat gggttaagtt    2100
ctctgccctc cccaggggtc tgaggaggct ctgggtttct cagatctgtc tcttgctgcg    2160
ttttcacatc agctgtgctg cttggtgcct ctctgatacg aatacactga cacgtcaaag    2220
taacctaatg tggacaccat ccagaaaact ccagttcatg ctggatctta accaaaaatg    2280
attcaatact gttatcacta aaacagcacc aagacctgaa gccatcttcc cttggagtca    2340
actgactacc acctctataa gcctagtcaa tgagcagacc ccttccagta tttgtaaaag    2400
tagtactagg ttgccttttt ggcaattttt attgacctgt tgaatcttga ctataaaatg    2460
atctgagaag taaggaaggc tgggctgatg tgtggctctc atataccttc tgcaaggggg    2520
cagtctcccc agctccctga tgatgctcac ccccgccccc ccacctcagg tgctgctggt    2580
gtgagccaaa gactggagtt ttttccagctg gggtgggagt ggagagacaa caggaacaac    2640
gctgcaccaa agaaaggtc agaataaaag gcagcacagc tggtgacctt attttctaga    2700
tgttacaaat caggtcacta tgcaaactag aatatcctca gcaggtggcc tggccactct    2760
ggagaaagaa acccaaggaa agtgagcacc caactggatg ccaagacacc cgggttctga    2820
aaatgtgctg tgttcctacc tcggcaagat caccagcact gaggggccca gctggagaat    2880
gattctgcta caaaaggaga cagttgagac ttttgcttgt tggaaatcaa acttcttatt    2940
tgtctaaatt gcccctttt ctgttcctaa aaggaaggat aagagagaac attccaggtg    3000
aggcacttca aagtttcctt agaccctata gtgttaagag gtattttaaa cactaaaagg    3060
acaaagctct tcccaatcct tatgcttccc taagtggtat ctgcagcagt tgttgtgtg    3120 cagtttgatg gcagctgcaa actggaggtg aggcggagga aagcaggta ggaaggagta    3180 aggatggaga tgctcagaat caagagcatg gcggagtagg agaagaagcc ctgcacacag    3240
ggcagtgtcc acagccagaa aactcctgct gggcaccaac cactacgagc ataccccatg    3300
cccaccgtgg agctgcaact cctcgacagc actgagtttg atagtctcac tggaagcaga    3360
tcagctgatg tagaacagag acctcggcca taaaggtgag aagacatagg gatttcaacc    3420
acacagttgg gacagaaggg acagtgcatc tgttcatcca tcctgcactt ggcccacgtt    3480
```

-continued

```
gaactccatg gtgcctgaga gagactagtt aagggttggt cttctgtatc ctctgctgtt      3540
gagcctctgg taagctttca tctcccatga actcatttcc ccataaatga aatgggtaaa      3600
taatgcccca tttgtagaag tgggccctca tgactgaggt agcttccaga taggccagag      3660
tagagtgtag agtgtgcccc gtgacatccc tccatcttct cctccattat catctagcag      3720
ggtcagactg ggaaacctgg ttggccacgc cacaccatga ccgaggagcc aactgggact      3780
tctggctgtt tgacatcctc atgttcccgt tggtcttccg gagaatagtg ctaccctcac      3840
atcccctgga gcacagcctt cctgaaatgc cctcacccca tgcctttgcc attgtgtgct      3900
ctcagatttc ttccactgtt tgacaccctc cttagagggc tgctcttttt tttccagaga      3960
taatcctagc catcctctcc actcccacgg ctggggacaa tggccactta ctacctgtgc      4020
actttgccac tcgggacacc tggatggttt ctcttaggac tttgcccacc tccttctcat      4080
ggcacttgct gtggaaaatg cctggctggc ctcgtgggc ctgtctcact tttccaggag       4140
acatgaccca ctaacgtggc aactttaacc caaaggcccc tcagacatgt tacagcaaat      4200
ctggagccac agacaggttc cctccattgg cagcccattg tgtttgaaat tccatgtcgg      4260
gtttacttgg aatgaaagat acttgaatta ttgtgcgcct gtgagcgccc agcttctgtt      4320
tcatagtctt aacaggtggc cattgtcgtg aaacgagtga tgcctgaaga tctcagtgat      4380
gtttgaacct tctgtgtaac ttttattaa gtctttgtat ctctcgactg attaataaag       4440
aagagaaaca cgta                                                         4454

<210> SEQ ID NO 18
<211> LENGTH: 4010
<212> TYPE: DNA
<213> ORGANISM: Homo sapiens

<400> SEQUENCE: 18
attggttgcg gcggatgcct cgcgggccgg tggctatgga ggcggcggcg gttgatggtt        60
gaccgttggc tccggggtgg gggtcgccgt tcgagtgatc tgctcagacc cgaccagagg      120
gcgcgggctg ctgatgcttg gcttggagcc cgtggggag acctagttcg gctccgccat        180
gccggccgcc gggagtaacg agccggacgg cgtcctcagc tatcagagac cagatgaaga      240
agctgtggtg gatcagggtg ggaccagtac aattctcaac attcactatg aaaaagaaga      300 gctgaaggt cacagaactc tgtatgtggg agttcggatg ccgcttggcc ggcagagcca       360
tcggcatcac cgcactcatg ccagaagca ccggagacga gggcggggca aaggagccag       420 ccaggggag gaaggcctgg aagccctggc cacgacaca ccatctcagc gtgttcagtt        480
cattcttggc accgaggaag atgaagagca tgtgcctcat gagctgttta cagagctgga      540
tgagatctgt atgaaagagg gagaagatgc tgagtgaag gaaacagcca ggtggctgaa       600
gtttgaagaa gatgttgaag atgggggaga acgctggagc aagccttatg tggcaaccct      660
ttcattgcac agcctgtttg agctaaggag ctgccttatt aatggaacag tcctcctgga     720
tatgcatgca aatagcatag aagaaatttc agacctgatc ctggatcagc aagaactgtc      780
cagtgacctg aatgacagca tgagggttaa agtgcgggaa gcccttctca aaaagcatca      840
tcatcagaat gaaaagaaga gaaacaacct cattcccatt gttcgctcct tgctgaggt      900 tggcaagaag cagtctgatc ctcatttgat ggataaacat ggtcaaaccg tgtctcctca      960
gtctgttcca actacaaatc ttgaagtaaa aaatggagtg aattgtgaac atagtcctgt     1020
ggatttaagc aaggtagacc ttcatttcat gaaaaaatt cctactgggg ccgaggcctc     1080
caatgtcctg gttggagagg tggatatttt ggaccgtccc attgttgcct ttgtgaggct     1140
```

```
gtctccagct gttcttctct caggcctaac agaagtgcca atcccaacaa gattttttgtt    1200
tatcttattg ggtccagtag ggaaaggtca gcagtaccat gagattggca gatccatggc    1260
caccatcatg acagatgaga tttttcatga cgtagcatat aaggcaaaag agcgagatga    1320
tctcctggcg gggattgatg agttcctaga ccaggtgacg gtgctccctc caggagagtg    1380
ggatccctcc attagaattg agccacccaa aaatgtccct tcccaggaga aaggaaaat     1440
gcctggagtt ccaaatggaa atgtttgcca catagaacag gaaccacatg ggggtcacag    1500
tgggccagaa cttcagcgca ctgggcggct atttgggggc ttggtgctgg acatcaagcg    1560
gaaggccccc tggtactgga gcgactaccg agatgcactc agcttacagt gtttggcttc    1620
ctttctgttc ctgtactgtg cctgcatgtc acctgtcatc acctttgggg gactgcttgg    1680
agaagccact gagggacgca taagtgcaat tgaatccttg tttggagctt ccatgactgg    1740
gattgcttat tccttgtttg cgggacaggc tctcaccatc ctgggaagta ctggaccagt    1800
gcttgtgttt gaaaagattt tgttcaaatt ctgcaaagac tatgctcttt catacctctc    1860
cctgcgagct tgtattggac tgtggaccgc tttcctgtgt attgtccttg tggcaactga    1920
tgccagttcc cttgtctgct acattacccg tttcactgaa gaagcatttg cctcccctaat   1980
ttgcattatt ttcatctatg aagcaataga aaaactgatt cacctggcag agacctaccc    2040
catccacatg cacagccagc tggaccacct tagcctctat tactgcaggt gtactctgcc    2100
agagaatcca acaatcaca ccctccagta ctggaaggac cacaacatcg tgacagcaga     2160
agtccactgg gctaacctga ctgtcagtga atgccaggag atgcatggag agttcatggg    2220
atctgcgtgc ggccatcatg gaccctacac tcctgatgtc ctcttttggt cctgtattct    2280
cttttttcacc accttcatcc tctcaagcac cttaaagacg tttaagacga gccgttattt    2340
cccaaccaga gtacgctcca tggtgagtga cttttgctgtt ttcctcacta tcttcacaat    2400
ggtgattatt gattttttga ttggagtccc atcaccaaag cttcaagttc ccagtgtgtt    2460
caagccaaca agggatgatc gcggatggat tattaatccc attggcccca atccctggtg    2520
gactgtgata gctgcaatta tcccagctct tctctgtact atcttgatat tcatggatca    2580
gcagatcaca gccgtcatta ttaacaggaa ggaacataag ctcaagaaag gctgtggcta    2640
ccacctggac ctactgatgg tggccatcat gctgggtgtc tgctccatca tgggcctgcc    2700
ctggtttgta gctgcaactg tcttgtccat cacacatgtg aacagcctca gctagaatc     2760
tgaatgctct gctcctggag aacagcccaa gttcctgggc atccgagaac agagagtgac    2820
aggcctttatg atctttgtgc tgatgggctg ctcagtcttc atgacggcta tcttaaagtt    2880
tattccaatg ccagtactct acggagtttt cctttacatg ggagtttctt cactacaggg    2940
aattcagttc tttgatcgtc taaagctctt tgggatgccc gcaaagcacc agccagtttt    3000
catctacctg cggcatgtgc cgctgcgcaa agtgcacctc ttcaccctca tccagttgac    3060
ctgtctcgtc ctgctctggg tcatcaaggc atctccagct gccattgttt tcccaatgat    3120
ggttttggcc ttggtctttg tcaggaaagt catggatctc tgtttctcta agcgagagct    3180
gagctggcta gatgatctca tgcctgaaag caaaaagaag aagttggatg atgccaaaaa    3240
gaaggccaag gaggaagagg tcatagtcct tgcaccaact gtataccgtg gggcctcaaa    3300
ttacagaaca taggaagggt catgtgaaaa gtcagcatgt ctggaatccc gagggttata    3360
tttaggagct gggaagatta cccccaaaga tgttctcagc taagaatgga ttagggattc    3420
ttgcttctgt ctgttcttaa ttttttgggtt tgacaaccac ttatttttc ctttgtttac     3480
aatctactca ccaggctcat acctacaatg tgaacataca gtatgccctt attagcagat    3540
```

| | |
|---|---|
| tcaatggctc acattctttc aaaaggtcta atttgacaaa tacataagac ccattatttc | 3600 |
| ctagaatgtt tgtaatatat ctaattgcaa atggtgctgt ggttggcacc atgcaaagat | 3660 |
| aacttgcata ggactttctg tctttttttca tttccctcag cacttggcat cttgtcatct | 3720 |
| acacaatgga ccctcaataa atggcctata tgtgcaaaga aagaatgtgt agcaaatgaa | 3780 |
| aataccagac caagaaatga gtgagctggg aagtgtttcc aaatacagtt agtgcctaaa | 3840 |
| atagtgtcct ttgaaaaaac ttttaaaaga ctttttttta ggccaggcat aatgggttat | 3900 |
| ccctgtaatt ccagggcttt tgggagttga agctggagga ttacttgagg ccagaagttt | 3960 |
| gagactagcc taggcaatat aatgagaccc tgtctctaca aaaaaaaaa | 4010 |

<210> SEQ ID NO 19
<211> LENGTH: 3276
<212> TYPE: DNA
<213> ORGANISM: Homo sapiens

<400> SEQUENCE: 19

| | |
|---|---|
| aatagactaa acccagagcc tcaaagcagt gcactccgtg aaggcaaaga gaacacgctg | 60 |
| caaaaggctt tccaagaatc ctcgacatgg caaggaggag ctcgttccag tcgtgtcaga | 120 |
| taatatccct gttcactttt gccgttggag tcaatatctg cttaggattc actgcacatc | 180 |
| gaattaagag agcagaagga tgggaggaag gtcctcctac agtgctatca gactcccccct | 240 |
| ggaccaacat ctccggatct tgcaagggca ggtgctttga acttcaagag gctggaccctc | 300 |
| ctgattgtcg ctgtgacaac ttgtgtaaga gctataccag ttgctgccat gactttgatg | 360 |
| agctgtgttt gaagacagcc cgtggctggg agtgtactaa ggacagatgt ggagaagtca | 420 |
| gaaatgaaga aaatgcctgt cactgctcag aggactgctt ggccagggga gactgctgta | 480 |
| ccaattacca agtggtttgc aaaggagagt cgcattgggt tgatgatgac tgtgaggaaa | 540 |
| taaaggccgc agaatgccct gcagggtttg ttcgccctcc attaatcatc ttctccgtgg | 600 |
| atggcttccg tgcatcatac atgaagaaag gcagcaaagt catgcctaat attgaaaaac | 660 |
| taaggtcttg tggcacacac tctcccctaca tgaggccggt gtacccaact aaaaacctttc | 720 |
| ctaacttata cactttggcc actgggctat atccagaatc acatggaatt gttggcaatt | 780 |
| caatgtatga tcctgtattt gatgccactt ttcatctgcg agggcgagag aaatttaatc | 840 |
| atagatggtg gggaggtcaa ccgctatgga ttacagccac caagcaaggg gtgaaagctg | 900 |
| gaacattctt ttggtctgtt gtcatccctc acgagcggag aatattaacc atattgcagt | 960 |
| ggctcaccct gccagatcat gagaggcctt cggtctatgc cttctattct gagcaacctg | 1020 |
| atttctctgg acacaaatat ggcccttttcg gccctgagga gagtagttat ggctcaccctt | 1080 |
| ttactccggc taagagacct aagaggaaag ttgcccctaa gaggagacag gaaagaccag | 1140 |
| ttgctcctcc aaagaaaaga agaagaaaaa tacataggat ggatcattat gctgcggaaa | 1200 |
| ctcgtcagga caaaatgaca aatcctctga gggaaatcga caaaattgtg gggcaattaa | 1260 |
| tggatggact gaaacaacta aaactgcatc ggtgtgtcaa cgtcatcttt gtcggagacc | 1320 |
| atggaatgga agatgtcaca tgtgatagaa ctgagttctt gagtaattac ctaactaatg | 1380 |
| tggatgatat tactttagtg cctggaactc taggaagaat tcgatccaaa tttagcaaca | 1440 |
| atgctaaata tgaccccaaa gccattattg ccaatctcac gtgtaaaaaa ccagatcagc | 1500 |
| actttaagcc ttacttgaaa cagcaccttc ccaaacgttt gcactatgcc aacaacagaa | 1560 |
| gaattgagga tatccatttta ttggtggaac gcagatggca tgttcaagg aaacctttgg | 1620 |
| atgtttataa gaaaccatca ggaaaatgct ttttccaggg agaccacgga tttgataaca | 1680 |

-continued

```
aggtcaacag catgcagact gtttttgtag gttatggctc aacatttaag tacaagacta      1740
aagtgcctcc atttgaaaac attgaacttt acaatgttat gtgtgatctc ctgggattga      1800
agccagctcc taataatggg acccatggaa gtttgaatca tctcctgcgc actaatacct      1860
tcaggccaac catgccagag gaagttacca gacccaatta tccagggatt atgtaccttc      1920
agtctgattt tgacctgggc tgcacttgtg atgataaggt agagccaaag aacaagttgg      1980
atgaactcaa caaacggctt catacaaaag ggtctacaga agagagacac ctcctctatg      2040
ggcgacctgc agtgctttat cggactagat atgatatctt atatcacact gactttgaaa      2100
gtggttatag tgaaatattc ctaatgccac tctggacatc atatactgtt tccaaacagg      2160
ctgaggtttc cagcgttcct gaccatctga ccagttgcgt ccggcctgat gtccgtgttt      2220
ctccgagttt cagtcagaac tgtttggcct acaaaaatga taagcagatg tcctacggat      2280
tcctctttcc tccttatctg agctcttcac cagaggctaa atatgatgca ttccttgtaa      2340
ccaatatggt tccaatgtat cctgctttca acgggtctg gaattatttc caaagggtat      2400
tggtgaagaa atatgcttcg gaaagaaatg gagttaacgt gataagtgga ccaatcttcg      2460
actatgacta tgatggctta catgacacag aagacaaaat aaaacagtac gtggaaggca      2520
gttccattcc tgttccaact cactactaca gcatcatcac cagctgtctg gatttcactc      2580
agcctgccga caagtgtgac ggccctctct ctgtgtcctc cttcatcctg cctcaccggc      2640
ctgacaacga ggagagctgc aatagctcag aggacgaatc aaaaatggga gaagaactca      2700
tgaagatgca cacagctagg gtgcgtgaca ttgaacatct caccagcctg acttcttcc      2760 gaaagaccag ccgcagctac ccagaaatcc tgacactcaa gacatacctg catacatatg      2820
agagcgagat ttaactttct gagcatctgc agtacagtct tatcaactgg ttgtatattt      2880
ttatattgtt tttgtattta ttaatttgaa accaggacat taaaaatgtt agtattttaa      2940
tcctgtacca aatctgacat attatgcctg aatgactcca ctgttttct ctaatgcttg       3000 atttaggtag ccttgtgttc tgagtagagc ttgtaataaa tactgcagct tgagttttta      3060
gtggaagctt ctaaatggtg ctgcagattt gatatttgca ttgaggaaat attaattttc      3120
caatgcacag ttgccacatt tagtcctgta ctgtatggaa acactgattt tgtaaagttg      3180
cctttatttg ctgttaactg ttaactatga cagatatatt taagccttat aaaccaatct      3240
taaacataat aaatcacaca ttcagttttt tctggt      3276
```

`<210>` SEQ ID NO 20
`<211>` LENGTH: 4750
`<212>` TYPE: DNA
`<213>` ORGANISM: Homo sapiens

`<400>` SEQUENCE: 20

```
gagaacggtg gccggacgga gagactgcgg gtctgaggga ctggcgggcg ggcgggccga       60
gcggcgccgc cgaggccggg ctgggccgag cccaggagcg cccggatgt agcgggccac       120 cctgccgatg ccacagcgcc cggccgcggg cggagccgga gccggagcct ggggaggcgg      180
cgggggccca gagcgcagcc cgcgcccccc gcgcggagcc aggcccgctg ccgtccccgc      240
cgcccgggcc cccggcatgc agccccggct gcggaggtga cactcacgga ccttagccac      300
cgccgccgcc atcgccacca tggacgaaca ggaggcattg aactcaatca tgaacgatct      360
ggtggccctc cagatgaacc gacgtcaccg gatgcctgga tatgagacca tgaagaacaa      420
agacacaggt cactcaaata ggcagagtga cgtcagaatc aagttcgagc acaacgggga      480
gaggcgaatt atagcgttca gccggcctgt gaaatatgaa gatgtggagc acaaggtgac      540
```

```
aacagtattt ggacaacctc ttgatctaca ttacatgaac aatgagctct ccatcctgct    600
gaaaaaccaa gatgatcttg ataaagcaat tgacatttta gatagaagct caagcatgaa    660
aagccttagg atattgctgt tgtcccagga cagaaaccat aacagttcct ctccccactc    720
tggggtgtcc agacaggtgc ggatcaaggc ttcccagtcc gcaggggata taaatactat    780
ctaccagccc cccgagccca aagcaggca cctctctgtc agctcccaga accctggccg    840
aagctcacct ccccctggct atgttcctga gcggcagcag cacattgccc ggcaggggtc    900
ctacaccagc atcaacagtg agggggagtt catcccagag accagcgagc agtgcatgct    960 ggatccctg agcagtgcag aaaattcctt gtctggaagc tgccaatcct tggacaggtc   1020
agcagacagc ccatccttcc ggaaatcacg aatgtcccgt gcccagagct ccctgacaa   1080 cagacaggaa tactcagatc gggaaactca gctttatgac aaaggggtca aaggtggaac   1140 ctaccccgg cgctaccacg tgtctgtgca ccacaaggac tacagtgatg gcagaagaac   1200
atttccccga atacggcgtc atcaaggcaa cttgttcacc ctggtgccct ccagccgctc   1260
cctgagcaca aatggcgaga acatgggtct ggctgtgcaa tacctggacc cccgtgggcg   1320
cctgcggagt gcggacagcg agaatgccct ctctgtgcag gagaggaatg tgccaaccaa   1380
gtctcccagt gcccccatca actggcgccg gggaaagctc ctgggccagg gtgccttcgg   1440
cagggtctat ttgtgctatg acgtggacac gggacgtgaa cttgcttcca agcaggtcca   1500
atttgatcca gacagtcctg agacaagcaa ggaggtgagt gctctggagt gcgagatcca   1560
gttgctaaag aacttgcagc atgagcgcat cgtgcagtac tatggctgtc tgcgggaccg   1620
cgctgagaag accctgacca tcttcatgga gtacatgcca gggggctcgg tgaaagacca   1680
gttgaaggct tacggtgctc tgacagagag cgtgacccga aagtacacgc ggcagatcct   1740
ggagggcatg tcctacctgc acagcaacat gattgttcac cgggacatta agggagccaa   1800
catcctccga gactctgctg ggaatgtaaa gctgggggac tttggggcca gcaaacgcct   1860
gcagacgatc tgtatgtcgg ggacgggcat gcgctccgtc actggcacac cctactggat   1920
gagccctgag gtgatcagcg gcgagggcta tggaaggaaa gcagacgtgt ggagcctggg   1980
ctgcactgtg gtggagatgc tgacagagaa accaccgtgg gcagagtatg aagctatggc   2040
cgccatcttc aagattgcca cccagcccac caatcctcag ctgccctccc acatctctga   2100
acatggccgg gacttcctga ggcgcatttt tgtggaggct cgccagagac ttcagctga   2160 ggagctgctc acacaccact ttgcacagct catgtactga gctctcacgg ccacacagct   2220
gccggtcgcc ctttgctgca tggcaggggg ctgctgctgg gctcagtgaa gttgctgctt   2280
ctcccaggca aggctgtgga ccatggagtg gcagcccagc cagcgtcggt ctgtgcccct   2340
tccgccactg gggctcagag ccggggtggg gtggctgcag cctcaggact gggagccccc   2400
agcctgtcag atccaggagc tccagtgtcc tgagctcagc gtggaggggt aggggctggg   2460
aacagtgtgc aaggcagccg tgggccccac cctcggggat gtgtcctgac actgcaattg   2520
gcaccgaagc ccagagggtc tggggcaca agactgacgc cagggtatga agagtgttat   2580
tttcattcaa agtgttattt tgttttttcct tccaatgtct ggagaccacc agggcatctc   2640
tgggctggat gagctcccac aagcctgagg gaaaggccag cactcgctag cagtggcagg   2700
cagaggccca ggctgccgtc ccctagagtc ccaggttggc tctgccagtc ctgtcctttta   2760 ccaaagatga atgaagcaaa tgtcatgctg ccttattcag ggaaggagga gcctgtcctg   2820
cctgtggcca tgaccctgcc tctcccaggc aggggcccgc gatgtggaac tgctgccact   2880 gagggggggat ccagttttgt caatgcagtt gtctctgttt tacaagttgg agtcactctt   2940
```

| | |
|---|---|
| atgctgtacc cagtttctaa actggagact gtgtgtgccc tctgggctct gagtacccct | 3000 |
| gctttgggct tgggcctagg ctgcattgaa aagagctgaa ggttgtgtgcc tttgcgctcc | 3060 |
| tggcccagcc tttgttcccc actggagcag aaggggagat ggacgacacg gtcggggcat | 3120 |
| ctggcctggc cagtgccctg atcccagaga gcccgaggag gtgtctcagg ctgcctgagt | 3180 |
| cgtgacctgc taggccagag cccactccat ctggtagaag ggaaagccca tatgctacca | 3240 |
| ccagctgtgt ccaaaaccgc cagctctgtt cttcctcagc cagcctcgcc catcccttg | 3300 |
| aggtctcagc ccctttccct tgtagctcct cccctggagg gggaatggca gcaggggttg | 3360 |
| gggaaacagc atctccaagc agcttagagt tggccatatt tacctcagcc tgggcgctgg | 3420 |
| tcctttcttc cggcccctcc cctccaaaat gtgcctattg ctagagctcc tccctctcaa | 3480 |
| cacccagttt ccttgggagt tgtcattaaa ggaaaaaaaa aaaaaaaaaa gccagtgccc | 3540 |
| agggatgggc atctccaggg agctggggat tagtgccagg cagccctgcc agccatgcct | 3600 |
| acatccccat gggcacagaa caagccaaag ccttcgttgt atgttgacga tgcacttta | 3660 |
| tgaatgtagt ttctatcgct gttttagcc ttttcacatc atgtaatgtg aggccttgta | 3720 |
| cttgttaatt tatatctcag atcatatttg atggttttta tatatatcaa ttctagactg | 3780 |
| ttacaggtga cggacgcctc aagagagaga agagaaaatg aaagcagctg gttttgcaga | 3840 |
| agtgtgtgtc gcatgcgcca gttgggcctg gaccctcctg tgtccatccc tgttcccca | 3900 |
| ggggctctat cagcccctgt accccacact gccctctgaa gacaacacag gctcctgctt | 3960 |
| ccacctcggc ccttgcccag ggtggggcct ggccctcatc ttgaccaaag ctgctgtgtg | 4020 |
| gcagctcggc ctctctacga ccccatcttg gtggctgcac actcttcctg gcccgcaccc | 4080 |
| ccatccccag tccctgttcc caagaggat acagagcacg gtgctggctg actcaactgt | 4140 |
| gcgtcccagg ttcagggtct tacagagctc caccccctgg ggtcttacct cactgggaat | 4200 |
| gtgtttgaa aatgaatttg aagacaagcc aacaaaccct gcactccaaa aaagcaaaac | 4260 |
| agaccctaat ttttttgtgc caaaaactgt ggacatgctg gctcagcatc ctcaggacca | 4320 |
| agttgttgct taatttattg ttttttaata actaatccag ataaaaagtt gtggggcttc | 4380 |
| agggtgacct gggcccaaag gttctgaagg gcagttcctg gcagcccag gcttgctgtg | 4440 |
| ggaaggggcc gtgccgtcac tttctcatca ttccatgggg tgtgtctgcc tgggccaact | 4500 |
| ctgcatggag aggccagggc tggggacagt ccgcactctg ccaccctcct gccccttcca | 4560 |
| cccaccccag ctctatgtct gtgtctgaat tgtggatcgt gcagccatgg ttattgtgga | 4620 |
| actgtggaac ctgcagccat agttatttga ctatatcttg accgagggct tgcagtgcaa | 4680 |
| agccaggcca gtgttgcgca ttacttacaa taaagggat catttatatc agaaaaaaaa | 4740 |
| aaaaaaaaaa | 4750 |

<210> SEQ ID NO 21
<211> LENGTH: 4843
<212> TYPE: DNA
<213> ORGANISM: Homo sapiens

<400> SEQUENCE: 21

| | |
|---|---|
| gagaacggtg gccggacgga gagactgcgg gtctgaggga ctggcgggcg ggcgggccga | 60 |
| gcggcgccgc cgaggccggg ctgggccgag cccaggagcg cccggatgt agcgggccac | 120 |
| cctgccgatg ccacagcgcc cggccgcggg cggagccgga gccggagcct ggggaggcgg | 180 |
| cgggggccca gagcgcagcc cgcgccccc gcgcggagcc aggcccgctg ccgtccccgc | 240 |
| cgcccgggcc cccggcatgc agccccggct gcggaggtga cactcacgga ccttagccac | 300 |

-continued

| | |
|---|---|
| cgccgccgcc atcgccacca tggacgaaca ggaggcattg aactcaatca tgaacgatct | 360 |
| ggtggccctc cagatgaacc gacgtcaccg gatgcctgga tatgagacca tgaagaacaa | 420 |
| agacacaggt cactcaaata ggcagaaaaa acacaacagc agcagctcag cccttctgaa | 480 |
| cagccccaca gtaacaacaa gctcatgtgc agggccagt gagaaaaaga aattttgag | 540 |
| tgacgtcaga atcaagttcg agcacaacgg ggagaggcga attatagcgt tcagccggcc | 600 |
| tgtgaaatat gaagatgtgg agcacaaggt gacaacagta tttggacaac ctcttgatct | 660 |
| acattacatg aacaatgagc tctccatcct gctgaaaaac caagatgatc ttgataaagc | 720 |
| aattgacatt ttagatagaa gctcaagcat gaaaagcctt aggatattgc tgttgtccca | 780 |
| ggacagaaac cataacagtt cctctcccca ctctggggtg tccagacagg tgcggatcaa | 840 |
| ggcttcccag tccgcagggg atataaatac tatctaccag ccccccgagc ccagaagcag | 900 |
| gcacctctct gtcagctccc agaaccctgg ccgaagctca cctcccctg gctatgttcc | 960 |
| tgagcggcag cagcacattg cccggcaggg gtcctacacc agcatcaaca gtgagggga | 1020 |
| gttcatccca gagaccagcg agcagtgcat gctggatccc ctgagcagtg cagaaaattc | 1080 |
| cttgtctgga agctgccaat ccttggacag gtcagcagac agcccatcct tccggaaatc | 1140 |
| acgaatgtcc cgtgcccaga gcttccctga caacagacag gaatactcag atcgggaaac | 1200 |
| tcagctttat gacaaagggg tcaaaggtgg aacctacccc cggcgctacc acgtgtctgt | 1260 |
| gcaccacaag gactacagtg atggcagaag aacatttccc cgaatacggc gtcatcaagg | 1320 |
| caacttgttc accctggtgc cctccagccg ctccctgagc acaaatggcg agaacatggg | 1380 |
| tctggctgtg caatacctgg accccgtgg gcgcctgcgg agtgcggaca gcgagaatgc | 1440 |
| cctctctgtg caggagagga atgtgccaac caagtctccc agtgccccca tcaactggcg | 1500 |
| ccggggaaag ctcctgggcc agggtgcctt cggcagggtc tatttgtgct atgacgtgga | 1560 |
| cacgggacgt gaacttgctt ccaagcaggt ccaatttgat ccagacagtc ctgagacaag | 1620 |
| caaggaggtg agtgctctgg agtgcgagat ccagttgcta aagaacttgc agcatgagcg | 1680 |
| catcgtgcag tactatggct gtctgcggga ccgcgctgag aagaccctga ccatcttcat | 1740 |
| ggagtacatg ccagggggct cggtgaaaga ccagttgaag gcttacggtg tctctgacaga | 1800 |
| gagcgtgacc cgaaagtaca cgcggcagat cctggagggc atgtcctacc tgcacagcaa | 1860 |
| catgattgtt caccgggaca ttaagggagc caacatcctc cgagactctg ctgggaatgt | 1920 |
| aaagctgggg gactttgggg ccagcaaacg cctgcagacg atctgtatgt cggggacggg | 1980 |
| catgcgctcc gtcactggca caccctactg gatgagccct gaggtgatca gcggcgaggg | 2040 |
| ctatggaagg aaagcagacg tgtggagcct gggctgcact gtggtggaga tgctgacaga | 2100 |
| gaaaccaccg tggcagagt atgaagctat ggccgccatc ttcaagattg ccacccagcc | 2160 |
| caccaatcct cagctgcccct cccacatctc tgaacatggc cgggacttcc tgaggcgcat | 2220 |
| ttttgtggag gctcgccaga gaccttcagc tgaggagctg ctcacacacc actttgcaca | 2280 |
| gctcatgtac tgagctctca cggccacaca gctgccggtc gccctttgct gcatggcagg | 2340 |
| gggctgctgc tgggctcagt gaagttgctg cttctcccag gcaaggctgt ggaccatgga | 2400 |
| gtggcagccc agccagcgtc ggtctgtgcc ccttccgcca ctgggctca gagccgggt | 2460 |
| ggggtggctg cagcctcagg actgggagcc cccagcctgt cagatccagg agctccagtg | 2520 |
| tcctgagctc agcgtggagg ggtagggct gggaacagtg tgcaaggcag ccgtgggccc | 2580 |
| caccctcggg gatgtgtcct gacactgcaa ttggcaccga agcccagagg gtctgggggc | 2640 |
| acaagactga cgccagggta tgaagagtgt tattttcatt caaagtgtta ttttgttttt | 2700 |

-continued

```
ccttccaatg tctggagacc accagggcat ctctgggctg gatgagctcc cacaagcctg      2760
agggaaaggc cagcactcgc tagcagtggc aggcagaggc ccaggctgcc gtcccctaga      2820
gtcccaggtt ggctctgcca gtcctgtcct ttaccaaaga tgaatgaagc aaatgtcatg      2880
ctgccttatt cagggaagga ggagcctgtc ctgcctgtgg ccatgaccct gcctctccca      2940
ggcaggggcc cgcgatgtgg aactgctgcc actgagggg gatccagttt tgtcaatgca       3000
gttgtctctg ttttacaagt tggagtcact cttatgctgt acccagtttc taaactggag      3060
actgtgtgtg ccctctgggc tctgagtacc cctgctttgg gcttgggcct aggctgcatt      3120
gaaaagagct gaaggttgtg cctttgcgc tcctggccca gcctttgttc cccactggag       3180
cagaagggga gatggacgac acggtcgggg catctggcct ggccagtgcc ctgatcccag      3240
agagcccgag gaggtgtctc aggctgcctg agtcgtgacc tgctaggcca gagcccactc      3300
catctggtag aagggaaagc ccatatgcta ccaccagctg tgtccaaaac cgccagctct      3360
gttcttcctc agccagcctc gcccatcccc ttgaggtctc agccccttc ccttgtagct      3420 cctcccctgg aggggaatg gcagcagggg ttggggaaac agcatctcca agcagcttag      3480
agttggccat atttacctca gcctgggcgc tggtcctttc ttccggcccc tccctccaa      3540 aatgtgccta ttgctagagc tcctccctct caacacccag tttccttggg agttgtcatt       3600
aaaggaaaaa aaaaaaaaaa aaagccagtg cccaggggatg gcatctcca gggagctggg      3660 gattagtgcc aggcagccct gccagccatg cctacatccc catgggcaca gaacaagcca      3720
aagccttcgt tgtatgttga cgatgcactt ttatgaatgt agtttctatc gctgttttta      3780
gccttttcac atcatgtaat gtgaggcctt gtacttgtta atttatatct cagatcatat      3840
ttgatggttt ttatatatat caattctaga ctgttacagg tgacggacgc ctcaagagag      3900
agaagagaaa atgaaagcag ctggttttgc agaagtgtgt gtcgcatgcg ccagttgggc      3960
ctggaccctc ctgtgtccat ccctgttccc cagggggctc tatcagcccc tgtaccccac      4020
actgccctct gaagacaaca caggctcctg cttccacctc ggcccttgcc cagggtgggg      4080
cctggccctc atcttgacca aagctgctgt gtggcagctc ggcctctcta cgaccccatc      4140
ttggtggctg cacactcttc ctggcccgca ccccatccc cagtccctgt tccccaagag       4200
gatacagagc acggtgctgg ctgactcaac tgtgcgtccc aggttcaggg tcttacagag      4260
ctccaccccc tggggtctta cctcactggg aatgtgtttt gaaatgaat ttgaagacaa       4320 gccaacaaac cctgcactcc aaaaaagcaa aacagaccct aattttttg tgccaaaaac      4380 tgtggacatg ctggctcagc atcctcagga ccaagttgtt gcttaattta ttgttttta       4440 ataactaatc cagataaaaa gttgtggggc ttcagggtga cctgggccca aaggttctga      4500
agggcagttc ctggcagccc caggcttgct gtgggaaggg gccgtgccgt cactttctca      4560
tcattccatg gggtgtgtct gcctgggcca actctgcatg gagaggccag ggctggggac      4620
agtccgcact ctgccaccct cctgccccctt ccacccaccc cagctctatg tctgtgtctg      4680
aattgtggat cgtgcagcca tggttattgt ggaactgtgg aacctgcagc catagttatt      4740
tgactatatc ttgaccgagg gcttgcagtg caaagccagg ccagtgttgc gcattactta      4800
caataaaagg gatcatttat atcagaaaaa aaaaaaaaaa aaa                        4843
```

<210> SEQ ID NO 22
<211> LENGTH: 2504
<212> TYPE: DNA
<213> ORGANISM: Homo sapiens

<400> SEQUENCE: 22

```
gggacccact atcttgtggt ttctgtcaag ttcctgattt tcatccgtag ttgaagatga    60
gcaagaactc tgtaacagtg ttaccttgga gcctacaatg agaggtattt caaaatgagt   120
gaagcatgac tctcacagat gaaggcctag acgcaggatc tttaatgaaa aaacacttgg   180
gccacttcaa gacgacaaac gctcactggg caaaacacct tcactgaaaa gagacctcat   240
attatgcaaa aaaatcttaa aaaggcctct gccttcagaa gttacaagat gatcaattca   300
acctccacac agcctccaga tgaatcctgc tctcagaacc tcctgatcac tcagcagatc   360
attcctgtgc tgtactgtat ggtcttcatt gcaggaatcc tactcaatgg agtgtcagga   420
tggatattct tttacgtgcc cagctctaag agtttcatca tctatctcaa gaacattgtt   480
attgctgact ttgtgatgag cctgactttt cctttcaaga tccttggtga ctcaggcctt   540 ggtcccggc agctgaacgt gtttgtgtgc agggtctctg ccgtgctctt ctacgtcaac   600
atgtacgtca gcattgtgtt cttttgggctc atcagctttg acagatatta taaaattgta   660
aagcctcttt ggacttcttt catccagtca gtgagttaca gcaaacttct gtcagtgata   720
gtatggatgc tcatgctcct ccttgctgtt ccaaatatta ttctcaccaa ccagagtgtt   780
agggaggtta cacaaataaa atgtatagaa ctgaaaagtg aactgggacg gaagtggcac   840
aaagcatcaa actacatctt cgtggccatc ttctggattg tgtttctttt gttaatcgtt   900
ttctatactg ctatcacaaa gaaaatcttt aagtcccacc ttaagtcaag tcggaattcc   960
acttcggtca aaaagaaatc tagccgcaac atattcagca tcgtgtttgt gttttttgtc  1020
tgttttgtac cttaccatat tgccagaatc ccctacacaa agagtcagac cgaagctcat  1080
tacagctgcc agtcaaaaga aatcttgcgg tatatgaaag aattcactct gctactatct  1140
gctgcaaatg tatgcttgga ccctattatt tatttctttc tatgccagcc gtttagggaa  1200
atcttatgta agaaattgca cattccatta aaagctcaga atgacctaga catttccaga  1260
atcaaaagag gaaatacaac acttgaaagc acagatactt tgtgagttcc taccctcttc  1320
caaagaaaga ccacgtgtgc atgttgtcat cttcaattac ataacagaaa tcaataagat  1380
atgtgccctc atcataaata tcatctctag cactgccatc caatttagtt caataaaatt  1440
caaatataag tttccatgct ttttttgtaac atcaaagaaa acatacccat cagtaatttc  1500
tctaatactg acctttctat tctctattaa taaaaaatta atacatacaa ttattcaatt  1560
ctattatatt aaaataagtt aaagtttata accactagtc tggtcagtta atgtagaaat  1620
ttaaatagta aataaaacac aacataatca aagacaactc actcaggcat cttctttctc  1680
taaataccag aatctagtat gtaattgttt tcaacactgt ccttaaagac taacttgaaa  1740
gcaggcacag tttgatgaag ggctagagag ctgtttgcaa taaaaagtca ggttttttttc  1800 ctgatttgaa gaagcaggaa aagctgacac ccagacaatc acttaagaaa ccccttattg  1860
atgtatttca tggcactgca aaggaagagg aatattaatt gtatacttag caagaaaatt  1920 tttttttttct gatagcactt tgaggatatt agatacatgc taaatatgtt ttctacaaag  1980
acttacgtca tttaatgagc ctggggttct ggtgttagaa tatttttaag taggctttac  2040
tgagagaaac taaatattgg catacgttat cagcaacttc ccctgttcaa tagtatggga  2100
aaaataagat gactgggaaa aagacacacc cacaccgtag aacatatatt aatctactgg  2160
cgaatgggaa aggagaccat tttccttagaa agcaaataaa cttgattttt ttaaatctaa  2220
aatttacatt aatgagtgca aaataacaca taaaatgaaa attcacacat cacatttttc  2280
tggaaaacag acggatttta cttctggaga catggcatac ggttactgac ttatgagcta  2340
ccaaaactaa attctttctc tgctattaac tggctagaag acattcatct attttttcaaa  2400
```

```
tgttctttca aaacattttt ataagtaatg tttgtatcta tttcatgctt tactgtctat      2460
atactaataa agaaatgttt taatactgaa aaaaaaaaa aaaa                        2504

<210> SEQ ID NO 23
<211> LENGTH: 2396
<212> TYPE: DNA
<213> ORGANISM: Homo sapiens

<400> SEQUENCE: 23
cacatagcta gtaagttcta gctagcactg agtgctgtgc ccgtgaaatt tatctacata       60
ggctttcact taacctgcag acagaactca gttagtcggg gacaatttcc ctcaatgtta      120
acagcactgt tccaccgcaa cgtggaacaa cagctttaaa acgtgctctt cgtaggcccg      180
gctactccaa gaacagtgcc tcccgccaga cccaggcggc ttccttcacc cgcaacccga      240
gagacgaccc gccgggcccg ccccgcggaa gccgccggtt gccaggccaa ggagtggact      300
agggtcgccg gggaagcggt ttgggagagc ccatggtgac tgcgtgagtg gagcccagct      360
gtgtggatgc cccagcatgg atgactacat ggtcctgaga atgattgggg agggctcctt      420
cggcagagct ctttggttc agcatgaaag cagtaatcag atgtttgcca tgaaagaaat      480
aaggcttccc aagtctttct ctaatacaca gaattctagg aaggaggctg ttcttttagc      540
caaaatgaaa caccctaata ttgttgcctt caaagaatca tttgaagctg aaggacactt      600
gtatattgtg atggaatact gtgatggagg ggatctaatg caaaagatta acagcagaa      660 aggaaagtta tttcctgaag acatgatact taattggttt acccaaatgt gccttggagt      720
aaatcacatt cacaagaaac gtgtgctaca cagagatatc aagtccaaga atatcttcct      780
cactcagaat ggaaaagtga aattgggaga cttttggatct gcccgtcttc tctccaatcc      840
gatggcattt gcttgtacct atgtgggaac tccttattat gtgcctccag aaatttggga      900
aaacctgcct tataacaata aaagtgacat ctggtccttg ggttgcatcc tgtatgaact      960 ctgtacccttt aagcatccat ttcaggcaaa tagttggaaa atcttatcc tcaaagtatg     1020 tcaagggtgc atcagtccac tgccgtctca ttactcctat gaacttcagt tcctagtcaa     1080
gcagatgttt aaaaggaatc cctcacatcg cccctcggct acaacgcttc tctctcgagg     1140
catcgtagct cggcttgtcc agaagtgctt acccccgag atcatcatgg aatatggtga     1200
ggaagtatta gaagaaataa aaaattcgaa gcataacaca ccaagaaaaa aaacaaaccc     1260
cagcagaatc aggatagctt tgggaaatga agcaagcaca gtgcaagagg aagaacaaga     1320
tagaaagggt agccatactg atttggaaag cattaatgaa aatttagttg aaagtgcatt     1380
gagaagagta aacagagaag aaaaaggtaa taagtcagtc catctgagga aagccagttc     1440
accaaatctt catagacgac agtgggagaa aaatgtaccc aatacagctc ttacagcttt     1500
ggaaaatgca tccatactca cctccagttt aacagcagag gacgatagag gtggttctgt     1560
aataaagtac agcaaaaata ctactcgtaa gcagtggctc aaagagaccc ctgacacttt     1620
gttgaacatc cttaagaatg ctgatctcag cttggctttt caaacataca caatatatag     1680
accaggttca gaagggttct tgaaaggccc cctgtctgaa gaaacagaag catcggacag     1740
tgttgatgga ggtcacgatt ctgtcatttt ggatccagag cgacttgagc ctgggctaga     1800
tgaggaggac acggactttg aggaggaaga tgacaacccc gactgggtgt cagagctgaa     1860
gaagcgagct ggatggcaag gcctgtgcga cagataatgc ctgaggaaat gttcctgagt     1920
cacgctgagg agaggcttca ctcaggagtt catgctgaga tgatcatgag ttcatgcgac     1980
gtatattttc cttggaaac agaatgaagc agaggaaact cttaatactt aaaatcgttc     2040
```

```
ttgattagta tcgtgagttt gaaaagtcta gaactcctgt aagttttgga actcaaggga    2100
gaaggtatag tggaatgagt gtgagcatcg ggctttgcag tcccatagaa cagaaatggg    2160
atgctagcgt gccactacct acttgtgtga ttgtgggaaa ttacttaacc tcttcaagcc    2220
ccaatttcct caaccataaa atgaagataa taatgcctac ctcagaggga tgctgaccac    2280
agacctttat agcagcccgt atgatattat tcacattatg atatgtgttt attattatgt    2340
gactcttttt acatttccta aaggtttgag aattaaatat atttaattat gattta        2396

<210> SEQ ID NO 24
<211> LENGTH: 2255
<212> TYPE: DNA
<213> ORGANISM: Homo sapiens

<400> SEQUENCE: 24
cgccgccttg gggtctgggc gcgcggtgcc gtggggtca gcagggcgga gcggcttttc      60
caggagaaag ggccctcacg ggtgagcggg gcgactgggc tcccccgcgg tgcagttgcc    120
ccgcgggcgc cggccccggc tcaacggatt cttctcgctc gctgcccgga agaaccatt    180 tgggagagcc catggtgact gcgtgagtgg agcccagctg tgtggatgcc ccagcatgga    240
tgactacatg gtcctgagaa tgattgggga gggctccttc ggcagagctc tttttggttca    300 gcatgaaagc agtaatcaga tgtttgccat gaaagaaata aggcttccca agtctttctc    360
taatacacag aattctagga aggaggctgt tcttttagcc aaaatgaaac accctaatat    420
tgttgccttc aaagaatcat ttgaagctga aggacacttg tatattgtga tggaatactg    480
tgatggaggg gatctaatgc aaaagattaa acagcagaaa ggaaagttat ttcctgaaga    540
catgatactt aattggttta cccaaatgtg ccttggagta aatcacattc acaagaaacg    600
tgtgctacac agagatatca agtccaagaa tatcttcctc actcagaatg gaaaagtgaa    660
attgggagac tttggatctg cccgtcttct ctccaatccg atggcatttg cttgtaccta    720
tgtgggaact ccttattatg tgcctccaga aatttgggaa aacctgcctt ataacaataa    780
aagtgacatc tggtccttgg gttgcatcct gtatgaactc tgtaccctta agcatccatt    840
tcaggcaaat agttggaaaa atcttatcct caaagtatgt caagggtgca tcagtccact    900
gccgtctcat tactcctatg aacttcagtt cctagtcaag cagatgttta aaaggaatcc    960
ctcacatcgc ccctcggcta caacgcttct ctctcgaggc atcgtagctc ggcttgtcca   1020
gaagtgctta ccccccgaga tcatcatgga atatggtgag gaagtattag aagaaataaa    1080
aaattcgaag cataacacac caagaaaaaa aacaaacccc agcagaatca ggatagcttt    1140
gggaaatgaa gcaagcacag tgcaagagga agaacaagat agaaagggta gccatactga    1200
tttggaaagc attaatgaaa atttagttga aagtgcattg agaagagtaa acagagaaga    1260
aaaaggtaat aagtcagtcc atctgaggaa agccagttca ccaaatcttc atagacgaca    1320
gtgggagaaa aatgtaccca atacagctct tacagctttg gaaatgcat ccatactcac    1380 ctccagttta acagcagagg acgatagagg tggttctgta ataaagtaca gcaaaaatac    1440
tactcgtaag cagtggctca agagaccccc tgacactttg ttgaacatcc ttaagaatgc    1500
tgatctcagc ttggcttttc aaacatacac aatatataga ccaggttcag aagggttctt    1560
gaaaggcccc ctgtctgaag aaacagaagc atcggacagt gttgatggag gtcacgattc    1620
tgtcattttg gatccagagc gacttgagcc tgggctagat gaggaggaca cggactttga    1680
ggaggaagat gacaaccccg actgggtgtc agagctgaag aagcgagctg gatggcaagg    1740
cctgtgcgac agataatgcc tgaggaaatg ttcctgagtc acgctgagga gaggcttcac   1800
```

| | |
|---|---|
| tcaggagttc atgctgagat gatcatgagt tcatgcgacg tatattttcc tttggaaaca | 1860 |
| gaatgaagca gaggaaactc ttaatactta aaatcgttct tgattagtat cgtgagtttg | 1920 |
| aaaagtctag aactcctgta agttttttgaa ctcaagggag aaggtatagt ggaatgagtg | 1980 |
| tgagcatcgg gctttgcagt cccatagaac agaaatggga tgctagcgtg ccactaccta | 2040 |
| cttgtgtgat tgtgggaaat tacttaacct cttcaagccc caatttcctc aaccataaaa | 2100 |
| tgaagataat aatgcctacc tcagagggat gctgaccaca gacctttata gcagcccgta | 2160 |
| tgatattatt cacattatga tatgtgttta ttattatgtg actcttttta catttcctaa | 2220 |
| aggtttgaga attaaatata tttaattatg attta | 2255 |

<210> SEQ ID NO 25
<211> LENGTH: 2252
<212> TYPE: DNA
<213> ORGANISM: Homo sapiens

<400> SEQUENCE: 25

| | |
|---|---|
| agaacagctt gaagaccgtt cattttttaag tgacaagaga ctcacctcca agaagcaatt | 60 |
| gtgttttcag aatgatttta ttcaagcaag caacttattt catttccttg tttgctacag | 120 |
| tttcctgtgg atgtctgact caactctatg aaaacgcctt cttcagaggt ggggatgtag | 180 |
| cttccatgta caccccaaat gcccaatact gccagatgag gtgcacattc cacccaaggt | 240 |
| gtttgctatt cagtttttctt ccagcaagtt caatcaatga catggagaaa aggtttggtt | 300 |
| gcttcttgaa agatagtgtt acaggaaccc tgccaaaagt acatcgaaca ggtgcagttt | 360 |
| ctggacattc cttgaagcaa tgtggtcatc aaataagtgc ttgccatcga gacatttata | 420 |
| aaggagttga tatgagagga gtcaatttta atgtgtctaa ggttagcagt gttgaagaat | 480 |
| gccaaaaaag gtgcaccagt aacattcgct gccagttttt ttcatatgcc acgcaaacat | 540 |
| ttcacaaggc agagtaccgg aacaattgcc tattaaagta cagtcccgga ggaacaccta | 600 |
| ccgctataaa ggtgctgagt aacgtggaat ctggattctc actgaagccc tgtgcccttt | 660 |
| cagaaattgg ttgccacatg aacatcttcc agcatcttgc gttctcagat gtggatgttg | 720 |
| ccagggttct cactccagat gcttttgtgt gtcggaccat ctgcacctat caccccaact | 780 |
| gcctcttctt tacattctat acaaatgtat ggaaatcga gtcacaaaga atgtttgtc | 840 |
| ttcttaaaac atctgaaagt ggcacaccaa gttcctctac tcctcaagaa acaccatat | 900 |
| ctggatatag cctttttaacc tgcaaaagaa cttttacctga accctgccat tctaaaattt | 960 |
| acccgggagt tgactttgga ggagaagaat tgaatgtgac ttttgttaaa ggagtgaatg | 1020 |
| tttgccaaga gacttgcaca aagatgattc gctgtcagtt tttcacttat tctttactcc | 1080 |
| cagaagactg taaggaagag aagtgtaagt gtttcttaag attatctatg gatggttctc | 1140 |
| caactaggat tgcgtatggg acacaaggga gctctggtta ctcctttgaga ttgtgtaaca | 1200 |
| ctggggacaa ctctgtctgc acaacaaaaa caagcacacg cattgttgga ggaacaaact | 1260 |
| cttcttgggg agagtggccc tggcaggtga gcctgcaggt gaagctgaca gctcagaggc | 1320 |
| acctgtgtgg agggtcactc ataggacacc agtgggtcct cactgctgcc cactgctttg | 1380 |
| atgggcttcc cctgcaggat gtttggcgca tctatagtgg cattttaaat ctgtcagaca | 1440 |
| ttacaaaaga tacacctttc tcacaaataa aagagattat tattcaccaa aactataaag | 1500 |
| tctcagaagg gaatcatgat atcgccttga taaaactcca ggctcctttg aattacactg | 1560 |
| aattccaaaa accaatatgc ctaccttcca aaggtgacac aagcacaatt tataccaact | 1620 |
| gttgggtaac cggatggggc ttctcgaagg agaaaggtga aatccaaaat attctacaaa | 1680 |

-continued

| | |
|---|---|
| aggtaaatat tcctttggta acaaatgaag aatgccagaa aagatatcaa gattataaaa | 1740 |
| taacccaacg gatggtctgt gctggctata aagaaggggg aaaagatgct tgtaagggag | 1800 |
| attcaggtgg tcccttagtt tgcaaacaca atggaatgtg gcgtttggtg ggcatcacca | 1860 |
| gctggggtga aggctgtgcc cgcagggagc aacctggtgt ctacaccaaa gtcgctgagt | 1920 |
| acatggactg gattttagag aaaacacaga gcagtgatgg aaaagctcag atgcagtcac | 1980 |
| cagcatgaga agcagtccag agtctaggca atttttacaa cctgagttca agtcaaattc | 2040 |
| tgagcctggg gggtcctcat ctgcaaagca tggagagtgg catcttcttt gcatcctaag | 2100 |
| gacgaaaaac acagtgcact cagagctgct gaggacaatg tctggctgaa gcccgctttc | 2160 |
| agcacgccgt aaccaggggc tgacaatgcg aggtcgcaac tgagatctcc atgactgtgt | 2220 |
| gttgtgaaat aaaatggtga aagatcaaaa aa | 2252 |

<210> SEQ ID NO 26
<211> LENGTH: 1710
<212> TYPE: DNA
<213> ORGANISM: Homo sapiens

<400> SEQUENCE: 26

| | |
|---|---|
| gggaggggcg gggcctccgc caccacctca gctgcggacc gaggcgagat ggcggccacc | 60 |
| gaggggtcg gggaggctgc gcaagggggc gagcccgggc agccggcgca accccgccc | 120 |
| cagccgcacc caccgccgcc ccagcagcag cacaaggaag agatggcggc cgaggctggg | 180 |
| gaagccgtgg cgtcccccat ggacgacggg tttgtgagcc tggactcgcc ctcctatgtc | 240 |
| ctgtacaggg acagagcaga atgggctgat atagatccgg tgccgcagaa tgatggcccc | 300 |
| aatcccgtgg tccagatcat ttatagtgac aaatttagag atgttttatga ttacttccga | 360 |
| gctgtcctgc agcgtgatga agaagtgaa cgagcttta agctaacccg ggatgctatt | 420 |
| gagttaaatg cagccaatta tacagtgtgg catttccgga gagttctttt gaagtcactt | 480 |
| cagaaggatc tacatgagga aatgaactac atcactgcaa taattgagga gcagcccaaa | 540 |
| aactatcaag tttggcatca taggcgagta ttagtggaat ggctaagaga tccatctcag | 600 |
| gagcttgaat ttattgctga tattcttaat caggatgcaa agaattatca tgcctggcag | 660 |
| catcgacaat gggttattca ggaatttaaa ctttgggata tgagctgca gtatgtggac | 720 |
| caacttctga agaggatgt gagaaataac tctgtctgga accaaagata cttcgttatt | 780 |
| tctaacacca ctggctacaa tgatcgtgct gtattggaga gaagtccaa atacactctg | 840 |
| gaaatgatta aactagtacc acataatgaa agtgcatgga actatttgaa agggatttg | 900 |
| caggatcgtg gtcttttccaa atatcctaat ctgttaaatc aattacttga tttacaacca | 960 |
| agtcatagtt cccctaccct aattgccttt cttgtggata tctatgaaga catgctagaa | 1020 |
| aatcagtgtg acaataagga agacattctt aataaagcat tagagttatg tgaaatccta | 1080 |
| gctaaagaaa aggacactat aagaaaggaa tattggagat acattggaag atccccttcaa | 1140 |
| agcaaacaca gcacagaaaa tgactcacca acaaatgtac agcaataaca ccatccagaa | 1200 |
| gaacttgatg gaatgctttt attttttatt aagggaccct gcaggagttt cacacgagag | 1260 |
| tggtccttcc ctttgcctgt ggtgtaaaag tgcatcacac aggtattgct ttttaacaag | 1320 |
| aactgatgct ccttgggtgc tgctgctact cagactagct ctaagtaatg tgattcttct | 1380 |
| aaagcaaagt cattggatgg gaggaggaag aaaaagtccc ataaggaac ttttgtagtc | 1440 |
| ttatcaacat ataatctaat cccttagcat cagctcctcc ctcagtggta catgcgtcaa | 1500 |
| gatttgtagc agtaataact gcaggtcact tgtatgtaat ggatgtgagg tagccgaagt | 1560 |

```
ttggttcagt aagcagggaa tacagtcgtt ccatcagagc tggtctgcac actcacatta   1620
tcttgctatc actgtaacca actaatgcca aagaacggt  tttgtaataa aattatagct   1680
gtatctaaaa acaaaaaaaa aaaaaaaaaa                                    1710

<210> SEQ ID NO 27
<211> LENGTH: 1624
<212> TYPE: DNA
<213> ORGANISM: Homo sapiens

<400> SEQUENCE: 27
gggaggggcg gggcctccgc caccacctca gctgcggacc gaggcgagat ggcggccacc     60 gaggggtcg  gggaggctgc gcaaggggc  gagcccgggc agccggcgca accccgcccc    120
cagccgcacc caccgccgcc ccagcagcag cacaaggaag agatggcggc cgaggctggg    180
gaagccgtgg cgtcccccat ggacgacggg tttgtgagcc tggactcgcc ctcctatgtc    240
ctgtacagtt agagatgttt atgattactt ccgagctgtc ctgcagcgtg atgaaagaag    300
tgaacgagct tttaagctaa cccgggatgc tattgagtta aatgcagcca attatacagt    360
gtggcatttc cggagagttc ttttgaagtc acttcagaag gatctacatg aggaaatgaa    420
ctacatcact gcaataattg aggagcagcc caaaaactat caagtttggc atcataggcg    480
agtattagtg gaatggctaa gagatccatc tcaggagctt gaatttattg ctgatattct    540
taatcaggat gcaagaatt  atcatgcctg gcagcatcga caatgggtta ttcaggaatt    600
taaactttgg gataatgagc tgcagtatgt ggaccaactt ctgaaagagg atgtgagaaa    660
taactctgtc tggaaccaaa gatacttcgt tatttctaac accactggct acaatgatcg    720
tgctgtattg gagagagaag tccaatacac tctggaaatg attaaactag taccacataa    780
tgaaagtgca tggaactatt tgaaagggat tttgcaggat cgtggtcttt ccaaatatcc    840
taatctgtta aatcaattac ttgatttaca accaagtcat agttccccct acctaattgc    900 cttcttgtg  gatatctatg aagacatgct agaaaatcag tgtgacaata aggaagacat    960
tcttaataaa gcattagagt tatgtgaaat cctagctaaa gaaaaggaca ctataagaaa   1020
ggaatattgg agatacattg gaagatccct tcaaagcaaa cacagcacag aaaatgactc   1080
accaacaaat gtacagcaat aacaccatcc agaagaactt gatggaatgc ttttatttt    1140 tattaaggga ccctgcagga gtttcacacg agagtggtcc ttcccttgc  ctgtggtgta   1200 aaagtgcatc acacaggtat tgcttttaa  caagaactga tgctccttgg gtgctgctgc   1260
tactcagact agctctaagt aatgtgattc ttctaaagca aagtcattgg atgggaggag   1320
gaagaaaaag tcccataaag gaacttttgt agtcttatca acatataatc taatccctta   1380
gcatcagctc ctccctcagt ggtacatgcg tcaagatttg tagcagtaat aactgcaggt   1440
cacttgtatg taatggatgt gaggtagccg aagtttggtt cagtaagcag ggaatacagt   1500
cgttccatca gagctggtct gcacactcac attatcttgc tatcactgta accaactaat   1560
gccaaaagaa cggttttgta ataaaattat agctgtatct aaaacaaaa  aaaaaaaaaa   1620 aaaa                                                                1624

<210> SEQ ID NO 28
<211> LENGTH: 1509
<212> TYPE: DNA
<213> ORGANISM: Homo sapiens

<400> SEQUENCE: 28
gggaggggcg gggcctccgc caccacctca gctgcggacc gaggcgagat ggcggccacc     60
```

| | |
|---|---|
| gagggggtcg gggaggctgc gcaaggggggc gagcccgggc agccggcgca accccccgccc | 120 |
| cagccgcacc caccgccgcc ccagcagcag cacaaggaag agatggcggc cgaggctggg | 180 |
| gaagccgtgg cgtcccccat ggacgacggg tttgtgagcc tggactcgcc ctcctatgtc | 240 |
| ctgtacaggc atttccggag agttcttttg aagtcacttc agaaggatct acatgaggaa | 300 |
| atgaactaca tcactgcaat aattgaggag cagcccaaaa actatcaagt ttggcatcat | 360 |
| aggcgagtat tagtggaatg gctaagagat ccatctcagg agcttgaatt tattgctgat | 420 |
| attcttaatc aggatgcaaa gaattatcat gcctggcagc atcgacaatg ggttattcag | 480 |
| gaatttaaac tttgggataa tgagctgcag tatgtggacc aacttctgaa agaggatgtg | 540 |
| agaaataact ctgtctggaa ccaaagatac ttcgttattt ctaacaccac tggctacaat | 600 |
| gatcgtgctg tattggagag agaagtccaa tacactctgg aaatgattaa actagtacca | 660 |
| cataatgaaa gtgcatggaa ctatttgaaa gggattttgc aggatcgtgg tctttccaaa | 720 |
| tatcctaatc tgttaaatca attacttgat ttacaaccaa gtcatagttc cccctaccta | 780 |
| attgcctttc ttgtggatat ctatgaagac atgctagaaa tcagtgtga caataaggaa | 840 |
| gacattctta ataaagcatt agagttatgt gaaatcctag ctaaagaaaa ggacactata | 900 |
| agaaaggaat attggagata cattggaaga tcccttcaaa gcaaacacag cacagaaaat | 960 |
| gactcaccaa caaatgtaca gcaataacac catccagaag aacttgatgg aatgctttta | 1020 |
| tttttatta agggaccctg caggagtttc acacgagagt ggtccttccc tttgcctgtg | 1080 |
| gtgtaaaagt gcatcacaca ggtattgctt tttaacaaga actgatgctc cttgggtgct | 1140 |
| gctgctactc agactagctc taagtaatgt gattcttcta aagcaaagtc attggatggg | 1200 |
| aggaggaaga aaaagtccca taaaggaact tttgtagtct tatcaacata taatctaatc | 1260 |
| ccttagcatc agctcctccc tcagtggtac atgcgtcaag atttgtagca gtaataactg | 1320 |
| caggtcactt gtatgtaatg gatgtgaggt agccgaagtt tggttcagta agcagggaat | 1380 |
| acagtcgttc catcagagct ggtctgcaca ctcacattat cttgctatca ctgtaaccaa | 1440 |
| ctaatgccaa aagaacggtt ttgtaataaa attatagctg tatctaaaaa caaaaaaaaa | 1500 |
| aaaaaaaaa | 1509 |

```
<210> SEQ ID NO 29
<211> LENGTH: 936
<212> TYPE: DNA
<213> ORGANISM: Homo sapiens

<400> SEQUENCE: 29
```

| | |
|---|---|
| atggcggcca ccgagggggt cggggaggct gcgcaaggcg gtgagccccg gcagctggag | 60 |
| cagcccccgc cccagccgca cccaccgctg cccaggagc agcacgagga agagatggca | 120 |
| gcagaggctg gggaagccgt ggcgtccccc atggacgacg ggtttctgag cctggattcg | 180 |
| ccctcctatg tcccgtacag gcatttccgg agagttctct aaagtcact tcagaaggat | 240 |
| ctacatgagg aaatgaacta catcactgaa ataattgagg ggcagcccaa aaactatcta | 300 |
| gtttgtcaca ataggcgagt aatagtggaa tggctaagag atccatctca ggagcctgaa | 360 |
| tttattgata atattcttaa tcaggatgca aagaattatc atgcctggca gcatcgacaa | 420 |
| tgggttattc aggaatttaa actttgggat aatgagctgc agtatgtgga ccaacttctc | 480 |
| aaagaggatg tgagaaataa ctctgtctgg aaccgaagat atttttgttat ttccaacacc | 540 |
| actggctaca atgattgtgc tgtattggag agagaagtcc aatacactct ggaaatgatt | 600 |
| caactagtac cacataatag ttcatggaac tatttgaaag gaattttgca ggatcgtggt | 660 |

-continued

```
ctttccaaat atcctaatct gttaaatcaa ttacttgatt tacaaccaag tcatagttcc    720
ccctacctaa ttgcctttct tgtgggtatc tatgaagaca tgctagaaaa ccagtgtgtc    780
aataaggaag acattcttaa taatgcatta gggttatgtg aaatcctagc taaagaaaag    840
gacatgataa gaaaggaata ttggagataa attggaagat cctttcaaag caaacacagc    900
acagaaaatg actcaccaac aaatgtacag caataa                              936

<210> SEQ ID NO 30
<211> LENGTH: 10048
<212> TYPE: DNA
<213> ORGANISM: Homo sapiens

<400> SEQUENCE: 30
tgaataattg aactttgttt atttctccat attttttgcag tggtaattcc attataaaac    60
ctaatgaaac aatgttttta tagatggtgt ggaaagactt ttctgggctc agaggtgaaa   120
ctgacccttg tgtatcagca gcatttctga ctgactgaga gagtgtagtg attaacagag   180
ttgtgatgtt agttaagaaa cttagatttg ccattgtagc ttttctacca attagcagat   240
tgtttaactc actgaaattg taaagtggta gacgtggact tagtcattac tgggcagctt   300
atgaattgta ttcatttact catgatgtaa aaatggttag tctccacttt taaggctcta   360
gttctagtgg ctaaataggt acttatttat acagtatgat aactgctgta ttaaaataca   420
tgtctcaaat gtggaatagt agaagaggtg aagaaaatca tagtttgagg tagaatactg   480
tttgctggtc ttaaaaactg tggtattttg gtgattccat aaattaggtc agatacttcc   540
actggaggga aacagtttaa aggatatatg tgatactatt aatagaatga ggaagacaca   600
ccagatattt aggagggaat tagcgagctt gaaactaaga gctggtttga atgagactgg   660
gtcataagtg atttcaagta ccagattaag gcactgagat tttatttta agcactgaag   720 tcagattttt tccttttaaa agaaaggatt catgatgaaa tctgcttttt gttttgcaga   780
gagcttggag ataattctgg tggctgtgtg gagtatgtgt tggaggtatt aaattttcac   840
agtatatata aggcagcaat tgataggcct ttcacagatt cttctgataa ctacataaag   900
agacaaaaaa agaaaaaag agcaaagatc tgtgctgtgt caagtatgac agccatcact   960
catggctctc cagtaggagg gaacgacagc cagggccagg ttcttgatgg ccagtctcag  1020
catctcttcc aacagaacca gacttcatca cctgattctt ccaatgagaa ttccgtagca  1080
actcctcctc cagaggaaca agggcaaggt gatgccccac cacagcatga agatgaagag  1140
cctgcatttc cacatactga gctggcaaac ctggatgaca tgatcaacag gcctcgatgg  1200
gtggttcctg ttttgccaaa aggggaatta gaagtgcttt tagaagctgc tattgatctt  1260
agtgtaaaag gccttgatgt taaaagtgaa gcatgccaac gttttttttcg agatggacta  1320 acaatatctt tcactaaaat tcttatggat gaggctgtga gtggctggaa gtttgaaatt  1380
catagatgta ttattaacaa tactcatcgc ctagtggagc tttgtgtggc caagttgtcc  1440
caagattggt ttccacttct agaacttctc gccatggcct taaatcctca ctgcaagttt  1500
catatctaca atggtacacg tccgtgtgaa ttaatttcct caaatgctca gttgcctgaa  1560
gatgaattat ttgctcgttc ttcagatcct cgatcaccaa aaggttggct agtggatctc  1620
atcaataaat ttggcacatt aaatgggttc cagattttgc atgatcgttt ttttaatgga  1680
tcagcattaa atattcaaat aattgcagct cttattaaac catttggaca atgctatgag  1740
tttctcagtc aacatacact gaaaagtac ttcattccag ttatagaaat agttccacat  1800
ttattggaaa acttaactga tgaagaactg aaaaggagg caaagaatga agccaaaaat  1860
```

```
gatgccctttt caatgattat taaatctttg aagaacttag cttcaagaat ttcaggacaa    1920
gatgagacta taaaaaattt ggaaatttttt aggttaaaga tgatactcag attgttgcaa    1980
atttcctctt ttaatggaaa gatgaatgca ctgaatgaaa taaataaggt tatatctagt    2040
gtatcatatt atactcatcg gcatagtaat cctgaggagg aagaatggct gacagctgag    2100
cgaatggcag aatggataca gcaaaataat atcttatcca tagtcttgca agacagtctt    2160
catcaaccac aatatgtaga aaagctagag aaaattcttc gttttgtgat taaagaaaag    2220
gctcttacat tacaggacct tgataatatc tgggcagcac aggcaggaaa acatgaagcc    2280
attgtgaaga atgtacatga tctgctagca aagttggctt gggattttttc tcctggacaa    2340 cttgatcatc tttttgattg ctttaaggca agttggacaa atgcaagtaa aaagcaacgt    2400
gaaaagctcc ttgagttgat acgccgtctt gcagaagatg ataaagatgg tgtgatggca    2460
cacaaagtgt tgaaccttct ttggaacctg gctcagagtg atgatgtgcc tgtagacatc    2520
atggaccttg ctcttagtgc ccacataaaa atactagatt atagttgttc ccaggatcga    2580
gatgcacaga agatccagtg gatagatcac tttatagaag aacttcgcac aaatgacaag    2640
tgggtaattc ctgctctgaa acaaataaga gaaatttgta gtttgtttgg tgaagcatct    2700
caaaatttga gtcaaactca gcgaagtccc cacatatttt atcgccatga tttaatcaac    2760
cagcttcaac aaaatcatgc tttagttact ttggtagcag aaaaccttgc aacctacatg    2820
aatagcatca gattgtatgc tggagatcat gaagactatg atccacaaac agtgaggctt    2880
ggaagtcgat acagtcatgt tcaagaagtt caagaacgac taaacttcct tagattttta    2940
ctgaaggatg ccaactgtgt gctctgtgct cctcaggcaa aacaaatatg gaagtgctta    3000
gcagaaaatg cagtttatct ttgtgatcgt gaagcctgtt ttaagtggta ttccaagtta    3060
atgggggatg aaccagactt ggatcctgat attaataagg acttctttga aagtaatgta    3120
cttcagcttg atccttccct tttaactgaa aatggaatga aatgctttga aagatttttc    3180
aaagctgtca attgtcgaga aaggaaacta atagcaaaaa gaagatccta tatgatggat    3240
gatttggaat taattggact agactacctt tggagggttg tgattcagag tagtgacgag    3300
attgctaaca gagctataga tcttcttaaa gagatatcaa caaaccttgg cccaagatta    3360
aaagccaatc aggtggttat ccatgaagac ttcattcagt cttgctttga tcgtttaaaa    3420
gcatcatatg atacactgtg tgtttttgat ggtgacaaaa acagcattaa ttgtgcaaga    3480
caagaagcca ttcgaatggt tagagtatta actgttataa aagagtacat taatgaatgt    3540
gacagtgatt atcacaagga aagaatgatt ctacctatgt cgagagcatt tcgtggcaaa    3600
cacctctctc ttatagttcg gtttccaaac cagggcagac aggttgatga gttggatata    3660
tggtctcata cgaatgacac aattggttca gtacggcgat gtattgttaa tcgtattaaa    3720
gccaatgtag cccacaaaaa aattgaactt tttgtgggtg gtgagctgat agattctgaa    3780
gatgacagaa agctaattgg acaattaaac ttaaaagata atctctaat tacagccaaa    3840 cttacacaaa taaatttcaa tatgccatca agtcctgata gctcttccga ttcctcaact    3900
gcatctcctg gaaccaccg taatcattac aatgatggtc ccaatctaga ggtgaaagt    3960 tgtttgcctg gggtgataat gtcagtgcat cccagataca tctctttcct ttggcaagtt    4020
gcagacttag gtagcaacct gaatatgcca cctcttagag atggagcaag agtacttatg    4080
aaacttatgc caccagatag aacagctgta gaaaaattac gagctgtttg tttggaccat    4140
gcaaaacttg gagaaggcaa acttagtcca ccccttgact ctctttttctt tggtccttct    4200 gcctcccaag ttctatacct aacagaggta gtttatgcct tgttaatgcc tgctggtgtg    4260
```

```
cctctaactg atgggtcctc tgactttcaa gttcacttct tgaaaagtgg tggcttacct    4320
cttgtactga gtatgctaat aagaaataac ttcttgccaa atacagatat ggaaactcga    4380
aggggtgctt atttaaatgc tcttaaaata gccaaactgt tgttaactgc gattggctat    4440
ggccatgttc gagctgtagc agaagcttgt cagccagttg tagatggtac agaccccata    4500
acacagatta accaagttac tcatgatcaa gcagtggtgc tacaaagtgc ccttcagagc    4560
attcctaatc cctcatccga gtgcgtactt agaaatgagt ccatacttct tgctcaggaa    4620
atatctaatg aggcttcaag atatatgcct gatatttgtg taattagggc tatacagaaa    4680
attatctggg catcagcatg tggggcatta ggactagttt ttagcccaaa tgaagaaata    4740
actaaaattt atcagatgac caccaatgga agcaataagc tggaggtgga agatgaacaa    4800
gtttgctgtg aagcactgga agtgatgacc ttatgttttg ctttacttcc aacagcgttg    4860
gatgcactta gtaaagaaaa agcctggcag accttcatca ttgacttatt attgcactgt    4920
ccaagcaaaa ctgttcgtca gttggcacag gagcagttct ttttaatgtg caccagatgt    4980
tgcatgggac acaggcctct gcttttcttc attacttttac tctttaccat actggggagc    5040
acagcaagag agaagggtaa atattcaggt gattatttca cacttttacg gcaccttctc    5100
aattatgctt acaatggcaa tattaacata cccaatgctg aagttcttct tgtcagtgaa    5160
attgattggc tcaaaaggat tagggataat gttaaaaaca caggtgaaac aggtgtcgaa    5220
gagccaatac tggaaggcca ccttggggta acaaaagagt tattggcctt tcaaacttct    5280
gagaaaaagt atcactttgg ttgtgaaaaa ggaggtgcta atctcattaa agaattaatt    5340
gatgatttca tctttcccgc atccaaagtt tacctgcagt atttaagaag tggagaacta    5400
ccagctgagc aggctattcc agtctgtagt tcacccgtta ccatcaatgc cggttttgag    5460
ctacttgtag cattagctat tggctgtgtg aggaatctca acagatagt agactgtttg    5520 actgaaatgt attacatggg cacagcaatt actacttgtg aagcacttac tgagtgggaa    5580
tatctgcccc ctgttggacc ccgcccacca aaaggatttg tgggactcaa aaatgctggt    5640
gctacgtgtt acatgaactc tgtgatccag cagctataca tgattccttc tatcaggaac    5700
agtattcttg caattgaagg cacaggtagt gatttacacg atgatatgtt cggggatgag    5760
aagcaggaca gtgagagtaa tgttgatccc cgagatgatg tatttggata tcctcatcaa    5820
tttgaagaca agccagcatt aagtaagaca gaagatagga aagagtataa tattggtgtc    5880
ctaagacacc ttcaggtcat ctttggtcat ttagctgctt cccaactaca atactatgta    5940
cccagaggat tttggaaaca gttcaggctt tggggtgaac tgttaatct ccgtgaacaa    6000 catgatgcct tagagttttt taattctttg gtggatagtt tagatgaagc tttaaaagct    6060
ttaggacacc cggctatact aagtaaagtc ctaggaggct cctttgctga tcagaagatc    6120
tgccaaggct gcccacatag gtatgaatgt gaagaatctt ttacaacttt gaatgtggat    6180
attagaaatc atcaaaatct tcttgactct ttggaacagt atatcaaagg agatttattg    6240
gaaggtgcaa atgcatatca ttgtgaaaaa tgtgataaaa aggttgacac agtaaagcgc    6300
ctgctaatta aaaaattgcc tcgggttctt gctatccaac tcaaacgatt tgactatgac    6360
tgggaaagag aatgtgcaat taaattcaat gattatttg aatttcctcg agagctggat    6420
atgggacctt acacagtagc aggtgttgca aacctggaaa gggataatgt aaactcagaa    6480
aatgagttga ttgaacagaa agagcagtct gacaatgaaa ctgcaggagg cacaaagtac    6540
agacttgtag gagtgcttgt acacagtggt caagcaagcg gtgggcatta ttattcttac    6600
atcattcaaa ggaatggtaa agatgatcag acagatcact ggtataaatt tgatgatgga    6660
```

```
gatgtaacag aatgcaaaat ggatgatgat gaagaaatga aaaatcagtg ttttggtgga    6720
gagtacatgg gagaagtatt tgatcacatg atgaagcgca tgtcatatag gcgacagaag    6780
aggtggtgga atgcttacat acttttttat gaacaaatgg atatgataga tgaagatgat    6840
gagatgataa gatacatatc agagctaact attgcaagac cccatcagat cattatgtca    6900
ccagccattg agagaagtgt acggaaacaa aatgtgaaat ttatgcataa ccgattgcaa    6960
tatagtttag agtattttca gtttgtgaaa aaactgctta catgtaatgg tgtttatttta   7020 aaccctgctc cagggcagga ttatttgttg cctgaagcag aagaaattac tatgattagt    7080
attcagcttg ctgctagatt cctctttacc actggatttc acaccaagaa aatagttcgt    7140
ggtcctgcca gtgactggta tgatgcactg tgcgttcttc tccgtcacag caaaaatgta    7200 cgttttggt ttactcataa tgtccttttt aatgtatcaa atcgcttctc tgaataacctt    7260 ctggagtgcc ctagtgcaga agtgaggggt gcatttgcaa aacttatagt gtttattgca    7320
cacttttcct tgcaagatgg gtcttgtcct tctccttttg catctccagg accttctagt    7380
caggcatgtg ataacttgag cttgagtgac cacttactaa gagccacact aaatctcttg    7440
agaagggaag tttcagagca tggacatcat ttacagcaat attttaattt gtttgtaatg    7500
tatgccaatt taggtgtggc agaaaaaaca cagcttctga aattgaatgt acctgctacc    7560
tttatgcttg tgtctttaga cgaaggacca ggtcctccaa tcaaatatca gtatgctgaa    7620
ttaggcaagt tatattcagt agtgtctcag ctgattcgtt gttgcaatgt gtcatcaaca    7680
atgcagtctt caatcaatgg taatccccct ctccccaatc ctttcggtga ccttaattta    7740
tcacagccta taatgccaat tcagcagaat gtgttagaca ttttatttgt gagaacaagt    7800
tatgtgaaga aaattattga agactgcagt aactcagagg ataccatcaa attacttcgc    7860
ttttgctctt gggagaatcc tcagttctca tctactgtcc tcagcgaact tctctggcag    7920
gttgcatatt catataccta tgaacttcgg ccatatttag atctactttt ccaaatttta    7980
ctgattgagg actcctggca gactcacaga attcataatg cacttaaagg aattccagat    8040
gacagagatg ggctgttcga tacaatacag cgctcgaaga atcactatca aaaacgagca    8100
tatcagtgca taaaatgtat ggtagctcta tttagcagtt gtcctgttgc ttaccagatc    8160
ttacagggta acggagatct taaaagaaaa tggacctggg cagtggaatg gctaggagat    8220
gaacttgaaa aagaccata tactggcaat cctcagtata gttacaacaa ttggtctcct    8280
ccagtacaaa gcaatgaaac agcaaatggt tatttcttag aaagatcaca tagtgctagg    8340 atgcacttg caaaagcttg tgaactctgt ccagaagagg agccagatga ccaggatgcc    8400
ccagatgagc atgagccctc tccatcagaa gatgccccat tatatcctca ttcacctgcc    8460
tctcagtatc aacagaataa tcatgtacat ggacagccat atacaggacc agcagcacat    8520
cacttgaaca accctcagaa aacaggccaa cgaacacaag aaaattatga aggcaatgaa    8580
gaagtatcct cacctcagat gaaggatcag tgaaaagcaa taattaactg cttcctttat    8640
gactatgcac taaggtctta tagtccaaac tttctctgtg tctggctagt attgaaaact    8700
agataaactg ctccaaacca acatggagta aagagcatat tcactggttt atttgcagta    8760
atttgcaatt tgtcagtgta taagacacat gcagggtgaa gtgtacagag ttttgtaaca    8820
aatgactggt cctaatctgt aaatgagaaa ggtatatata ctatgttaat gtctgactgt    8880
taattcttaa gcaagaaact ttttttgatg aaaacaagtc agatctacac agtcacacaa    8940 ttatttttg ttgtgttcac tacattgtgc aattgatatt gcctgctttg agcagtttgg    9000
tcaacttacc aacttccccc caaaaaaggg aacataaaag agcccatctt tgtcagttta    9060
```

```
caccaatagt tccttgttaa tccttctttc ctggatatat aaggctggtg gtaacttttg    9120
aattatatgg ttgatgtgga aaattggcag tgtaacattt ctagatactt ttcattacct    9180
ttttattctg gtatataggc taaccacttt aaagctattc ttatgctgta acagttagca    9240
tggcttcaca ctgtttgtgt agccaagagg acagaattac atgaatgaca gtgcccagag    9300
tgacagctgt atattgctca gagcttttat ttcttatacc tagaataaat ataaaatggg    9360
ggaaaaatgt gacagacaag cagttttttca ttgcacacat attcttcaca tttaatgttt    9420
gatagttcaa tttcttgagc tgaagaatat caaagtatcg ataatacgaa ttttaaaata    9480
ttaaaaccaa tacacaaaat tttcctatgt cagaatgtgg tggagcataa tagattgtat    9540
ttggtgtgct tgcgattttt ttttttccata gaatttatta agtgaagttt ctaaaacttt    9600
gcttctcctg atcccggtga agtgtacatc ataagaatcc atagtacttt gaagtaccat    9660
tgcaccaaga tgtctgactg aattcatagt cacactttta tttgaaagaa agaattgttg    9720 tagtttttttt tcattattct aaaactcttg ttgttagata caagatttaa ttaagatcta    9780
agctcctgct tatttaatgt aattctaagg taccatttta gaaaaaacat ttgttttaag    9840
attccaagaa acctgtgagt taatactata tttaaaagag aattggtaaa ttttgaatgt    9900
gtgtaatatt ttggaacctg tttaaaaacc aaatatacct gcaaatagat acagcctatc    9960
ctatactatt taaatgtttg gctgttttgt tttatagaaa ttattttgct gaattcacaa    10020
ataaaattta agaagacttt aaaaaaaa                                        10048

<210> SEQ ID NO 31
<211> LENGTH: 3178
<212> TYPE: DNA
<213> ORGANISM: Homo sapiens

<400> SEQUENCE: 31
gatctcttgg agacggcgac ccaggcatct ggggagccac agaagtcgta ctcccttaaa      60
ccctgctttg ctcccccctgt ggatgtaacc ccttagctgg cattttgcat ctcaattggc    120
ttgtgatgga ggcgtctttg gggattcaga tggatgagcc aatggctttt tctccccagc     180
gtgaccggtt tcaggctgaa ggctcttaaa aaaaaaacga gcagaatttt aaacttgcag     240
gtgttaaaaa agatattgag aagctttatg aagctgtacc acagcttagt aatgtgttta     300
agattgagga caaaattgga gaaggcactt tcagctctgt ttatttggcc acagcacagt     360
tacaagtagg acctgaagag aaaaattgctc taaaacactt gattccaaca agtcatccta     420
taagaattgc agctgaactt cagtgcctaa cagtggctgg ggggcaagat aatgtcatgg     480
gagttaaata ctgctttagg aagaatgatc atgtagttat tgctatgcca tatctggagc     540
atgagtcgtt tttggacatt ctgaattctc tttcctttca agaagtacgg gaatatatgc     600
ttaatctgtt caaagctttg aaacgcattc atcagtttgg tattgttcac cgtgatgtta     660
agcccagcaa tttttatat aataggcgcc tgaaaaagta tgccttggta gactttggtt     720
tggcccaagg aaccccatgat acgaaaatag agcttcttaa atttgtccag tctgaagctc     780
agcaggaaag gtgttcacaa acaaatccc acataatcac aggaaacaag attccactga      840
gtggcccagt acctaaggag ctggatcagc agtccaccac aaaagcttct gttaaaagac      900
cctacacaaa tgcacaaatt cagattaaac aaggaaaaga cggaaaggag ggatctgtag     960
gcctttctgt ccagcgctct gttttttggag aaagaaattt caatatacac agctccattt    1020
cacatgagag ccctgcagtg aaactcatga agcagtcaaa gactgtggat gtactgtcta   1080
gaaagttagc aacaaaaaag aaggctattt ctacgaaagt tatgaatagt gctgtgatga   1140
```

```
ggaaaactgc cagttcttgc ccagctagcc tgacctgtga ctgctatgca acagataaag    1200
tttgtagtat ttgcctttca aggcgtcagc aggttgcccc tagggcaggt acaccaggat    1260
tcagagcacc agaggtcttg acaaagtgcc ccaatcaaac tacagcaatt gacatgtggt    1320
ctgcaggtgt catatttctt tctttgctta gtggacgata tccatttat aaagcaagtg     1380 atgatttaac tgctttggcc caaattatga caattagggg atccagagaa actatccaag    1440
ctgctaaaac ttttgggaaa tcaatattat gtagcaaaga agttccagca caagacttga    1500
gaaaactctg tgagagactc aggggtatgg attctagcac tcccaagtta acaagtgata    1560
tacaagggca tgcttctcat caaccagcta tttcagagaa gactgaccat aaagcttctt    1620
gcctcgttca aacacctcca ggacaatact cagggaattc atttaaaaag ggggatagta    1680
atagctgtga gcattgtttt gatgagtata ataccaattt agaaggctgg aatgaggtac    1740
ctgatgaagc ttatgacctg cttgataaac ttctagatct aaatccagct tcaagaataa    1800
cagcagaaga agctttgttg catccatttt ttaaagatat gagcttgtga taatggatct    1860
tcatttaatg tttactgtta tgaggtagaa taaaaagaa tactttgtaa tagccacaag     1920
ttcttgttta gagaccagag caggattaat aatttatttt aacattttag tgtttggtgg    1980
cacattctaa aatatagatt aagaatactt aaaatgcctg ggatagttct tgggactaac    2040
aacatgatct tctttgagtt aaacctacct aagtagattt taggtgggtt cctattaggt    2100 cagatttta gcttccctaa ttacctttca ctgacataca gaaaaaggag cagttttagt     2160
tttaattaat taaaattaac agatgtgatg aggattaaat gaatcaaaag acttaatttg    2220
tagattcttt tagagttatg agctaggtat agtttgggga aactcaacct ggtgctggtg    2280
ctcttaacaa ttttgtaaat aaagaagata atttccttt ctagaggtac atattaggcc     2340
ttttatgaac actaaaacaa tgaggaaatg ttggtcatgg ggcaaagtat cacttaaaat    2400
tgaattcatc cattttaaa aaacacttca tgaaagcatt ctggtgtgaa ttgccatttt     2460
tttcttactg gcttctcaat tttcttcctt ctctgcccct acctaaaaca ttctcctcgg    2520
aaattacatg gtgctgacca caaagttctt ggatgtttta ttaaatattg tacgtgttta    2580
cagttgggaa tttaaaataa tacatacact ggttgataaa gggaagctgc aggaccaagg    2640
tgaagattga tagtccaaat gctttcttt tttgagttgt atatttttc acaccatctt      2700 agatataatt aggtagctgc tgaaaggaaa agtgaataca gaattgacgg tattattgga    2760 gattttcct ctgcgtagag ccatccagat ctctgtatcc tgttttgact aagtcttagg     2820
tgggttggga agacagataa tgaagtaggc aaagagaaaa ggacccaaga tagaggttta    2880
tattcagaaa tggtatatat caatgacagc atatcaaact tcctatggga aaaagtctgg    2940
tgggtggtca gctgacagat ttcccattta gtagtcatag aatacagaaa tagtttaggg    3000
acatgtattc attttgttat tttgagcatt gataggtcag tatatctacc taatctgttt    3060
ggtaagtata ggatatataa accattacca ttgatctgtc ttatgccata tcttaaaaa     3120 aaaattgaat gctcttgaat ttgtatattc aataaagtta ccttttata aaaaaaaa      3178
```

```
<210> SEQ ID NO 32
<211> LENGTH: 2276
<212> TYPE: DNA
<213> ORGANISM: Homo sapiens

<400> SEQUENCE: 32
gaacgtggta taaagggggc gggaggccag gctcgtgccg ttttgcagac gccaccgccg      60
aggaaaaccg tgtactatta gccatggtca accccaccgt gttcttcgac attgccgtcg     120
```

| | |
|---|---|
| acggcgagcc cttgggccgc gtctcctttg agctgtttgc agacaaggtc ccaaagacag | 180 |
| cagaaaattt tcgtgctctg agcactggag agaaaggatt tggttataag ggttcctgct | 240 |
| ttcacagaat tattccaggg tttatgtgtc agggtggtga cttcacacgc cataatggca | 300 |
| ctggtggcaa gtccatctat ggggagaaat tgaagatga gaacttcatc ctaaagcata | 360 |
| cgggtcctgg catcttgtcc atggcaaatg ctggacccaa cacaaatggt tcccagtttt | 420 |
| tcatctgcac tgccaagact gagtggttgg atggcaagca tgtggtgttt ggcaaagtga | 480 |
| aagaaggcat gaatattgtg gaggccatgg agcgctttgg gtccaggaat ggcaagacca | 540 |
| gcaagaagat caccattgct gactgtggac aactcgaata agtttgactt gtgttttatc | 600 |
| ttaaccacca gatcattcct tctgtagctc aggagagcac ccctccaccc catttgctcg | 660 |
| cagtatccta gaatctttgt gctctcgctg cagttcccct tggggttccat gttttccttg | 720 |
| ttccctccca tgcctagctg gattgcagag ttaagtttat gattatgaaa taaaaactaa | 780 |
| ataacaattg tcctcgtttg agttaagagt gttgatgtag gctttatttt aagcagtaat | 840 |
| gggttacttc tgaaacatca cttgtttgct taattctaca cagtacttag atttttttta | 900 |
| ctttccagtc ccaggaagtg tcaatgtttg ttgagtggaa tattgaaaat gtaggcagca | 960 |
| actgggcatg gtggctcact gtctgtaatg tattacctga ggcagaagac cacctgaggg | 1020 |
| taggagtcaa gatcagcctg ggcaacatag tgagacgctg tctctacaaa aaataattag | 1080 |
| cctggcctgg tggtgcatgc ctagtcctag ctgatctgga ggctgacgtg ggaggattgc | 1140 |
| ttgagcctag agtgagctat tatcatgcca ctgtacagcc tggtgttca cagatcttgt | 1200 |
| gtctcaaagg taggcagagg caggaaaagc aaggagccag aattaagagg ttgggtcagt | 1260 |
| ctgcagtgag ttcatgcatt tagaggtgtt cttcaagatg actaatgtca aaaattgaga | 1320 |
| catctgttgc ggtttttttt tttttttttt cccctggaat gcagtggcgt gatctcagct | 1380 |
| cactgcagcc tccgcctcct ggggttcaagt gattctagtg cctcagcctc ctgagtagct | 1440 |
| gggataatgg gcgtgtgcca ccatgcccag ctaattttg tattttagt atagatgggg | 1500 |
| tttcatcatt ttgaccaggc tggtctcaaa ctcttgacct cagctgatgc gcctgccttg | 1560 |
| gcctcccaaa ctgctgagat tacagatgtg agccaccgca ccctacctca ttttctgtaa | 1620 |
| caaagctaag cttgaacact gttgatgttc ttgagggaag catattgggc tttaggctgt | 1680 |
| aggtcaagtt tatacatctt aattatggtg gaattcctat gtagagtcta aaaagccagg | 1740 |
| tacttggtgc tacagtcagt ctccctgcag agggttaagg cgcagactac ctgcagtgag | 1800 |
| gaggtactgc ttgtagcata tagagcctct ccctagcttt ggttatggag ctttgaggt | 1860 |
| tttgcaaacc tgaccaattt aagccataag atctggtcaa agggataccc ttcccactaa | 1920 |
| ggacttggtt tctcaggaaa ttatatgtac agtgcttgct ggcagttaga tgtcaggaca | 1980 |
| atctaagctg agaaaacccc ttctctgccc accttaacag acctctaggg ttcttaaccc | 2040 |
| agcaatcaag tttgcctatc ctagaggtgg cggatttgat catttggtgt gttgggcaat | 2100 |
| ttttgtttta ctgtctggtt ccttctgcgt gaattaccac caccaccact tgtgcatctc | 2160 |
| agtcttgtgt gttgtctggt tacgtattcc ctgggtgata ccattcaatg tcttaatgta | 2220 |
| cttgtggctc agacctgagt gcaaggtgga aataaacatc aaacatcttt tcatta | 2276 |

<210> SEQ ID NO 33
<211> LENGTH: 5189
<212> TYPE: DNA
<213> ORGANISM: Homo sapiens

<400> SEQUENCE: 33

-continued

```
atggccaagt cgggtggctg cggcgcggga gccggcgtgg gcggcggcaa cggggcactg    60
acctgggtga acaatgctgc aaaaaaagaa gagtcagaaa ctgccaacaa aaatgattct   120
tcaaagaagt tgtctgttga gagagtgtat cagaagaaga cacaacttga acacattctt   180
cttcgtcctg atacatatat tgggtcagtg gagccattga cgcagttcat gtgggtgtat   240
gatgaagatg taggaatgaa ttgcagggag gttacctttg tgccaggttt atacaagatc   300
tttgatgaaa ttttggttaa tgctgctgac aataaacaga gggataagaa catgacttgt   360
attaaagttt ctattgatcc tgaatctaac attataagca tttggaataa tgggaaaggc   420
attccagtag tagaacacaa ggtagagaaa gtttatgttc ctgctttaat ttttggacag   480
cttttaacat ccagtaacta tgatgatgat gagaaaaaag ttacaggtgg tcgtaatggt   540
tatggtgcaa actttgtaa tattttcagt acaaagttta cagtagaaac agcttgcaaa   600
gaatacaaac acagttttaa gcagacatgg atgaataata tgatgaagac ttctgaagcc   660
aaaattaaac attttgatgg tgaagattac acatgcataa cattccaacc agatctgtcc   720
aaatttaaga tggaaaaact tgacaaggat attgtggccc tcatgactag aagggcatat   780
gatttggctg gttcgtgtag aggggtcaag gtcatgttta tggaaagaa attgcctgta   840
aatggatttc gcagttatgt agatctttat gtgaaagaca aattggatga aactggggtg   900
gccctgaaag ttattcatga gcttgcaaat gaaagatggg atgtttgtct cacattgagt   960
gaaaaaggat tccagcaaat cagctttgta atagtattg caactacaaa aggtggacgg  1020
cacgtggatt atgtgtagga tcaagttgtt ggtaaactga ttgaagtagt taagaaaaag  1080
aacaaagctg gtgtatcagt gaaaccattt caagtaaaaa accatatatg gttttttatt  1140
aattgcctta ttgaaaatcc aacttttgat tctcagacta aggaaaacat gactctgcag  1200
cccaaaagtt ttgggtctaa atgccagctg tcagaaaaat ttttaaagc agcctctaat  1260
tgtggcattg tagaaagtat cctgaactgg gtgaaattta aggctcagac tcagctgaat  1320
aagaagtgtt catcagtaaa atacagtaaa atcaaaggta ttcccaaact ggatgatgct  1380
aatgatgctg gtggtaaaca ttccctggag tgtacactga tattaacaga gggagactct  1440
gccaaatcac tggctgtgtc tggattaggt gtgattggac gagacagata cggagttttt  1500
ccactcaggg gcaaaattct taatgtacgg gaagcttctc ataaacagat catggaaaat  1560
gctgaaataa ataatattat taaaatagtt ggtctacaat ataagaaaag ttacgatgat  1620
gcagaatctc tgaaaccctt acgctatgga agattatga ttatgaccga tcaggatcaa  1680
gatggttctc acataaaagg cctgcttatt aatttcatcc atcacaattg ccatcactt   1740
ttgaagcatg gttttcttga agagttcatt actcctattg taaaggcaag caaaaataag  1800
caggaacttt ccttctacag tattcctgaa tttgacgaat ggaaaaaaca tatagaaaac  1860
cagaaagcct ggaaaataaa gtactataaa ggattgggta ctagtacagc taaagaagca  1920
aaggaatatt tgctgatat ggaaaggcat cgcatcttgt ttagatatgc tggtcctgaa  1980
gatgatgctg ccattacctt ggcatttagt aagaagaaga ttgatgacag aaaagaatgg  2040
ttaacaaatt ttatggaaga ccggagacag cgtaggctac atggcttacc agagcaattt  2100
ttatatggta ctgcaacaaa gcatttgact tataatgatt tcatcaacaa ggaattgatt  2160
ctcttctcaa actcagacaa tgaaagatct ataccatctc ttgttgatgg ctttaaacct  2220
ggccagcgga aagtttttatt tacctgtttc aagaggaatg ataaacgtga agtaaaagtt  2280
gcccagttgg ctggctctgt tgctgagatg tcggcttatc atcatggaga acaagcattg  2340
atgatgacta ttgtgaattt ggctcagaac tttgtgggaa gtaacaacat taacttgctt  2400
```

```
cagcctattg gtcagtttgg aactcggctt catggtggca aagatgctgc aagccctcgt    2460
tatattttca caatgttaag cactttagca aggctacttt ttcctgctgt ggatgacaac    2520
ctccttaagt tcctttatga tgataatcaa cgtgtagagc ctgagtggta tattcctata    2580
attcccatgg ttttaataaa tggtgctgag ggcattggta ctggatgggc ttgtaaacta    2640
cccaactatg atgctaggga aattgtgaac aatgtcagac gaatgctaga tggcctggat    2700
cctcatccca tgcttccaaa ctacaaaaac tttaaaggca cgattcaaga acttggtcaa    2760
aaccagtatg cagtcagtgg tgaaatattt gtagtggaca gaaacacagt agaaattaca    2820
gagcttccag ttagaacttg gacacaggta tataaagaac aggttttaga acctatgcta    2880
aatggaacag ataaaacacc agcattaatt tctgattata agaatatca tactgacaca    2940 actgtgaaat ttgtggtgaa aatgactgaa gagaaactag cacaagcaga agctgctgga    3000
ctgcataaag ttttttaaact tcaaactact cttacttgta attccatggt actttttgat    3060
catatgggat gtctgaagaa atatgaaact gtgcaagaca ttctgaaaga attctttgat    3120
ttacgattaa gttattacgg tttacgtaag gagtggcttg tgggaatgtt gggagcagaa    3180
tctacaaagc ttaacaatca agcccgtttc attttagaga agatacaagg gaaaattact    3240
atagagaata ggtcaaagaa agatttgatt caaatgttag tccagagagg ttatgaatct    3300
gacccagtga aagcctggaa agaagcacaa gaaaaggcag cagaagagga tgaaacacaa    3360
aaccagcatg atgatagttc ctccgattca ggaactcctt caggcccaga ttttaattat    3420
attttaaata tgtctctgtg gtctcttact aaagaaaaag ttgaagaact gattaaacag    3480
agagatgcaa aagggcgaga ggtcaatgat cttaaaagaa aatctccttc agatctttgg    3540
aaagaggatt tagcggcatt tgttgaagaa ctggataaag tggaatctca agaacgagaa    3600
gatgttctgg ctggaatgtc tggaaaagca attaaaggta agttggcaa acctaaggtg    3660 aagaaactcc agttggaaga gacaatgccc tcaccttatg gcagaagaat aattcctgaa    3720
attacagcta tgaaggcaga tgccagcaaa aagttgctga agaagaagaa gggtgatctt    3780
gatactgcag cagtaaaagt ggaatttgat gaagaattca gtggagcacc agtagaaggt    3840
gcaggagaag aggcattgac tccatcagtt cctataaata aaggtcccaa acctaagagg    3900
gagaagaagg agcctggtac cagagtgaga aaaacaccta catcatctgg taaacctagt    3960
gcaaagaaag tgaagaaacg gaatccttgg tcagatgatg aatccaagtc agaaagtgat    4020
ttggaagaaa cagaacctgt ggttattcca agagattctt tgcttaggag agcagcagcc    4080
gaaagaccta aatacacatt tgatttctca gaagaagagg atgatgatgc tgatgatgat    4140
gatgatgaca ataatgattt agaggaattg aaagttaaag catctcccat aacaaatgat    4200
ggggaagatg aatttgttcc ttcagatggg ttagataaag atgaatatac attttcacca    4260
ggcaaatcaa aagccactcc agaaaaatct ttgcatgaca aaaaaagtca ggattttgga    4320
aatctcttct catttccttc atattctcag aagtcagaag atgattcagc taaatttgac    4380
agtaatgaag aagattctgc ttctgttttt tcaccatcat ttggtctgaa acagacagat    4440
aaagttccaa gtaaacggt agctgctaaa aagggaaaac cgtcttcaga tacagtccct    4500
aagcccaaga gagcccccaaa acagaagaaa gtagtagagg ctgtaaactc tgactcggat    4560
tcagaatttg gcattccaaa gaagactaca acaccaaaag gtaaaggccg aggggcaaag    4620
aaaaggaaag catctggctc tgaaaatgaa ggcgattata cctggcag gaaaacatcc    4680 aaaacaacaa gcaagaaacc gaagaagaca cttttttgatc aggattcaga tgtggacatc    4740 ttccctcag acttccctac tgagccacct tctctgccac gaaccggtcg ggctaggaaa    4800
```

| | |
|---|---:|
| gaagtaaaat attttgcaga gtctgatgaa gaagaagatg atgttgattt tgcaatgttt | 4860 |
| aattaagtgc ccaaagagca caaacatttt tcaacaaata tcttgtgttg tccttttgtc | 4920 |
| ttctctgtct cagactttg tacatctggc ttattttaat gtgatgatgt aattgacggt | 4980 |
| ttttattat tgtggtaggc cttttaacat tttgttctta cacatacagt tttatgctct | 5040 |
| tttttactca ttgaaatgtc acgtactgtc tgattggctt gtagaattgt tatagactgc | 5100 |
| cgtgcattag cacagatttt aattgtcatg gttacaaact acagacctgc ttttgaaat | 5160 |
| gaaatttaaa cattaaaaat ggaactgtg | 5189 |

<210> SEQ ID NO 34
<211> LENGTH: 1807
<212> TYPE: DNA
<213> ORGANISM: Homo sapiens

<400> SEQUENCE: 34

| | |
|---|---:|
| ggaggggaga gaaagagcga gagaagggga aagacaagtc gggagaggcc ggtaggcgtg | 60 |
| aggcgggcct gaagcggcag cgggcggcct tcgtccggcg agagctaggc cgaggacccg | 120 |
| cgccgcgctc cccggcacct caccgcgtcc ttcaccgact cccgcggcgc gcggccgggc | 180 |
| ggggaagggc ggcggccggg ctggggctcg ggatccgcat cgggatcggg ccgccatgga | 240 |
| cgacaaggcg ttcaccaagg agctggacca gtgggtcgag cagctgaacg agtgtaagca | 300 |
| gctgaacgag aaccaagtgc ggacgctgtg cgagaaggca aaggaaattt taacaaaaga | 360 |
| atcaaatgtg caagaggttc gttgccctgt tactgtctgt ggagatgtgc atggtcaatt | 420 |
| tcatgatctt atggaactct ttagaattgg tggaaaatca ccggatacaa actacttatt | 480 |
| catgggtgac tatgtagaca gaggatatta ttcagtggag actgtgactc ttcttgtagc | 540 |
| attaaaggtg cgttatccag aacgcattac aatattgaga ggaaatcacg aaagccgaca | 600 |
| aattacccaa gtatatggct tttatgatga atgtctgcga aagtatggga atgccaacgt | 660 |
| ttggaaatat tttacagatc tctttgatta tcttccactt acagctttag tagatggaca | 720 |
| gatattctgc ctccatggtg gcctctctcc atccatagac acactggatc atataagagc | 780 |
| cctggatcgt ttacaggaag ttccacatga gggcccaatg tgtgatctgt tatggtcaga | 840 |
| tccagatgat cgtggtggat ggggtatttc accacgtggt gctggctaca catttggaca | 900 |
| agacatttct gaaacctta accatgccaa tggtctcaca ctggtttctc gtgcccacca | 960 |
| gcttgtaatg gagggataca attggtgtca tgatcggaat gtggttacca ttttcagtgc | 1020 |
| acccaattac tgttatcgtt gtgggaacca ggctgctatc atggaattag atgacacttt | 1080 |
| aaaatattcc ttccttcaat ttgacccagc gcctcgtcgt ggtgagcctc atgttacacg | 1140 |
| gcgcacccca gactacttcc tataaatttc tcctgggaaa cctgcctttg tatgtggaag | 1200 |
| tatacctggc ttttaaaat atatgtattt aaaaacaaaa agcaacagta atctatgtgt | 1260 |
| ttctgtaaca aattgggatc tgtccttggca ttaaaccaca tcatggacca aatgtgccat | 1320 |
| actaatgatg agcatttagc acaatttgag actgaaattt agtacactat gttctaggtc | 1380 |
| agtctaacag tttgcctgct gtatttatag taaccatttt cctttggact gttcaagcaa | 1440 |
| aaaaggtaac taactgcttc atctcctttt gcgcttattt ggaaatttta gttatagtgt | 1500 |
| ttaactggca tggattaata gagttggagt tttattttta agaaaaattc acaagctaac | 1560 |
| ttccactaat ccattatcct ttattttatt gaaatgtata attaacttaa ctgaagaaaa | 1620 |
| ggttcttctt gggagtatgt tgtcataaca tttaaagaga tttccttca tttaaactaa | 1680 |
| attactgttt tatgttgatc tgcatatttc tgtatatttg tcatgacagt gcttgcatcc | 1740 |

| tatttggtgt actcagcaaa taaacttttc attttaaaca aaaacattca aaaaaaaaaa | 1800 |
| aaaaaaa | 1807 |

<210> SEQ ID NO 35
<211> LENGTH: 1987
<212> TYPE: DNA
<213> ORGANISM: Homo sapiens

<400> SEQUENCE: 35

| ggaggggaga gaaagagcga gagaagggga aagacaagtc gggagaggcc ggtaggcgtg | 60 |
| aggcgggcct gaagcggcag cgggcggcct tcgtccggcg agagctaggc cgaggacccg | 120 |
| cgccgcgctc cccggcacct caccgcgtcc ttcaccgact cccgcggcgc gcggccgggc | 180 |
| ggggaagggc gggcggggt ctcctccagg ctgcgcgctc ggagccgcct gctgggcttg | 240 |
| ggcggggcgc ggggcccgcg gccgccctac ccggctcagt cctccccctg tgggacctgg | 300 |
| cgacggcggc ggagggagag gggagcggcg cccgggccgg ggccggggc gggtggggag | 360 |
| gggggagggc ggcggccggg ctggggctcg ggatccgcat cgggatcggg ccgccatgga | 420 |
| cgacaaggcg ttcaccaagg agctggacca gtgggtcgag cagctgaacg agtgtaagca | 480 |
| gctgaacgag aaccaagtgc ggacgctgtg cgagaaggca aaggaaattt taacaaaaga | 540 |
| atcaaatgtg caagaggttc gttgccctgt tactgtctgt ggagatgtgc atggtcaatt | 600 |
| tcatgatctt atggaactct tagaattggg tggaaaatca ccggatacaa actacttatt | 660 |
| catgggtgac tatgtagaca gaggatatta ttcagtggag actgtgactc ttcttgtagc | 720 |
| attaaaggtg cgttatccag aacgcattac aatattgaga ggaaatcacg aaagccgaca | 780 |
| aattacccaa gtatggctt tttatgatga atgtctgcga agtatggga atgccaacgt | 840 |
| ttggaaatat tttacagatc tctttgatta tcttccactt acagctttag tagatggaca | 900 |
| gatattctgc ctccatggtg gcctctctcc atccatagac acactggatc atataagagc | 960 |
| cctggatcgt ttacaggaag ttccacatga gggcccaatg tgtgatctgt tatggtcaga | 1020 |
| tccagatgat cgtggtggat ggggtatttc accacgtggt gctggctaca catttggaca | 1080 |
| agacatttct gaaaccttta accatgccaa tggtctcaca ctggtttctc gtgcccacca | 1140 |
| gcttgtaatg gagggataca attggtgtca tgatcggaat gtggttacca ttttcagtgc | 1200 |
| acccaattac tgttatcgtt gtgggaacca ggctgctatc atggaattag atgacacttt | 1260 |
| aaaatattcc ttccttcaat ttgacccagc gcctcgtcgt ggtgagcctc atgttacacg | 1320 |
| gcgcacccca gactacttcc tataaatttc tcctgggaaa cctgcctttg tatgtggaag | 1380 |
| tatacctggc tttttaaaat atatgtattt aaaaacaaaa agcaacagta atctatgtgt | 1440 |
| ttctgtaaca aattgggatc tgtcttggca ttaaaccaca tcatggacca aatgtgccat | 1500 |
| actaatgatg agcatttagc acaatttgag actgaaattt agtacactat gttctaggtc | 1560 |
| agtctaacag tttgcctgct gtatttatag taaccatttt cctttggact gttcaagcaa | 1620 |
| aaaaggtaac taactgcttc atctcctttt gcgcttattt ggaaatttta gttatagtgt | 1680 |
| ttaactggca tggattaata gagttggagt tttatttta agaaaattc acaagctaac | 1740 |
| ttccactaat ccattatcct ttattttatt gaaatgtata attaacttaa ctgaagaaaa | 1800 |
| ggttcttctt gggagtatgt tgtcataaca tttaaagaga tttcccttca tttaaactaa | 1860 |
| attactgttt tatgttgatc tgcatatttc tgtatatttg tcatgacagt gcttgcatcc | 1920 |
| tatttggtgt actcagcaaa taaacttttc attttaaaca aaaacattca aaaaaaaaa | 1980 |
| aaaaaaa | 1987 |

<210> SEQ ID NO 36
<211> LENGTH: 3016
<212> TYPE: DNA
<213> ORGANISM: Homo sapiens

<400> SEQUENCE: 36

| | | | | | |
|---|---|---|---|---|---|
| ctcagacctg | tcagcccgcc | acactccagc | cagtcccttc | cgatcacctc | cagacaccac | 60 |
| gctctccttt | cggagcccgc | ccgccggaag | tggcggcccg | gaactactcc | cacaggggg | 120 |
| cggggaagga | agatggcggc | gcccagcgtc | ccgtgaggag | agaggacaca | gggatcccgg | 180 |
| ggagcggccc | cagactcgta | aattatggcc | gcatctccgc | acactctctc | ctcacgcctc | 240 |
| ctgacaggtt | gcgtaggagg | ctctgtctgg | tatcttgaaa | gaagaactat | acaggactcc | 300 |
| cctcacaagt | tcttacatct | tctcaggaat | gtcaataagc | agtggattac | atttcagcac | 360 |
| tttagcttcc | tcaaacgcat | gtatgtcaca | cagctgaaca | gaagccacaa | ccagcaagta | 420 |
| agacccaagc | cagaaccagt | agcatctcct | ttccttgaaa | aaacatcttc | aggtcaagcc | 480 |
| aaagcagaaa | tatatgagat | gagacctctc | tcaccgccca | gcctatcttt | gtccagaaag | 540 |
| ccaaatgaaa | aggaattgat | agaactagag | ccagactcag | taattgaaga | ctcaatagat | 600 |
| gtagggaaag | agacaaaaga | ggaaaagcgg | tggaaagaga | tgaagctgca | agtgtatgat | 660 |
| ttgccaggaa | ttttggctcg | actatccaaa | atcaaactca | cagctctggt | tgtaagtacc | 720 |
| actgcagctg | gatttgcatt | ggctccgggc | ccttttgact | ggccctgttt | cctgcttact | 780 |
| tctgttggga | caggccttgc | atcctgtgct | gccaactcca | tcaatcagtt | ttttgaggtg | 840 |
| ccatttgact | caaacatgaa | taggacaaag | aacagaccgc | tggttcgtgg | acagatcagc | 900 |
| ccattgctag | ctgtgtcctt | tgccacttgt | tgtgctgttc | cgggagttgc | cattctgacc | 960 |
| tgggggtga | atccactcac | aggagccctg | gggctcttca | acattttcct | gtatacctgc | 1020 |
| tgctacacac | cactgaaaag | gatcagcatt | gccaacacat | gggtcggagc | tgtggttggg | 1080 |
| gccatcccgc | ctgtcatggg | ctggacagcg | gccacgggca | gcctcgatgc | tggcgcattt | 1140 |
| ctcctgggag | gaatcctcta | ctcctggcag | tttcctcatt | tcaacgccct | gagctggggc | 1200 |
| ctccgtgaag | actactcccg | gggcggctac | tgcatgatgt | cggtcaccca | cccgggcctg | 1260 |
| tgccggcgcg | tggcgctgcg | ccactgcctg | gccctgctcg | tgctgtccgc | agcagcccct | 1320 |
| gtgctggaca | tcaccacatg | gaccttcccc | atcatggccc | ttcccatcaa | tgcgtacatc | 1380 |
| tcctacctcg | gcttccgctt | ctacgtggac | gcagaccgca | ggagctcgcg | gagactgttc | 1440 |
| ttctgcagcc | tgtggcacct | gccgctgctg | ctgctgctca | tgctcacctg | caagcggccg | 1500 |
| agcggaggcg | gggacgcagg | gccccctccc | agctgagagc | actgggacgc | ccaccgcccc | 1560 |
| tttccctccg | ctgccaggcg | agcatgttgt | ggtaattctg | gaacacaaga | agagaaattg | 1620 |
| ctgggtttag | aacaagatta | taaacgaatt | cggtgctcag | tgatcacttg | acagtttttt | 1680 |
| tttttttaa | atattaccca | aaatgctccc | caaataagaa | atgcatcagc | tcagtcagtg | 1740 |
| aatacaaaaa | aggaattatt | tttcccttg | agggtcttta | tacatctctc | ctccaacccc | 1800 |
| accctctatt | ctgtttcttc | ctcctcacat | gggggtacac | atacacagct | tcctcttttg | 1860 |
| gttccatcct | taccaccaca | ccacacgcac | actccacatg | cccagcagag | tggcacttgg | 1920 |
| tggccagaaa | gtgtgagcct | catgatctgc | tgtctgtagt | tctgtgagct | caggtccctc | 1980 |
| aaaggcctcg | gagcaccccc | ttcctggtga | ctgagccagg | gcctgcattt | tggttttcc | 2040 |
| ccaccccaca | cattctcaac | catagtcctt | ctaacaatac | caatagctag | acccggctg | 2100 |
| ctgtgcactg | ggactgggga | ttccacatgt | ttgccttggg | agtctcaagc | tggactgcca | 2160 |

-continued

| | |
|---|---|
| gcccctgtcc tcccttcacc cccattgcgt atgagcattt cagaactcca aggagtcaca | 2220 |
| ggcatcttta tagttcacgt taacatatag acactgttgg aagcagttcc ttctaaaagg | 2280 |
| gtagccctgg acttaatacc agccggatac ctctggcccc caccccatta ctgtacctct | 2340 |
| ggagtcacta ctgtgggtcg ccactcctct gctacacagc acggcttttt caaggctgta | 2400 |
| ttgagaaggg aagttaggaa aagggtgtg ctgggctaac cagcccacag agctcacatt | 2460 |
| cctgtccctt gggtgaaaaa tacatgtcca tcctgatatc tcctgaattc agaaattagc | 2520 |
| ctccacatgt gcaatggctt taagagccag aagcagggtt ctgggaattt tgcaagttat | 2580 |
| cctgtggcca ggtgtggtct cggttaccaa atacggttac ctgcagcttt ttagtccttt | 2640 |
| gtgctcccac gggtctgcag agtcccatct gcccaaaggt cttgaagctt gacaggatgt | 2700 |
| tttcattact cagtctccca gggcactgct ggtccgtagg gattcattgg tcggggtggg | 2760 |
| agagttaaac aacatttaaa cagagttctc tcaaaaatgt ctaaagggat tgtaggtaga | 2820 |
| taacatccaa tcactgtttg cacttatctg aaatcttccc tcttggctgc cccaggtat | 2880 |
| ttactgtgga gaacattgca taggaatgtc tggaaaaagc ctctacaact tgttacagcc | 2940 |
| ttcacatttg tacaattcat tgattctctt ttccttccac aataaaatgg tatacaagaa | 3000 |
| caaaaaaaaa aaaaaa | 3016 |

<210> SEQ ID NO 37
<211> LENGTH: 2690
<212> TYPE: DNA
<213> ORGANISM: Homo sapiens

<400> SEQUENCE: 37

| | |
|---|---|
| ataaaaaccc agaaagcccc agaaacaaag acttcacgga caaagtccct tggaaccaga | 60 |
| gagaagccgg gatggaaact ccaaacacca cagaggacta tgacacgacc acagagtttg | 120 |
| actatgggga tgcaactccg tgccagaagg tgaacgagag ggcctttggg gcccaactgc | 180 |
| tgccccctct gtactccttg gtatttgtca ttggcctggt tggaaacatc ctggtggtcc | 240 |
| tggtccttgt gcaatacaag aggctaaaaa acatgaccag catctacctc ctgaacctgg | 300 |
| ccatttctga cctgctcttc ctgttcacgc ttccccttct gatcgactac aagttgaagg | 360 |
| atgactgggt ttttggtgat gccatgtgta gatcctctc tgggttttat tacacaggct | 420 |
| tgtacagcga gatcttttc atcatcctgc tgacgattga caggtacctg gccatcgtcc | 480 |
| acgccgtgtt tgccttgcgg gcacggaccg tcactttttgg tgtcatcacc agcatcatca | 540 |
| tttgggccct ggccatcttg gcttccatgc caggcttata cttttccaag acccaatggg | 600 |
| aattcactca ccacacctgc agccttcact ttcctcacga aagcctacga gagtggaagc | 660 |
| tgtttcaggc tctgaaactg aacctctttg ggctggtatt gcctttgttg gtcatgatca | 720 |
| tctgctacac agggattata aagattctgc taagacgacc aaatgagaag aaatccaaag | 780 |
| ctgtccgttt gattttgtc atcatgatca tctttttttct cttttggacc cctacaatt | 840 |
| tgactatact tatttctgtt ttccaagact tcctgttcac ccatgagtgt gagcagagca | 900 |
| gacatttgga cctggctgtg caagtgacgg aggtgatcgc ctacacgcac tgctgtgtca | 960 |
| acccagtgat ctacgccttc gttggtgaga ggttccggaa gtacctgcgg cagttgttcc | 1020 |
| acaggcgtgt ggctgtgcac ctggttaaat ggctccccctt cctctccgtg gacaggctgg | 1080 |
| agagggtcag ctccacatct ccctccacag gggagcatga actctctgct gggttctgac | 1140 |
| tcagaccata ggaggccaac ccaaaataag caggcgtgac ctgccaggca cactgagcca | 1200 |
| gcagcctggc tctcccagcc aggttctgac tcttggcaca gcatggagtc acagccactt | 1260 |

-continued

| | |
|---|---|
| gggatagaga gggaatgtaa tggtggcctg gggcttctga ggcttctggg gcttcagtct | 1320 |
| tttccatgaa cttctcccct ggtagaaaga agatgaatga gcaaaaccaa atattccaga | 1380 |
| gactgggact aagtgtacca gagaagggct tggactcaag caagatttca gatttgtgac | 1440 |
| cattagcatt tgtcaacaaa gtcacccact tcccactatt gcttgcacaa accaattaaa | 1500 |
| cccagtagtg gtgactgtgg gctccattca aagtgagctc ctaagccatg ggagacactg | 1560 |
| atgtatgagg aatttctgtt cttccatcac ctcccccccc ccgccaccct cccactgcca | 1620 |
| aagaacttgg aaatagtgat tccacagtg actccactct gagtcccaga gccaatcagt | 1680 |
| agccagcatc tgcctcccct tcactcccac cgcaggattt gggctcttgg aatcctgggg | 1740 |
| aacatagaac tcatgacgga agagttgaga cctaacgaga aatagaaatg gggaactact | 1800 |
| gctggcagtg gaactaagaa agcccttagg aagaattttt atatccacta aaatcaaaca | 1860 |
| attcagggag tgggctaagc acgggccata tgaataacat ggtgtgcttc ttaaaatagc | 1920 |
| cataaagggg agggactcat catttccatt taccccttctt ttctgactat ttttcagaat | 1980 |
| ctctcttctt ttcaagttgg gtgatatgtt ggtagattct aatggcttta ttgcagcgat | 2040 |
| taataacagg caaaggaag caggttggt ttcccttctt tttgttcttc atctaagcct | 2100 |
| tctggtttta tgggtcagag ttccgactgc catcttggac ttgtcagcaa aaaaaaaaaa | 2160 |
| taataataat aataaggcct gctgtgtaag ctgacagtat ttgtagctga taggggttg | 2220 |
| ggaggaaagt gtctactagg agggtggggt gagattctgt gttgatgtag gaggccgaga | 2280 |
| aggccccttaa ctcaaagtag cttatttatc caaaatgttc tggatgcatc atctccaacc | 2340 |
| aaggacccct tatttatcat gcctttgttc tcttttccct cagatgtata tttctttaaa | 2400 |
| ataattttc ctaataacaa aacttatttc taaaacagct taaaaattca agaaaaacc | 2460 |
| ccaaacactg acattaccta cacttccact acccaaagac aaaatgtgcc cactgtgtgc | 2520 |
| ttttgagtgt attttctttt agtttgtttt ttgttgggtg catatttatg ataataacaa | 2580 |
| tgatggactt caattgtact cactgttcta ttgttggttt taattagcag caagttgtga | 2640 |
| tcactttccc aggtgaataa atcatttcaa agcattaaaa aaaaaaaaa | 2690 |

<210> SEQ ID NO 38
<211> LENGTH: 2168
<212> TYPE: DNA
<213> ORGANISM: Homo sapiens

<400> SEQUENCE: 38

| | |
|---|---|
| ggctacgcag cttgctcctg gcacgggcac cttgaatctc ctcctcacac agatggagac | 60 |
| catgcttgat ttcctgaact tgtagtaaga agaaggaaaa cacagcacgc tggagccaac | 120 |
| agagttaaga ggaagattta tgagtcatgg aaccctccat cagatttgga agaaagtaga | 180 |
| atgagcgcag aggtgacaga cagccactga ggcccatgga caatctccac ctcacgcttc | 240 |
| tctatcaaac ttgaagattt attagtaata tgctgccttt ggaagatgaa acaaaactag | 300 |
| tgccaaggag gcgtattctt caatatttgg aatagacgtg ttctcaagac aatggcttca | 360 |
| aaggtctcct gtttgtatgt tttgacagtt gtgtgctggg ccagcgctct ctggtacttg | 420 |
| agtataactc gccctacttc ttcttacact ggctccaaac cattcagcca cctaacagtt | 480 |
| gccaggaaaa acttcacctt tggcaacata agaactcgac ctatcaaccc acattctttt | 540 |
| gaatttctta tcaacgagcc caataaatgt gagaaaaaca ttccttttct tgttatcctc | 600 |
| atcagcacca ctcacaagga atttgatgcc cgtcaggcaa tcagagagac gtgggggat | 660 |
| gagaacaact ttaaggggat caagatagcc accctgttcc tcctgggcaa gaatgctgat | 720 |

-continued

```
cctgttctca atcagatggt ggagcaagag agccaaatct tccatgatat catcgtggag      780
gactttattg actcctacca taaccttacc ctcaaaacat taatggggat gagatgggtg      840
gccactttt gttcaaaagc caagtatgtc atgaaaacag acagcgacat ttttgtaaac       900
atggacaatc ttatttataa attactgaaa ccctccacca agccacgaag aaggtatttt      960
actggctatg tcattaatgg aggaccgatt cgggatgtcc gcagtaaatg gtatatgccc     1020
agggatttgt acccagacag taactaccca ccttctgtt cggggactgg ctacatcttt      1080
tcagccgatg tagctgaact catttacaag acctcactcc acacaaggct gcttcacctt     1140
gaagacgtat atgtgggact gtgtcttcga aagctgggca tacatccttt ccagaacagt     1200
ggcttcaatc actggaaaat ggcctacagt ttgtgtaggt atcgccgagt tatcactgtg     1260
catcagatct ctccagaaga aatgcacaga atctggaatg acatgtcaag caagaaacat     1320
ctcagatgtt aggattttta ccaatgtaaa tatgtttctt ttcttttttt aagaaatggg     1380
acctaaggtg ttggtatttt ccaggtgtcg ggggaaatga actggtgaag gggttttgta     1440
aagttttgc ttcctgctat aagttctttt cttggattac caatttatga atgttagact      1500
ctggtcatag aaacaataaa tgagttagaa gggccagatt tcattctcag tcccagagca     1560
ttgctattta tctcaaaaag tgacttccaa acaactctta ggattgacgt accgtgcatc     1620
tgagataaaa atttggttct gggaaactga aactcacagt aatgtgtcat atcatccctg     1680
caaaaattaa tacacaaata gaaaccattt tcaaaagcaa ttcagaaagg atgcacagtc     1740
aggaagacac actggatgtg attattaata tcgtgtgtgt tgttacatta tattttaca     1800
tatattccca tgtaatgtgt acagtctttg cagttccacc aagaaatgaa cttggtacct     1860
gcagagtggc tgcagttaaa tagatgggag tttaaatttg agaatcaaac attctatgtg     1920
tttggaagac aactctgctt gctcatccaa ggattaaatc tggtcagcag gtggaatgtg     1980
tataaaatgc tacttaacaa agtaaacaaa gattttttt tttctttttt tttctttctt      2040
ttttgttttg ctctttcaga acaaacatta aatggtgcct ccaaggaaac tttgccaaat     2100
ataatctcac ctgcttcctt ccagacagtg tcgctaagtg catttcacag ttttttggatc    2160
tggcaggc                                                              2168
```

<210> SEQ ID NO 39
<211> LENGTH: 6255
<212> TYPE: DNA
<213> ORGANISM: Homo sapiens

<400> SEQUENCE: 39

```
ccgaaagccc cgagagagac taagaagcaa tcctcccacg cgctttctcc caccctcggg      60
ccactgagac ggagggacag agggccgccc tcgcgcggcc gaggcccgc ctcccgctcg      120
cccgcccgcg cctccagcgg aagccggaag caaaagcggg ttctgctagc cccgcggctc     180
cgaactcggt ggtcctggaa gctccgcagg atggggaga gatggcgga agaggagagg       240
ttccccaata caactcatga gggtttcaat gtcaccctcc acaccaccct ggttgtcacg     300
acgaaactgg tgctcccgac ccctggcaag cccatcctcc ccgtgcagac aggggagcag     360
gcccagcaag aggagcagtc cagcggcatg accattttct tcagcctcct tgtcctagct     420
atctgcatca tattggtgca tttactgatc cgatacagat acatttctt gccagagagt     480
gttgctgttg tttctttagg tattctcatg ggagcagtta taaaaattat agagtttaaa     540
aaactggcga attggaagga agaagaaatg tttcgtccaa acatgttttt cctcctcctg     600
cttccccta ttatctttga gtctggatat tcattacaca agggtaactt cttcaaaat      660
```

-continued

```
attggttcca tcaccctgtt tgctgttttt gggacggcaa tctccgcttt tgtagtaggt    720
ggaggaattt attttctggg tcaggctgat gtaatctcta aactcaacat gacagacagt    780
tttgcgtttg gctccctaat atctgctgtc gatccagtgg ccactattgc cattttcaat    840
gcacttcatg tggaccccgt gctcaacatg ctggtctttg gagaaagtat tctcaacgat    900
gcagtctcca ttgttctgac caacacagct gaaggtttaa caagaaaaaa tatgtcagat    960
gtcagtgggt ggcaaacatt tttacaagcc cttgactact tcctcaaaat gttctttggc   1020
tctgcagcgc tcggcactct cactggctta atttctgcat tagtgctgaa gcatattgac   1080
ttgaggaaaa cgccttcctt ggagtttggc atgatgatca tttttgctta tctgccttat   1140
gggcttgcag aaggaatctc actctcaggc atcatggcca tccttttctc aggcatcgtg   1200
atgtcccact acacgcacca taacctctcc ccagtcaccc agatcctcat gcagcagacc   1260
ctccgcaccg tggccttctt atgtgaaaca tgtgtgtttg catttcttgg cctgtccatt   1320
tttagttttc ctcacaagtt tgaaatttcc tttgtcatct ggtgcatagt gcttgtacta   1380
tttggcagag cggtaaacat tttccctctt tcctacctcc tgaatttctt ccgggatcat   1440
aaaatcacac cgaagatgat gttcatcatg tggtttagtg gcctgcgggg agccatcccc   1500
tatgccctga gcctacacct ggacctggag cccatggaga agcggcagct catcggcacc   1560
accaccatcg tcatcgtgct cttcaccatc ctgctgctgg gcggcagcac catgcccctc   1620
attcgcctca tggacatcga ggacgccaag gcacaccgca ggaacaagaa ggacgtcaac   1680
ctcagcaaga ctgagaagat gggcaacact gtggagtcgg agcacctgtc ggagctcacg   1740
gaggaggagt acgaggccca ctacatcagg cggcaggacc ttaagggctt cgtgtggctg   1800
gacgccaagt acctgaaccc cttcttcact cggaggctga cgcaggagga cctgcaccac   1860
gggcgcatcc agatgaaaac tctcaccaac aagtggtacg aggaggtacg ccagggcccc   1920
tccggctccg aggacgacga gcaggagctg ctctgacgcc aggtgccaag gcttcaggca   1980
ggcaggccca ggatgggcgt tgctgcgca cagacactca gcggggcct cgcagagatg   2040 cgtgcatcca gcagcccctt caagacataa gagggcgggg cgaggtactg gctgcagagt   2100
cgccttagtc cagaacctga caggcctctg gagccaggcg acttcttggg aaactgtcat   2160
ctcccgactc ctccctgagc cagcctccgc tcagtgtggc tcctcagccc acagagggga   2220
gggagcatgg ggccaggtgc cagtcatctg tgaagctagg gcgcctaccc cccacccgg   2280 aggacccctg cggccccctg cctagaggag caccatctac agttgtgcca ttccccagcc   2340
actgccttca tgctgccccc gccggactgg cagagccagg ggtcagccac ctgcctttga   2400
gtcatcaaga tgcctctgca gccacaattc tgacctaagt ggcagggccc agaaatcctg   2460
aaaacctccc gctgcctttt tgtgatactt cctgtgctcc tcagagagaa acggagtgac   2520
cttttgtcct ttacctgatt ggcacttcgc agtctatctc cctgggtagc agacggctgc   2580
tgcccttctc tgggcatgtt ctgaatgttt acactggtac cttctggtat cttctttaga   2640 gcccctgca agctgcaact ctaggctttt atcttgcggg gtcagagcgc cctctagagg   2700
gaaaagctag aggcacaggg tttctgccgg cccacaactg ctgtcttgat ttgcatttta   2760
cagcaaagtg ctgagagcct ctagtcgcct cctgccatct gatctccctc cccaccattc   2820
ccgtactcag ttgttctttt gtctaatcgg aggccactgt gctgaggccc tgcagtgtct   2880
gctcactgct gccatcttcg ctgctagtca gggttccatc ctctttcccc tctcccagtt   2940
ccctaccacg ttggatccca ttcgtcaccc atgctagggt ccccaaagca ctggggcagg   3000
ggccagagca gcagcaccca gtgctccctc ctctactctg acctgggcc ccagcatcct   3060
```

```
ggagcacacg ctccacgcac acacacccca gccctgtccc aggggcctgg cccctcagc    3120
catctcaggg tgaggagctg ccagtcatgt ccagatggaa tgactccat cctctcctca    3180
tctcccottt gacgagcctc aaactgctca gctcatcaaa gagccattgc caacttccgt   3240
atgtggttct gggtcccagg gagccttgga acctggcacc ctggggtggt ttaattcatc   3300
attaagaagc attcctgctt ctcaagggac acagtggcct gcatgggcca gcatggaccc   3360
tgggctgatc atgtgcattc ctgcttctct ggggacacag tgggcccaca tgggccagca   3420
tggaccctgg gctagagcaa gcacatctcc atctcttcca cctcaggcag tgtggctcca   3480
gatgtcagga gggactgacc tcaggacctt ccaggttcct ctgtgccagg aatgagaggc   3540
caggcccgat cctaccacct cgccttgacc ctgaagtcag agcaggccag ccaagcagga   3600
agcacactgt ttacttttg catgaaaagt aaatgtgtac ttgatagagc taaaatatga    3660
tctttttaa tttctcaacc ccataatttg agccattgcc ttgcttaatt ttggtttcca    3720
ccatttcctt ttagtggaga agagaggaag tcagaggta gggacctttg cctgcccctg    3780
ggcgagtgcg ggcagggatc tgagaccaga ttgttctcgc accctgcca gaactcactc    3840
tcccctgaag tttagggtcc catctcccag atgtaagttg ttttgcaaac tcagtttgcc   3900
aggattctt tctttcctaa tcttaaattc acagataaag caatgaaaag agtcagatcc    3960
catttccgtc tgcccctcg tcaccaggtg tgatagcccc agccaggtca cctggcct     4020
cacactttga gctgagactt gaaaacgatg ctgtggcgga agagcatgtg gggcttggtg   4080
gaggggcccc aggatttgtt gggggcaaag ggggtggcgg gaccgttccc aggaggtacc   4140
agcacctgcc tcgatctcct ctgagcctct tctgcccct gtcggccagg tgaggtcagc    4200
agcctgggag agtgccccca agagatgagg gcaccccgtg ttccttggca atcttggctc   4260
accttggtaa caaaaggcca tagaagtctg tttttctggg tcagtttttt ttgcctgaga   4320
ataacaaatt gctgctgtct accttagca cacccaataa ttctatttgg ggcagtgaat    4380
gcatagaaga tataaaaata cgcagcttaa ctatatcttc ctgcgtgtgt atttatttttc   4440
ttctgggtct aggccatggt acaggagaac tgtggcgtgt aggaggaata cttcaggatg   4500
agtgaaggct ggagccaggg agcgctggag gaaaccagcc ctttagccag cagcccctcc   4560
accacaggca ctgctgtgtg aacgagttc ttggaatgaa tcccatgctt tctgcagcct    4620
gtagttgtta tgacccctcg gaacaaccac cccgtggctt gtgtgggtc tcgcagggaa    4680
aagggctggc ttctaggtcc ccgagataag tgtgcagggg gatgggccag gccaggcta    4740
agggtggctc agttccatca tctggaggtc agacacactg tccagaggca gaactgaagc   4800
cctctcggcc cctaccctaa gccagccacc cctcttcaca gtgggtgagc tgggctgggc   4860
tggctggcat gaggccaagg ggtaggcctg agcgccagag tcgcccaggt tagcccacag   4920
gattcctttg tgtgccatgg aatgctgaaa gatgggtgac tggggaccct tcttaaaacc   4980
tttggcaaag gtgccatcgg cagggcttgg cctcatgaag tctcaggtcc gtgttccgc    5040
agggcgcaca tgcttggaga gtcctcagca gggtagccga ggccaggcca cttctgctga   5100
ggatggggca ggctggggtg tgggtgtggc ctggggtggc tcagggctgg aactgctgcc   5160
tgattcctgt gtgggagaa gctcagtggc cgtttgctgc cactgacaag gatttcacat    5220
gcagaagaga aaaggccccc ctccaccccc cgcattccct gccgagtgag agccagtgtt   5280
tgctgccctt gctggggcg ggtaggaaac cctgagcttc ctgatgcgga gtcatgaagc    5340
agagtcctcg ggaaggcatc tccacagccc cgggtcctct gtctaacgcc ctccatttca   5400
cgccctccat ctcacagtca agataaaggc ctcgagaata aagagccagc ccccttccat   5460
```

```
ttagtctcct gccgtttccc aaacagttgt ccaacagtta gacattgagg ggcttcactg    5520
ttaccaggca tgtaacagaa ggaggaagac taacacacac cccctgcccc atcccatccc    5580
cctctcccga gctatttttct tgctgtggcc tctggtgccc ttgagttggt ctccccggct   5640
gctctgcggg ggcttcactg gcttcggagt gagcgcgaag tgctggtgag cagtgggcct    5700
gtgattggat gggaagatgt gcatccgtgg tcaaaagtca gctgccagcc ctgcggaacc    5760
agagcctcag gctgggatgg ggaggcctcc ctgcttccac ctgcatggtg ggcatggcct    5820
ggcttacacc aaaggctttg acggtttctc caagtaagga tctgcaaatc ttgaatcgtc    5880
ctcaaaatga cgaagcttga attgtcctca agatggatgt gaatcttaca ttcctttttca   5940 tcatttcctt tgtaaaaatg acgagtgctg ggttttttgtt ttaagaagca ttatgaaggc   6000
cagacttact cattttttctc ccccaagtga gctgcaagag gcccctgtta ggcccctgtt   6060
tcctgagcag tgatgtgctg ctcttcttgg tggggctttg ggctgggagg ggaaggcggg   6120
tcagagatgg gggacctgtg gctgccatgc aggagcccct gcgtcatctc gttggactct    6180
ttaagggagt caggaataga tgtatgaaca gtcgtgtcac tggatgccta tttagaaata    6240
aagtgtatgc tgctg                                                     6255

<210> SEQ ID NO 40
<211> LENGTH: 1953
<212> TYPE: DNA
<213> ORGANISM: Homo sapiens

<400> SEQUENCE: 40
gcagaccttg cttcatgagc aagctcatct ctggaacaaa ctggcaaagc atctctgctg     60
gtgttcatca gaacagacac catggcagag catgattacc atgaagacta tgggttcagc    120
agtttcaatg acagcagcca ggaggagcat caagacttcc tgcagttcag caaggtcttt    180
ctgccctgca tgtacctggt ggtgtttgtc tgtggtctgg tggggaactc tctggtgctg    240
gtcatatcca tcttctacca taagttgcag agcctgacgg atgtgttcct ggtgaaccta    300
cccctggctg acctggtgtt tgtctgcact ctgcccttct gggcctatgc aggcatccat    360
gaatgggtgt ttggccaggt catgtgcaag agcctactgg gcatctacac tattaacttc    420
tacacgtcca tgctcatcct cacctgcatc actgtggatc gtttcattgt agtggttaag    480
gccaccaagg cctacaacca gcaagccaag aggatgacct ggggcaaggt caccagcttg    540
ctcatctggg tgatatccct gctggttttcc ttgccccaaa ttatctatgg caatgtcttt    600
aatctcgaca agctccatatg tggttaccat gacgaggcaa tttccactgt ggttcttgcc    660
acccagatga cactggggtt cttcttgcca ctgctcacca tgattgtctg ctattcagtc    720
ataatcaaaa cactgcttca tgctggaggc ttccagaagc acagatctct aaagatcatc    780
ttcctggtga tggctgtgtt cctgctgacc cagatgccct tcaacctcat gaagttcatc    840
cgcagcacac actgggaata ctatgccatg accagctttc actacaccat catggtgaca    900
gaggccatcg cataccctga ggcctgcctt aaccctgtgc tctatgcctt tgtcagcctg    960
aagtttcgaa agaacttctg gaaacttgtg aaggacattg ttgcctccc ttaccttggg   1020 gtctcacatc aatggaaatc ttctgaggac aattccaaga ctttttctgc ctcccacaat    1080
gtggaggcca ccagcatgtt ccagttatag gccttgccag ggtttcgaga agctgctctg    1140
gaatttgcaa gtcatggctg tgccctcttg atgtggtgag gcaggctttg tttatagctt    1200
gcgcattctc atgagaagt tatcagacac tctggctggt ttggaatgct tcttctcagg    1260
catgaacatg tactgttctc ttcttgaaca ctcatgctga aagcccaagt aggggggtcta   1320
```

```
aaattttaa ggactttcct tcctccatct ccaagaatgc tgaaaccaag ggggatgaca    1380
tgtgactcct atgatctcag gttctccttg attgggactg gggctgaagg ttgaagaggt    1440
gagcacggcc aacaaagctg ttgatggtag gtggcacact gggtgcccaa gctcagaagg    1500
ctcttctgac tactgggcaa agagtgtaga tcagagcagc agtgaaaaca gtgctggca    1560 ccaccaggca cctcacagaa atgagatcag gctctgcctc accttggggc ttgacttttg    1620
tataggtaga tgttcagatt gctttgatta atccagaata actagcacca gggactatga    1680
atgggcaaaa ctgaattata agaggctgat aattccagtg gtccatggaa tgcttgaaaa    1740
atgtgcaaaa cagcgtttaa gactgtaatg aatctaagca gcatttctga agtggactct    1800
ttggtggctt tgcattttaa aaatgaaatt ttccaatgtc tgccacacaa acgtatgtaa    1860
atgtatatac ccacacacat acacacatat gtcatatatt actagcatat gagtttcata    1920
gctaagaaat aaaactgtta aagtctccaa act                                 1953

<210> SEQ ID NO 41
<211> LENGTH: 838
<212> TYPE: PRT
<213> ORGANISM: Homo sapiens

<400> SEQUENCE: 41

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
                20                  25                  30

Pro Thr Ser Cys Lys Cys Ser Ala Ser Arg Ile Trp Cys Ser Asp Pro
            35                  40                  45

Ser Pro Gly Ile Val Ala Phe Pro Arg Leu Glu Pro Asn Ser Val Asp
        50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270
```

-continued

Gly Glu Asp Gln Asp Ser Val Asn Leu Thr Val His Phe Ala Pro Thr
            275                 280                 285

Ile Thr Phe Leu Glu Ser Pro Thr Ser Asp His His Trp Cys Ile Pro
        290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Ile Ala Ser Val Val Gly Phe Cys Leu Leu
        435                 440                 445

Val Met Leu Phe Leu Leu Lys Leu Ala Arg His Ser Lys Phe Gly Met
    450                 455                 460

Lys Asp Phe Ser Trp Phe Gly Phe Gly Lys Val Lys Ser Arg Gln Gly
465                 470                 475                 480

Val Gly Pro Ala Ser Val Ile Ser Asn Asp Asp Ser Ala Ser Pro
                485                 490                 495

Leu His His Ile Ser Asn Gly Ser Asn Thr Pro Ser Ser Ser Glu Gly
            500                 505                 510

Gly Pro Asp Ala Val Ile Ile Gly Met Thr Lys Ile Pro Val Ile Glu
        515                 520                 525

Asn Pro Gln Tyr Phe Gly Ile Thr Asn Ser Gln Leu Lys Pro Asp Thr
    530                 535                 540

Phe Val Gln His Ile Lys Arg His Asn Ile Val Leu Lys Arg Glu Leu
545                 550                 555                 560

Gly Glu Gly Ala Phe Gly Lys Val Phe Leu Ala Glu Cys Tyr Asn Leu
                565                 570                 575

Cys Pro Glu Gln Asp Lys Ile Leu Val Ala Val Lys Thr Leu Lys Asp
            580                 585                 590

Ala Ser Asp Asn Ala Arg Lys Asp Phe His Arg Glu Ala Glu Leu Leu
        595                 600                 605

Thr Asn Leu Gln His Glu His Ile Val Lys Phe Tyr Gly Val Cys Val
    610                 615                 620

Glu Gly Asp Pro Leu Ile Met Val Phe Glu Tyr Met Lys His Gly Asp
625                 630                 635                 640

Leu Asn Lys Phe Leu Arg Ala His Gly Pro Asp Ala Val Leu Met Ala
                645                 650                 655

Glu Gly Asn Pro Pro Thr Glu Leu Thr Gln Ser Gln Met Leu His Ile
            660                 665                 670

Ala Gln Gln Ile Ala Ala Gly Met Val Tyr Leu Ala Ser Gln His Phe
        675                 680                 685

Val His Arg Asp Leu Ala Thr Arg Asn Cys Leu Val Gly Glu Asn Leu

```
                690                 695                 700
Leu Val Lys Ile Gly Asp Phe Gly Met Ser Arg Asp Val Tyr Ser Thr
705                 710                 715                 720

Asp Tyr Tyr Arg Val Gly Gly His Thr Met Leu Pro Ile Arg Trp Met
                725                 730                 735

Pro Pro Glu Ser Ile Met Tyr Arg Lys Phe Thr Thr Glu Ser Asp Val
                740                 745                 750

Trp Ser Leu Gly Val Val Leu Trp Glu Ile Phe Thr Tyr Gly Lys Gln
                755                 760                 765

Pro Trp Tyr Gln Leu Ser Asn Asn Glu Val Ile Glu Cys Ile Thr Gln
                770                 775                 780

Gly Arg Val Leu Gln Arg Pro Arg Thr Cys Pro Gln Glu Val Tyr Glu
785                 790                 795                 800

Leu Met Leu Gly Cys Trp Gln Arg Glu Pro His Met Arg Lys Asn Ile
                805                 810                 815

Lys Gly Ile His Thr Leu Leu Gln Asn Leu Ala Lys Ala Ser Pro Val
                820                 825                 830

Tyr Leu Asp Ile Leu Gly
                835

<210> SEQ ID NO 42
<211> LENGTH: 477
<212> TYPE: PRT
<213> ORGANISM: Homo sapiens

<400> SEQUENCE: 42

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
                20                  25                  30

Pro Thr Ser Cys Lys Cys Ser Ala Ser Arg Ile Trp Cys Ser Asp Pro
                35                  40                  45

Ser Pro Gly Ile Val Ala Phe Pro Arg Leu Glu Pro Asn Ser Val Asp
                50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
                100                 105                 110

Lys Asn Ser Asn Leu Gln His Ile Asn Phe Thr Arg Asn Lys Leu Thr
                115                 120                 125

Ser Leu Ser Arg Lys His Phe Arg His Leu Asp Leu Ser Glu Leu Ile
                130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
                180                 185                 190

Asn Cys Gly Leu Pro Ser Ala Asn Leu Ala Ala Pro Asn Leu Thr Val
                195                 200                 205

Glu Glu Gly Lys Ser Ile Thr Leu Ser Cys Ser Val Ala Gly Asp Pro
                210                 215                 220

Val Pro Asn Met Tyr Trp Asp Val Gly Asn Leu Val Ser Lys His Met
```

```
                    225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
        435                 440                 445

Val Met Leu Phe Leu Leu Lys Leu Ala Arg His Ser Lys Phe Gly Met
    450                 455                 460

Lys Gly Phe Val Leu Phe His Lys Ile Pro Leu Asp Gly
465                 470                 475

<210> SEQ ID NO 43
<211> LENGTH: 822
<212> TYPE: PRT
<213> ORGANISM: Homo sapiens

<400> SEQUENCE: 43

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
```

```
                130                 135                 140
Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
                180                 185                 190

Asn Cys Gly Leu Pro Ser Ala Asn Leu Ala Ala Pro Asn Leu Thr Val
                195                 200                 205

Glu Glu Gly Lys Ser Ile Thr Leu Ser Cys Ser Val Ala Gly Asp Pro
210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
                260                 265                 270

Gly Glu Asp Gln Asp Ser Val Asn Leu Thr Val His Phe Ala Pro Thr
                275                 280                 285

Ile Thr Phe Leu Glu Ser Pro Thr Ser Asp His His Trp Cys Ile Pro
290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
                340                 345                 350

His Met Asn Asn Gly Asp Tyr Thr Leu Ile Ala Lys Asn Glu Tyr Gly
                355                 360                 365

Lys Asp Glu Lys Gln Ile Ser Ala His Phe Met Gly Trp Pro Gly Ile
370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
                420                 425                 430

Val Tyr Ala Val Val Ile Ala Ser Val Val Gly Phe Cys Leu Leu
                435                 440                 445

Val Met Leu Phe Leu Leu Lys Leu Ala Arg His Ser Lys Phe Gly Met
450                 455                 460

Lys Gly Pro Ala Ser Val Ile Ser Asn Asp Asp Asp Ser Ala Ser Pro
465                 470                 475                 480

Leu His His Ile Ser Asn Gly Ser Asn Thr Pro Ser Ser Glu Gly
                485                 490                 495

Gly Pro Asp Ala Val Ile Ile Gly Met Thr Lys Ile Pro Val Ile Glu
                500                 505                 510

Asn Pro Gln Tyr Phe Gly Ile Thr Asn Ser Gln Leu Lys Pro Asp Thr
                515                 520                 525

Phe Val Gln His Ile Lys Arg His Asn Ile Val Leu Lys Arg Glu Leu
                530                 535                 540

Gly Glu Gly Ala Phe Gly Lys Val Phe Leu Ala Glu Cys Tyr Asn Leu
545                 550                 555                 560
```

```
Cys Pro Glu Gln Asp Lys Ile Leu Val Ala Val Lys Thr Leu Lys Asp
                565                 570                 575

Ala Ser Asp Asn Ala Arg Lys Asp Phe His Arg Glu Ala Glu Leu Leu
            580                 585                 590

Thr Asn Leu Gln His Glu His Ile Val Lys Phe Tyr Gly Val Cys Val
        595                 600                 605

Glu Gly Asp Pro Leu Ile Met Val Phe Glu Tyr Met Lys His Gly Asp
    610                 615                 620

Leu Asn Lys Phe Leu Arg Ala His Gly Pro Asp Ala Val Leu Met Ala
625                 630                 635                 640

Glu Gly Asn Pro Pro Thr Glu Leu Thr Gln Ser Gln Met Leu His Ile
                645                 650                 655

Ala Gln Gln Ile Ala Ala Gly Met Val Tyr Leu Ala Ser Gln His Phe
            660                 665                 670

Val His Arg Asp Leu Ala Thr Arg Asn Cys Leu Val Gly Glu Asn Leu
        675                 680                 685

Leu Val Lys Ile Gly Asp Phe Gly Met Ser Arg Asp Val Tyr Ser Thr
    690                 695                 700

Asp Tyr Tyr Arg Val Gly Gly His Thr Met Leu Pro Ile Arg Trp Met
705                 710                 715                 720

Pro Pro Glu Ser Ile Met Tyr Arg Lys Phe Thr Thr Glu Ser Asp Val
                725                 730                 735

Trp Ser Leu Gly Val Val Leu Trp Glu Ile Phe Thr Tyr Gly Lys Gln
            740                 745                 750

Pro Trp Tyr Gln Leu Ser Asn Asn Glu Val Ile Glu Cys Ile Thr Gln
        755                 760                 765

Gly Arg Val Leu Gln Arg Pro Arg Thr Cys Pro Gln Glu Val Tyr Glu
    770                 775                 780

Leu Met Leu Gly Cys Trp Gln Arg Glu Pro His Met Arg Lys Asn Ile
785                 790                 795                 800

Lys Gly Ile His Thr Leu Leu Gln Asn Leu Ala Lys Ala Ser Pro Val
                805                 810                 815

Tyr Leu Asp Ile Leu Gly
            820

<210> SEQ ID NO 44
<211> LENGTH: 553
<212> TYPE: PRT
<213> ORGANISM: Homo sapiens

<400> SEQUENCE: 44

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110
```

-continued

```
Lys Asn Ser Asn Leu Gln His Ile Asn Phe Thr Arg Asn Lys Leu Thr
        115                 120                 125
Ser Leu Ser Arg Lys His Phe Arg His Leu Asp Leu Ser Glu Leu Ile
130                 135                 140
Leu Val Gly Asn Pro Phe Thr Cys Ser Cys Asp Ile Met Trp Ile Lys
145                 150                 155                 160
Thr Leu Gln Glu Ala Lys Ser Ser Pro Asp Thr Gln Asp Leu Tyr Cys
                165                 170                 175
Leu Asn Glu Ser Ser Lys Asn Ile Pro Leu Ala Asn Leu Gln Ile Pro
            180                 185                 190
Asn Cys Gly Leu Pro Ser Ala Asn Leu Ala Ala Pro Asn Leu Thr Val
                195                 200                 205
Glu Glu Gly Lys Ser Ile Thr Leu Ser Cys Ser Val Ala Gly Asp Pro
210                 215                 220
Val Pro Asn Met Tyr Trp Asp Val Gly Asn Leu Val Ser Lys His Met
225                 230                 235                 240
Asn Glu Thr Ser His Thr Gln Gly Ser Leu Arg Ile Thr Asn Ile Ser
                245                 250                 255
Ser Asp Asp Ser Gly Lys Gln Ile Ser Cys Val Ala Glu Asn Leu Val
                260                 265                 270
Gly Glu Asp Gln Asp Ser Val Asn Leu Thr Val His Phe Ala Pro Thr
            275                 280                 285
Ile Thr Phe Leu Glu Ser Pro Thr Ser Asp His His Trp Cys Ile Pro
290                 295                 300
Phe Thr Val Lys Gly Asn Pro Lys Pro Ala Leu Gln Trp Phe Tyr Asn
305                 310                 315                 320
Gly Ala Ile Leu Asn Glu Ser Lys Tyr Ile Cys Thr Lys Ile His Val
                325                 330                 335
Thr Asn His Thr Glu Tyr His Gly Cys Leu Gln Leu Asp Asn Pro Thr
                340                 345                 350
His Met Asn Asn Gly Asp Tyr Thr Leu Ile Ala Lys Asn Glu Tyr Gly
            355                 360                 365
Lys Asp Glu Lys Gln Ile Ser Ala His Phe Met Gly Trp Pro Gly Ile
370                 375                 380
Asp Asp Gly Ala Asn Pro Asn Tyr Pro Asp Val Ile Tyr Glu Asp Tyr
385                 390                 395                 400
Gly Thr Ala Ala Asn Asp Ile Gly Asp Thr Thr Asn Arg Ser Asn Glu
                405                 410                 415
Ile Pro Ser Thr Asp Val Thr Asp Lys Thr Gly Arg Glu His Leu Ser
            420                 425                 430
Val Tyr Ala Val Val Ile Ala Ser Val Val Gly Phe Cys Leu Leu
                435                 440                 445
Val Met Leu Phe Leu Leu Lys Leu Ala Arg His Ser Lys Phe Gly Met
450                 455                 460
Lys Asp Phe Ser Trp Phe Gly Phe Gly Lys Val Lys Ser Arg Gln Gly
465                 470                 475                 480
Val Gly Pro Ala Ser Val Ile Ser Asn Asp Asp Ser Ala Ser Pro
                485                 490                 495
Leu His His Ile Ser Asn Gly Ser Asn Thr Pro Ser Ser Glu Gly
            500                 505                 510
Gly Pro Asp Ala Val Ile Ile Gly Met Thr Lys Ile Pro Val Ile Glu
            515                 520                 525
Asn Pro Gln Tyr Phe Gly Ile Thr Asn Ser Gln Leu Lys Pro Asp Thr
530                 535                 540
```

```
Trp Pro Arg Gly Ser Pro Lys Thr Ala
545                 550

<210> SEQ ID NO 45
<211> LENGTH: 537
<212> TYPE: PRT
<213> ORGANISM: Homo sapiens

<400> SEQUENCE: 45

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365
```

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
                420                 425                 430

Val Tyr Ala Val Val Val Ile Ala Ser Val Val Gly Phe Cys Leu Leu
                435                 440                 445

Val Met Leu Phe Leu Leu Lys Leu Ala Arg His Ser Lys Phe Gly Met
    450                 455                 460

Lys Gly Pro Ala Ser Val Ile Ser Asn Asp Asp Asp Ser Ala Ser Pro
465                 470                 475                 480

Leu His His Ile Ser Asn Gly Ser Asn Thr Pro Ser Ser Ser Glu Gly
                485                 490                 495

Gly Pro Asp Ala Val Ile Ile Gly Met Thr Lys Ile Pro Val Ile Glu
                500                 505                 510

Asn Pro Gln Tyr Phe Gly Ile Thr Asn Ser Gln Leu Lys Pro Asp Thr
                515                 520                 525

Trp Pro Arg Gly Ser Pro Lys Thr Ala
    530                 535

<210> SEQ ID NO 46
<211> LENGTH: 1166
<212> TYPE: PRT
<213> ORGANISM: Homo sapiens

<400> SEQUENCE: 46

Met Ala Asn Asp Ser Pro Ala Lys Ser Leu Val Asp Ile Asp Leu Ser
1               5                   10                  15

Ser Leu Arg Asp Pro Ala Gly Ile Phe Glu Leu Val Glu Val Val Gly
                20                  25                  30

Asn Gly Thr Tyr Gly Gln Val Tyr Lys Gly Arg His Val Lys Thr Gly
                35                  40                  45

Gln Leu Ala Ala Ile Lys Val Met Asp Val Thr Glu Asp Glu Glu Glu
    50                  55                  60

Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

His Asp Asp Gln Leu Trp Leu Val Met Glu Phe Cys Gly Ala Gly Ser
                100                 105                 110

Ile Thr Asp Leu Val Lys Asn Thr Lys Gly Asn Thr Leu Lys Glu Asp
                115                 120                 125

Trp Ile Ala Tyr Ile Ser Arg Glu Ile Leu Arg Gly Leu Ala His Leu
    130                 135                 140

His Ile His His Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
                180                 185                 190

Tyr Trp Met Ala Pro Glu Val Ile Ala Cys Asp Glu Asn Pro Asp Ala
                195                 200                 205

```
Thr Tyr Asp Tyr Arg Ser Asp Leu Trp Ser Cys Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
                245                 250                 255

Lys Trp Ser Lys Lys Phe Phe Ser Phe Ile Glu Gly Cys Leu Val Lys
                260                 265                 270

Asn Tyr Met Gln Arg Pro Ser Thr Glu Gln Leu Leu Lys His Pro Phe
            275                 280                 285

Ile Arg Asp Gln Pro Asn Glu Arg Gln Val Arg Ile Gln Leu Lys Asp
        290                 295                 300

His Ile Asp Arg Thr Arg Lys Lys Arg Gly Glu Lys Asp Glu Thr Glu
305                 310                 315                 320

Tyr Glu Tyr Ser Gly Ser Glu Glu Glu Glu Glu Val Pro Glu Gln
                325                 330                 335

Glu Gly Glu Pro Ser Ser Ile Val Asn Val Pro Gly Glu Ser Thr Leu
                340                 345                 350

Arg Arg Asp Phe Leu Arg Leu Gln Gln Glu Asn Lys Glu Arg Ser Glu
            355                 360                 365

Ala Leu Arg Arg Gln Gln Leu Leu Gln Glu Gln Leu Arg Glu Gln
370                 375                 380

Glu Glu Tyr Lys Arg Gln Leu Leu Ala Glu Arg Gln Lys Arg Ile Glu
385                 390                 395                 400

Gln Gln Lys Glu Gln Arg Arg Arg Leu Glu Glu Gln Arg Arg Glu
                405                 410                 415

Arg Glu Ala Arg Arg Gln Gln Glu Arg Glu Gln Arg Arg Glu Gln
            420                 425                 430

Glu Glu Lys Arg Arg Leu Glu Glu Leu Glu Arg Arg Lys Glu Glu
                435                 440                 445

Glu Glu Arg Arg Arg Ala Glu Glu Lys Arg Arg Val Glu Arg Glu
            450                 455                 460

Gln Glu Tyr Ile Arg Arg Gln Leu Glu Glu Glu Gln Arg His Leu Glu
465                 470                 475                 480

Val Leu Gln Gln Gln Leu Leu Gln Glu Gln Ala Met Leu Leu His Asp
                485                 490                 495

His Arg Arg Pro His Pro Gln His Ser Gln Gln Pro Pro Pro Gln
            500                 505                 510

Gln Glu Arg Ser Lys Pro Ser Phe His Ala Pro Glu Pro Lys Ala His
                515                 520                 525

Tyr Glu Pro Ala Asp Arg Ala Arg Glu Val Pro Val Arg Thr Thr Ser
            530                 535                 540

Arg Ser Pro Val Leu Ser Arg Arg Asp Ser Pro Leu Gln Gly Ser Gly
545                 550                 555                 560

Gln Gln Asn Ser Gln Ala Gly Gln Arg Asn Ser Thr Ser Ser Ile Glu
                565                 570                 575

Pro Arg Leu Leu Trp Glu Arg Val Glu Lys Leu Val Pro Arg Pro Gly
                580                 585                 590

Ser Gly Ser Ser Ser Gly Ser Ser Asn Ser Gly Ser Gln Pro Gly Ser
            595                 600                 605

His Pro Gly Ser Gln Ser Gly Ser Gly Glu Arg Phe Arg Val Arg Ser
            610                 615                 620

Ser Ser Lys Ser Glu Gly Ser Pro Ser Gln Arg Leu Glu Asn Ala Val
```

```
                625                 630                 635                 640
Lys Lys Pro Glu Asp Lys Lys Glu Val Phe Arg Pro Leu Lys Pro Ala
                    645                 650                 655
Gly Glu Val Asp Leu Thr Ala Leu Ala Lys Glu Leu Arg Ala Val Glu
                    660                 665                 670
Asp Val Arg Pro Pro His Lys Val Thr Asp Tyr Ser Ser Ser Ser Glu
                675                 680                 685
Glu Ser Gly Thr Thr Asp Glu Glu Asp Asp Val Glu Gln Glu Gly
            690                 695                 700
Ala Asp Glu Ser Thr Ser Gly Pro Glu Asp Thr Arg Ala Ala Ser Ser
705                 710                 715                 720
Leu Asn Leu Ser Asn Gly Glu Thr Glu Ser Val Lys Thr Met Ile Val
                    725                 730                 735
His Asp Asp Val Glu Ser Glu Pro Ala Met Thr Pro Ser Lys Glu Gly
                740                 745                 750
Thr Leu Ile Val Arg Gln Thr Gln Ser Ala Ser Ser Thr Leu Gln Lys
                755                 760                 765
His Lys Ser Ser Ser Ser Phe Thr Pro Phe Ile Asp Pro Arg Leu Leu
    770                 775                 780
Gln Ile Ser Pro Ser Ser Gly Thr Thr Val Thr Ser Val Val Gly Phe
785                 790                 795                 800
Ser Cys Asp Gly Met Arg Pro Glu Ala Ile Arg Gln Asp Pro Thr Arg
                805                 810                 815
Lys Gly Ser Val Val Asn Val Asn Pro Thr Asn Thr Arg Pro Gln Ser
                820                 825                 830
Asp Thr Pro Glu Ile Arg Lys Tyr Lys Lys Arg Phe Asn Ser Glu Ile
                835                 840                 845
Leu Cys Ala Ala Leu Trp Gly Val Asn Leu Leu Val Gly Thr Glu Ser
    850                 855                 860
Gly Leu Met Leu Leu Asp Arg Ser Gly Gln Gly Lys Val Tyr Pro Leu
865                 870                 875                 880
Ile Asn Arg Arg Arg Phe Gln Gln Met Asp Val Leu Glu Gly Leu Asn
                885                 890                 895
Val Leu Val Thr Ile Ser Gly Lys Lys Asp Lys Leu Arg Val Tyr Tyr
                900                 905                 910
Leu Ser Trp Leu Arg Asn Lys Ile Leu His Asn Asp Pro Glu Val Glu
                915                 920                 925
Lys Lys Gln Gly Trp Thr Thr Val Gly Asp Leu Glu Gly Cys Val His
                930                 935                 940
Tyr Lys Val Val Lys Tyr Glu Arg Ile Lys Phe Leu Val Ile Ala Leu
945                 950                 955                 960
Lys Ser Ser Val Glu Val Tyr Ala Trp Ala Pro Lys Pro Tyr His Lys
                    965                 970                 975
Phe Met Ala Phe Lys Ser Phe Gly Glu Leu Val His Lys Pro Leu Leu
                980                 985                 990
Val Asp Leu Thr Val Glu Glu Gly  Gln Arg Leu Lys Val  Ile Tyr Gly
                995                 1000                1005
Ser Cys  Ala Gly Phe His Ala  Val Asp Val Asp Ser  Gly Ser Val
    1010                1015                1020
Tyr Asp  Ile Tyr Leu Pro Thr  His Val Arg Lys Asn  Pro His Ser
    1025                1030                1035
Met Ile  Gln Cys Ser Ile Lys  Pro His Ala Ile Ile  Ile Leu Pro
    1040                1045                1050
```

```
Asn Thr Asp Gly Met Glu Leu Leu Val Cys Tyr Glu Asp Glu Gly
    1055                1060                1065

Val Tyr Val Asn Thr Tyr Gly Arg Ile Thr Lys Asp Val Val Leu
    1070                1075                1080

Gln Trp Gly Glu Met Pro Thr Ser Val Ala Tyr Ile Arg Ser Asn
    1085                1090                1095

Gln Thr Met Gly Trp Gly Glu Lys Ala Ile Glu Ile Arg Ser Val
    1100                1105                1110

Glu Thr Gly His Leu Asp Gly Val Phe Met His Lys Arg Ala Gln
    1115                1120                1125

Arg Leu Lys Phe Leu Cys Glu Arg Asn Asp Lys Val Phe Phe Ala
    1130                1135                1140

Ser Val Arg Ser Gly Gly Ser Ser Gln Val Tyr Phe Met Thr Leu
    1145                1150                1155

Gly Arg Thr Ser Leu Leu Ser Trp
    1160                1165

<210> SEQ ID NO 47
<211> LENGTH: 1320
<212> TYPE: PRT
<213> ORGANISM: Homo sapiens

<400> SEQUENCE: 47

Met Ala Asn Asp Ser Pro Ala Lys Ser Leu Val Asp Ile Asp Leu Ser
  1               5                  10                  15

Ser Leu Arg Asp Pro Ala Gly Ile Phe Glu Leu Val Glu Val Val Gly
                 20                  25                  30

Asn Gly Thr Tyr Gly Gln Val Tyr Lys Gly Arg His Val Lys Thr Gly
             35                  40                  45

Gln Leu Ala Ala Ile Lys Val Met Asp Val Thr Glu Asp Glu Glu Glu
         50                  55                  60

Glu Ile Lys Leu Glu Ile Asn Met Leu Lys Lys Tyr Ser His His Arg
     65                  70                  75                  80

Asn Ile Ala Thr Tyr Tyr Gly Ala Phe Ile Lys Lys Ser Pro Pro Gly
                 85                  90                  95

His Asp Asp Gln Leu Trp Leu Val Met Glu Phe Cys Gly Ala Gly Ser
                100                 105                 110

Ile Thr Asp Leu Val Lys Asn Thr Lys Gly Asn Thr Leu Lys Glu Asp
            115                 120                 125

Trp Ile Ala Tyr Ile Ser Arg Glu Ile Leu Arg Gly Leu Ala His Leu
        130                 135                 140

His Ile His His Val Ile His Arg Asp Ile Lys Gly Gln Asn Val Leu
    145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Tyr Arg Ser Asp Leu Trp Ser Cys Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Pro Arg Leu Lys Ser Lys
                245                 250                 255
```

-continued

```
Lys Trp Ser Lys Lys Phe Phe Ser Phe Ile Glu Gly Cys Leu Val Lys
                260                 265                 270

Asn Tyr Met Gln Arg Pro Ser Thr Glu Gln Leu Leu Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Arg Lys Lys Arg Gly Glu Lys Asp Glu Thr Glu
305                 310                 315                 320

Tyr Glu Tyr Ser Gly Ser Glu Glu Glu Glu Val Pro Glu Gln
                325                 330                 335

Glu Gly Glu Pro Ser Ser Ile Val Asn Val Pro Gly Glu Ser Thr Leu
                340                 345                 350

Arg Arg Asp Phe Leu Arg Leu Gln Gln Glu Asn Lys Glu Arg Ser Glu
        355                 360                 365

Ala Leu Arg Arg Gln Gln Leu Leu Gln Glu Gln Leu Arg Glu Gln
    370                 375                 380

Glu Glu Tyr Lys Arg Gln Leu Leu Ala Glu Arg Gln Lys Arg Ile Glu
385                 390                 395                 400

Gln Gln Lys Glu Gln Arg Arg Arg Leu Glu Glu Gln Arg Arg Glu
                405                 410                 415

Arg Glu Ala Arg Arg Gln Gln Glu Arg Glu Gln Arg Arg Glu Gln
            420                 425                 430

Glu Glu Lys Arg Arg Leu Glu Glu Leu Glu Arg Arg Lys Glu Glu
                435                 440                 445

Glu Glu Arg Arg Arg Ala Glu Glu Lys Arg Arg Val Glu Arg Glu
    450                 455                 460

Gln Glu Tyr Ile Arg Arg Gln Leu Glu Glu Gln Arg His Leu Glu
465                 470                 475                 480

Val Leu Gln Gln Gln Leu Leu Gln Glu Gln Ala Met Leu Leu Glu Cys
                485                 490                 495

Arg Trp Arg Glu Met Glu Glu His Arg Gln Ala Glu Arg Leu Gln Arg
                500                 505                 510

Gln Leu Gln Gln Glu Gln Ala Tyr Leu Leu Ser Leu Gln His Asp His
        515                 520                 525

Arg Arg Pro His Pro Gln His Ser Gln Gln Pro Pro Pro Gln Gln
    530                 535                 540

Glu Arg Ser Lys Pro Ser Phe His Ala Pro Glu Pro Lys Ala His Tyr
545                 550                 555                 560

Glu Pro Ala Asp Arg Ala Arg Glu Val Glu Asp Arg Phe Arg Lys Thr
                565                 570                 575

Asn His Ser Ser Pro Glu Ala Gln Ser Lys Gln Thr Gly Arg Val Leu
        580                 585                 590

Glu Pro Pro Val Pro Ser Arg Ser Glu Ser Phe Ser Asn Gly Asn Ser
    595                 600                 605

Glu Ser Val His Pro Ala Leu Gln Arg Pro Ala Glu Pro Gln Val Gln
610                 615                 620

Trp Ser His Leu Ala Ser Leu Lys Asn Asn Val Ser Pro Val Ser Arg
625                 630                 635                 640

Ser His Ser Phe Ser Asp Pro Ser Pro Lys Phe Ala His His Leu
                645                 650                 655

Arg Ser Gln Asp Pro Cys Pro Pro Ser Arg Ser Glu Val Leu Ser Gln
        660                 665                 670

Ser Ser Asp Ser Lys Ser Glu Ala Pro Asp Pro Thr Gln Lys Ala Trp
    675                 680                 685
```

-continued

```
Ser Arg Ser Asp Ser Asp Glu Val Pro Pro Arg Val Pro Val Arg Thr
    690                 695                 700
Thr Ser Arg Ser Pro Val Leu Ser Arg Arg Asp Ser Pro Leu Gln Gly
705                 710                 715                 720
Ser Gly Gln Gln Asn Ser Gln Ala Gly Gln Arg Asn Ser Thr Ser Ser
                725                 730                 735
Ile Glu Pro Arg Leu Leu Trp Glu Arg Val Glu Lys Leu Val Pro Arg
            740                 745                 750
Pro Gly Ser Gly Ser Ser Ser Gly Ser Ser Asn Ser Gly Ser Gln Pro
        755                 760                 765
Gly Ser His Pro Gly Ser Gln Ser Gly Ser Gly Glu Arg Phe Arg Val
    770                 775                 780
Arg Ser Ser Ser Lys Ser Glu Gly Ser Pro Ser Gln Arg Leu Glu Asn
785                 790                 795                 800
Ala Val Lys Lys Pro Glu Asp Lys Lys Glu Val Phe Arg Pro Leu Lys
                805                 810                 815
Pro Ala Gly Glu Val Asp Leu Thr Ala Leu Ala Lys Glu Leu Arg Ala
            820                 825                 830
Val Glu Asp Val Arg Pro Pro His Lys Val Thr Asp Tyr Ser Ser Ser
        835                 840                 845
Ser Glu Glu Ser Gly Thr Thr Asp Glu Glu Asp Asp Val Glu Gln
    850                 855                 860
Glu Gly Ala Asp Glu Ser Thr Ser Gly Pro Glu Asp Thr Arg Ala Ala
865                 870                 875                 880
Ser Ser Leu Asn Leu Ser Asn Gly Glu Thr Glu Ser Val Lys Thr Met
                885                 890                 895
Ile Val His Asp Asp Val Glu Ser Glu Pro Ala Met Thr Pro Ser Lys
            900                 905                 910
Glu Gly Thr Leu Ile Val Arg Gln Thr Gln Ser Ala Ser Ser Thr Leu
        915                 920                 925
Gln Lys His Lys Ser Ser Ser Ser Phe Thr Pro Phe Ile Asp Pro Arg
    930                 935                 940
Leu Leu Gln Ile Ser Pro Ser Ser Gly Thr Thr Val Thr Ser Val Val
945                 950                 955                 960
Gly Phe Ser Cys Asp Gly Met Arg Pro Glu Ala Ile Arg Gln Asp Pro
                965                 970                 975
Thr Arg Lys Gly Ser Val Val Asn Val Asn Pro Thr Asn Thr Arg Pro
            980                 985                 990
Gln Ser Asp Thr Pro Glu Ile Arg Lys Tyr Lys Lys Arg Phe Asn Ser
        995                 1000                1005
Glu Ile Leu Cys Ala Ala Leu Trp Gly Val Asn Leu Leu Val Gly
    1010                1015                1020
Thr Glu Ser Gly Leu Met Leu Leu Asp Arg Ser Gly Gln Gly Lys
    1025                1030                1035
Val Tyr Pro Leu Ile Asn Arg Arg Arg Phe Gln Gln Met Asp Val
    1040                1045                1050
Leu Glu Gly Leu Asn Val Leu Val Thr Ile Ser Gly Lys Lys Asp
    1055                1060                1065
Lys Leu Arg Val Tyr Tyr Leu Ser Trp Leu Arg Asn Lys Ile Leu
    1070                1075                1080
His Asn Asp Pro Glu Val Glu Lys Lys Gln Gly Trp Thr Thr Val
    1085                1090                1095
Gly Asp Leu Glu Gly Cys Val His Tyr Lys Val Val Lys Tyr Glu
```

-continued

```
                1100                1105                1110

Arg Ile Lys Phe Leu Val Ile Ala Leu Lys Ser Ser Val Glu Val
            1115                1120                1125

Tyr Ala Trp Ala Pro Lys Pro Tyr His Lys Phe Met Ala Phe Lys
        1130                1135                1140

Ser Phe Gly Glu Leu Val His Lys Pro Leu Leu Val Asp Leu Thr
    1145                1150                1155

Val Glu Glu Gly Gln Arg Leu Lys Val Ile Tyr Gly Ser Cys Ala
1160                1165                1170

Gly Phe His Ala Val Asp Val Asp Ser Gly Ser Val Tyr Asp Ile
    1175                1180                1185

Tyr Leu Pro Thr His Ile Gln Cys Ser Ile Lys Pro His Ala Ile
    1190                1195                1200

Ile Ile Leu Pro Asn Thr Asp Gly Met Glu Leu Leu Val Cys Tyr
    1205                1210                1215

Glu Asp Glu Gly Val Tyr Val Asn Thr Tyr Gly Arg Ile Thr Lys
    1220                1225                1230

Asp Val Val Leu Gln Trp Gly Glu Met Pro Thr Ser Val Ala Tyr
    1235                1240                1245

Ile Arg Ser Asn Gln Thr Met Gly Trp Gly Glu Lys Ala Ile Glu
    1250                1255                1260

Ile Arg Ser Val Glu Thr Gly His Leu Asp Gly Val Phe Met His
    1265                1270                1275

Lys Arg Ala Gln Arg Leu Lys Phe Leu Cys Glu Arg Asn Asp Lys
    1280                1285                1290

Val Phe Phe Ala Ser Val Arg Ser Gly Gly Ser Ser Gln Val Tyr
    1295                1300                1305

Phe Met Thr Leu Gly Arg Thr Ser Leu Leu Ser Trp
    1310                1315                1320

<210> SEQ ID NO 48
<211> LENGTH: 1212
<212> TYPE: PRT
<213> ORGANISM: Homo sapiens

<400> SEQUENCE: 48

Met Ala Asn Asp Ser Pro Ala Lys Ser Leu Val Asp Ile Asp Leu Ser
1               5                   10                  15

Ser Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Glu Asp Glu Glu Glu
    50                  55                  60

Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

His Asp Asp Gln Leu Trp Leu Val Met Glu Phe Cys Gly Ala Gly Ser
            100                 105                 110

Ile Thr Asp Leu Val Lys Asn Thr Lys Gly Asn Thr Leu Lys Glu Asp
        115                 120                 125

Trp Ile Ala Tyr Ile Ser Arg Glu Ile Leu Arg Gly Leu Ala His Leu
    130                 135                 140

His Ile His His Val Ile His Arg Asp Ile Lys Gly Gln Asn Val Leu
```

```
            145                 150                 155                 160
Leu Thr Glu Asn Ala Glu Val Lys Leu Val Asp Phe Gly Val Ser Ala
                165                 170                 175
Gln Leu Asp Arg Thr Val Gly Arg Arg Asn Thr Phe Ile Gly Thr Pro
                180                 185                 190
Tyr Trp Met Ala Pro Glu Val Ile Ala Cys Asp Glu Asn Pro Asp Ala
                195                 200                 205
Thr Tyr Asp Tyr Arg Ser Asp Leu Trp Ser Cys Gly Ile Thr Ala Ile
                210                 215                 220
Glu Met Ala Glu Gly Ala Pro Pro Leu Cys Asp Met His Pro Met Arg
225                 230                 235                 240
Ala Leu Phe Leu Ile Pro Arg Asn Pro Pro Arg Leu Lys Ser Lys
                245                 250                 255
Lys Trp Ser Lys Lys Phe Phe Ser Phe Ile Glu Gly Cys Leu Val Lys
                260                 265                 270
Asn Tyr Met Gln Arg Pro Ser Thr Glu Gln Leu Leu Lys His Pro Phe
                275                 280                 285
Ile Arg Asp Gln Pro Asn Glu Arg Gln Val Arg Ile Gln Leu Lys Asp
                290                 295                 300
His Ile Asp Arg Thr Arg Lys Lys Arg Gly Glu Lys Asp Glu Thr Glu
305                 310                 315                 320
Tyr Glu Tyr Ser Gly Ser Glu Glu Glu Glu Val Pro Glu Gln
                325                 330                 335
Glu Gly Glu Pro Ser Ser Ile Val Asn Val Pro Gly Glu Ser Thr Leu
                340                 345                 350
Arg Arg Asp Phe Leu Arg Leu Gln Gln Glu Asn Lys Glu Arg Ser Glu
                355                 360                 365
Ala Leu Arg Arg Gln Gln Leu Leu Gln Glu Gln Leu Arg Glu Gln
                370                 375                 380
Glu Glu Tyr Lys Arg Gln Leu Leu Ala Glu Arg Gln Lys Arg Ile Glu
385                 390                 395                 400
Gln Gln Lys Glu Gln Arg Arg Leu Glu Glu Gln Arg Arg Glu
                405                 410                 415
Arg Glu Ala Arg Arg Gln Gln Glu Arg Glu Gln Arg Arg Glu Gln
                420                 425                 430
Glu Glu Lys Arg Arg Leu Glu Glu Leu Glu Arg Arg Lys Glu Glu
                435                 440                 445
Glu Glu Arg Arg Arg Ala Glu Glu Lys Arg Arg Val Glu Arg Glu
                450                 455                 460
Gln Glu Tyr Ile Arg Arg Gln Leu Glu Glu Gln Arg His Leu Glu
465                 470                 475                 480
Val Leu Gln Gln Gln Leu Leu Gln Glu Gln Ala Met Leu Leu His Asp
                485                 490                 495
His Arg Arg Pro His Pro Gln His Ser Gln Gln Pro Pro Pro Gln
                500                 505                 510
Gln Glu Arg Ser Lys Pro Ser Phe His Ala Pro Glu Pro Lys Ala His
                515                 520                 525
Tyr Glu Pro Ala Asp Arg Ala Arg Glu Val Glu Asp Arg Phe Arg Lys
                530                 535                 540
Thr Asn His Ser Ser Pro Glu Ala Gln Ser Lys Gln Thr Gly Arg Val
545                 550                 555                 560
Leu Glu Pro Pro Val Pro Ser Arg Ser Glu Ser Phe Ser Asn Gly Asn
                565                 570                 575
```

-continued

```
Ser Glu Ser Val His Pro Ala Leu Gln Arg Pro Ala Glu Pro Gln Val
            580                 585                 590

Pro Val Arg Thr Thr Ser Arg Ser Pro Val Leu Ser Arg Asp Ser
        595                 600                 605

Pro Leu Gln Gly Ser Gly Gln Gln Asn Ser Gln Ala Gly Gln Arg Asn
610                 615                 620

Ser Thr Ser Ser Ile Glu Pro Arg Leu Leu Trp Glu Arg Val Glu Lys
625                 630                 635                 640

Leu Val Pro Arg Pro Gly Ser Gly Ser Ser Gly Ser Ser Asn Ser
            645                 650                 655

Gly Ser Gln Pro Gly Ser His Pro Gly Ser Gln Ser Gly Ser Gly Glu
                660                 665                 670

Arg Phe Arg Val Arg Ser Ser Lys Ser Glu Gly Ser Pro Ser Gln
        675                 680                 685

Arg Leu Glu Asn Ala Val Lys Lys Pro Glu Asp Lys Lys Glu Val Phe
        690                 695                 700

Arg Pro Leu Lys Pro Ala Gly Glu Val Asp Leu Thr Ala Leu Ala Lys
705                 710                 715                 720

Glu Leu Arg Ala Val Glu Asp Val Arg Pro Pro His Lys Val Thr Asp
            725                 730                 735

Tyr Ser Ser Ser Ser Glu Glu Ser Gly Thr Thr Asp Glu Glu Asp Asp
                740                 745                 750

Asp Val Glu Gln Glu Gly Ala Asp Glu Ser Thr Ser Gly Pro Glu Asp
        755                 760                 765

Thr Arg Ala Ala Ser Ser Leu Asn Leu Ser Asn Gly Glu Thr Glu Ser
770                 775                 780

Val Lys Thr Met Ile Val His Asp Asp Val Glu Ser Glu Pro Ala Met
785                 790                 795                 800

Thr Pro Ser Lys Glu Gly Thr Leu Ile Val Arg Gln Thr Gln Ser Ala
            805                 810                 815

Ser Ser Thr Leu Gln Lys His Lys Ser Ser Ser Phe Thr Pro Phe
                820                 825                 830

Ile Asp Pro Arg Leu Leu Gln Ile Ser Pro Ser Ser Gly Thr Thr Val
        835                 840                 845

Thr Ser Val Val Gly Phe Ser Cys Asp Gly Met Arg Pro Glu Ala Ile
850                 855                 860

Arg Gln Asp Pro Thr Arg Lys Gly Ser Val Val Asn Val Asn Pro Thr
865                 870                 875                 880

Asn Thr Arg Pro Gln Ser Asp Thr Pro Glu Ile Arg Lys Tyr Lys Lys
            885                 890                 895

Arg Phe Asn Ser Glu Ile Leu Cys Ala Ala Leu Trp Gly Val Asn Leu
                900                 905                 910

Leu Val Gly Thr Glu Ser Gly Leu Met Leu Leu Asp Arg Ser Gly Gln
        915                 920                 925

Gly Lys Val Tyr Pro Leu Ile Asn Arg Arg Phe Gln Gln Met Asp
        930                 935                 940

Val Leu Glu Gly Leu Asn Val Leu Val Thr Ile Ser Gly Lys Lys Asp
945                 950                 955                 960

Lys Leu Arg Val Tyr Tyr Leu Ser Trp Leu Arg Asn Lys Ile Leu His
            965                 970                 975

Asn Asp Pro Glu Val Glu Lys Lys Gln Gly Trp Thr Thr Val Gly Asp
                980                 985                 990

Leu Glu Gly Cys Val His Tyr Lys  Val Val Lys Tyr Glu  Arg Ile Lys
        995                 1000                 1005
```

Phe Leu Val Ile Ala Leu Lys Ser Ser Val Glu Val Tyr Ala Trp
    1010                1015                1020

Ala Pro Lys Pro Tyr His Lys Phe Met Ala Phe Lys Ser Phe Gly
    1025                1030                1035

Glu Leu Val His Lys Pro Leu Leu Val Asp Leu Thr Val Glu Glu
    1040                1045                1050

Gly Gln Arg Leu Lys Val Ile Tyr Gly Ser Cys Ala Gly Phe His
    1055                1060                1065

Ala Val Asp Val Asp Ser Gly Ser Val Tyr Asp Ile Tyr Leu Pro
    1070                1075                1080

Thr His Ile Gln Cys Ser Ile Lys Pro His Ala Ile Ile Leu
    1085                1090                1095

Pro Asn Thr Asp Gly Met Glu Leu Leu Val Cys Tyr Glu Asp Glu
    1100                1105                1110

Gly Val Tyr Val Asn Thr Tyr Gly Arg Ile Thr Lys Asp Val Val
    1115                1120                1125

Leu Gln Trp Gly Glu Met Pro Thr Ser Val Ala Tyr Ile Arg Ser
    1130                1135                1140

Asn Gln Thr Met Gly Trp Gly Glu Lys Ala Ile Glu Ile Arg Ser
    1145                1150                1155

Val Glu Thr Gly His Leu Asp Gly Val Phe Met His Lys Arg Ala
    1160                1165                1170

Gln Arg Leu Lys Phe Leu Cys Glu Arg Asn Asp Lys Val Phe Phe
    1175                1180                1185

Ala Ser Val Arg Ser Gly Gly Ser Ser Gln Val Tyr Phe Met Thr
    1190                1195                1200

Leu Gly Arg Thr Ser Leu Leu Ser Trp
    1205                1210

<210> SEQ ID NO 49
<211> LENGTH: 1392
<212> TYPE: PRT
<213> ORGANISM: Homo sapiens

<400> SEQUENCE: 49

Met Ala Asn Asp Ser Pro Ala Lys Ser Leu Val Asp Ile Asp Leu Ser
1               5                   10                  15

Ser Leu Arg Asp Pro Ala Gly Ile Phe Glu Leu Val Glu Val Val Gly
                20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Glu Asp Glu Glu Glu
        50                  55                  60

Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

His Asp Asp Gln Leu Trp Leu Val Met Glu Phe Cys Gly Ala Gly Ser
                100                 105                 110

Ile Thr Asp Leu Val Lys Asn Thr Lys Gly Asn Thr Leu Lys Glu Asp
            115                 120                 125

Trp Ile Ala Tyr Ile Ser Arg Glu Ile Leu Arg Gly Leu Ala His Leu
        130                 135                 140

His Ile His His Val Ile His Arg Asp Ile Lys Gly Gln Asn Val Leu
145                 150                 155                 160

```
Leu Thr Glu Asn Ala Glu Val Lys Leu Val Asp Phe Gly Val Ser Ala
            165                 170                 175

Gln Leu Asp Arg Thr Val Gly Arg Arg Asn Thr Phe Ile Gly Thr Pro
        180                 185                 190

Tyr Trp Met Ala Pro Glu Val Ile Ala Cys Asp Glu Asn Pro Asp Ala
            195                 200                 205

Thr Tyr Asp Tyr Arg Ser Asp Leu Trp Ser Cys Gly Ile Thr Ala Ile
        210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
            245                 250                 255

Lys Trp Ser Lys Lys Phe Phe Ser Phe Ile Glu Gly Cys Leu Val Lys
            260                 265                 270

Asn Tyr Met Gln Arg Pro Ser Thr Glu Gln Leu Leu Lys His Pro Phe
        275                 280                 285

Ile Arg Asp Gln Pro Asn Glu Arg Gln Val Arg Ile Gln Leu Lys Asp
        290                 295                 300

His Ile Asp Arg Thr Arg Lys Lys Arg Gly Glu Lys Asp Glu Thr Glu
305                 310                 315                 320

Tyr Glu Tyr Ser Gly Ser Glu Glu Glu Glu Val Pro Glu Gln
            325                 330                 335

Glu Gly Glu Pro Ser Ser Ile Val Asn Val Pro Gly Glu Ser Thr Leu
            340                 345                 350

Arg Arg Asp Phe Leu Arg Leu Gln Gln Glu Asn Lys Glu Arg Ser Glu
        355                 360                 365

Ala Leu Arg Arg Gln Gln Leu Leu Gln Glu Gln Leu Arg Glu Gln
            370                 375                 380

Glu Glu Tyr Lys Arg Gln Leu Leu Ala Glu Arg Gln Lys Arg Ile Glu
385                 390                 395                 400

Gln Gln Lys Glu Gln Arg Arg Leu Glu Glu Gln Arg Arg Glu
            405                 410                 415

Arg Glu Ala Arg Arg Gln Glu Arg Glu Arg Arg Glu Gln
            420                 425                 430

Glu Glu Lys Arg Arg Leu Glu Glu Leu Glu Arg Arg Lys Glu Glu
            435                 440                 445

Glu Glu Arg Arg Arg Ala Glu Glu Lys Arg Arg Val Glu Arg Glu
            450                 455                 460

Gln Glu Tyr Ile Arg Arg Gln Leu Glu Glu Gln Arg His Leu Glu
465                 470                 475                 480

Val Leu Gln Gln Gln Leu Leu Gln Glu Gln Ala Met Leu Leu Glu Cys
            485                 490                 495

Arg Trp Arg Glu Met Glu Glu His Arg Gln Ala Glu Arg Leu Gln Arg
            500                 505                 510

Gln Leu Gln Gln Glu Gln Ala Tyr Leu Leu Ser Leu Gln His Asp His
        515                 520                 525

Arg Arg Pro His Pro Gln His Ser Gln Gln Pro Pro Pro Gln Gln
            530                 535                 540

Glu Arg Ser Lys Pro Ser Phe His Ala Pro Glu Pro Lys Ala His Tyr
545                 550                 555                 560

Glu Pro Ala Asp Arg Ala Arg Glu Val Glu Asp Arg Phe Arg Lys Thr
            565                 570                 575

Asn His Ser Ser Pro Glu Ala Gln Ser Lys Gln Thr Gly Arg Val Leu
```

```
                580             585             590
Glu Pro Pro Val Pro Ser Arg Ser Glu Ser Phe Ser Asn Gly Asn Ser
            595                 600             605
Glu Ser Val His Pro Ala Leu Gln Arg Pro Ala Glu Pro Gln Val Gln
            610                 615             620
Trp Ser His Leu Ala Ser Leu Lys Asn Asn Val Ser Pro Val Ser Arg
625                 630                 635                 640
Ser His Ser Phe Ser Asp Pro Pro Lys Phe Ala His His His Leu
            645                 650             655
Arg Ser Gln Asp Pro Cys Pro Pro Ser Arg Ser Glu Val Leu Ser Gln
            660                 665             670
Ser Ser Asp Ser Lys Ser Glu Ala Pro Asp Pro Thr Gln Lys Ala Trp
            675                 680             685
Ser Arg Ser Asp Ser Asp Glu Val Pro Pro Arg Val Pro Val Arg Thr
            690                 695             700
Thr Ser Arg Ser Pro Val Leu Ser Arg Arg Asp Ser Pro Leu Gln Gly
705                 710                 715                 720
Ser Gly Gln Gln Asn Ser Gln Ala Gly Gln Arg Asn Ser Thr Ser Ser
            725                 730             735
Ile Glu Pro Arg Leu Leu Trp Glu Arg Val Glu Lys Leu Val Pro Arg
            740                 745             750
Pro Gly Ser Gly Ser Ser Ser Gly Ser Ser Asn Ser Gly Ser Gln Pro
            755                 760             765
Gly Ser His Pro Gly Ser Gln Ser Gly Ser Gly Glu Arg Phe Arg Val
            770                 775             780
Arg Ser Ser Ser Lys Ser Glu Gly Ser Pro Ser Gln Arg Leu Glu Asn
785                 790                 795                 800
Ala Val Lys Lys Pro Glu Asp Lys Lys Glu Val Phe Arg Pro Leu Lys
            805                 810             815
Pro Ala Gly Glu Val Asp Leu Thr Ala Leu Ala Lys Glu Leu Arg Ala
            820                 825             830
Val Glu Asp Val Arg Pro Pro His Lys Val Thr Asp Tyr Ser Ser Ser
            835                 840             845
Ser Glu Glu Ser Gly Thr Thr Asp Glu Glu Asp Asp Val Glu Gln
850                 855                 860
Glu Gly Ala Asp Glu Ser Thr Ser Gly Pro Glu Asp Thr Arg Ala Ala
865                 870                 875                 880
Ser Ser Leu Asn Leu Ser Asn Gly Glu Thr Glu Ser Val Lys Thr Met
            885                 890             895
Ile Val His Asp Asp Val Glu Ser Glu Pro Ala Met Thr Pro Ser Lys
            900                 905             910
Glu Gly Thr Leu Ile Val Arg Gln Ser Thr Val Asp Gln Lys Arg Ala
            915                 920             925
Ser His His Glu Ser Asn Gly Phe Ala Gly Arg Ile His Leu Leu Pro
            930                 935             940
Asp Leu Leu Gln Gln Ser His Ser Ser Thr Ser Ser Thr Ser Ser
945                 950                 955                 960
Ser Pro Ser Ser Ser Gln Pro Thr Pro Thr Met Ser Pro Gln Thr Pro
            965                 970             975
Gln Asp Lys Leu Thr Ala Asn Glu Thr Gln Ser Ala Ser Ser Thr Leu
            980                 985             990
Gln Lys His Lys Ser Ser Ser Phe Thr Pro Phe Ile Asp Pro Arg
            995                 1000                1005
```

```
Leu Leu Gln Ile Ser Pro Ser Ser Gly Thr Thr Val Thr Ser Val
    1010                1015                1020

Val Gly Phe Ser Cys Asp Gly Met Arg Pro Glu Ala Ile Arg Gln
    1025                1030                1035

Asp Pro Thr Arg Lys Gly Ser Val Val Asn Val Asn Pro Thr Asn
    1040                1045                1050

Thr Arg Pro Gln Ser Asp Thr Pro Glu Ile Arg Lys Tyr Lys Lys
    1055                1060                1065

Arg Phe Asn Ser Glu Ile Leu Cys Ala Ala Leu Trp Gly Val Asn
    1070                1075                1080

Leu Leu Val Gly Thr Glu Ser Gly Leu Met Leu Leu Asp Arg Ser
    1085                1090                1095

Gly Gln Gly Lys Val Tyr Pro Leu Ile Asn Arg Arg Arg Phe Gln
    1100                1105                1110

Gln Met Asp Val Leu Glu Gly Leu Asn Val Leu Val Thr Ile Ser
    1115                1120                1125

Gly Lys Lys Asp Lys Leu Arg Val Tyr Tyr Leu Ser Trp Leu Arg
    1130                1135                1140

Asn Lys Ile Leu His Asn Asp Pro Glu Val Glu Lys Lys Gln Gly
    1145                1150                1155

Trp Thr Thr Val Gly Asp Leu Glu Gly Cys Val His Tyr Lys Val
    1160                1165                1170

Val Lys Tyr Glu Arg Ile Lys Phe Leu Val Ile Ala Leu Lys Ser
    1175                1180                1185

Ser Val Glu Val Tyr Ala Trp Ala Pro Lys Pro Tyr His Lys Phe
    1190                1195                1200

Met Ala Phe Lys Ser Phe Gly Glu Leu Val His Lys Pro Leu Leu
    1205                1210                1215

Val Asp Leu Thr Val Glu Glu Gly Gln Arg Leu Lys Val Ile Tyr
    1220                1225                1230

Gly Ser Cys Ala Gly Phe His Ala Val Asp Val Asp Ser Gly Ser
    1235                1240                1245

Val Tyr Asp Ile Tyr Leu Pro Thr His Val Arg Lys Asn Pro His
    1250                1255                1260

Ser Met Ile Gln Cys Ser Ile Lys Pro His Ala Ile Ile Ile Leu
    1265                1270                1275

Pro Asn Thr Asp Gly Met Glu Leu Leu Val Cys Tyr Glu Asp Glu
    1280                1285                1290

Gly Val Tyr Val Asn Thr Tyr Gly Arg Ile Thr Lys Asp Val Val
    1295                1300                1305

Leu Gln Trp Gly Glu Met Pro Thr Ser Val Ala Tyr Ile Arg Ser
    1310                1315                1320

Asn Gln Thr Met Gly Trp Gly Glu Lys Ala Ile Glu Ile Arg Ser
    1325                1330                1335

Val Glu Thr Gly His Leu Asp Gly Val Phe Met His Lys Arg Ala
    1340                1345                1350

Gln Arg Leu Lys Phe Leu Cys Glu Arg Asn Asp Lys Val Phe Phe
    1355                1360                1365

Ala Ser Val Arg Ser Gly Gly Ser Ser Gln Val Tyr Phe Met Thr
    1370                1375                1380

Leu Gly Arg Thr Ser Leu Leu Ser Trp
    1385                1390

<210> SEQ ID NO 50
```

```
<211> LENGTH: 603
<212> TYPE: PRT
<213> ORGANISM: Homo sapiens

<400> SEQUENCE: 50

Met Arg Arg Arg Ala Ala Arg Gly Pro Gly Pro Pro Pro Gly Pro
1               5                   10                  15

Gly Leu Ser Arg Leu Pro Leu Pro Leu Leu Leu Leu Ala Leu Gly
                20                  25                  30

Thr Arg Gly Gly Cys Ala Ala Pro Ala Pro Ala Pro Arg Ala Glu Asp
            35                  40                  45

Leu Ser Leu Gly Val Glu Trp Leu Ser Arg Phe Gly Tyr Leu Pro Pro
50                  55                  60

Ala Asp Pro Thr Thr Gly Gln Leu Gln Thr Gln Glu Glu Leu Ser Lys
65                  70                  75                  80

Ala Ile Thr Ala Met Gln Gln Phe Gly Gly Leu Glu Ala Thr Gly Ile
                85                  90                  95

Leu Asp Glu Ala Thr Leu Ala Leu Met Lys Thr Pro Arg Cys Ser Leu
                100                 105                 110

Pro Asp Leu Pro Val Leu Thr Gln Ala Arg Arg Arg Gln Ala Pro
                115                 120                 125

Ala Pro Thr Lys Trp Asn Lys Arg Asn Leu Ser Trp Arg Val Arg Thr
130                 135                 140

Phe Pro Arg Asp Ser Pro Leu Gly His Asp Thr Val Arg Ala Leu Met
145                 150                 155                 160

Tyr Tyr Ala Leu Lys Val Trp Ser Asp Ile Ala Pro Leu Asn Phe His
                165                 170                 175

Glu Val Ala Gly Ser Ala Ala Asp Ile Gln Ile Asp Phe Ser Lys Ala
                180                 185                 190

Asp His Asn Asp Gly Tyr Pro Phe Asp Gly Pro Gly Gly Thr Val Ala
                195                 200                 205

His Ala Phe Phe Pro Gly His His Thr Ala Gly Asp Thr His Phe
210                 215                 220

Asp Asp Asp Glu Ala Trp Thr Phe Arg Ser Ser Asp Ala His Gly Met
225                 230                 235                 240

Asp Leu Phe Ala Val Ala Val His Glu Phe Gly His Ala Ile Gly Leu
                245                 250                 255

Ser His Val Ala Ala Ala His Ser Ile Met Arg Pro Tyr Tyr Gln Gly
                260                 265                 270

Pro Val Gly Asp Pro Leu Arg Tyr Gly Leu Pro Tyr Glu Asp Lys Val
                275                 280                 285

Arg Val Trp Gln Leu Tyr Gly Val Arg Glu Ser Val Ser Pro Thr Ala
290                 295                 300

Gln Pro Glu Glu Pro Pro Leu Leu Pro Glu Pro Pro Asp Asn Arg Ser
305                 310                 315                 320

Ser Ala Pro Pro Arg Lys Asp Val Pro His Arg Cys Ser Thr His Phe
                325                 330                 335

Asp Ala Val Ala Gln Ile Arg Gly Glu Ala Phe Phe Phe Lys Gly Lys
                340                 345                 350

Tyr Phe Trp Arg Leu Thr Arg Asp Arg His Leu Val Ser Leu Gln Pro
                355                 360                 365

Ala Gln Met His Arg Phe Trp Arg Gly Leu Pro Leu His Leu Asp Ser
                370                 375                 380

Val Asp Ala Val Tyr Glu Arg Thr Ser Asp His Lys Ile Val Phe Phe
385                 390                 395                 400
```

-continued

Lys Gly Asp Arg Tyr Trp Val Phe Lys Asp Asn Asn Val Glu Glu Gly
                405                 410                 415

Tyr Pro Arg Pro Val Ser Asp Phe Ser Leu Pro Pro Gly Gly Ile Asp
            420                 425                 430

Ala Ala Phe Ser Trp Ala His Asn Asp Arg Thr Tyr Phe Phe Lys Asp
        435                 440                 445

Gln Leu Tyr Trp Arg Tyr Asp Asp His Thr Arg His Met Asp Pro Gly
    450                 455                 460

Tyr Pro Ala Gln Ser Pro Leu Trp Arg Gly Val Pro Ser Thr Leu Asp
465                 470                 475                 480

Asp Ala Met Arg Trp Ser Asp Gly Ala Ser Tyr Phe Phe Arg Gly Gln
                485                 490                 495

Glu Tyr Trp Lys Val Leu Asp Gly Glu Leu Glu Val Ala Pro Gly Tyr
                500                 505                 510

Pro Gln Ser Thr Ala Arg Asp Trp Leu Val Cys Gly Asp Ser Gln Ala
            515                 520                 525

Asp Gly Ser Val Ala Ala Gly Val Asp Ala Ala Glu Gly Pro Arg Ala
        530                 535                 540

Pro Pro Gly Gln His Asp Gln Ser Arg Ser Glu Asp Gly Tyr Glu Val
545                 550                 555                 560

Cys Ser Cys Thr Ser Gly Ala Ser Ser Pro Gly Ala Pro Gly Pro
                565                 570                 575

Leu Val Ala Ala Thr Met Leu Leu Leu Pro Pro Leu Ser Pro Gly
                580                 585                 590

Ala Leu Trp Thr Ala Ala Gln Ala Leu Thr Leu
                595                 600

<210> SEQ ID NO 51
<211> LENGTH: 189
<212> TYPE: PRT
<213> ORGANISM: Homo sapiens

<400> SEQUENCE: 51

Met Ala Leu Leu Ser Arg Pro Ala Leu Thr Leu Leu Leu Leu Leu Met
1               5                   10                  15

Ala Ala Val Val Arg Cys Gln Glu Gln Ala Gln Thr Thr Asp Trp Arg
                20                  25                  30

Ala Thr Leu Lys Thr Ile Arg Asn Gly Val His Lys Ile Asp Thr Tyr
            35                  40                  45

Leu Asn Ala Ala Leu Asp Leu Leu Gly Gly Glu Asp Gly Leu Cys Gln
        50                  55                  60

Tyr Lys Cys Ser Asp Gly Ser Lys Pro Phe Pro Arg Tyr Gly Tyr Lys
65                  70                  75                  80

Pro Ser Pro Pro Asn Gly Cys Gly Ser Pro Leu Phe Gly Val His Leu
                85                  90                  95

Asn Ile Gly Ile Pro Ser Leu Thr Lys Cys Cys Asn Gln His Asp Arg
                100                 105                 110

Cys Tyr Glu Thr Cys Gly Lys Ser Lys Asn Asp Cys Asp Glu Glu Phe
            115                 120                 125

Gln Tyr Cys Leu Ser Lys Ile Cys Arg Asp Val Gln Lys Thr Leu Gly
        130                 135                 140

Leu Thr Gln His Val Gln Ala Cys Glu Thr Thr Val Glu Leu Leu Phe
145                 150                 155                 160

Asp Ser Val Ile His Leu Gly Cys Lys Pro Tyr Leu Asp Ser Gln Arg
                165                 170                 175

Ala Ala Cys Arg Cys His Tyr Glu Glu Lys Thr Asp Leu
            180                 185

<210> SEQ ID NO 52
<211> LENGTH: 313
<212> TYPE: PRT
<213> ORGANISM: Homo sapiens

<400> SEQUENCE: 52

Met Glu Thr Gly Pro Glu Pro Ser Ser Met Pro Glu Ser Ser
1               5                   10                  15

Pro Arg Arg Thr Pro Gln Ser Ile Pro Tyr Gln Asp Leu Pro His Leu
            20                  25                  30

Val Asn Ala Asp Gly Gln Tyr Leu Phe Cys Arg Tyr Trp Lys Pro Thr
        35                  40                  45

Gly Thr Pro Lys Ala Leu Ile Phe Val Ser His Gly Ala Gly Glu His
    50                  55                  60

Ser Gly Arg Tyr Glu Glu Leu Ala Arg Met Leu Met Gly Leu Asp Leu
65                  70                  75                  80

Leu Val Phe Ala His Asp His Val Gly His Gly Gln Ser Glu Gly Glu
                85                  90                  95

Arg Met Val Val Ser Asp Phe His Val Phe Val Arg Asp Val Leu Gln
            100                 105                 110

His Val Asp Ser Met Gln Lys Asp Tyr Pro Gly Leu Pro Val Phe Leu
        115                 120                 125

Leu Gly His Ser Met Gly Gly Ala Ile Ala Ile Leu Thr Ala Ala Glu
    130                 135                 140

Arg Pro Gly His Phe Ala Gly Met Val Leu Ile Ser Pro Leu Val Leu
145                 150                 155                 160

Ala Asn Pro Glu Ser Ala Thr Thr Phe Lys Val Leu Ala Ala Lys Val
                165                 170                 175

Leu Asn Leu Val Leu Pro Asn Leu Ser Leu Gly Pro Ile Asp Ser Ser
            180                 185                 190

Val Leu Ser Arg Asn Lys Thr Glu Val Asp Ile Tyr Asn Ser Asp Pro
        195                 200                 205

Leu Ile Cys Arg Ala Gly Leu Lys Val Cys Phe Gly Ile Gln Leu Leu
    210                 215                 220

Asn Ala Val Ser Arg Val Glu Arg Ala Leu Pro Lys Leu Thr Val Pro
225                 230                 235                 240

Phe Leu Leu Leu Gln Gly Ser Ala Asp Arg Leu Cys Asp Ser Lys Gly
                245                 250                 255

Ala Tyr Leu Leu Met Glu Leu Ala Lys Ser Gln Asp Lys Thr Leu Lys
            260                 265                 270

Ile Tyr Glu Gly Ala Tyr His Val Leu His Lys Glu Leu Pro Glu Val
        275                 280                 285

Thr Asn Ser Val Phe His Glu Ile Asn Met Trp Val Ser Gln Arg Thr
    290                 295                 300

Ala Thr Ala Gly Thr Ala Ser Pro Pro
305                 310

<210> SEQ ID NO 53
<211> LENGTH: 303
<212> TYPE: PRT
<213> ORGANISM: Homo sapiens

<400> SEQUENCE: 53

```
Met Pro Glu Glu Ser Ser Pro Arg Arg Thr Pro Gln Ser Ile Pro Tyr
1               5                   10                  15

Gln Asp Leu Pro His Leu Val Asn Ala Asp Gly Gln Tyr Leu Phe Cys
            20                  25                  30

Arg Tyr Trp Lys Pro Thr Gly Thr Pro Lys Ala Leu Ile Phe Val Ser
            35                  40                  45

His Gly Ala Gly Glu His Ser Gly Arg Tyr Glu Glu Leu Ala Arg Met
50                  55                  60

Leu Met Gly Leu Asp Leu Leu Val Phe Ala His Asp His Val Gly His
65                  70                  75                  80

Gly Gln Ser Glu Gly Glu Arg Met Val Val Ser Asp Phe His Val Phe
                85                  90                  95

Val Arg Asp Val Leu Gln His Val Asp Ser Met Gln Lys Asp Tyr Pro
                100                 105                 110

Gly Leu Pro Val Phe Leu Leu Gly His Ser Met Gly Gly Ala Ile Ala
            115                 120                 125

Ile Leu Thr Ala Ala Glu Arg Pro Gly His Phe Ala Gly Met Val Leu
        130                 135                 140

Ile Ser Pro Leu Val Leu Ala Asn Pro Glu Ser Ala Thr Thr Phe Lys
145                 150                 155                 160

Val Leu Ala Ala Lys Val Leu Asn Leu Val Leu Pro Asn Leu Ser Leu
                165                 170                 175

Gly Pro Ile Asp Ser Ser Val Leu Ser Arg Asn Lys Thr Glu Val Asp
            180                 185                 190

Ile Tyr Asn Ser Asp Pro Leu Ile Cys Arg Ala Gly Leu Lys Val Cys
        195                 200                 205

Phe Gly Ile Gln Leu Leu Asn Ala Val Ser Arg Val Glu Arg Ala Leu
210                 215                 220

Pro Lys Leu Thr Val Pro Phe Leu Leu Leu Gln Gly Ser Ala Asp Arg
225                 230                 235                 240

Leu Cys Asp Ser Lys Gly Ala Tyr Leu Leu Met Glu Leu Ala Lys Ser
                245                 250                 255

Gln Asp Lys Thr Leu Lys Ile Tyr Glu Gly Ala Tyr His Val Leu His
            260                 265                 270

Lys Glu Leu Pro Glu Val Thr Asn Ser Val Phe His Glu Ile Asn Met
275                 280                 285

Trp Val Ser Gln Arg Thr Ala Thr Ala Gly Thr Ala Ser Pro Pro
290                 295                 300

<210> SEQ ID NO 54
<211> LENGTH: 395
<212> TYPE: PRT
<213> ORGANISM: Homo sapiens

<400> SEQUENCE: 54

Met Ser Ala Asn Ala Thr Leu Lys Pro Leu Cys Pro Ile Leu Glu Gln
1               5                   10                  15

Met Ser Arg Leu Gln Ser His Ser Asn Thr Ser Ile Arg Tyr Ile Asp
            20                  25                  30

His Ala Ala Val Leu Leu His Gly Leu Ala Ser Leu Leu Gly Leu Val
            35                  40                  45

Glu Asn Gly Val Ile Leu Phe Val Val Gly Cys Arg Met Arg Gln Thr
        50                  55                  60

Val Val Thr Thr Trp Val Leu His Leu Ala Leu Ser Asp Leu Leu Ala
65                  70                  75                  80
```

-continued

Ser Ala Ser Leu Pro Phe Phe Thr Tyr Phe Leu Ala Val Gly His Ser
                85                  90                  95

Trp Glu Leu Gly Thr Thr Phe Cys Lys Leu His Ser Ile Phe Phe
            100                 105                 110

Leu Asn Met Phe Ala Ser Gly Phe Leu Leu Ser Ala Ile Ser Leu Asp
            115                 120                 125

Arg Cys Leu Gln Val Val Arg Pro Val Trp Ala Gln Asn His Arg Thr
            130                 135                 140

Val Ala Ala Ala His Lys Val Cys Leu Val Leu Trp Ala Leu Ala Val
145                 150                 155                 160

Leu Asn Thr Val Pro Tyr Phe Val Phe Arg Asp Thr Ile Ser Arg Leu
            165                 170                 175

Asp Gly Arg Ile Met Cys Tyr Tyr Asn Val Leu Leu Leu Asn Pro Gly
            180                 185                 190

Pro Asp Arg Asp Ala Thr Cys Asn Ser Arg Gln Val Ala Leu Ala Val
            195                 200                 205

Ser Lys Phe Leu Leu Ala Phe Leu Val Pro Leu Ala Ile Ile Ala Ser
            210                 215                 220

Ser His Ala Ala Val Ser Leu Arg Leu Gln His Arg Gly Arg Arg Arg
225                 230                 235                 240

Pro Gly Arg Phe Val Arg Leu Val Ala Ala Val Val Ala Ala Phe Ala
            245                 250                 255

Leu Cys Trp Gly Pro Tyr His Val Phe Ser Leu Leu Glu Ala Arg Ala
            260                 265                 270

His Ala Asn Pro Gly Leu Arg Pro Leu Val Trp Arg Gly Leu Pro Phe
            275                 280                 285

Val Thr Ser Leu Ala Phe Phe Asn Ser Val Ala Asn Pro Val Leu Tyr
290                 295                 300

Val Leu Thr Cys Pro Asp Met Leu Arg Lys Leu Arg Arg Ser Leu Arg
305                 310                 315                 320

Thr Val Leu Glu Ser Val Leu Val Asp Asp Ser Glu Leu Gly Gly Ala
            325                 330                 335

Gly Ser Ser Arg Arg Arg Arg Thr Ser Ser Thr Ala Arg Ser Ala Ser
            340                 345                 350

Pro Leu Ala Leu Cys Ser Arg Pro Glu Glu Pro Arg Gly Pro Ala Arg
            355                 360                 365

Leu Leu Gly Trp Leu Leu Gly Ser Cys Ala Ala Ser Pro Gln Thr Gly
            370                 375                 380

Pro Leu Asn Arg Ala Leu Ser Ser Thr Ser Ser
385                 390                 395

<210> SEQ ID NO 55
<211> LENGTH: 331
<212> TYPE: PRT
<213> ORGANISM: Homo sapiens

<400> SEQUENCE: 55

Met Trp Leu Trp Glu Asp Gln Gly Gly Leu Leu Gly Pro Phe Ser Phe
1               5                   10                  15

Leu Leu Leu Val Leu Leu Leu Val Thr Arg Ser Pro Val Asn Ala Cys
            20                  25                  30

Leu Leu Thr Gly Ser Leu Phe Val Leu Leu Arg Val Phe Ser Phe Glu
            35                  40                  45

Pro Val Pro Ser Cys Arg Ala Leu Gln Val Leu Lys Pro Arg Asp Arg
            50                  55                  60

```
Ile Ser Ala Ile Ala His Arg Gly Gly Ser His Asp Ala Pro Glu Asn
 65                  70                  75                  80

Thr Leu Ala Ala Ile Arg Gln Ala Ala Lys Asn Gly Ala Thr Gly Val
                 85                  90                  95

Glu Leu Asp Ile Glu Phe Thr Ser Asp Gly Ile Pro Val Leu Met His
            100                 105                 110

Asp Asn Thr Val Asp Arg Thr Thr Asp Gly Thr Gly Arg Leu Cys Asp
        115                 120                 125

Leu Thr Phe Glu Gln Ile Arg Lys Leu Asn Pro Ala Ala Asn His Arg
130                 135                 140

Leu Arg Asn Asp Phe Pro Asp Glu Lys Ile Pro Thr Leu Arg Glu Ala
145                 150                 155                 160

Val Ala Glu Cys Leu Asn His Asn Leu Thr Ile Phe Phe Asp Val Lys
                165                 170                 175

Gly His Ala His Lys Ala Thr Glu Ala Leu Lys Lys Met Tyr Met Glu
            180                 185                 190

Phe Pro Gln Leu Tyr Asn Asn Ser Val Val Cys Ser Phe Leu Pro Glu
        195                 200                 205

Val Ile Tyr Lys Met Arg Gln Thr Asp Arg Asp Val Ile Thr Ala Leu
210                 215                 220

Thr His Arg Pro Trp Ser Leu Ser His Thr Gly Asp Gly Lys Pro Arg
225                 230                 235                 240

Tyr Asp Thr Phe Trp Lys His Phe Ile Phe Val Met Met Asp Ile Leu
                245                 250                 255

Leu Asp Trp Ser Met His Asn Ile Leu Trp Tyr Leu Cys Gly Ile Ser
            260                 265                 270

Ala Phe Leu Met Gln Lys Asp Phe Val Ser Pro Ala Tyr Leu Lys Lys
        275                 280                 285

Trp Ser Ala Lys Gly Ile Gln Val Val Gly Trp Thr Val Asn Thr Phe
290                 295                 300

Asp Glu Lys Ser Tyr Tyr Glu Ser His Leu Gly Ser Ser Tyr Ile Thr
305                 310                 315                 320

Asp Ser Met Val Glu Asp Cys Glu Pro His Phe
                325                 330

<210> SEQ ID NO 56
<211> LENGTH: 451
<212> TYPE: PRT
<213> ORGANISM: Homo sapiens

<400> SEQUENCE: 56

Met Val Ser Arg Asp Gln Ala His Leu Gly Pro Lys Tyr Val Gly Leu
 1               5                  10                  15

Trp Asp Phe Lys Ser Arg Thr Asp Glu Glu Leu Ser Phe Arg Ala Gly
                20                  25                  30

Asp Val Phe His Val Ala Arg Lys Glu Glu Gln Trp Trp Trp Ala Thr
            35                  40                  45

Leu Leu Asp Glu Ala Gly Gly Ala Val Ala Gln Gly Tyr Val Pro His
        50                  55                  60

Asn Tyr Leu Ala Glu Arg Glu Thr Val Glu Ser Glu Pro Trp Phe Phe
 65                  70                  75                  80

Gly Cys Ile Ser Arg Ser Glu Ala Val Arg Leu Gln Ala Glu Gly
                85                  90                  95

Asn Ala Thr Gly Ala Phe Leu Ile Arg Val Ser Glu Lys Pro Ser Ala
            100                 105                 110
```

```
Asp Tyr Val Leu Ser Val Arg Asp Thr Gln Ala Val Arg His Tyr Lys
        115                 120                 125
Ile Trp Arg Arg Ala Gly Gly Arg Leu His Leu Asn Glu Ala Val Ser
130                 135                 140
Phe Leu Ser Leu Pro Glu Leu Val Asn Tyr His Arg Ala Gln Ser Leu
145                 150                 155                 160
Ser His Gly Leu Arg Leu Ala Ala Pro Cys Arg Lys His Glu Pro Glu
                165                 170                 175
Pro Leu Pro His Trp Asp Asp Trp Glu Arg Pro Arg Glu Glu Phe Thr
            180                 185                 190
Leu Cys Arg Lys Leu Gly Ser Gly Tyr Phe Gly Glu Val Phe Glu Gly
        195                 200                 205
Leu Trp Lys Asp Arg Val Gln Val Ala Ile Lys Val Ile Ser Arg Asp
210                 215                 220
Asn Leu Leu His Gln Gln Met Leu Gln Ser Glu Ile Gln Ala Met Lys
225                 230                 235                 240
Lys Leu Arg His Lys His Ile Leu Ala Leu Tyr Ala Val Val Ser Val
                245                 250                 255
Gly Asp Pro Val Tyr Ile Ile Thr Glu Leu Met Ala Lys Gly Ser Leu
            260                 265                 270
Leu Glu Leu Leu Arg Asp Ser Asp Glu Lys Val Leu Pro Val Ser Glu
        275                 280                 285
Leu Leu Asp Ile Ala Trp Gln Val Ala Glu Gly Met Cys Tyr Leu Glu
290                 295                 300
Ser Gln Asn Tyr Ile His Arg Asp Leu Ala Ala Arg Asn Ile Leu Val
305                 310                 315                 320
Gly Glu Asn Thr Leu Cys Lys Val Gly Asp Phe Gly Leu Ala Arg Leu
                325                 330                 335
Ile Lys Glu Asp Val Tyr Leu Ser His Asp His Asn Ile Pro Tyr Lys
            340                 345                 350
Trp Thr Ala Pro Glu Ala Leu Ser Arg Gly His Tyr Ser Thr Lys Ser
        355                 360                 365
Asp Val Trp Ser Phe Gly Ile Leu Leu His Glu Met Phe Ser Arg Gly
370                 375                 380
Gln Val Pro Tyr Pro Gly Met Ser Asn His Glu Ala Phe Leu Arg Val
385                 390                 395                 400
Asp Ala Gly Tyr Arg Met Pro Cys Pro Leu Glu Cys Pro Pro Ser Val
                405                 410                 415
His Lys Leu Met Leu Thr Cys Trp Cys Arg Asp Pro Glu Gln Arg Pro
            420                 425                 430
Cys Phe Lys Ala Leu Arg Glu Arg Leu Ser Ser Phe Thr Ser Tyr Glu
        435                 440                 445
Asn Pro Thr
    450

<210> SEQ ID NO 57
<211> LENGTH: 208
<212> TYPE: PRT
<213> ORGANISM: Homo sapiens

<400> SEQUENCE: 57

Met Ala Thr Ser Ala Val Pro Ser Asp Asn Leu Pro Thr Tyr Lys Leu
1               5                   10                  15
Val Val Val Gly Asp Gly Gly Val Gly Lys Ser Ala Leu Thr Ile Gln
            20                  25                  30
```

```
Phe Phe Gln Lys Ile Phe Val Pro Asp Tyr Asp Pro Thr Ile Glu Asp
        35                  40                  45

Ser Tyr Leu Lys His Thr Glu Ile Asp Asn Gln Trp Ala Ile Leu Asp
    50                  55                  60

Val Leu Asp Thr Ala Gly Gln Glu Glu Phe Ser Ala Met Arg Glu Gln
65                  70                  75                  80

Tyr Met Arg Thr Gly Asp Gly Phe Leu Ile Val Tyr Ser Val Thr Asp
                85                  90                  95

Lys Ala Ser Phe Glu His Val Asp Arg Phe His Gln Leu Ile Leu Arg
                100                 105                 110

Val Lys Asp Arg Glu Ser Phe Pro Met Ile Leu Val Ala Asn Lys Val
            115                 120                 125

Asp Leu Met His Leu Arg Lys Ile Thr Arg Glu Gln Gly Lys Glu Met
        130                 135                 140

Ala Thr Lys His Asn Ile Pro Tyr Ile Glu Thr Ser Ala Lys Asp Pro
145                 150                 155                 160

Pro Leu Asn Val Asp Lys Ala Phe His Asp Leu Val Arg Val Ile Arg
                165                 170                 175

Gln Gln Ile Pro Glu Lys Ser Gln Lys Lys Lys Lys Thr Lys Trp
                180                 185                 190

Arg Gly Asp Arg Ala Thr Gly Thr His Lys Leu Gln Cys Val Ile Leu
            195                 200                 205

<210> SEQ ID NO 58
<211> LENGTH: 1044
<212> TYPE: PRT
<213> ORGANISM: Homo sapiens

<400> SEQUENCE: 58

Met Pro Ala Ala Gly Ser Asn Glu Pro Asp Gly Val Leu Ser Tyr Gln
1                   5                   10                  15

Arg Pro Asp Glu Glu Ala Val Val Asp Gln Gly Gly Thr Ser Thr Ile
                20                  25                  30

Leu Asn Ile His Tyr Glu Lys Glu Leu Glu Gly His Arg Thr Leu
            35                  40                  45

Tyr Val Gly Val Arg Met Pro Leu Gly Arg Gln Ser His Arg His
    50                  55                  60

Arg Thr His Gly Gln Lys His Arg Arg Gly Arg Gly Lys Gly Ala
65                  70                  75                  80

Ser Gln Gly Glu Glu Gly Leu Glu Ala Leu Ala His Asp Thr Pro Ser
                85                  90                  95

Gln Arg Val Gln Phe Ile Leu Gly Thr Glu Glu Asp Glu His Val
            100                 105                 110

Pro His Glu Leu Phe Thr Glu Leu Asp Glu Ile Cys Met Lys Glu Gly
        115                 120                 125

Glu Asp Ala Glu Trp Lys Glu Thr Ala Arg Trp Leu Lys Phe Glu Glu
        130                 135                 140

Asp Val Glu Asp Gly Gly Glu Arg Trp Ser Lys Pro Tyr Val Ala Thr
145                 150                 155                 160

Leu Ser Leu His Ser Leu Phe Glu Leu Arg Ser Cys Leu Ile Asn Gly
                165                 170                 175

Thr Val Leu Leu Asp Met His Ala Asn Ser Ile Glu Glu Ile Ser Asp
            180                 185                 190

Leu Ile Leu Asp Gln Gln Glu Leu Ser Ser Asp Leu Asn Asp Ser Met
        195                 200                 205
```

-continued

```
Arg Val Lys Val Arg Glu Ala Leu Leu Lys Lys His His Gln Asn
    210                 215                 220

Glu Lys Lys Arg Asn Asn Leu Ile Pro Ile Val Arg Ser Phe Ala Glu
225                 230                 235                 240

Val Gly Lys Lys Gln Ser Asp Pro His Leu Met Asp Lys His Gly Gln
                245                 250                 255

Thr Val Ser Pro Gln Ser Val Pro Thr Thr Asn Leu Glu Val Lys Asn
            260                 265                 270

Gly Val Asn Cys Glu His Ser Pro Val Asp Leu Ser Lys Val Asp Leu
            275                 280                 285

His Phe Met Lys Lys Ile Pro Thr Gly Ala Glu Ala Ser Asn Val Leu
        290                 295                 300

Val Gly Glu Val Asp Ile Leu Asp Arg Pro Ile Val Ala Phe Val Arg
305                 310                 315                 320

Leu Ser Pro Ala Val Leu Leu Ser Gly Leu Thr Glu Val Pro Ile Pro
                325                 330                 335

Thr Arg Phe Leu Phe Ile Leu Leu Gly Pro Val Gly Lys Gly Gln Gln
            340                 345                 350

Tyr His Glu Ile Gly Arg Ser Met Ala Thr Ile Met Thr Asp Glu Ile
        355                 360                 365

Phe His Asp Val Ala Tyr Lys Ala Lys Glu Arg Asp Asp Leu Leu Ala
    370                 375                 380

Gly Ile Asp Glu Phe Leu Asp Gln Val Thr Val Leu Pro Pro Gly Glu
385                 390                 395                 400

Trp Asp Pro Ser Ile Arg Ile Glu Pro Pro Lys Asn Val Pro Ser Gln
                405                 410                 415

Glu Lys Arg Lys Met Pro Gly Val Pro Asn Gly Asn Val Cys His Ile
            420                 425                 430

Glu Gln Glu Pro His Gly Gly His Ser Gly Pro Glu Leu Gln Arg Thr
        435                 440                 445

Gly Arg Leu Phe Gly Gly Leu Val Leu Asp Ile Lys Arg Lys Ala Pro
    450                 455                 460

Trp Tyr Trp Ser Asp Tyr Arg Asp Ala Leu Ser Leu Gln Cys Leu Ala
465                 470                 475                 480

Ser Phe Leu Phe Leu Tyr Cys Ala Cys Met Ser Pro Val Ile Thr Phe
                485                 490                 495

Gly Gly Leu Leu Gly Glu Ala Thr Glu Gly Arg Ile Ser Ala Ile Glu
            500                 505                 510

Ser Leu Phe Gly Ala Ser Met Thr Gly Ile Ala Tyr Ser Leu Phe Ala
        515                 520                 525

Gly Gln Ala Leu Thr Ile Leu Gly Ser Thr Gly Pro Val Leu Val Phe
    530                 535                 540

Glu Lys Ile Leu Phe Lys Phe Cys Lys Asp Tyr Ala Leu Ser Tyr Leu
545                 550                 555                 560

Ser Leu Arg Ala Cys Ile Gly Leu Trp Thr Ala Phe Leu Cys Ile Val
                565                 570                 575

Leu Val Ala Thr Asp Ala Ser Ser Leu Val Cys Tyr Ile Thr Arg Phe
            580                 585                 590

Thr Glu Glu Ala Phe Ala Ser Leu Ile Cys Ile Ile Phe Ile Tyr Glu
        595                 600                 605

Ala Ile Glu Lys Leu Ile His Leu Ala Glu Thr Tyr Pro Ile His Met
    610                 615                 620

His Ser Gln Leu Asp His Leu Ser Leu Tyr Tyr Cys Arg Cys Thr Leu
625                 630                 635                 640
```

-continued

```
Pro Glu Asn Pro Asn Asn His Thr Leu Gln Tyr Trp Lys Asp His Asn
            645                 650                 655

Ile Val Thr Ala Glu Val His Trp Ala Asn Leu Thr Val Ser Glu Cys
            660                 665                 670

Gln Glu Met His Gly Glu Phe Met Gly Ser Ala Cys Gly His His Gly
            675                 680                 685

Pro Tyr Thr Pro Asp Val Leu Phe Trp Ser Cys Ile Leu Phe Phe Thr
            690                 695                 700

Thr Phe Ile Leu Ser Ser Thr Leu Lys Thr Phe Lys Thr Ser Arg Tyr
705                 710                 715                 720

Phe Pro Thr Arg Val Arg Ser Met Val Ser Asp Phe Ala Val Phe Leu
            725                 730                 735

Thr Ile Phe Thr Met Val Ile Ile Asp Phe Leu Ile Gly Val Pro Ser
            740                 745                 750

Pro Lys Leu Gln Val Pro Ser Val Phe Lys Pro Thr Arg Asp Asp Arg
            755                 760                 765

Gly Trp Ile Ile Asn Pro Ile Gly Pro Asn Pro Trp Trp Thr Val Ile
            770                 775                 780

Ala Ala Ile Ile Pro Ala Leu Leu Cys Thr Ile Leu Ile Phe Met Asp
785                 790                 795                 800

Gln Gln Ile Thr Ala Val Ile Ile Asn Arg Lys Glu His Lys Leu Lys
            805                 810                 815

Lys Gly Cys Gly Tyr His Leu Asp Leu Leu Met Val Ala Ile Met Leu
            820                 825                 830

Gly Val Cys Ser Ile Met Gly Leu Pro Trp Phe Val Ala Ala Thr Val
            835                 840                 845

Leu Ser Ile Thr His Val Asn Ser Leu Lys Leu Glu Ser Glu Cys Ser
850                 855                 860

Ala Pro Gly Glu Gln Pro Lys Phe Leu Gly Ile Arg Glu Gln Arg Val
865                 870                 875                 880

Thr Gly Leu Met Ile Phe Val Leu Met Gly Cys Ser Val Phe Met Thr
            885                 890                 895

Ala Ile Leu Lys Phe Ile Pro Met Pro Val Leu Tyr Gly Val Phe Leu
            900                 905                 910

Tyr Met Gly Val Ser Ser Leu Gln Gly Ile Gln Phe Phe Asp Arg Leu
            915                 920                 925

Lys Leu Phe Gly Met Pro Ala Lys His Gln Pro Asp Phe Ile Tyr Leu
            930                 935                 940

Arg His Val Pro Leu Arg Lys Val His Leu Phe Thr Leu Ile Gln Leu
945                 950                 955                 960

Thr Cys Leu Val Leu Leu Trp Val Ile Lys Ala Ser Pro Ala Ala Ile
            965                 970                 975

Val Phe Pro Met Met Val Leu Ala Leu Val Phe Val Arg Lys Val Met
            980                 985                 990

Asp Leu Cys Phe Ser Lys Arg Glu  Leu Ser Trp Leu Asp  Asp Leu Met
            995                 1000                1005

Pro Glu  Ser Lys Lys Lys Lys  Leu Asp Asp Ala Lys  Lys Lys Ala
    1010                1015                1020

Lys Glu  Glu Glu Val Ile Val  Leu Ala Pro Thr Val  Tyr Leu Gly
    1025                1030                1035

Ala Ser  Asn Tyr Arg Thr
    1040
```

-continued

```
<210> SEQ ID NO 59
<211> LENGTH: 915
<212> TYPE: PRT
<213> ORGANISM: Homo sapiens

<400> SEQUENCE: 59

Met Ala Arg Arg Ser Ser Phe Gln Ser Cys Gln Ile Ile Ser Leu Phe
1               5                   10                  15

Thr Phe Ala Val Gly Val Asn Ile Cys Leu Gly Phe Thr Ala His Arg
            20                  25                  30

Ile Lys Arg Ala Glu Gly Trp Glu Gly Pro Pro Thr Val Leu Ser
        35                  40                  45

Asp Ser Pro Trp Thr Asn Ile Ser Gly Ser Cys Lys Gly Arg Cys Phe
50                  55                  60

Glu Leu Gln Glu Ala Gly Pro Pro Asp Cys Arg Cys Asp Asn Leu Cys
65                  70                  75                  80

Lys Ser Tyr Thr Ser Cys Cys His Asp Phe Asp Glu Leu Cys Leu Lys
                85                  90                  95

Thr Ala Arg Gly Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
        115                 120                 125

Asp Cys Cys Thr Asn Tyr Gln Val Val Cys Lys Gly Glu Ser His Trp
130                 135                 140

Val Asp Asp Asp Cys Glu Glu Ile Lys Ala Ala Glu Cys Pro Ala Gly
145                 150                 155                 160

Phe Val Arg Pro Pro Leu Ile Ile Phe Ser Val Asp Gly Phe Arg Ala
                165                 170                 175

Ser Tyr Met Lys Lys Gly Ser Lys Val Met Pro Asn Ile Glu Lys Leu
            180                 185                 190

Arg Ser Cys Gly Thr His Ser Pro Tyr Met Arg Pro Val Tyr Pro Thr
        195                 200                 205

Lys Thr Phe Pro Asn Leu Tyr Thr Leu Ala Thr Gly Leu Tyr Pro Glu
    210                 215                 220

Ser His Gly Ile Val Gly Asn Ser Met Tyr Asp Pro Val Phe Asp Ala
225                 230                 235                 240

Thr Phe His Leu Arg Gly Arg Glu Lys Phe Asn His Arg Trp Trp Gly
                245                 250                 255

Gly Gln Pro Leu Trp Ile Thr Ala Thr Lys Gln Gly Val Lys Ala Gly
            260                 265                 270

Thr Phe Phe Trp Ser Val Val Ile Pro His Glu Arg Arg Ile Leu Thr
        275                 280                 285

Ile Leu Gln Trp Leu Thr Leu Pro Asp His Glu Arg Pro Ser Val Tyr
    290                 295                 300

Ala Phe Tyr Ser Glu Gln Pro Asp Phe Ser Gly His Lys Tyr Gly Pro
305                 310                 315                 320

Phe Gly Pro Glu Glu Ser Ser Tyr Gly Ser Pro Phe Thr Pro Ala Lys
                325                 330                 335

Arg Pro Lys Arg Lys Val Ala Pro Lys Arg Arg Gln Glu Arg Pro Val
            340                 345                 350

Ala Pro Pro Lys Lys Arg Arg Lys Ile His Arg Met Asp His Tyr
        355                 360                 365

Ala Ala Glu Thr Arg Gln Asp Lys Met Thr Asn Pro Leu Arg Glu Ile
    370                 375                 380

Asp Lys Ile Val Gly Gln Leu Met Asp Gly Leu Lys Gln Leu Lys Leu
```

```
                385                 390                 395                 400
His Arg Cys Val Asn Val Ile Phe Val Gly Asp His Gly Met Glu Asp
                    405                 410                 415

Val Thr Cys Asp Arg Thr Glu Phe Leu Ser Asn Tyr Leu Thr Asn Val
                    420                 425                 430

Asp Asp Ile Thr Leu Val Pro Gly Thr Leu Gly Arg Ile Arg Ser Lys
                    435                 440                 445

Phe Ser Asn Asn Ala Lys Tyr Asp Pro Lys Ala Ile Ile Ala Asn Leu
                450                 455                 460

Thr Cys Lys Lys Pro Asp Gln His Phe Lys Pro Tyr Leu Lys Gln His
465                 470                 475                 480

Leu Pro Lys Arg Leu His Tyr Ala Asn Asn Arg Arg Ile Glu Asp Ile
                    485                 490                 495

His Leu Leu Val Glu Arg Arg Trp His Val Ala Arg Lys Pro Leu Asp
                500                 505                 510

Val Tyr Lys Lys Pro Ser Gly Lys Cys Phe Phe Gln Gly Asp His Gly
                515                 520                 525

Phe Asp Asn Lys Val Asn Ser Met Gln Thr Val Phe Val Gly Tyr Gly
                530                 535                 540

Ser Thr Phe Lys Tyr Lys Thr Lys Val Pro Pro Phe Glu Asn Ile Glu
545                 550                 555                 560

Leu Tyr Asn Val Met Cys Asp Leu Leu Gly Leu Lys Pro Ala Pro Asn
                    565                 570                 575

Asn Gly Thr His Gly Ser Leu Asn His Leu Leu Arg Thr Asn Thr Phe
                    580                 585                 590

Arg Pro Thr Met Pro Glu Glu Val Thr Arg Pro Asn Tyr Pro Gly Ile
                    595                 600                 605

Met Tyr Leu Gln Ser Asp Phe Asp Leu Gly Cys Thr Cys Asp Asp Lys
                    610                 615                 620

Val Glu Pro Lys Asn Lys Leu Asp Glu Leu Asn Lys Arg Leu His Thr
625                 630                 635                 640

Lys Gly Ser Thr Glu Glu Arg His Leu Leu Tyr Gly Arg Pro Ala Val
                    645                 650                 655

Leu Tyr Arg Thr Arg Tyr Asp Ile Leu Tyr His Thr Asp Phe Glu Ser
                    660                 665                 670

Gly Tyr Ser Glu Ile Phe Leu Met Pro Leu Trp Thr Ser Tyr Thr Val
                    675                 680                 685

Ser Lys Gln Ala Glu Val Ser Ser Val Pro Asp His Leu Thr Ser Cys
                    690                 695                 700

Val Arg Pro Asp Val Arg Val Ser Pro Ser Phe Ser Gln Asn Cys Leu
705                 710                 715                 720

Ala Tyr Lys Asn Asp Lys Gln Met Ser Tyr Gly Phe Leu Phe Pro Pro
                    725                 730                 735

Tyr Leu Ser Ser Ser Pro Glu Ala Lys Tyr Asp Ala Phe Leu Val Thr
                    740                 745                 750

Asn Met Val Pro Met Tyr Pro Ala Phe Lys Arg Val Trp Asn Tyr Phe
                    755                 760                 765

Gln Arg Val Leu Val Lys Lys Tyr Ala Ser Glu Arg Asn Gly Val Asn
                    770                 775                 780

Val Ile Ser Gly Pro Ile Phe Asp Tyr Asp Tyr Asp Gly Leu His Asp
785                 790                 795                 800

Thr Glu Asp Lys Ile Lys Gln Tyr Val Glu Gly Ser Ser Ile Pro Val
                    805                 810                 815
```

```
Pro Thr His Tyr Tyr Ser Ile Ile Thr Ser Cys Leu Asp Phe Thr Gln
            820                 825                 830

Pro Ala Asp Lys Cys Asp Gly Pro Leu Ser Val Ser Ser Phe Ile Leu
        835                 840                 845

Pro His Arg Pro Asp Asn Glu Glu Ser Cys Asn Ser Ser Glu Asp Glu
    850                 855                 860

Ser Lys Trp Val Glu Glu Leu Met Lys Met His Thr Ala Arg Val Arg
865                 870                 875                 880

Asp Ile Glu His Leu Thr Ser Leu Asp Phe Phe Arg Lys Thr Ser Arg
                885                 890                 895

Ser Tyr Pro Glu Ile Leu Thr Leu Lys Thr Tyr Leu His Thr Tyr Glu
            900                 905                 910

Ser Glu Ile
        915

<210> SEQ ID NO 60
<211> LENGTH: 626
<212> TYPE: PRT
<213> ORGANISM: Homo sapiens

<400> SEQUENCE: 60

Met Asp Glu Gln Glu Ala Leu Asn Ser Ile Met Asn Asp Leu Val Ala
1               5                   10                  15

Leu Gln Met Asn Arg Arg His Arg Met Pro Gly Tyr Glu Thr Met Lys
            20                  25                  30

Asn Lys Asp Thr Gly His Ser Asn Arg Gln Ser Asp Val Arg Ile Lys
        35                  40                  45

Phe Glu His Asn Gly Glu Arg Arg Ile Ile Ala Phe Ser Arg Pro Val
    50                  55                  60

Lys Tyr Glu Asp Val Glu His Lys Val Thr Thr Val Phe Gly Gln Pro
65                  70                  75                  80

Leu Asp Leu His Tyr Met Asn Asn Glu Leu Ser Ile Leu Leu Lys Asn
                85                  90                  95

Gln Asp Asp Leu Asp Lys Ala Ile Asp Ile Leu Asp Arg Ser Ser Ser
            100                 105                 110

Met Lys Ser Leu Arg Ile Leu Leu Leu Ser Gln Asp Arg Asn His Asn
        115                 120                 125

Ser Ser Ser Pro His Ser Gly Val Ser Arg Gln Val Arg Ile Lys Ala
    130                 135                 140

Ser Gln Ser Ala Gly Asp Ile Asn Thr Ile Tyr Gln Pro Pro Glu Pro
145                 150                 155                 160

Arg Ser Arg His Leu Ser Val Ser Ser Gln Asn Pro Gly Arg Ser Ser
                165                 170                 175

Pro Pro Pro Gly Tyr Val Pro Glu Arg Gln Gln His Ile Ala Arg Gln
            180                 185                 190

Gly Ser Tyr Thr Ser Ile Asn Ser Glu Gly Glu Phe Ile Pro Glu Thr
        195                 200                 205

Ser Glu Gln Cys Met Leu Asp Pro Leu Ser Ser Ala Glu Asn Ser Leu
    210                 215                 220

Ser Gly Ser Cys Gln Ser Leu Asp Arg Ser Ala Asp Ser Pro Ser Phe
225                 230                 235                 240

Arg Lys Ser Arg Met Ser Arg Ala Gln Ser Phe Pro Asp Asn Arg Gln
                245                 250                 255

Glu Tyr Ser Asp Arg Glu Thr Gln Leu Tyr Asp Lys Gly Val Lys Gly
            260                 265                 270
```

```
Gly Thr Tyr Pro Arg Arg Tyr His Val Ser Val His Lys Asp Tyr
            275                 280                 285

Ser Asp Gly Arg Arg Thr Phe Pro Arg Ile Arg Arg His Gln Gly Asn
    290                 295                 300

Leu Phe Thr Leu Val Pro Ser Ser Arg Ser Leu Ser Thr Asn Gly Glu
305                 310                 315                 320

Asn Met Gly Leu Ala Val Gln Tyr Leu Asp Pro Arg Gly Arg Leu Arg
                325                 330                 335

Ser Ala Asp Ser Glu Asn Ala Leu Ser Val Gln Glu Arg Asn Val Pro
                340                 345                 350

Thr Lys Ser Pro Ser Ala Pro Ile Asn Trp Arg Arg Gly Lys Leu Leu
            355                 360                 365

Gly Gln Gly Ala Phe Gly Arg Val Tyr Leu Cys Tyr Asp Val Asp Thr
    370                 375                 380

Gly Arg Glu Leu Ala Ser Lys Gln Val Gln Phe Asp Pro Asp Ser Pro
385                 390                 395                 400

Glu Thr Ser Lys Glu Val Ser Ala Leu Glu Cys Glu Ile Gln Leu Leu
                405                 410                 415

Lys Asn Leu Gln His Glu Arg Ile Val Gln Tyr Tyr Gly Cys Leu Arg
                420                 425                 430

Asp Arg Ala Glu Lys Thr Leu Thr Ile Phe Met Glu Tyr Met Pro Gly
            435                 440                 445

Gly Ser Val Lys Asp Gln Leu Lys Ala Tyr Gly Ala Leu Thr Glu Ser
    450                 455                 460

Val Thr Arg Lys Tyr Thr Arg Gln Ile Leu Glu Gly Met Ser Tyr Leu
465                 470                 475                 480

His Ser Asn Met Ile Val His Arg Asp Ile Lys Gly Ala Asn Ile Leu
                485                 490                 495

Arg Asp Ser Ala Gly Asn Val Lys Leu Gly Asp Phe Gly Ala Ser Lys
            500                 505                 510

Arg Leu Gln Thr Ile Cys Met Ser Gly Thr Gly Met Arg Ser Val Thr
    515                 520                 525

Gly Thr Pro Tyr Trp Met Ser Pro Glu Val Ile Ser Gly Glu Gly Tyr
530                 535                 540

Gly Arg Lys Ala Asp Val Trp Ser Leu Gly Cys Thr Val Val Glu Met
545                 550                 555                 560

Leu Thr Glu Lys Pro Pro Trp Ala Glu Tyr Glu Ala Met Ala Ala Ile
                565                 570                 575

Phe Lys Ile Ala Thr Gln Pro Thr Asn Pro Gln Leu Pro Ser His Ile
                580                 585                 590

Ser Glu His Gly Arg Asp Phe Leu Arg Arg Ile Phe Val Glu Ala Arg
            595                 600                 605

Gln Arg Pro Ser Ala Glu Glu Leu Leu Thr His His Phe Ala Gln Leu
    610                 615                 620

Met Tyr
625

<210> SEQ ID NO 61
<211> LENGTH: 657
<212> TYPE: PRT
<213> ORGANISM: Homo sapiens

<400> SEQUENCE: 61

Met Asp Glu Gln Glu Ala Leu Asn Ser Ile Met Asn Asp Leu Val Ala
1               5                   10                  15
```

-continued

```
Leu Gln Met Asn Arg Arg His Arg Met Pro Gly Tyr Glu Thr Met Lys
         20                  25                  30
Asn Lys Asp Thr Gly His Ser Asn Arg Gln Lys Lys His Asn Ser Ser
             35                  40                  45
Ser Ser Ala Leu Leu Asn Ser Pro Thr Val Thr Ser Ser Cys Ala
 50                  55                  60
Gly Ala Ser Glu Lys Lys Lys Phe Leu Ser Asp Val Arg Ile Lys Phe
 65                  70                  75                  80
Glu His Asn Gly Glu Arg Arg Ile Ile Ala Phe Ser Arg Pro Val Lys
                 85                  90                  95
Tyr Glu Asp Val Glu His Lys Val Thr Thr Val Phe Gly Gln Pro Leu
             100                 105                 110
Asp Leu His Tyr Met Asn Asn Glu Leu Ser Ile Leu Leu Lys Asn Gln
         115                 120                 125
Asp Asp Leu Asp Lys Ala Ile Asp Ile Leu Asp Arg Ser Ser Ser Met
         130                 135                 140
Lys Ser Leu Arg Ile Leu Leu Leu Ser Gln Asp Arg Asn His Asn Ser
145                 150                 155                 160
Ser Ser Pro His Ser Gly Val Ser Arg Gln Val Arg Ile Lys Ala Ser
                 165                 170                 175
Gln Ser Ala Gly Asp Ile Asn Thr Ile Tyr Gln Pro Pro Glu Pro Arg
             180                 185                 190
Ser Arg His Leu Ser Val Ser Ser Gln Asn Pro Gly Arg Ser Ser Pro
         195                 200                 205
Pro Pro Gly Tyr Val Pro Glu Arg Gln Gln His Ile Ala Arg Gln Gly
         210                 215                 220
Ser Tyr Thr Ser Ile Asn Ser Glu Gly Glu Phe Ile Pro Glu Thr Ser
225                 230                 235                 240
Glu Gln Cys Met Leu Asp Pro Leu Ser Ser Ala Glu Asn Ser Leu Ser
                 245                 250                 255
Gly Ser Cys Gln Ser Leu Asp Arg Ser Ala Asp Ser Pro Ser Phe Arg
             260                 265                 270
Lys Ser Arg Met Ser Arg Ala Gln Ser Phe Pro Asp Asn Arg Gln Glu
         275                 280                 285
Tyr Ser Asp Arg Glu Thr Gln Leu Tyr Asp Lys Gly Val Lys Gly Gly
         290                 295                 300
Thr Tyr Pro Arg Arg Tyr His Val Ser Val His His Lys Asp Tyr Ser
305                 310                 315                 320
Asp Gly Arg Arg Thr Phe Pro Arg Ile Arg Arg His Gln Gly Asn Leu
                 325                 330                 335
Phe Thr Leu Val Pro Ser Ser Arg Ser Leu Ser Thr Asn Gly Glu Asn
             340                 345                 350
Met Gly Leu Ala Val Gln Tyr Leu Asp Pro Arg Gly Arg Leu Arg Ser
         355                 360                 365
Ala Asp Ser Glu Asn Ala Leu Ser Val Gln Glu Arg Asn Val Pro Thr
         370                 375                 380
Lys Ser Pro Ser Ala Pro Ile Asn Trp Arg Arg Gly Lys Leu Leu Gly
385                 390                 395                 400
Gln Gly Ala Phe Gly Arg Val Tyr Leu Cys Tyr Asp Val Asp Thr Gly
                 405                 410                 415
Arg Glu Leu Ala Ser Lys Gln Val Gln Phe Asp Pro Asp Ser Pro Glu
             420                 425                 430
Thr Ser Lys Glu Val Ser Ala Leu Glu Cys Glu Ile Gln Leu Leu Lys
         435                 440                 445
```

```
Asn Leu Gln His Glu Arg Ile Val Gln Tyr Tyr Gly Cys Leu Arg Asp
    450                 455                 460

Arg Ala Glu Lys Thr Leu Thr Ile Phe Met Glu Tyr Met Pro Gly Gly
465                 470                 475                 480

Ser Val Lys Asp Gln Leu Lys Ala Tyr Gly Ala Leu Thr Glu Ser Val
                485                 490                 495

Thr Arg Lys Tyr Thr Arg Gln Ile Leu Glu Gly Met Ser Tyr Leu His
            500                 505                 510

Ser Asn Met Ile Val His Arg Asp Ile Lys Gly Ala Asn Ile Leu Arg
        515                 520                 525

Asp Ser Ala Gly Asn Val Lys Leu Gly Asp Phe Gly Ala Ser Lys Arg
530                 535                 540

Leu Gln Thr Ile Cys Met Ser Gly Thr Gly Met Arg Ser Val Thr Gly
545                 550                 555                 560

Thr Pro Tyr Trp Met Ser Pro Glu Val Ile Ser Gly Glu Gly Tyr Gly
                565                 570                 575

Arg Lys Ala Asp Val Trp Ser Leu Gly Cys Thr Val Val Glu Met Leu
            580                 585                 590

Thr Glu Lys Pro Pro Trp Ala Glu Tyr Glu Ala Met Ala Ala Ile Phe
        595                 600                 605

Lys Ile Ala Thr Gln Pro Thr Asn Pro Gln Leu Pro Ser His Ile Ser
610                 615                 620

Glu His Gly Arg Asp Phe Leu Arg Arg Ile Phe Val Glu Ala Arg Gln
625                 630                 635                 640

Arg Pro Ser Ala Glu Glu Leu Leu Thr His Phe Ala Gln Leu Met
                645                 650                 655
Tyr

<210> SEQ ID NO 62
<211> LENGTH: 338
<212> TYPE: PRT
<213> ORGANISM: Homo sapiens

<400> SEQUENCE: 62

Met Ile Asn Ser Thr Ser Thr Gln Pro Pro Asp Glu Ser Cys Ser Gln
1               5                   10                  15

Asn Leu Leu Ile Thr Gln Gln Ile Ile Pro Val Leu Tyr Cys Met Val
                20                  25                  30

Phe Ile Ala Gly Ile Leu Leu Asn Gly Val Ser Gly Trp Ile Phe Phe
            35                  40                  45

Tyr Val Pro Ser Ser Lys Ser Phe Ile Ile Tyr Leu Lys Asn Ile Val
    50                  55                  60

Ile Ala Asp Phe Val Met Ser Leu Thr Phe Pro Phe Lys Ile Leu Gly
65                  70                  75                  80

Asp Ser Gly Leu Gly Pro Trp Gln Leu Asn Val Phe Val Cys Arg Val
                85                  90                  95

Ser Ala Val Leu Phe Tyr Val Asn Met Tyr Val Ser Ile Val Phe Phe
            100                 105                 110

Gly Leu Ile Ser Phe Asp Arg Tyr Tyr Lys Ile Val Lys Pro Leu Trp
        115                 120                 125

Thr Ser Phe Ile Gln Ser Val Ser Tyr Ser Lys Leu Leu Ser Val Ile
    130                 135                 140

Val Trp Met Leu Met Leu Leu Leu Ala Val Pro Asn Ile Ile Leu Thr
145                 150                 155                 160
```

```
Asn Gln Ser Val Arg Glu Val Thr Gln Ile Lys Cys Ile Glu Leu Lys
            165                 170                 175

Ser Glu Leu Gly Arg Lys Trp His Lys Ala Ser Asn Tyr Ile Phe Val
            180                 185                 190

Ala Ile Phe Trp Ile Val Phe Leu Leu Ile Val Phe Tyr Thr Ala
            195                 200                 205

Ile Thr Lys Lys Ile Phe Lys Ser His Leu Lys Ser Ser Arg Asn Ser
210                 215                 220

Thr Ser Val Lys Lys Ser Ser Arg Asn Ile Phe Ser Ile Val Phe
225             230                 235                 240

Val Phe Phe Val Cys Phe Val Pro Tyr His Ile Ala Arg Ile Pro Tyr
                245                 250                 255

Thr Lys Ser Gln Thr Glu Ala His Tyr Ser Cys Gln Ser Lys Glu Ile
            260                 265                 270

Leu Arg Tyr Met Lys Glu Phe Thr Leu Leu Ser Ala Ala Asn Val
            275                 280                 285

Cys Leu Asp Pro Ile Ile Tyr Phe Phe Leu Cys Gln Pro Phe Arg Glu
            290                 295                 300

Ile Leu Cys Lys Lys Leu His Ile Pro Leu Lys Ala Gln Asn Asp Leu
305                 310                 315                 320

Asp Ile Ser Arg Ile Lys Arg Gly Asn Thr Thr Leu Glu Ser Thr Asp
                325                 330                 335

Thr Leu

<210> SEQ ID NO 63
<211> LENGTH: 506
<212> TYPE: PRT
<213> ORGANISM: Homo sapiens

<400> SEQUENCE: 63

Met Asp Asp Tyr Met Val Leu Arg Met Ile Gly Glu Gly Ser Phe Gly
1               5                   10                  15

Arg Ala Leu Leu Val Gln His Glu Ser Ser Asn Gln Met Phe Ala Met
            20                  25                  30

Lys Glu Ile Arg Leu Pro Lys Ser Phe Ser Asn Thr Gln Asn Ser Arg
        35                  40                  45

Lys Glu Ala Val Leu Leu Ala Lys Met Lys His Pro Asn Ile Val Ala
    50                  55                  60

Phe Lys Glu Ser Phe Glu Ala Glu Gly His Leu Tyr Ile Val Met Glu
65                  70                  75                  80

Tyr Cys Asp Gly Gly Asp Leu Met Gln Lys Ile Lys Gln Gln Lys Gly
                85                  90                  95

Lys Leu Phe Pro Glu Asp Met Ile Leu Asn Trp Phe Thr Gln Met Cys
            100                 105                 110

Leu Gly Val Asn His Ile His Lys Lys Arg Val Leu His Arg Asp Ile
        115                 120                 125

Lys Ser Lys Asn Ile Phe Leu Thr Gln Asn Gly Lys Val Lys Leu Gly
    130                 135                 140

Asp Phe Gly Ser Ala Arg Leu Leu Ser Asn Pro Met Ala Phe Ala Cys
145                 150                 155                 160

Thr Tyr Val Gly Thr Pro Tyr Tyr Val Pro Pro Glu Ile Trp Glu Asn
                165                 170                 175

Leu Pro Tyr Asn Asn Lys Ser Asp Ile Trp Ser Leu Gly Cys Ile Leu
            180                 185                 190

Tyr Glu Leu Cys Thr Leu Lys His Pro Phe Gln Ala Asn Ser Trp Lys
```

```
                195                 200                 205
Asn Leu Ile Leu Lys Val Cys Gln Gly Cys Ile Ser Pro Leu Pro Ser
210                 215                 220

His Tyr Ser Tyr Glu Leu Gln Phe Leu Val Lys Gln Met Phe Lys Arg
225                 230                 235                 240

Asn Pro Ser His Arg Pro Ser Ala Thr Thr Leu Leu Ser Arg Gly Ile
            245                 250                 255

Val Ala Arg Leu Val Gln Lys Cys Leu Pro Pro Glu Ile Ile Met Glu
        260                 265                 270

Tyr Gly Glu Glu Val Leu Glu Glu Ile Lys Asn Ser Lys His Asn Thr
    275                 280                 285

Pro Arg Lys Lys Thr Asn Pro Ser Arg Ile Arg Ile Ala Leu Gly Asn
290                 295                 300

Glu Ala Ser Thr Val Gln Glu Glu Gln Asp Arg Lys Gly Ser His
305                 310                 315                 320

Thr Asp Leu Glu Ser Ile Asn Glu Asn Leu Val Glu Ser Ala Leu Arg
            325                 330                 335

Arg Val Asn Arg Glu Glu Lys Gly Asn Lys Ser Val His Leu Arg Lys
        340                 345                 350

Ala Ser Ser Pro Asn Leu His Arg Arg Gln Trp Glu Lys Asn Val Pro
    355                 360                 365

Asn Thr Ala Leu Thr Ala Leu Glu Asn Ala Ser Ile Leu Thr Ser Ser
370                 375                 380

Leu Thr Ala Glu Asp Asp Arg Gly Gly Ser Val Ile Lys Tyr Ser Lys
385                 390                 395                 400

Asn Thr Thr Arg Lys Gln Trp Leu Lys Glu Thr Pro Asp Thr Leu Leu
            405                 410                 415

Asn Ile Leu Lys Asn Ala Asp Leu Ser Leu Ala Phe Gln Thr Tyr Thr
        420                 425                 430

Ile Tyr Arg Pro Gly Ser Glu Gly Phe Leu Lys Gly Pro Leu Ser Glu
    435                 440                 445

Glu Thr Glu Ala Ser Asp Ser Val Asp Gly Gly His Asp Ser Val Ile
450                 455                 460

Leu Asp Pro Glu Arg Leu Glu Pro Gly Leu Glu Glu Asp Thr Asp
465                 470                 475                 480

Phe Glu Glu Glu Asp Asp Asn Pro Asp Trp Val Ser Glu Leu Lys Lys
            485                 490                 495

Arg Ala Gly Trp Gln Gly Leu Cys Asp Arg
        500                 505

<210> SEQ ID NO 64
<211> LENGTH: 506
<212> TYPE: PRT
<213> ORGANISM: Homo sapiens

<400> SEQUENCE: 64

Met Asp Asp Tyr Met Val Leu Arg Met Ile Gly Glu Gly Ser Phe Gly
1               5                   10                  15

Arg Ala Leu Leu Val Gln His Glu Ser Ser Asn Gln Met Phe Ala Met
            20                  25                  30

Lys Glu Ile Arg Leu Pro Lys Ser Phe Ser Asn Thr Gln Asn Ser Arg
        35                  40                  45

Lys Glu Ala Val Leu Leu Ala Lys Met Lys His Pro Asn Ile Val Ala
    50                  55                  60

Phe Lys Glu Ser Phe Glu Ala Glu Gly His Leu Tyr Ile Val Met Glu
```

```
                65                  70                  75                  80
Tyr Cys Asp Gly Gly Asp Leu Met Gln Lys Ile Lys Gln Gln Lys Gly
                    85                  90                  95
Lys Leu Phe Pro Glu Asp Met Ile Leu Asn Trp Phe Thr Gln Met Cys
                    100                 105                 110
Leu Gly Val Asn His Ile His Lys Lys Arg Val Leu His Arg Asp Ile
                    115                 120                 125
Lys Ser Lys Asn Ile Phe Leu Thr Gln Asn Gly Lys Val Lys Leu Gly
                    130                 135                 140
Asp Phe Gly Ser Ala Arg Leu Leu Ser Asn Pro Met Ala Phe Ala Cys
145                 150                 155                 160
Thr Tyr Val Gly Thr Pro Tyr Tyr Val Pro Pro Glu Ile Trp Glu Asn
                    165                 170                 175
Leu Pro Tyr Asn Asn Lys Ser Asp Ile Trp Ser Leu Gly Cys Ile Leu
                    180                 185                 190
Tyr Glu Leu Cys Thr Leu Lys His Pro Phe Gln Ala Asn Ser Trp Lys
                    195                 200                 205
Asn Leu Ile Leu Lys Val Cys Gln Gly Cys Ile Ser Pro Leu Pro Ser
210                 215                 220
His Tyr Ser Tyr Glu Leu Gln Phe Leu Val Lys Gln Met Phe Lys Arg
225                 230                 235                 240
Asn Pro Ser His Arg Pro Ser Ala Thr Thr Leu Leu Ser Arg Gly Ile
                    245                 250                 255
Val Ala Arg Leu Val Gln Lys Cys Leu Pro Pro Glu Ile Ile Met Glu
                    260                 265                 270
Tyr Gly Glu Glu Val Leu Glu Glu Ile Lys Asn Ser Lys His Asn Thr
                    275                 280                 285
Pro Arg Lys Lys Thr Asn Pro Ser Arg Ile Arg Ile Ala Leu Gly Asn
                    290                 295                 300
Glu Ala Ser Thr Val Gln Glu Glu Gln Asp Arg Lys Gly Ser His
305                 310                 315                 320
Thr Asp Leu Glu Ser Ile Asn Glu Asn Leu Val Glu Ser Ala Leu Arg
                    325                 330                 335
Arg Val Asn Arg Glu Glu Lys Gly Asn Lys Ser Val His Leu Arg Lys
                    340                 345                 350
Ala Ser Ser Pro Asn Leu His Arg Arg Gln Trp Glu Lys Asn Val Pro
                    355                 360                 365
Asn Thr Ala Leu Thr Ala Leu Glu Asn Ala Ser Ile Leu Thr Ser Ser
                    370                 375                 380
Leu Thr Ala Glu Asp Asp Arg Gly Gly Ser Val Ile Lys Tyr Ser Lys
385                 390                 395                 400
Asn Thr Thr Arg Lys Gln Trp Leu Lys Glu Thr Pro Asp Thr Leu Leu
                    405                 410                 415
Asn Ile Leu Lys Asn Ala Asp Leu Ser Leu Ala Phe Gln Thr Tyr Thr
                    420                 425                 430
Ile Tyr Arg Pro Gly Ser Glu Gly Phe Leu Lys Gly Pro Leu Ser Glu
                    435                 440                 445
Glu Thr Glu Ala Ser Asp Ser Val Asp Gly His Asp Ser Val Ile
                    450                 455                 460
Leu Asp Pro Glu Arg Leu Glu Pro Gly Leu Asp Glu Asp Thr Asp
465                 470                 475                 480
Phe Glu Glu Glu Asp Asp Asn Pro Asp Trp Val Ser Glu Leu Lys Lys
                    485                 490                 495
```

Arg Ala Gly Trp Gln Gly Leu Cys Asp Arg
            500                 505

<210> SEQ ID NO 65
<211> LENGTH: 638
<212> TYPE: PRT
<213> ORGANISM: Homo sapiens

<400> SEQUENCE: 65

Met Ile Leu Phe Lys Gln Ala Thr Tyr Phe Ile Ser Leu Phe Ala Thr
1               5                   10                  15

Val Ser Cys Gly Cys Leu Thr Gln Leu Tyr Glu Asn Ala Phe Phe Arg
            20                  25                  30

Gly Gly Asp Val Ala Ser Met Tyr Thr Pro Asn Ala Gln Tyr Cys Gln
        35                  40                  45

Met Arg Cys Thr Phe His Pro Arg Cys Leu Leu Phe Ser Phe Leu Pro
    50                  55                  60

Ala Ser Ser Ile Asn Asp Met Glu Lys Arg Phe Gly Cys Phe Leu Lys
65                  70                  75                  80

Asp Ser Val Thr Gly Thr Leu Pro Lys Val His Arg Thr Gly Ala Val
                85                  90                  95

Ser Gly His Ser Leu Lys Gln Cys Gly His Gln Ile Ser Ala Cys His
            100                 105                 110

Arg Asp Ile Tyr Lys Gly Val Asp Met Arg Gly Val Asn Phe Asn Val
        115                 120                 125

Ser Lys Val Ser Ser Val Glu Glu Cys Gln Lys Arg Cys Thr Ser Asn
130                 135                 140

Ile Arg Cys Gln Phe Phe Ser Tyr Ala Thr Gln Thr Phe His Lys Ala
145                 150                 155                 160

Glu Tyr Arg Asn Asn Cys Leu Leu Lys Tyr Ser Pro Gly Gly Thr Pro
                165                 170                 175

Thr Ala Ile Lys Val Leu Ser Asn Val Glu Ser Gly Phe Ser Leu Lys
            180                 185                 190

Pro Cys Ala Leu Ser Glu Ile Gly Cys His Met Asn Ile Phe Gln His
        195                 200                 205

Leu Ala Phe Ser Asp Val Asp Val Ala Arg Val Leu Thr Pro Asp Ala
    210                 215                 220

Phe Val Cys Arg Thr Ile Cys Thr Tyr His Pro Asn Cys Leu Phe Phe
225                 230                 235                 240

Thr Phe Tyr Thr Asn Val Trp Lys Ile Glu Ser Gln Arg Asn Val Cys
                245                 250                 255

Leu Leu Lys Thr Ser Glu Ser Gly Thr Pro Ser Ser Thr Pro Gln
            260                 265                 270

Glu Asn Thr Ile Ser Gly Tyr Ser Leu Leu Thr Cys Lys Arg Thr Leu
        275                 280                 285

Pro Glu Pro Cys His Ser Lys Ile Tyr Pro Gly Val Asp Phe Gly Gly
    290                 295                 300

Glu Glu Leu Asn Val Thr Phe Val Lys Gly Val Asn Val Cys Gln Glu
305                 310                 315                 320

Thr Cys Thr Lys Met Ile Arg Cys Gln Phe Phe Thr Tyr Ser Leu Leu
                325                 330                 335

Pro Glu Asp Cys Lys Glu Lys Cys Lys Cys Phe Leu Arg Leu Ser
            340                 345                 350

Met Asp Gly Ser Pro Thr Arg Ile Ala Tyr Gly Thr Gln Gly Ser Ser
        355                 360                 365

```
Gly Tyr Ser Leu Arg Leu Cys Asn Thr Gly Asp Asn Ser Val Cys Thr
        370                 375                 380

Thr Lys Thr Ser Thr Arg Ile Val Gly Gly Thr Asn Ser Ser Trp Gly
385                 390                 395                 400

Glu Trp Pro Trp Gln Val Ser Leu Gln Val Lys Leu Thr Ala Gln Arg
                405                 410                 415

His Leu Cys Gly Gly Ser Leu Ile Gly His Gln Trp Val Leu Thr Ala
            420                 425                 430

Ala His Cys Phe Asp Gly Leu Pro Leu Gln Asp Val Trp Arg Ile Tyr
        435                 440                 445

Ser Gly Ile Leu Asn Leu Ser Asp Ile Thr Lys Asp Thr Pro Phe Ser
450                 455                 460

Gln Ile Lys Glu Ile Ile Ile His Gln Asn Tyr Lys Val Ser Glu Gly
465                 470                 475                 480

Asn His Asp Ile Ala Leu Ile Lys Leu Gln Ala Pro Leu Asn Tyr Thr
                485                 490                 495

Glu Phe Gln Lys Pro Ile Cys Leu Pro Ser Lys Gly Asp Thr Ser Thr
                500                 505                 510

Ile Tyr Thr Asn Cys Trp Val Thr Gly Trp Gly Phe Ser Lys Glu Lys
                515                 520                 525

Gly Glu Ile Gln Asn Ile Leu Gln Lys Val Asn Ile Pro Leu Val Thr
530                 535                 540

Asn Glu Glu Cys Gln Lys Arg Tyr Gln Asp Tyr Lys Ile Thr Gln Arg
545                 550                 555                 560

Met Val Cys Ala Gly Tyr Lys Glu Gly Lys Asp Ala Cys Lys Gly
                565                 570                 575

Asp Ser Gly Gly Pro Leu Val Cys Lys His Asn Gly Met Trp Arg Leu
                580                 585                 590

Val Gly Ile Thr Ser Trp Gly Glu Gly Cys Ala Arg Arg Glu Gln Pro
                595                 600                 605

Gly Val Tyr Thr Lys Val Ala Glu Tyr Met Asp Trp Ile Leu Glu Lys
            610                 615                 620

Thr Gln Ser Ser Asp Gly Lys Ala Gln Met Gln Ser Pro Ala
625                 630                 635

<210> SEQ ID NO 66
<211> LENGTH: 379
<212> TYPE: PRT
<213> ORGANISM: Homo sapiens

<400> SEQUENCE: 66

Met Ala Ala Thr Glu Gly Val Gly Glu Ala Ala Gln Gly Gly Glu Pro
1               5                   10                  15

Gly Gln Pro Ala Gln Pro Pro Gln Pro His Pro Pro Pro Pro Gln
            20                  25                  30

Gln Gln His Lys Glu Glu Met Ala Ala Glu Ala Gly Glu Ala Val Ala
        35                  40                  45

Ser Pro Met Asp Asp Gly Phe Val Ser Leu Asp Ser Pro Ser Tyr Val
    50                  55                  60

Leu Tyr Arg Asp Arg Ala Glu Trp Ala Asp Ile Asp Pro Val Pro Gln
65                  70                  75                  80

Asn Asp Gly Pro Asn Pro Val Val Gln Ile Ile Tyr Ser Asp Lys Phe
                85                  90                  95

Arg Asp Val Tyr Asp Tyr Phe Arg Ala Val Leu Gln Arg Asp Glu Arg
                100                 105                 110
```

```
Ser Glu Arg Ala Phe Lys Leu Thr Arg Asp Ala Ile Glu Leu Asn Ala
        115                 120                 125

Ala Asn Tyr Thr Val Trp His Phe Arg Arg Val Leu Leu Lys Ser Leu
    130                 135                 140

Gln Lys Asp Leu His Glu Glu Met Asn Tyr Ile Thr Ala Ile Ile Glu
145                 150                 155                 160

Glu Gln Pro Lys Asn Tyr Gln Val Trp His His Arg Arg Val Leu Val
                165                 170                 175

Glu Trp Leu Arg Asp Pro Ser Gln Glu Leu Glu Phe Ile Ala Asp Ile
            180                 185                 190

Leu Asn Gln Asp Ala Lys Asn Tyr His Ala Trp Gln His Arg Gln Trp
        195                 200                 205

Val Ile Gln Glu Phe Lys Leu Trp Asp Asn Glu Leu Gln Tyr Val Asp
    210                 215                 220

Gln Leu Leu Lys Glu Asp Val Arg Asn Asn Ser Val Trp Asn Gln Arg
225                 230                 235                 240

Tyr Phe Val Ile Ser Asn Thr Thr Gly Tyr Asn Asp Arg Ala Val Leu
                245                 250                 255

Glu Arg Glu Val Gln Tyr Thr Leu Glu Met Ile Lys Leu Val Pro His
            260                 265                 270

Asn Glu Ser Ala Trp Asn Tyr Leu Lys Gly Ile Leu Gln Asp Arg Gly
        275                 280                 285

Leu Ser Lys Tyr Pro Asn Leu Leu Asn Gln Leu Leu Asp Leu Gln Pro
    290                 295                 300

Ser His Ser Ser Pro Tyr Leu Ile Ala Phe Leu Val Asp Ile Tyr Glu
305                 310                 315                 320

Asp Met Leu Glu Asn Gln Cys Asp Asn Lys Glu Asp Ile Leu Asn Lys
                325                 330                 335

Ala Leu Glu Leu Cys Glu Ile Leu Ala Lys Glu Lys Asp Thr Ile Arg
            340                 345                 350

Lys Glu Tyr Trp Arg Tyr Ile Gly Arg Ser Leu Gln Ser Lys His Ser
        355                 360                 365

Thr Glu Asn Asp Ser Pro Thr Asn Val Gln Gln
    370                 375

<210> SEQ ID NO 67
<211> LENGTH: 288
<212> TYPE: PRT
<213> ORGANISM: Homo sapiens

<400> SEQUENCE: 67

Met Ser Cys Thr Val Arg Asp Val Tyr Asp Tyr Phe Arg Ala Val Leu
1               5                   10                  15

Gln Arg Asp Glu Arg Ser Glu Arg Ala Phe Lys Leu Thr Arg Asp Ala
            20                  25                  30

Ile Glu Leu Asn Ala Ala Asn Tyr Thr Val Trp His Phe Arg Arg Val
        35                  40                  45

Leu Leu Lys Ser Leu Gln Lys Asp Leu His Glu Glu Met Asn Tyr Ile
    50                  55                  60

Thr Ala Ile Ile Glu Glu Gln Pro Lys Asn Tyr Gln Val Trp His His
65                  70                  75                  80

Arg Arg Val Leu Val Glu Trp Leu Arg Asp Pro Ser Gln Glu Leu Glu
                85                  90                  95

Phe Ile Ala Asp Ile Leu Asn Gln Asp Ala Lys Asn Tyr His Ala Trp
            100                 105                 110
```

```
Gln His Arg Gln Trp Val Ile Gln Glu Phe Lys Leu Trp Asp Asn Glu
        115                 120                 125
Leu Gln Tyr Val Asp Gln Leu Leu Lys Glu Asp Val Arg Asn Asn Ser
130                 135                 140
Val Trp Asn Gln Arg Tyr Phe Val Ile Ser Asn Thr Thr Gly Tyr Asn
145                 150                 155                 160
Asp Arg Ala Val Leu Glu Arg Glu Val Gln Tyr Thr Leu Glu Met Ile
                165                 170                 175
Lys Leu Val Pro His Asn Glu Ser Ala Trp Asn Tyr Leu Lys Gly Ile
            180                 185                 190
Leu Gln Asp Arg Gly Leu Ser Lys Tyr Pro Asn Leu Leu Asn Gln Leu
        195                 200                 205
Leu Asp Leu Gln Pro Ser His Ser Ser Pro Tyr Leu Ile Ala Phe Leu
210                 215                 220
Val Asp Ile Tyr Glu Asp Met Leu Glu Asn Gln Cys Asp Asn Lys Glu
225                 230                 235                 240
Asp Ile Leu Asn Lys Ala Leu Glu Leu Cys Glu Ile Leu Ala Lys Glu
                245                 250                 255
Lys Asp Thr Ile Arg Lys Glu Tyr Trp Arg Tyr Ile Gly Arg Ser Leu
            260                 265                 270
Gln Ser Lys His Ser Thr Glu Asn Asp Ser Pro Thr Asn Val Gln Gln
        275                 280                 285

<210> SEQ ID NO 68
<211> LENGTH: 312
<212> TYPE: PRT
<213> ORGANISM: Homo sapiens

<400> SEQUENCE: 68

Met Ala Ala Thr Glu Gly Val Gly Glu Ala Ala Gln Gly Gly Glu Pro
1               5                   10                  15
Gly Gln Pro Ala Gln Pro Pro Gln Pro His Pro Pro Pro Gln
            20                  25                  30
Gln Gln His Lys Glu Glu Met Ala Ala Glu Ala Gly Glu Ala Val Ala
        35                  40                  45
Ser Pro Met Asp Asp Gly Phe Val Ser Leu Asp Ser Pro Ser Tyr Val
    50                  55                  60
Leu Tyr Arg His Phe Arg Val Leu Leu Lys Ser Leu Gln Lys Asp
65                  70                  75                  80
Leu His Glu Glu Met Asn Tyr Ile Thr Ala Ile Ile Glu Glu Gln Pro
                85                  90                  95
Lys Asn Tyr Gln Val Trp His His Arg Arg Val Leu Val Glu Trp Leu
            100                 105                 110
Arg Asp Pro Ser Gln Glu Leu Glu Phe Ile Ala Asp Ile Leu Asn Gln
        115                 120                 125
Asp Ala Lys Asn Tyr His Ala Trp Gln His Arg Gln Trp Val Ile Gln
    130                 135                 140
Glu Phe Lys Leu Trp Asp Asn Glu Leu Gln Tyr Val Asp Gln Leu Leu
145                 150                 155                 160
Lys Glu Asp Val Arg Asn Asn Ser Val Trp Asn Gln Arg Tyr Phe Val
                165                 170                 175
Ile Ser Asn Thr Thr Gly Tyr Asn Asp Arg Ala Val Leu Glu Arg Glu
            180                 185                 190
Val Gln Tyr Thr Leu Glu Met Ile Lys Leu Val Pro His Asn Glu Ser
        195                 200                 205
```

-continued

```
Ala Trp Asn Tyr Leu Lys Gly Ile Leu Gln Asp Arg Gly Leu Ser Lys
    210                 215                 220

Tyr Pro Asn Leu Leu Asn Gln Leu Leu Asp Leu Gln Pro Ser His Ser
225                 230                 235                 240

Ser Pro Tyr Leu Ile Ala Phe Leu Val Asp Ile Tyr Glu Asp Met Leu
                245                 250                 255

Glu Asn Gln Cys Asp Asn Lys Glu Asp Ile Leu Asn Lys Ala Leu Glu
            260                 265                 270

Leu Cys Glu Ile Leu Ala Lys Glu Lys Asp Thr Ile Arg Lys Glu Tyr
        275                 280                 285

Trp Arg Tyr Ile Gly Arg Ser Leu Gln Ser Lys His Ser Thr Glu Asn
    290                 295                 300

Asp Ser Pro Thr Asn Val Gln Gln
305                 310

<210> SEQ ID NO 69
<211> LENGTH: 311
<212> TYPE: PRT
<213> ORGANISM: Homo sapiens
<220> FEATURE:
<221> NAME/KEY: misc_feature
<222> LOCATION: (290)..(290)
<223> OTHER INFORMATION: Xaa can be any naturally occurring amino acid

<400> SEQUENCE: 69

Met Ala Ala Thr Glu Gly Val Gly Glu Ala Gln Gly Gly Glu Pro
1               5                   10                  15

Arg Gln Leu Glu Gln Pro Pro Gln Pro His Pro Leu Pro Gln
            20                  25                  30

Glu Gln His Glu Glu Glu Met Ala Ala Glu Ala Gly Glu Ala Val Ala
            35                  40                  45

Ser Pro Met Asp Asp Gly Phe Leu Ser Leu Asp Ser Pro Ser Tyr Val
    50                  55                  60

Pro Tyr Arg His Phe Arg Arg Val Leu Leu Lys Ser Leu Gln Lys Asp
65                  70                  75                  80

Leu His Glu Glu Met Asn Tyr Ile Thr Glu Ile Glu Gly Gln Pro
                85                  90                  95

Lys Asn Tyr Leu Val Cys His Asn Arg Arg Val Ile Val Glu Trp Leu
            100                 105                 110

Arg Asp Pro Ser Gln Glu Pro Glu Phe Ile Asp Asn Ile Leu Asn Gln
        115                 120                 125

Asp Ala Lys Asn Tyr His Ala Trp Gln His Arg Trp Val Ile Gln
    130                 135                 140

Glu Phe Lys Leu Trp Asp Asn Glu Leu Gln Tyr Val Asp Gln Leu Leu
145                 150                 155                 160

Lys Glu Asp Val Arg Asn Asn Ser Val Trp Asn Arg Arg Tyr Phe Val
                165                 170                 175

Ile Ser Asn Thr Thr Gly Tyr Asn Asp Cys Ala Val Leu Glu Arg Glu
            180                 185                 190

Val Gln Tyr Thr Leu Glu Met Ile Gln Leu Val Pro His Asn Ser Ser
        195                 200                 205

Trp Asn Tyr Leu Lys Gly Ile Leu Gln Asp Arg Gly Leu Ser Lys Tyr
    210                 215                 220

Pro Asn Leu Leu Asn Gln Leu Leu Asp Leu Gln Pro Ser His Ser Ser
225                 230                 235                 240

Pro Tyr Leu Ile Ala Phe Leu Val Gly Ile Tyr Glu Asp Met Leu Glu
                245                 250                 255
```

```
Asn Gln Cys Val Asn Lys Glu Asp Ile Leu Asn Asn Ala Leu Gly Leu
        260                 265                 270

Cys Glu Ile Leu Ala Lys Glu Lys Asp Met Ile Arg Lys Glu Tyr Trp
        275                 280                 285

Arg Xaa Ile Gly Arg Ser Phe Gln Ser Lys His Ser Thr Glu Asn Asp
        290                 295                 300

Ser Pro Thr Asn Val Gln Gln
305                 310

<210> SEQ ID NO 70
<211> LENGTH: 2555
<212> TYPE: PRT
<213> ORGANISM: Homo sapiens

<400> SEQUENCE: 70

Met Thr Ala Ile Thr His Gly Ser Pro Val Gly Gly Asn Asp Ser Gln
1               5                   10                  15

Gly Gln Val Leu Asp Gly Gln Ser Gln His Leu Phe Gln Gln Asn Gln
            20                  25                  30

Thr Ser Ser Pro Asp Ser Ser Asn Glu Asn Ser Val Ala Thr Pro Pro
        35                  40                  45

Pro Glu Glu Gln Gly Gln Gly Asp Ala Pro Gln His Glu Asp Glu
    50                  55                  60

Glu Pro Ala Phe Pro His Thr Glu Leu Ala Asn Leu Asp Asp Met Ile
65                  70                  75                  80

Asn Arg Pro Arg Trp Val Val Pro Val Leu Pro Lys Gly Glu Leu Glu
                85                  90                  95

Val Leu Leu Glu Ala Ala Ile Asp Leu Ser Val Lys Gly Leu Asp Val
            100                 105                 110

Lys Ser Glu Ala Cys Gln Arg Phe Phe Arg Asp Gly Leu Thr Ile Ser
        115                 120                 125

Phe Thr Lys Ile Leu Met Asp Glu Ala Val Ser Gly Trp Lys Phe Glu
    130                 135                 140

Ile His Arg Cys Ile Ile Asn Asn Thr His Arg Leu Val Glu Leu Cys
145                 150                 155                 160

Val Ala Lys Leu Ser Gln Asp Trp Phe Pro Leu Leu Glu Leu Leu Ala
                165                 170                 175

Met Ala Leu Asn Pro His Cys Lys Phe His Ile Tyr Asn Gly Thr Arg
            180                 185                 190

Pro Cys Glu Leu Ile Ser Ser Asn Ala Gln Leu Pro Glu Asp Glu Leu
        195                 200                 205

Phe Ala Arg Ser Ser Asp Pro Arg Ser Pro Lys Gly Trp Leu Val Asp
    210                 215                 220

Leu Ile Asn Lys Phe Gly Thr Leu Asn Gly Phe Gln Ile Leu His Asp
225                 230                 235                 240

Arg Phe Phe Asn Gly Ser Ala Leu Asn Ile Gln Ile Ile Ala Ala Leu
                245                 250                 255

Ile Lys Pro Phe Gly Gln Cys Tyr Glu Phe Leu Ser Gln His Thr Leu
            260                 265                 270

Lys Lys Tyr Phe Ile Pro Val Ile Glu Ile Val Pro His Leu Leu Glu
        275                 280                 285

Asn Leu Thr Asp Glu Glu Leu Lys Lys Glu Ala Lys Asn Glu Ala Lys
    290                 295                 300

Asn Asp Ala Leu Ser Met Ile Ile Lys Ser Leu Lys Asn Leu Ala Ser
305                 310                 315                 320
```

-continued

Arg Ile Ser Gly Gln Asp Glu Thr Ile Lys Asn Leu Glu Ile Phe Arg
                325                 330                 335

Leu Lys Met Ile Leu Arg Leu Leu Gln Ile Ser Ser Phe Asn Gly Lys
            340                 345                 350

Met Asn Ala Leu Asn Glu Ile Asn Lys Val Ile Ser Ser Val Ser Tyr
        355                 360                 365

Tyr Thr His Arg His Ser Asn Pro Glu Glu Glu Trp Leu Thr Ala
    370                 375                 380

Glu Arg Met Ala Glu Trp Ile Gln Gln Asn Asn Ile Leu Ser Ile Val
385                 390                 395                 400

Leu Gln Asp Ser Leu His Gln Pro Gln Tyr Val Lys Leu Glu Lys
            405                 410                 415

Ile Leu Arg Phe Val Ile Lys Glu Lys Ala Leu Thr Leu Gln Asp Leu
            420                 425                 430

Asp Asn Ile Trp Ala Ala Gln Ala Gly Lys His Glu Ala Ile Val Lys
            435                 440                 445

Asn Val His Asp Leu Leu Ala Lys Leu Ala Trp Asp Phe Ser Pro Gly
        450                 455                 460

Gln Leu Asp His Leu Phe Asp Cys Phe Lys Ala Ser Trp Thr Asn Ala
465                 470                 475                 480

Ser Lys Lys Gln Arg Glu Lys Leu Leu Glu Leu Ile Arg Arg Leu Ala
            485                 490                 495

Glu Asp Asp Lys Asp Gly Val Met Ala His Lys Val Leu Asn Leu Leu
            500                 505                 510

Trp Asn Leu Ala Gln Ser Asp Val Pro Val Asp Ile Met Asp Leu
        515                 520                 525

Ala Leu Ser Ala His Ile Lys Ile Leu Asp Tyr Ser Cys Ser Gln Asp
        530                 535                 540

Arg Asp Ala Gln Lys Ile Gln Trp Ile Asp His Phe Ile Glu Glu Leu
545                 550                 555                 560

Arg Thr Asn Asp Lys Trp Val Ile Pro Ala Leu Lys Gln Ile Arg Glu
            565                 570                 575

Ile Cys Ser Leu Phe Gly Glu Ala Ser Gln Asn Leu Ser Gln Thr Gln
            580                 585                 590

Arg Ser Pro His Ile Phe Tyr Arg His Asp Leu Ile Asn Gln Leu Gln
        595                 600                 605

Gln Asn His Ala Leu Val Thr Leu Val Ala Glu Asn Leu Ala Thr Tyr
        610                 615                 620

Met Asn Ser Ile Arg Leu Tyr Ala Gly Asp His Glu Asp Tyr Asp Pro
625                 630                 635                 640

Gln Thr Val Arg Leu Gly Ser Arg Tyr Ser His Val Gln Glu Val Gln
            645                 650                 655

Glu Arg Leu Asn Phe Leu Arg Phe Leu Leu Lys Asp Gly Gln Leu Trp
            660                 665                 670

Leu Cys Ala Pro Gln Ala Lys Gln Ile Trp Lys Cys Leu Ala Glu Asn
            675                 680                 685

Ala Val Tyr Leu Cys Asp Arg Glu Ala Cys Phe Lys Trp Tyr Ser Lys
        690                 695                 700

Leu Met Gly Asp Glu Pro Asp Leu Asp Pro Asp Ile Asn Lys Asp Phe
705                 710                 715                 720

Phe Glu Ser Asn Val Leu Gln Leu Asp Pro Ser Leu Leu Thr Glu Asn
            725                 730                 735

Gly Met Lys Cys Phe Glu Arg Phe Lys Ala Val Asn Cys Arg Glu

```
                    740                 745                 750
Arg Lys Leu Ile Ala Lys Arg Ser Tyr Met Met Asp Asp Leu Glu
            755                 760                 765
Leu Ile Gly Leu Asp Tyr Leu Trp Arg Val Val Ile Gln Ser Ser Asp
        770                 775                 780
Glu Ile Ala Asn Arg Ala Ile Asp Leu Leu Lys Glu Ile Tyr Thr Asn
785                 790                 795                 800
Leu Gly Pro Arg Leu Lys Ala Asn Gln Val Val Ile His Glu Asp Phe
                805                 810                 815
Ile Gln Ser Cys Phe Asp Arg Leu Lys Ala Ser Tyr Asp Thr Leu Cys
            820                 825                 830
Val Phe Asp Gly Asp Lys Asn Ser Ile Asn Cys Ala Arg Gln Glu Ala
            835                 840                 845
Ile Arg Met Val Arg Val Leu Thr Val Ile Lys Glu Tyr Ile Asn Glu
            850                 855                 860
Cys Asp Ser Asp Tyr His Lys Glu Arg Met Ile Leu Pro Met Ser Arg
865                 870                 875                 880
Ala Phe Arg Gly Lys His Leu Ser Leu Ile Val Arg Phe Pro Asn Gln
                885                 890                 895
Gly Arg Gln Val Asp Glu Leu Asp Ile Trp Ser His Thr Asn Asp Thr
            900                 905                 910
Ile Gly Ser Val Arg Arg Cys Ile Val Asn Arg Ile Lys Ala Asn Val
            915                 920                 925
Ala His Lys Lys Ile Glu Leu Phe Val Gly Gly Glu Leu Ile Asp Ser
        930                 935                 940
Glu Asp Asp Arg Lys Leu Ile Gly Gln Leu Asn Leu Lys Asp Lys Ser
945                 950                 955                 960
Leu Ile Thr Ala Lys Leu Thr Gln Ile Asn Phe Asn Met Pro Ser Ser
                965                 970                 975
Pro Asp Ser Ser Ser Asp Ser Ser Thr Ala Ser Pro Gly Asn His Arg
            980                 985                 990
Asn His Tyr Asn Asp Gly Pro Asn Leu Glu Val Glu Ser Cys Leu Pro
        995                 1000                1005
Gly Val Ile Met Ser Val His Pro Arg Tyr Ile Ser Phe Leu Trp
    1010                1015                1020
Gln Val Ala Asp Leu Gly Ser Asn Leu Asn Met Pro Pro Leu Arg
    1025                1030                1035
Asp Gly Ala Arg Val Leu Met Lys Leu Met Pro Pro Asp Arg Thr
    1040                1045                1050
Ala Val Glu Lys Leu Arg Ala Val Cys Leu Asp His Ala Lys Leu
    1055                1060                1065
Gly Glu Gly Lys Leu Ser Pro Pro Leu Asp Ser Leu Phe Phe Gly
    1070                1075                1080
Pro Ser Ala Ser Gln Val Leu Tyr Leu Thr Glu Val Val Tyr Ala
    1085                1090                1095
Leu Leu Met Pro Ala Gly Val Pro Leu Thr Asp Gly Ser Ser Asp
    1100                1105                1110
Phe Gln Val His Phe Leu Lys Ser Gly Gly Leu Pro Leu Val Leu
    1115                1120                1125
Ser Met Leu Ile Arg Asn Asn Phe Leu Pro Asn Thr Asp Met Glu
    1130                1135                1140
Thr Arg Arg Gly Ala Tyr Leu Asn Ala Leu Lys Ile Ala Lys Leu
    1145                1150                1155
```

```
Leu Leu Thr Ala Ile Gly Tyr Gly His Val Arg Ala Val Ala Glu
1160                 1165                 1170

Ala Cys Gln Pro Val Val Asp Gly Thr Asp Pro Ile Thr Gln Ile
1175                 1180                 1185

Asn Gln Val Thr His Asp Gln Ala Val Val Leu Gln Ser Ala Leu
1190                 1195                 1200

Gln Ser Ile Pro Asn Pro Ser Ser Glu Cys Val Leu Arg Asn Glu
1205                 1210                 1215

Ser Ile Leu Leu Ala Gln Glu Ile Ser Asn Glu Ala Ser Arg Tyr
1220                 1225                 1230

Met Pro Asp Ile Cys Val Ile Arg Ala Ile Gln Lys Ile Ile Trp
1235                 1240                 1245

Ala Ser Ala Cys Gly Ala Leu Gly Leu Val Phe Ser Pro Asn Glu
1250                 1255                 1260

Glu Ile Thr Lys Ile Tyr Gln Met Thr Thr Asn Gly Ser Asn Lys
1265                 1270                 1275

Leu Glu Val Glu Asp Glu Gln Val Cys Cys Glu Ala Leu Glu Val
1280                 1285                 1290

Met Thr Leu Cys Phe Ala Leu Leu Pro Thr Ala Leu Asp Ala Leu
1295                 1300                 1305

Ser Lys Glu Lys Ala Trp Gln Thr Phe Ile Ile Asp Leu Leu Leu
1310                 1315                 1320

His Cys Pro Ser Lys Thr Val Arg Gln Leu Ala Gln Glu Gln Phe
1325                 1330                 1335

Phe Leu Met Cys Thr Arg Cys Cys Met Gly His Arg Pro Leu Leu
1340                 1345                 1350

Phe Phe Ile Thr Leu Leu Phe Thr Ile Leu Gly Ser Thr Ala Arg
1355                 1360                 1365

Glu Lys Gly Lys Tyr Ser Gly Asp Tyr Phe Thr Leu Leu Arg His
1370                 1375                 1380

Leu Leu Asn Tyr Ala Tyr Asn Gly Asn Ile Asn Ile Pro Asn Ala
1385                 1390                 1395

Glu Val Leu Leu Val Ser Glu Ile Asp Trp Leu Lys Arg Ile Arg
1400                 1405                 1410

Asp Asn Val Lys Asn Thr Gly Glu Thr Gly Val Glu Glu Pro Ile
1415                 1420                 1425

Leu Glu Gly His Leu Gly Val Thr Lys Glu Leu Leu Ala Phe Gln
1430                 1435                 1440

Thr Ser Glu Lys Lys Tyr His Phe Gly Cys Glu Lys Gly Gly Ala
1445                 1450                 1455

Asn Leu Ile Lys Glu Leu Ile Asp Asp Phe Ile Phe Pro Ala Ser
1460                 1465                 1470

Lys Val Tyr Leu Gln Tyr Leu Arg Ser Gly Glu Leu Pro Ala Glu
1475                 1480                 1485

Gln Ala Ile Pro Val Cys Ser Ser Pro Val Thr Ile Asn Ala Gly
1490                 1495                 1500

Phe Glu Leu Leu Val Ala Leu Ala Ile Gly Cys Val Arg Asn Leu
1505                 1510                 1515

Lys Gln Ile Val Asp Cys Leu Thr Glu Met Tyr Tyr Met Gly Thr
1520                 1525                 1530

Ala Ile Thr Thr Cys Glu Ala Leu Thr Glu Trp Glu Tyr Leu Pro
1535                 1540                 1545

Pro Val Gly Pro Arg Pro Pro Lys Gly Phe Val Gly Leu Lys Asn
1550                 1555                 1560
```

```
Ala Gly Ala Thr Cys Tyr Met Asn Ser Val Ile Gln Gln Leu Tyr
1565                1570                1575

Met Ile Pro Ser Ile Arg Asn Ser Ile Leu Ala Ile Glu Gly Thr
1580                1585                1590

Gly Ser Asp Leu His Asp Asp Met Phe Gly Asp Glu Lys Gln Asp
1595                1600                1605

Ser Glu Ser Asn Val Asp Pro Arg Asp Val Phe Gly Tyr Pro
1610                1615                1620

His Gln Phe Glu Asp Lys Pro Ala Leu Ser Lys Thr Glu Asp Arg
1625                1630                1635

Lys Glu Tyr Asn Ile Gly Val Leu Arg His Leu Gln Val Ile Phe
1640                1645                1650

Gly His Leu Ala Ala Ser Gln Leu Gln Tyr Tyr Val Pro Arg Gly
1655                1660                1665

Phe Trp Lys Gln Phe Arg Leu Trp Gly Glu Pro Val Asn Leu Arg
1670                1675                1680

Glu Gln His Asp Ala Leu Glu Phe Phe Asn Ser Leu Val Asp Ser
1685                1690                1695

Leu Asp Glu Ala Leu Lys Ala Leu Gly His Pro Ala Ile Leu Ser
1700                1705                1710

Lys Val Leu Gly Gly Ser Phe Ala Asp Gln Lys Ile Cys Gln Gly
1715                1720                1725

Cys Pro His Arg Tyr Glu Cys Glu Glu Ser Phe Thr Thr Leu Asn
1730                1735                1740

Val Asp Ile Arg Asn His Gln Asn Leu Leu Asp Ser Leu Glu Gln
1745                1750                1755

Tyr Ile Lys Gly Asp Leu Leu Glu Gly Ala Asn Ala Tyr His Cys
1760                1765                1770

Glu Lys Cys Asp Lys Lys Val Asp Thr Val Lys Arg Leu Leu Ile
1775                1780                1785

Lys Lys Leu Pro Arg Val Leu Ala Ile Gln Leu Lys Arg Phe Asp
1790                1795                1800

Tyr Asp Trp Glu Arg Glu Cys Ala Ile Lys Phe Asn Asp Tyr Phe
1805                1810                1815

Glu Phe Pro Arg Glu Leu Asp Met Gly Pro Tyr Thr Val Ala Gly
1820                1825                1830

Val Ala Asn Leu Glu Arg Asp Asn Val Asn Ser Glu Asn Glu Leu
1835                1840                1845

Ile Glu Gln Lys Glu Gln Ser Asp Asn Glu Thr Ala Gly Gly Thr
1850                1855                1860

Lys Tyr Arg Leu Val Gly Val Leu Val His Ser Gly Gln Ala Ser
1865                1870                1875

Gly Gly His Tyr Tyr Ser Tyr Ile Ile Gln Arg Asn Gly Lys Asp
1880                1885                1890

Asp Gln Thr Asp His Trp Tyr Lys Phe Asp Asp Gly Asp Val Thr
1895                1900                1905

Glu Cys Lys Met Asp Asp Asp Glu Glu Met Lys Asn Gln Cys Phe
1910                1915                1920

Gly Gly Glu Tyr Met Gly Glu Val Phe Asp His Met Met Lys Arg
1925                1930                1935

Met Ser Tyr Arg Arg Gln Lys Arg Trp Trp Asn Ala Tyr Ile Leu
1940                1945                1950

Phe Tyr Glu Gln Met Asp Met Ile Asp Glu Asp Asp Glu Met Ile
```

|   |   |   |   |   |   |   |   |   |   |   |
|---|---|---|---|---|---|---|---|---|---|---|
|   |   |   | 1955 |   |   |   | 1960 |   |   | 1965 |
| Arg | Tyr | Ile | Ser | Glu | Leu | Thr | Ile | Ala | Arg | Pro | His | Gln | Ile | Ile |
|   | 1970 |   |   |   | 1975 |   |   |   | 1980 |   |
| Met | Ser | Pro | Ala | Ile | Glu | Arg | Ser | Val | Arg | Lys | Gln | Asn | Val | Lys |
|   | 1985 |   |   |   | 1990 |   |   |   | 1995 |   |
| Phe | Met | His | Asn | Arg | Leu | Gln | Tyr | Ser | Leu | Glu | Tyr | Phe | Gln | Phe |
|   | 2000 |   |   |   | 2005 |   |   |   | 2010 |   |
| Val | Lys | Lys | Leu | Leu | Thr | Cys | Asn | Gly | Val | Tyr | Leu | Asn | Pro | Ala |
|   | 2015 |   |   |   | 2020 |   |   |   | 2025 |   |
| Pro | Gly | Gln | Asp | Tyr | Leu | Leu | Pro | Glu | Ala | Glu | Ile | Thr | Met |
|   | 2030 |   |   |   | 2035 |   |   |   | 2040 |   |
| Ile | Ser | Ile | Gln | Leu | Ala | Ala | Arg | Phe | Leu | Phe | Thr | Thr | Gly | Phe |
|   | 2045 |   |   |   | 2050 |   |   |   | 2055 |   |
| His | Thr | Lys | Lys | Ile | Val | Arg | Gly | Pro | Ala | Ser | Asp | Trp | Tyr | Asp |
|   | 2060 |   |   |   | 2065 |   |   |   | 2070 |   |
| Ala | Leu | Cys | Val | Leu | Leu | Arg | His | Ser | Lys | Asn | Val | Arg | Phe | Trp |
|   | 2075 |   |   |   | 2080 |   |   |   | 2085 |   |
| Phe | Thr | His | Asn | Val | Leu | Phe | Asn | Val | Ser | Asn | Arg | Phe | Ser | Glu |
|   | 2090 |   |   |   | 2095 |   |   |   | 2100 |   |
| Tyr | Leu | Leu | Glu | Cys | Pro | Ser | Ala | Glu | Val | Arg | Gly | Ala | Phe | Ala |
|   | 2105 |   |   |   | 2110 |   |   |   | 2115 |   |
| Lys | Leu | Ile | Val | Phe | Ile | Ala | His | Phe | Ser | Leu | Gln | Asp | Gly | Ser |
|   | 2120 |   |   |   | 2125 |   |   |   | 2130 |   |
| Cys | Pro | Ser | Pro | Phe | Ala | Ser | Pro | Gly | Pro | Ser | Ser | Gln | Ala | Cys |
|   | 2135 |   |   |   | 2140 |   |   |   | 2145 |   |
| Asp | Asn | Leu | Ser | Leu | Ser | Asp | His | Leu | Leu | Arg | Ala | Thr | Leu | Asn |
|   | 2150 |   |   |   | 2155 |   |   |   | 2160 |   |
| Leu | Leu | Arg | Arg | Glu | Val | Ser | Glu | His | Gly | His | His | Leu | Gln | Gln |
|   | 2165 |   |   |   | 2170 |   |   |   | 2175 |   |
| Tyr | Phe | Asn | Leu | Phe | Val | Met | Tyr | Ala | Asn | Leu | Gly | Val | Ala | Glu |
|   | 2180 |   |   |   | 2185 |   |   |   | 2190 |   |
| Lys | Thr | Gln | Leu | Leu | Lys | Leu | Asn | Val | Pro | Ala | Thr | Phe | Met | Leu |
|   | 2195 |   |   |   | 2200 |   |   |   | 2205 |   |
| Val | Ser | Leu | Asp | Glu | Gly | Pro | Gly | Pro | Pro | Ile | Lys | Tyr | Gln | Tyr |
|   | 2210 |   |   |   | 2215 |   |   |   | 2220 |   |
| Ala | Glu | Leu | Gly | Lys | Leu | Tyr | Ser | Val | Val | Ser | Gln | Leu | Ile | Arg |
|   | 2225 |   |   |   | 2230 |   |   |   | 2235 |   |
| Cys | Cys | Asn | Val | Ser | Ser | Thr | Met | Gln | Ser | Ser | Ile | Asn | Gly | Asn |
|   | 2240 |   |   |   | 2245 |   |   |   | 2250 |   |
| Pro | Pro | Leu | Pro | Asn | Pro | Phe | Gly | Asp | Leu | Asn | Leu | Ser | Gln | Pro |
|   | 2255 |   |   |   | 2260 |   |   |   | 2265 |   |
| Ile | Met | Pro | Ile | Gln | Gln | Asn | Val | Leu | Asp | Ile | Leu | Phe | Val | Arg |
|   | 2270 |   |   |   | 2275 |   |   |   | 2280 |   |
| Thr | Ser | Tyr | Val | Lys | Lys | Ile | Ile | Glu | Asp | Cys | Ser | Asn | Ser | Glu |
|   | 2285 |   |   |   | 2290 |   |   |   | 2295 |   |
| Asp | Thr | Ile | Lys | Leu | Leu | Arg | Phe | Cys | Ser | Trp | Glu | Asn | Pro | Gln |
|   | 2300 |   |   |   | 2305 |   |   |   | 2310 |   |
| Phe | Ser | Ser | Thr | Val | Leu | Ser | Glu | Leu | Leu | Trp | Gln | Val | Ala | Tyr |
|   | 2315 |   |   |   | 2320 |   |   |   | 2325 |   |
| Ser | Tyr | Thr | Tyr | Glu | Leu | Arg | Pro | Tyr | Leu | Asp | Leu | Leu | Phe | Gln |
|   | 2330 |   |   |   | 2335 |   |   |   | 2340 |   |
| Ile | Leu | Leu | Ile | Glu | Asp | Ser | Trp | Gln | Thr | His | Arg | Ile | His | Asn |
|   | 2345 |   |   |   | 2350 |   |   |   | 2355 |   |

```
Ala Leu Lys Gly Ile Pro Asp Asp Arg Asp Gly Leu Phe Asp Thr
    2360            2365                2370

Ile Gln Arg Ser Lys Asn His Tyr Gln Lys Arg Ala Tyr Gln Cys
2375            2380                2385

Ile Lys Cys Met Val Ala Leu Phe Ser Ser Cys Pro Val Ala Tyr
2390            2395                2400

Gln Ile Leu Gln Gly Asn Gly Asp Leu Lys Arg Lys Trp Thr Trp
2405            2410                2415

Ala Val Glu Trp Leu Gly Asp Glu Leu Glu Arg Pro Tyr Thr
2420            2425                2430

Gly Asn Pro Gln Tyr Ser Tyr Asn Asn Trp Ser Pro Pro Val Gln
2435            2440                2445

Ser Asn Glu Thr Ala Asn Gly Tyr Phe Leu Glu Arg Ser His Ser
2450            2455                2460

Ala Arg Met Thr Leu Ala Lys Ala Cys Glu Leu Cys Pro Glu Glu
2465            2470                2475

Glu Pro Asp Asp Gln Asp Ala Pro Asp Glu His Glu Pro Ser Pro
2480            2485                2490

Ser Glu Asp Ala Pro Leu Tyr Pro His Ser Pro Ala Ser Gln Tyr
2495            2500                2505

Gln Gln Asn Asn His Val His Gly Gln Pro Tyr Thr Gly Pro Ala
2510            2515                2520

Ala His His Leu Asn Asn Pro Gln Lys Thr Gly Gln Arg Thr Gln
2525            2530                2535

Glu Asn Tyr Glu Gly Asn Glu Val Ser Ser Pro Gln Met Lys
2540            2545                2550

Asp Gln
2555

<210> SEQ ID NO 71
<211> LENGTH: 574
<212> TYPE: PRT
<213> ORGANISM: Homo sapiens

<400> SEQUENCE: 71

Met Glu Ala Ser Leu Gly Ile Gln Met Asp Glu Pro Met Ala Phe Ser
1               5                   10                  15

Pro Gln Arg Asp Arg Phe Gln Ala Glu Gly Ser Leu Lys Lys Asn Glu
            20                  25                  30

Gln Asn Phe Lys Leu Ala Gly Val Lys Lys Asp Ile Glu Lys Leu Tyr
        35                  40                  45

Glu Ala Val Pro Gln Leu Ser Asn Val Phe Lys Ile Glu Asp Lys Ile
    50                  55                  60

Gly Glu Gly Thr Phe Ser Ser Val Tyr Leu Ala Thr Ala Gln Leu Gln
65                  70                  75                  80

Val Gly Pro Glu Glu Lys Ile Ala Leu Lys His Leu Ile Pro Thr Ser
                85                  90                  95

His Pro Ile Arg Ile Ala Ala Glu Leu Gln Cys Leu Thr Val Ala Gly
            100                 105                 110

Gly Gln Asp Asn Val Met Gly Val Lys Tyr Cys Phe Arg Lys Asn Asp
        115                 120                 125

His Val Val Ile Ala Met Pro Tyr Leu Glu His Glu Ser Phe Leu Asp
    130                 135                 140

Ile Leu Asn Ser Leu Ser Phe Gln Glu Val Arg Glu Tyr Met Leu Asn
145                 150                 155                 160
```

```
Leu Phe Lys Ala Leu Lys Arg Ile His Gln Phe Gly Ile Val His Arg
            165                 170                 175

Asp Val Lys Pro Ser Asn Phe Leu Tyr Asn Arg Arg Leu Lys Lys Tyr
            180                 185                 190

Ala Leu Val Asp Phe Gly Leu Ala Gln Gly Thr His Asp Thr Lys Ile
            195                 200                 205

Glu Leu Leu Lys Phe Val Gln Ser Glu Ala Gln Gln Glu Arg Cys Ser
    210                 215                 220

Gln Asn Lys Ser His Ile Ile Thr Gly Asn Lys Ile Pro Leu Ser Gly
225                 230                 235                 240

Pro Val Pro Lys Glu Leu Asp Gln Gln Ser Thr Thr Lys Ala Ser Val
            245                 250                 255

Lys Arg Pro Tyr Thr Asn Ala Gln Ile Gln Ile Lys Gln Gly Lys Asp
            260                 265                 270

Gly Lys Glu Gly Ser Val Gly Leu Ser Val Gln Arg Ser Val Phe Gly
            275                 280                 285

Glu Arg Asn Phe Asn Ile His Ser Ser Ile Ser His Glu Ser Pro Ala
    290                 295                 300

Val Lys Leu Met Lys Gln Ser Lys Thr Val Asp Val Leu Ser Arg Lys
305                 310                 315                 320

Leu Ala Thr Lys Lys Ala Ile Ser Thr Lys Val Met Asn Ser Ala
            325                 330                 335

Val Met Arg Lys Thr Ala Ser Ser Cys Pro Ala Ser Leu Thr Cys Asp
            340                 345                 350

Cys Tyr Ala Thr Asp Lys Val Cys Ser Ile Cys Leu Ser Arg Arg Gln
            355                 360                 365

Gln Val Ala Pro Arg Ala Gly Thr Pro Gly Phe Arg Ala Pro Glu Val
    370                 375                 380

Leu Thr Lys Cys Pro Asn Gln Thr Thr Ala Ile Asp Met Trp Ser Ala
385                 390                 395                 400

Gly Val Ile Phe Leu Ser Leu Ser Gly Arg Tyr Pro Phe Tyr Lys
            405                 410                 415

Ala Ser Asp Asp Leu Thr Ala Leu Ala Gln Ile Met Thr Ile Arg Gly
            420                 425                 430

Ser Arg Glu Thr Ile Gln Ala Ala Lys Thr Phe Gly Lys Ser Ile Leu
            435                 440                 445

Cys Ser Lys Glu Val Pro Ala Gln Asp Leu Arg Lys Leu Cys Glu Arg
450                 455                 460

Leu Arg Gly Met Asp Ser Ser Thr Pro Lys Leu Thr Ser Asp Ile Gln
465                 470                 475                 480

Gly His Ala Ser His Gln Pro Ala Ile Ser Glu Lys Thr Asp His Lys
            485                 490                 495

Ala Ser Cys Leu Val Gln Thr Pro Pro Gly Gln Tyr Ser Gly Asn Ser
            500                 505                 510

Phe Lys Lys Gly Asp Ser Asn Ser Cys Glu His Cys Phe Asp Glu Tyr
    515                 520                 525

Asn Thr Asn Leu Glu Gly Trp Asn Glu Val Pro Asp Glu Ala Tyr Asp
            530                 535                 540

Leu Leu Asp Lys Leu Leu Asp Leu Asn Pro Ala Ser Arg Ile Thr Ala
545                 550                 555                 560

Glu Glu Ala Leu Leu His Pro Phe Phe Lys Asp Met Ser Leu
            565                 570

<210> SEQ ID NO 72
```

```
<211> LENGTH: 165
<212> TYPE: PRT
<213> ORGANISM: Homo sapiens

<400> SEQUENCE: 72

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
        35                  40                  45

Lys Gly Ser Cys Phe His Arg Ile Ile Pro Gly Phe Met Cys Gln Gly
50                  55                  60

Gly Asp Phe Thr Arg His Asn Gly Thr Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu
                165

<210> SEQ ID NO 73
<211> LENGTH: 1621
<212> TYPE: PRT
<213> ORGANISM: Homo sapiens

<400> SEQUENCE: 73

Met Ala Lys Ser Gly Cys Gly Ala Gly Ala Gly Val Gly Gly Gly
1               5                   10                  15

Asn Gly Ala Leu Thr Trp Val Asn Asn Ala Lys Lys Glu Glu Ser
            20                  25                  30

Glu Thr Ala Asn Lys Asn Asp Ser Ser Lys Lys Leu Ser Val Glu Arg
        35                  40                  45

Val Tyr Gln Lys Lys Thr Gln Leu Glu His Ile Leu Leu Arg Pro Asp
    50                  55                  60

Thr Tyr Ile Gly Ser Val Glu Pro Leu Thr Gln Phe Met Trp Val Tyr
65                  70                  75                  80

Asp Glu Asp Val Gly Met Asn Cys Arg Glu Val Thr Phe Val Pro Gly
                85                  90                  95

Leu Tyr Lys Ile Phe Asp Glu Ile Leu Val Asn Ala Ala Asp Asn Lys
            100                 105                 110

Gln Arg Asp Lys Asn Met Thr Cys Ile Lys Val Ser Ile Asp Pro Glu
        115                 120                 125

Ser Asn Ile Ile Ser Ile Trp Asn Asn Gly Lys Gly Ile Pro Val Val
    130                 135                 140

Glu His Lys Val Glu Lys Val Tyr Val Pro Ala Leu Ile Phe Gly Gln
145                 150                 155                 160

Leu Leu Thr Ser Ser Asn Tyr Asp Asp Asp Glu Lys Lys Val Thr Gly
                165                 170                 175
```

-continued

Gly Arg Asn Gly Tyr Gly Ala Lys Leu Cys Asn Ile Phe Ser Thr Lys
                180                 185                 190

Phe Thr Val Glu Thr Ala Cys Lys Glu Tyr Lys His Ser Phe Lys Gln
            195                 200                 205

Thr Trp Met Asn Asn Met Met Lys Thr Ser Glu Ala Lys Ile Lys His
        210                 215                 220

Phe Asp Gly Glu Asp Tyr Thr Cys Ile Thr Phe Gln Pro Asp Leu Ser
225                 230                 235                 240

Lys Phe Lys Met Glu Lys Leu Asp Lys Asp Ile Val Ala Leu Met Thr
                245                 250                 255

Arg Arg Ala Tyr Asp Leu Ala Gly Ser Cys Arg Gly Val Lys Val Met
                260                 265                 270

Phe Asn Gly Lys Lys Leu Pro Val Asn Gly Phe Arg Ser Tyr Val Asp
            275                 280                 285

Leu Tyr Val Lys Asp Lys Leu Asp Glu Thr Gly Val Ala Leu Lys Val
        290                 295                 300

Ile His Glu Leu Ala Asn Glu Arg Trp Asp Val Cys Leu Thr Leu Ser
305                 310                 315                 320

Glu Lys Gly Phe Gln Gln Ile Ser Phe Val Asn Ser Ile Ala Thr Thr
                325                 330                 335

Lys Gly Gly Arg His Val Asp Tyr Val Val Asp Gln Val Val Gly Lys
                340                 345                 350

Leu Ile Glu Val Val Lys Lys Asn Lys Ala Gly Val Ser Val Lys
            355                 360                 365

Pro Phe Gln Val Lys Asn His Ile Trp Val Phe Ile Asn Cys Leu Ile
        370                 375                 380

Glu Asn Pro Thr Phe Asp Ser Gln Thr Lys Glu Asn Met Thr Leu Gln
385                 390                 395                 400

Pro Lys Ser Phe Gly Ser Lys Cys Gln Leu Ser Glu Lys Phe Phe Lys
                405                 410                 415

Ala Ala Ser Asn Cys Gly Ile Val Glu Ser Ile Leu Asn Trp Val Lys
                420                 425                 430

Phe Lys Ala Gln Thr Gln Leu Asn Lys Lys Cys Ser Ser Val Lys Tyr
            435                 440                 445

Ser Lys Ile Lys Gly Ile Pro Lys Leu Asp Asp Ala Asn Asp Ala Gly
        450                 455                 460

Gly Lys His Ser Leu Glu Cys Thr Leu Ile Leu Thr Glu Gly Asp Ser
465                 470                 475                 480

Ala Lys Ser Leu Ala Val Ser Gly Leu Gly Val Ile Gly Arg Asp Arg
                485                 490                 495

Tyr Gly Val Phe Pro Leu Arg Gly Lys Ile Leu Asn Val Arg Glu Ala
                500                 505                 510

Ser His Lys Gln Ile Met Glu Asn Ala Glu Ile Asn Asn Ile Ile Lys
            515                 520                 525

Ile Val Gly Leu Gln Tyr Lys Lys Ser Tyr Asp Asp Ala Glu Ser Leu
        530                 535                 540

Lys Thr Leu Arg Tyr Gly Lys Ile Met Ile Met Thr Asp Gln Asp Gln
545                 550                 555                 560

Asp Gly Ser His Ile Lys Gly Leu Leu Ile Asn Phe Ile His Asn
                565                 570                 575

Trp Pro Ser Leu Leu Lys His Gly Phe Leu Glu Glu Phe Ile Thr Pro
            580                 585                 590

Ile Val Lys Ala Ser Lys Asn Lys Gln Glu Leu Ser Phe Tyr Ser Ile
        595                 600                 605

```
Pro Glu Phe Asp Glu Trp Lys Lys His Ile Glu Asn Gln Lys Ala Trp
    610                 615                 620
Lys Ile Lys Tyr Tyr Lys Gly Leu Gly Thr Ser Thr Ala Lys Glu Ala
625                 630                 635                 640
Lys Glu Tyr Phe Ala Asp Met Glu Arg His Arg Ile Leu Phe Arg Tyr
                645                 650                 655
Ala Gly Pro Glu Asp Asp Ala Ala Ile Thr Leu Ala Phe Ser Lys Lys
                660                 665                 670
Lys Ile Asp Asp Arg Lys Glu Trp Leu Thr Asn Phe Met Glu Asp Arg
        675                 680                 685
Arg Gln Arg Arg Leu His Gly Leu Pro Glu Gln Phe Leu Tyr Gly Thr
690                 695                 700
Ala Thr Lys His Leu Thr Tyr Asn Asp Phe Ile Asn Lys Glu Leu Ile
705                 710                 715                 720
Leu Phe Ser Asn Ser Asp Asn Glu Arg Ser Ile Pro Ser Leu Val Asp
                725                 730                 735
Gly Phe Lys Pro Gly Gln Arg Lys Val Leu Phe Thr Cys Phe Lys Arg
                740                 745                 750
Asn Asp Lys Arg Glu Val Lys Val Ala Gln Leu Ala Gly Ser Val Ala
            755                 760                 765
Glu Met Ser Ala Tyr His His Gly Glu Gln Ala Leu Met Met Thr Ile
770                 775                 780
Val Asn Leu Ala Gln Asn Phe Val Gly Ser Asn Asn Ile Asn Leu Leu
785                 790                 795                 800
Gln Pro Ile Gly Gln Phe Gly Thr Arg Leu His Gly Gly Lys Asp Ala
                805                 810                 815
Ala Ser Pro Arg Tyr Ile Phe Thr Met Leu Ser Thr Leu Ala Arg Leu
                820                 825                 830
Leu Phe Pro Ala Val Asp Asp Asn Leu Leu Lys Phe Leu Tyr Asp Asp
            835                 840                 845
Asn Gln Arg Val Glu Pro Glu Trp Tyr Ile Pro Ile Ile Pro Met Val
            850                 855                 860
Leu Ile Asn Gly Ala Glu Gly Ile Gly Thr Gly Trp Ala Cys Lys Leu
865                 870                 875                 880
Pro Asn Tyr Asp Ala Arg Glu Ile Val Asn Asn Val Arg Arg Met Leu
                885                 890                 895
Asp Gly Leu Asp Pro His Pro Met Leu Pro Asn Tyr Lys Asn Phe Lys
                900                 905                 910
Gly Thr Ile Gln Glu Leu Gly Gln Asn Gln Tyr Ala Val Ser Gly Glu
        915                 920                 925
Ile Phe Val Val Asp Arg Asn Thr Val Glu Ile Thr Glu Leu Pro Val
        930                 935                 940
Arg Thr Trp Thr Gln Val Tyr Lys Glu Gln Val Leu Glu Pro Met Leu
945                 950                 955                 960
Asn Gly Thr Asp Lys Thr Pro Ala Leu Ile Ser Asp Tyr Lys Glu Tyr
                965                 970                 975
His Thr Asp Thr Thr Val Lys Phe Val Val Lys Met Thr Glu Glu Lys
                980                 985                 990
Leu Ala Gln Ala Glu Ala Ala Gly Leu His Lys Val Phe Lys Leu Gln
            995                 1000                1005
Thr Thr Leu Thr Cys Asn Ser Met Val Leu Phe Asp His Met Gly
        1010                1015                1020
Cys Leu Lys Lys Tyr Glu Thr Val Gln Asp Ile Leu Lys Glu Phe
```

-continued

```
                1025                1030                1035

Phe Asp Leu Arg Leu Ser Tyr Tyr Gly Leu Arg Lys Glu Trp Leu
1040                1045                1050

Val Gly Met Leu Gly Ala Glu Ser Thr Lys Leu Asn Asn Gln Ala
1055                1060                1065

Arg Phe Ile Leu Glu Lys Ile Gln Gly Lys Ile Thr Ile Glu Asn
1070                1075                1080

Arg Ser Lys Lys Asp Leu Ile Gln Met Leu Val Gln Arg Gly Tyr
1085                1090                1095

Glu Ser Asp Pro Val Lys Ala Trp Lys Glu Ala Gln Glu Lys Ala
1100                1105                1110

Ala Glu Glu Asp Glu Thr Gln Asn Gln His Asp Ser Ser Ser
1115                1120                1125

Asp Ser Gly Thr Pro Ser Gly Pro Asp Phe Asn Tyr Ile Leu Asn
1130                1135                1140

Met Ser Leu Trp Ser Leu Thr Lys Glu Lys Val Glu Glu Leu Ile
1145                1150                1155

Lys Gln Arg Asp Ala Lys Gly Arg Glu Val Asn Asp Leu Lys Arg
1160                1165                1170

Lys Ser Pro Ser Asp Leu Trp Lys Glu Asp Leu Ala Ala Phe Val
1175                1180                1185

Glu Glu Leu Asp Lys Val Glu Ser Gln Glu Arg Glu Asp Val Leu
1190                1195                1200

Ala Gly Met Ser Gly Lys Ala Ile Lys Gly Lys Val Gly Lys Pro
1205                1210                1215

Lys Val Lys Lys Leu Gln Leu Glu Glu Thr Met Pro Ser Pro Tyr
1220                1225                1230

Gly Arg Arg Ile Ile Pro Glu Ile Thr Ala Met Lys Ala Asp Ala
1235                1240                1245

Ser Lys Lys Leu Leu Lys Lys Lys Gly Asp Leu Asp Thr Ala
1250                1255                1260

Ala Val Lys Val Glu Phe Asp Glu Glu Phe Ser Gly Ala Pro Val
1265                1270                1275

Glu Gly Ala Gly Glu Glu Ala Leu Thr Pro Ser Val Pro Ile Asn
1280                1285                1290

Lys Gly Pro Lys Pro Lys Arg Glu Lys Lys Glu Pro Gly Thr Arg
1295                1300                1305

Val Arg Lys Thr Pro Thr Ser Ser Gly Lys Pro Ser Ala Lys Lys
1310                1315                1320

Val Lys Lys Arg Asn Pro Trp Ser Asp Asp Glu Ser Lys Ser Glu
1325                1330                1335

Ser Asp Leu Glu Glu Thr Glu Pro Val Val Ile Pro Arg Asp Ser
1340                1345                1350

Leu Leu Arg Arg Ala Ala Ala Glu Arg Pro Lys Tyr Thr Phe Asp
1355                1360                1365

Phe Ser Glu Glu Glu Asp Asp Asp Ala Asp Asp Asp Asp Asp
1370                1375                1380

Asn Asn Asp Leu Glu Glu Leu Lys Val Lys Ala Ser Pro Ile Thr
1385                1390                1395

Asn Asp Gly Glu Asp Glu Phe Val Pro Ser Asp Gly Leu Asp Lys
1400                1405                1410

Asp Glu Tyr Thr Phe Ser Pro Gly Lys Ser Lys Ala Thr Pro Glu
1415                1420                1425
```

```
Lys Ser Leu His Asp Lys Lys Ser Gln Asp Phe Gly Asn Leu Phe
    1430            1435                1440

Ser Phe Pro Ser Tyr Ser Gln Lys Ser Glu Asp Ser Ala Lys
    1445            1450                1455

Phe Asp Ser Asn Glu Glu Asp Ser Ala Ser Val Phe Ser Pro Ser
    1460            1465                1470

Phe Gly Leu Lys Gln Thr Asp Lys Val Pro Ser Lys Thr Val Ala
    1475            1480                1485

Ala Lys Lys Gly Lys Pro Ser Ser Asp Thr Val Pro Lys Pro Lys
    1490            1495                1500

Arg Ala Pro Lys Gln Lys Lys Val Val Glu Ala Val Asn Ser Asp
    1505            1510                1515

Ser Asp Ser Glu Phe Gly Ile Pro Lys Lys Thr Thr Thr Pro Lys
    1520            1525                1530

Gly Lys Gly Arg Gly Ala Lys Lys Arg Lys Ala Ser Gly Ser Glu
    1535            1540                1545

Asn Glu Gly Asp Tyr Asn Pro Gly Arg Lys Thr Ser Lys Thr Thr
    1550            1555                1560

Ser Lys Lys Pro Lys Lys Thr Ser Phe Asp Gln Asp Ser Asp Val
    1565            1570                1575

Asp Ile Phe Pro Ser Asp Phe Pro Thr Glu Pro Pro Ser Leu Pro
    1580            1585                1590

Arg Thr Gly Arg Ala Arg Lys Glu Val Lys Tyr Phe Ala Glu Ser
    1595            1600                1605

Asp Glu Glu Glu Asp Asp Val Asp Phe Ala Met Phe Asn
    1610            1615                1620

<210> SEQ ID NO 74
<211> LENGTH: 309
<212> TYPE: PRT
<213> ORGANISM: Homo sapiens

<400> SEQUENCE: 74

Met Asp Asp Lys Ala Phe Thr Lys Glu Leu Asp Gln Trp Val Glu Gln
1               5                   10                  15

Leu Asn Glu Cys Lys Gln Leu Asn Glu Asn Gln Val Arg Thr Leu Cys
                20                  25                  30

Glu Lys Ala Lys Glu Ile Leu Thr Lys Glu Ser Asn Val Gln Glu Val
            35                  40                  45

Arg Cys Pro Val Thr Val Cys Gly Asp Val His Gly Gln Phe His Asp
        50                  55                  60

Leu Met Glu Leu Phe Arg Ile Gly Gly Lys Ser Pro Asp Thr Asn Tyr
65                  70                  75                  80

Leu Phe Met Gly Asp Tyr Val Asp Arg Gly Tyr Tyr Ser Val Glu Thr
                85                  90                  95

Val Thr Leu Leu Val Ala Leu Lys Val Arg Tyr Pro Glu Arg Ile Thr
            100                 105                 110

Ile Leu Arg Gly Asn His Glu Ser Arg Gln Ile Thr Gln Val Tyr Gly
        115                 120                 125

Phe Tyr Asp Glu Cys Leu Arg Lys Tyr Gly Asn Ala Asn Val Trp Lys
    130                 135                 140

Tyr Phe Thr Asp Leu Phe Asp Tyr Leu Pro Leu Thr Ala Leu Val Asp
145                 150                 155                 160

Gly Gln Ile Phe Cys Leu His Gly Gly Leu Ser Pro Ser Ile Asp Thr
                165                 170                 175
```

```
Leu Asp His Ile Arg Ala Leu Asp Arg Leu Gln Glu Val Pro His Glu
            180                 185                 190

Gly Pro Met Cys Asp Leu Leu Trp Ser Asp Pro Asp Arg Gly Gly
            195                 200                 205

Trp Gly Ile Ser Pro Arg Gly Ala Gly Tyr Thr Phe Gly Gln Asp Ile
            210                 215                 220

Ser Glu Thr Phe Asn His Ala Asn Gly Leu Thr Leu Val Ser Arg Ala
225                 230                 235                 240

His Gln Leu Val Met Glu Gly Tyr Asn Trp Cys His Asp Arg Asn Val
                245                 250                 255

Val Thr Ile Phe Ser Ala Pro Asn Tyr Cys Tyr Arg Cys Gly Asn Gln
            260                 265                 270

Ala Ala Ile Met Glu Leu Asp Asp Thr Leu Lys Tyr Ser Phe Leu Gln
            275                 280                 285

Phe Asp Pro Ala Pro Arg Arg Gly Glu Pro His Val Thr Arg Arg Thr
            290                 295                 300

Pro Asp Tyr Phe Leu
305

<210> SEQ ID NO 75
<211> LENGTH: 309
<212> TYPE: PRT
<213> ORGANISM: Homo sapiens

<400> SEQUENCE: 75

Met Asp Asp Lys Ala Phe Thr Lys Glu Leu Asp Gln Trp Val Glu Gln
1               5                   10                  15

Leu Asn Glu Cys Lys Gln Leu Asn Glu Asn Gln Val Arg Thr Leu Cys
            20                  25                  30

Glu Lys Ala Lys Glu Ile Leu Thr Lys Glu Ser Asn Val Gln Glu Val
        35                  40                  45

Arg Cys Pro Val Thr Val Cys Gly Asp Val His Gly Gln Phe His Asp
    50                  55                  60

Leu Met Glu Leu Phe Arg Ile Gly Gly Lys Ser Pro Asp Thr Asn Tyr
65                  70                  75                  80

Leu Phe Met Gly Asp Tyr Val Asp Arg Gly Tyr Tyr Ser Val Glu Thr
                85                  90                  95

Val Thr Leu Leu Val Ala Leu Lys Val Arg Tyr Pro Glu Arg Ile Thr
            100                 105                 110

Ile Leu Arg Gly Asn His Glu Ser Arg Gln Ile Thr Gln Val Tyr Gly
        115                 120                 125

Phe Tyr Asp Glu Cys Leu Arg Lys Tyr Gly Asn Ala Asn Val Trp Lys
    130                 135                 140

Tyr Phe Thr Asp Leu Phe Asp Tyr Leu Pro Leu Thr Ala Leu Val Asp
145                 150                 155                 160

Gly Gln Ile Phe Cys Leu His Gly Gly Leu Ser Pro Ser Ile Asp Thr
                165                 170                 175

Leu Asp His Ile Arg Ala Leu Asp Arg Leu Gln Glu Val Pro His Glu
            180                 185                 190

Gly Pro Met Cys Asp Leu Leu Trp Ser Asp Pro Asp Arg Gly Gly
            195                 200                 205

Trp Gly Ile Ser Pro Arg Gly Ala Gly Tyr Thr Phe Gly Gln Asp Ile
            210                 215                 220

Ser Glu Thr Phe Asn His Ala Asn Gly Leu Thr Leu Val Ser Arg Ala
225                 230                 235                 240
```

```
His Gln Leu Val Met Glu Gly Tyr Asn Trp Cys His Asp Arg Asn Val
                245                 250                 255

Val Thr Ile Phe Ser Ala Pro Asn Tyr Cys Tyr Arg Cys Gly Asn Gln
            260                 265                 270

Ala Ala Ile Met Glu Leu Asp Asp Thr Leu Lys Tyr Ser Phe Leu Gln
        275                 280                 285

Phe Asp Pro Ala Pro Arg Arg Gly Glu Pro His Val Thr Arg Thr
    290                 295                 300

Pro Asp Tyr Phe Leu
305
```

<210> SEQ ID NO 76
<211> LENGTH: 443
<212> TYPE: PRT
<213> ORGANISM: Homo sapiens

<400> SEQUENCE: 76

```
Met Ala Ala Ser Pro His Thr Leu Ser Ser Arg Leu Leu Thr Gly Cys
1               5                   10                  15

Val Gly Gly Ser Val Trp Tyr Leu Glu Arg Arg Thr Ile Gln Asp Ser
            20                  25                  30

Pro His Lys Phe Leu His Leu Leu Arg Asn Val Asn Lys Gln Trp Ile
        35                  40                  45

Thr Phe Gln His Phe Ser Phe Leu Lys Arg Met Tyr Val Thr Gln Leu
    50                  55                  60

Asn Arg Ser His Asn Gln Gln Val Arg Pro Lys Pro Glu Pro Val Ala
65                  70                  75                  80

Ser Pro Phe Leu Glu Lys Thr Ser Ser Gly Gln Ala Lys Ala Glu Ile
                85                  90                  95

Tyr Glu Met Arg Pro Leu Ser Pro Pro Ser Leu Ser Leu Ser Arg Lys
            100                 105                 110

Pro Asn Glu Lys Glu Leu Ile Glu Leu Glu Pro Asp Ser Val Ile Glu
        115                 120                 125

Asp Ser Ile Asp Val Gly Lys Glu Thr Lys Glu Glu Lys Arg Trp Lys
    130                 135                 140

Glu Met Lys Leu Gln Val Tyr Asp Leu Pro Gly Ile Leu Ala Arg Leu
145                 150                 155                 160

Ser Lys Ile Lys Leu Thr Ala Leu Val Val Ser Thr Thr Ala Ala Gly
                165                 170                 175

Phe Ala Leu Ala Pro Gly Pro Phe Asp Trp Pro Cys Phe Leu Leu Thr
            180                 185                 190

Ser Val Gly Thr Gly Leu Ala Ser Cys Ala Ala Asn Ser Ile Asn Gln
        195                 200                 205

Phe Phe Glu Val Pro Phe Asp Ser Asn Met Asn Arg Thr Lys Asn Arg
    210                 215                 220

Pro Leu Val Arg Gly Gln Ile Ser Pro Leu Leu Ala Val Ser Phe Ala
225                 230                 235                 240

Thr Cys Cys Ala Val Pro Gly Val Ala Ile Leu Thr Leu Gly Val Asn
                245                 250                 255

Pro Leu Thr Gly Ala Leu Gly Leu Phe Asn Ile Phe Leu Tyr Thr Cys
            260                 265                 270

Cys Tyr Thr Pro Leu Lys Arg Ile Ser Ile Ala Asn Thr Trp Val Gly
        275                 280                 285

Ala Val Val Gly Ala Ile Pro Pro Val Met Gly Trp Thr Ala Ala Thr
    290                 295                 300
```

-continued

```
Gly Ser Leu Asp Ala Gly Ala Phe Leu Leu Gly Ile Leu Tyr Ser
305                 310                 315                 320

Trp Gln Phe Pro His Phe Asn Ala Leu Ser Trp Gly Leu Arg Glu Asp
                325                 330                 335

Tyr Ser Arg Gly Gly Tyr Cys Met Met Ser Val Thr His Pro Gly Leu
            340                 345                 350

Cys Arg Arg Val Ala Leu Arg His Cys Leu Ala Leu Val Leu Ser
        355                 360                 365

Ala Ala Ala Pro Val Leu Asp Ile Thr Thr Trp Thr Phe Pro Ile Met
370                 375                 380

Ala Leu Pro Ile Asn Ala Tyr Ile Ser Tyr Leu Gly Phe Arg Phe Tyr
385                 390                 395                 400

Val Asp Ala Asp Arg Arg Ser Ser Arg Arg Leu Phe Phe Cys Ser Leu
                405                 410                 415

Trp His Leu Pro Leu Leu Leu Leu Met Leu Thr Cys Lys Arg Pro
            420                 425                 430

Ser Gly Gly Gly Asp Ala Gly Pro Pro Ser
        435                 440
```

<210> SEQ ID NO 77
<211> LENGTH: 355
<212> TYPE: PRT
<213> ORGANISM: Homo sapiens

<400> SEQUENCE: 77

```
Met Glu Thr Pro Asn Thr Thr Glu Asp Tyr Asp Thr Thr Glu Phe
1               5                   10                  15

Asp Tyr Gly Asp Ala Thr Pro Cys Gln Lys Val Asn Glu Arg Ala Phe
            20                  25                  30

Gly Ala Gln Leu Leu Pro Pro Leu Tyr Ser Leu Val Phe Val Ile Gly
        35                  40                  45

Leu Val Gly Asn Ile Leu Val Val Leu Val Leu Val Gln Tyr Lys Arg
    50                  55                  60

Leu Lys Asn Met Thr Ser Ile Tyr Leu Leu Asn Leu Ala Ile Ser Asp
65                  70                  75                  80

Leu Leu Phe Leu Phe Thr Leu Pro Phe Trp Ile Asp Tyr Lys Leu Lys
                85                  90                  95

Asp Asp Trp Val Phe Gly Asp Ala Met Cys Lys Ile Leu Ser Gly Phe
            100                 105                 110

Tyr Tyr Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Ile Ile Trp Ala Leu
145                 150                 155                 160

Ala Ile Leu Ala Ser Met Pro Gly Leu Tyr Phe Ser Lys Thr Gln Trp
                165                 170                 175

Glu Phe Thr His His Thr Cys Ser Leu His Phe Pro His Glu Ser Leu
            180                 185                 190

Arg Glu Trp Lys Leu Phe Gln Ala Leu Lys Leu Asn Leu Phe Gly Leu
        195                 200                 205

Val Leu Pro Leu Leu Val Met Ile Ile Cys Tyr Thr Gly Ile Ile Lys
    210                 215                 220

Ile Leu Leu Arg Arg Pro Asn Glu Lys Lys Ser Lys Ala Val Arg Leu
225                 230                 235                 240
```

```
Ile Phe Val Ile Met Ile Ile Phe Phe Leu Phe Trp Thr Pro Tyr Asn
                245                 250                 255

Leu Thr Ile Leu Ile Ser Val Phe Gln Asp Phe Leu Phe Thr His Glu
            260                 265                 270

Cys Glu Gln Ser Arg His Leu Asp Leu Ala Val Gln Val Thr Glu Val
        275                 280                 285

Ile Ala Tyr Thr His Cys Cys Val Asn Pro Val Ile Tyr Ala Phe Val
    290                 295                 300

Gly Glu Arg Phe Arg Lys Tyr Leu Arg Gln Leu Phe His Arg Arg Val
305                 310                 315                 320

Ala Val His Leu Val Lys Trp Leu Pro Phe Leu Ser Val Asp Arg Leu
                325                 330                 335

Glu Arg Val Ser Ser Thr Ser Pro Ser Thr Gly Glu His Glu Leu Ser
            340                 345                 350

Ala Gly Phe
        355

<210> SEQ ID NO 78
<211> LENGTH: 326
<212> TYPE: PRT
<213> ORGANISM: Homo sapiens

<400> SEQUENCE: 78

Met Ala Ser Lys Val Ser Cys Leu Tyr Val Leu Thr Val Val Cys Trp
1               5                   10                  15

Ala Ser Ala Leu Trp Tyr Leu Ser Ile Thr Arg Pro Thr Ser Ser Tyr
            20                  25                  30

Thr Gly Ser Lys Pro Phe Ser His Leu Thr Val Ala Arg Lys Asn Phe
        35                  40                  45

Thr Phe Gly Asn Ile Arg Thr Arg Pro Ile Asn Pro His Ser Phe Glu
    50                  55                  60

Phe Leu Ile Asn Glu Pro Asn Lys Cys Glu Lys Asn Ile Pro Phe Leu
65                  70                  75                  80

Val Ile Leu Ile Ser Thr Thr His Lys Glu Phe Asp Ala Arg Gln Ala
                85                  90                  95

Ile Arg Glu Thr Trp Gly Asp Glu Asn Asn Phe Lys Gly Ile Lys Ile
            100                 105                 110

Ala Thr Leu Phe Leu Leu Gly Lys Asn Ala Asp Pro Val Leu Asn Gln
        115                 120                 125

Met Val Glu Gln Glu Ser Gln Ile Phe His Asp Ile Ile Val Glu Asp
    130                 135                 140

Phe Ile Asp Ser Tyr His Asn Leu Thr Leu Lys Thr Leu Met Gly Met
145                 150                 155                 160

Arg Trp Val Ala Thr Phe Cys Ser Lys Ala Lys Tyr Val Met Lys Thr
                165                 170                 175

Asp Ser Asp Ile Phe Val Asn Met Asp Asn Leu Ile Tyr Lys Leu Leu
            180                 185                 190

Lys Pro Ser Thr Lys Pro Arg Arg Tyr Phe Thr Gly Tyr Val Ile
        195                 200                 205

Asn Gly Gly Pro Ile Arg Asp Val Arg Ser Lys Trp Tyr Met Pro Arg
    210                 215                 220

Asp Leu Tyr Pro Asp Ser Asn Tyr Pro Pro Phe Cys Ser Gly Thr Gly
225                 230                 235                 240

Tyr Ile Phe Ser Ala Asp Val Ala Glu Leu Ile Tyr Lys Thr Ser Leu
                245                 250                 255
```

-continued

His Thr Arg Leu Leu His Leu Glu Asp Val Tyr Val Gly Leu Cys Leu
            260                 265                 270

Arg Lys Leu Gly Ile His Pro Phe Gln Asn Ser Gly Phe Asn His Trp
            275                 280                 285

Lys Met Ala Tyr Ser Leu Cys Arg Tyr Arg Val Ile Thr Val His
290                 295                 300

Gln Ile Ser Pro Glu Glu Met His Arg Ile Trp Asn Asp Met Ser Ser
305                 310                 315                 320

Lys Lys His Leu Arg Cys
            325

<210> SEQ ID NO 79
<211> LENGTH: 581
<212> TYPE: PRT
<213> ORGANISM: Homo sapiens

<400> SEQUENCE: 79

Met Gly Glu Lys Met Ala Glu Glu Arg Phe Pro Asn Thr Thr His
1               5                   10                  15

Glu Gly Phe Asn Val Thr Leu His Thr Thr Leu Val Val Thr Thr Lys
                20                  25                  30

Leu Val Leu Pro Thr Pro Gly Lys Pro Ile Leu Pro Val Gln Thr Gly
            35                  40                  45

Glu Gln Ala Gln Gln Glu Gln Ser Ser Gly Met Thr Ile Phe Phe
        50                  55                  60

Ser Leu Leu Val Leu Ala Ile Cys Ile Ile Leu Val His Leu Leu Ile
65                  70                  75                  80

Arg Tyr Arg Leu His Phe Leu Pro Gly Ser Val Ala Val Val Ser Leu
                85                  90                  95

Gly Ile Leu Met Gly Ala Val Ile Lys Ile Ile Glu Phe Lys Lys Leu
            100                 105                 110

Ala Asn Trp Lys Glu Glu Glu Met Phe Arg Pro Asn Met Phe Phe Leu
        115                 120                 125

Leu Leu Leu Pro Pro Ile Ile Phe Glu Ser Gly Tyr Ser Leu His Lys
130                 135                 140

Gly Asn Phe Phe Gln Asn Ile Gly Ser Ile Thr Leu Phe Ala Val Phe
145                 150                 155                 160

Gly Thr Ala Ile Ser Ala Phe Val Val Gly Gly Ile Tyr Phe Leu
                165                 170                 175

Gly Gln Ala Asp Val Ile Ser Lys Leu Asn Met Thr Asp Ser Phe Ala
            180                 185                 190

Phe Gly Ser Leu Ile Ser Ala Val Asp Pro Val Ala Thr Ile Ala Ile
        195                 200                 205

Phe Asn Ala Leu His Val Asp Pro Val Leu Asn Met Leu Val Phe Gly
210                 215                 220

Glu Ser Ile Leu Asn Asp Ala Val Ser Ile Val Leu Thr Asn Thr Ala
225                 230                 235                 240

Glu Gly Leu Thr Arg Lys Asn Met Ser Asp Val Ser Gly Trp Gln Thr
                245                 250                 255

Phe Leu Gln Ala Leu Asp Tyr Phe Leu Lys Met Phe Phe Gly Ser Ala
            260                 265                 270

Ala Leu Gly Thr Leu Thr Gly Leu Ile Ser Ala Leu Val Leu Lys His
        275                 280                 285

Ile Asp Leu Arg Lys Thr Pro Ser Leu Glu Phe Gly Met Met Ile Ile
290                 295                 300

```
Phe Ala Tyr Leu Pro Tyr Gly Leu Ala Glu Gly Ile Ser Leu Ser Gly
305                 310                 315                 320

Ile Met Ala Ile Leu Phe Ser Gly Ile Val Met Ser His Tyr Thr His
                325                 330                 335

His Asn Leu Ser Pro Val Thr Gln Ile Leu Met Gln Gln Thr Leu Arg
            340                 345                 350

Thr Val Ala Phe Leu Cys Glu Thr Cys Val Phe Ala Phe Leu Gly Leu
        355                 360                 365

Ser Ile Phe Ser Phe Pro His Lys Phe Glu Ile Ser Phe Val Ile Trp
    370                 375                 380

Cys Ile Val Leu Val Leu Phe Gly Arg Ala Val Asn Ile Phe Pro Leu
385                 390                 395                 400

Ser Tyr Leu Leu Asn Phe Phe Arg Asp His Lys Ile Thr Pro Lys Met
                405                 410                 415

Met Phe Ile Met Trp Phe Ser Gly Leu Arg Gly Ala Ile Pro Tyr Ala
            420                 425                 430

Leu Ser Leu His Leu Asp Leu Glu Pro Met Glu Lys Arg Gln Leu Ile
        435                 440                 445

Gly Thr Thr Thr Ile Val Ile Val Leu Phe Thr Ile Leu Leu Leu Gly
    450                 455                 460

Gly Ser Thr Met Pro Leu Ile Arg Leu Met Asp Ile Glu Asp Ala Lys
465                 470                 475                 480

Ala His Arg Arg Asn Lys Lys Asp Val Asn Leu Ser Lys Thr Glu Lys
                485                 490                 495

Met Gly Asn Thr Val Glu Ser Glu His Leu Ser Glu Leu Thr Glu Glu
            500                 505                 510

Glu Tyr Glu Ala His Tyr Ile Arg Arg Gln Asp Leu Lys Gly Phe Val
        515                 520                 525

Trp Leu Asp Ala Lys Tyr Leu Asn Pro Phe Phe Thr Arg Arg Leu Thr
    530                 535                 540

Gln Glu Asp Leu His His Gly Arg Ile Gln Met Lys Thr Leu Thr Asn
545                 550                 555                 560

Lys Trp Tyr Glu Glu Val Arg Gln Gly Pro Ser Gly Ser Glu Asp Asp
                565                 570                 575

Glu Gln Glu Leu Leu
            580

<210> SEQ ID NO 80
<211> LENGTH: 342
<212> TYPE: PRT
<213> ORGANISM: Homo sapiens

<400> SEQUENCE: 80

Met Ala Glu His Asp Tyr His Glu Asp Tyr Gly Phe Ser Ser Phe Asn
1               5                   10                  15

Asp Ser Ser Gln Glu Glu His Gln Asp Phe Leu Gln Phe Ser Lys Val
                20                  25                  30

Phe Leu Pro Cys Met Tyr Leu Val Val Phe Val Cys Gly Leu Val Gly
            35                  40                  45

Asn Ser Leu Val Leu Val Ile Ser Ile Phe Tyr His Lys Leu Gln Ser
        50                  55                  60

Leu Thr Asp Val Phe Leu Val Asn Leu Pro Leu Ala Asp Leu Val Phe
65                  70                  75                  80

Val Cys Thr Leu Pro Phe Trp Ala Tyr Ala Gly Ile His Glu Trp Val
                85                  90                  95
```

```
Phe Gly Gln Val Met Cys Lys Ser Leu Leu Gly Ile Tyr Thr Ile Asn
                100                 105                 110

Phe Tyr Thr Ser Met Leu Ile Leu Thr Cys Ile Thr Val Asp Arg Phe
            115                 120                 125

Ile Val Val Lys Ala Thr Lys Ala Tyr Asn Gln Gln Ala Lys Arg
    130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
            195                 200                 205

Val Cys Tyr Ser Val Ile Ile Lys Thr Leu Leu His Ala Gly Gly Phe
    210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
            260                 265                 270

Thr Glu Ala Ile Ala Tyr Leu Arg Ala Cys Leu Asn Pro Val Leu Tyr
            275                 280                 285

Ala Phe Val Ser Leu Lys Phe Arg Lys Asn Phe Trp Lys Leu Val Lys
            290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
            340

<210> SEQ ID NO 81
<211> LENGTH: 19
<212> TYPE: DNA
<213> ORGANISM: Artificial
<220> FEATURE:
<223> OTHER INFORMATION: Target Knock-Down sequence

<400> SEQUENCE: 81
atgcagtgcc tctcggatc                                                19

<210> SEQ ID NO 82
<211> LENGTH: 19
<212> TYPE: DNA
<213> ORGANISM: Artificial
<220> FEATURE:
<223> OTHER INFORMATION: Target Knock-Down sequence

<400> SEQUENCE: 82
tggcacctat ggacaagtc                                                19

<210> SEQ ID NO 83
<211> LENGTH: 19
<212> TYPE: DNA
<213> ORGANISM: Artificial
<220> FEATURE:
<223> OTHER INFORMATION: Target Knock-Down sequence
```

<400> SEQUENCE: 83
ctgtttgcag tggctgtcc                                            19

<210> SEQ ID NO 84
<211> LENGTH: 19
<212> TYPE: DNA
<213> ORGANISM: Artificial
<220> FEATURE:
<223> OTHER INFORMATION: Target Knock-Down sequence

<400> SEQUENCE: 84
tgcagtgacg gatctaagc                                            19

<210> SEQ ID NO 85
<211> LENGTH: 19
<212> TYPE: DNA
<213> ORGANISM: Artificial
<220> FEATURE:
<223> OTHER INFORMATION: Target Knock-Down sequence

<400> SEQUENCE: 85
catgttctcc acaaggagc                                            19

<210> SEQ ID NO 86
<211> LENGTH: 19
<212> TYPE: DNA
<213> ORGANISM: Artificial
<220> FEATURE:
<223> OTHER INFORMATION: Target Knock-Down sequence

<400> SEQUENCE: 86
catgttcgcc agcggcttc                                            19

<210> SEQ ID NO 87
<211> LENGTH: 19
<212> TYPE: DNA
<213> ORGANISM: Artificial
<220> FEATURE:
<223> OTHER INFORMATION: Target Knock-Down sequence

<400> SEQUENCE: 87
gtggtcagct aaaggaatc                                            19

<210> SEQ ID NO 88
<211> LENGTH: 19
<212> TYPE: DNA
<213> ORGANISM: Artificial
<220> FEATURE:
<223> OTHER INFORMATION: Target Knock-Down sequence

<400> SEQUENCE: 88
gaagctgcgg cacaaacac                                            19

<210> SEQ ID NO 89
<211> LENGTH: 19
<212> TYPE: DNA
<213> ORGANISM: Artificial
<220> FEATURE:
<223> OTHER INFORMATION: Target Knock-Down sequence

<400> SEQUENCE: 89
agaaatggcg accaaacac                                            19

<210> SEQ ID NO 90
<211> LENGTH: 19
<212> TYPE: DNA

<210> SEQ ID NO 91
<211> LENGTH: 19
<212> TYPE: DNA
<213> ORGANISM: Artificial
<220> FEATURE:
<223> OTHER INFORMATION: Target Knock-Down sequence

<400> SEQUENCE: 90
agcatgaggg ttaaagtgc                                             19

<210> SEQ ID NO 91
<211> LENGTH: 19
<212> TYPE: DNA
<213> ORGANISM: Artificial
<220> FEATURE:
<223> OTHER INFORMATION: Target Knock-Down sequence

<400> SEQUENCE: 91
ctgcagtgct ttatcggac                                             19

<210> SEQ ID NO 92
<211> LENGTH: 19
<212> TYPE: DNA
<213> ORGANISM: Artificial
<220> FEATURE:
<223> OTHER INFORMATION: Target Knock-Down sequence

<400> SEQUENCE: 92
ttccttgtct ggaagctgc                                             19

<210> SEQ ID NO 93
<211> LENGTH: 19
<212> TYPE: DNA
<213> ORGANISM: Artificial
<220> FEATURE:
<223> OTHER INFORMATION: Target Knock-Down sequence

<400> SEQUENCE: 93
gatccttggt gactcaggc                                             19

<210> SEQ ID NO 94
<211> LENGTH: 19
<212> TYPE: DNA
<213> ORGANISM: Artificial
<220> FEATURE:
<223> OTHER INFORMATION: Target Knock-Down sequence

<400> SEQUENCE: 94
agctcagaat gacctagac                                             19

<210> SEQ ID NO 95
<211> LENGTH: 19
<212> TYPE: DNA
<213> ORGANISM: Artificial
<220> FEATURE:
<223> OTHER INFORMATION: Target Knock-Down sequence

<400> SEQUENCE: 95
gcagtggctc aaagagacc                                             19

<210> SEQ ID NO 96
<211> LENGTH: 19
<212> TYPE: DNA
<213> ORGANISM: Artificial
<220> FEATURE:
<223> OTHER INFORMATION: Target Knock-Down sequence

<400> SEQUENCE: 96
catctgcacc tatcacccc                                             19

```
<210> SEQ ID NO 97
<211> LENGTH: 19
<212> TYPE: DNA
<213> ORGANISM: Artificial
<220> FEATURE:
<223> OTHER INFORMATION: Target Knock-Down sequence

<400> SEQUENCE: 97
tggctaagag atccatctc                                                19

<210> SEQ ID NO 98
<211> LENGTH: 19
<212> TYPE: DNA
<213> ORGANISM: Artificial
<220> FEATURE:
<223> OTHER INFORMATION: Target knock-down sequence

<400> SEQUENCE: 98
atgaactctg tgatccagc                                                19

<210> SEQ ID NO 99
<211> LENGTH: 19
<212> TYPE: DNA
<213> ORGANISM: Artificial
<220> FEATURE:
<223> OTHER INFORMATION: Target Knock-Down sequence

<400> SEQUENCE: 99
ttcagtgcct aacagtggc                                                19

<210> SEQ ID NO 100
<211> LENGTH: 19
<212> TYPE: DNA
<213> ORGANISM: Artificial
<220> FEATURE:
<223> OTHER INFORMATION: Target knock-down sequence

<400> SEQUENCE: 100
gcatgaatat tgtggaggc                                                19

<210> SEQ ID NO 101
<211> LENGTH: 19
<212> TYPE: DNA
<213> ORGANISM: Artificial
<220> FEATURE:
<223> OTHER INFORMATION: Target knock-down sequence

<400> SEQUENCE: 101
agcatgatga tagttcctc                                                19

<210> SEQ ID NO 102
<211> LENGTH: 19
<212> TYPE: DNA
<213> ORGANISM: Artificial
<220> FEATURE:
<223> OTHER INFORMATION: Target knock-down sequence

<400> SEQUENCE: 102
tgtgcaagag gttcgttgc                                                19

<210> SEQ ID NO 103
<211> LENGTH: 19
<212> TYPE: DNA
<213> ORGANISM: Artificial
<220> FEATURE:
<223> OTHER INFORMATION: Target knock-down sequence
```

-continued

```
<400> SEQUENCE: 103
tgcatgatgt cggtcaccc                                                    19

<210> SEQ ID NO 104
<211> LENGTH: 19
<212> TYPE: DNA
<213> ORGANISM: Artificial
<220> FEATURE:
<223> OTHER INFORMATION: Target knock-down sequence

<400> SEQUENCE: 104
agcctacgag agtggaagc                                                    19

<210> SEQ ID NO 105
<211> LENGTH: 19
<212> TYPE: DNA
<213> ORGANISM: Artificial
<220> FEATURE:
<223> OTHER INFORMATION: Target knock-down sequence

<400> SEQUENCE: 105
agtttgtgta ggtatcgcc                                                    19

<210> SEQ ID NO 106
<211> LENGTH: 19
<212> TYPE: DNA
<213> ORGANISM: Artificial
<220> FEATURE:
<223> OTHER INFORMATION: Target knock-down sequence

<400> SEQUENCE: 106
tgttctttgg ctctgcagc                                                    19

<210> SEQ ID NO 107
<211> LENGTH: 19
<212> TYPE: DNA
<213> ORGANISM: Artificial
<220> FEATURE:
<223> OTHER INFORMATION: Target knock-down sequence

<400> SEQUENCE: 107
cttctacacg tccatgctc                                                    19

<210> SEQ ID NO 108
<211> LENGTH: 12
<212> TYPE: RNA
<213> ORGANISM: Artificial
<220> FEATURE:
<223> OTHER INFORMATION: Loop region

<400> SEQUENCE: 108
guuugcuaua ac                                                           12
```

MOLECULAR TARGETS AND COMPOUNDS, AND METHODS TO IDENTIFY THE SAME, USEFUL IN THE TREATMENT OF BONE AND JOINT DEGENERATIVE DISEASES

RELATED APPLICATIONS

The present application claims the benefit under 35 U.S.C. §119 of U.S. Provisional Application No. 60/936,569, filed Jun. 20, 2007, and the entire disclosure of said application is incorporated herein by reference in its entirety.

BACKGROUND OF THE INVENTION

The present invention relates to methods for identifying agents capable of inhibiting the expression or activity of proteins involved in the processes modulating osteoclastogenesis, which inhibition is useful in the prevention and/or treatment of bone and joint degenerative diseases and diseases involving aberrant activity of osteoclasts. In particular, the present invention provides methods for identifying agents for use in the prevention and/or treatment of rheumatoid arthritis.

Rheumatoid arthritis (RA) is a chronic joint degenerative disease, characterized by inflammation and destruction of the joint structures. When the disease is unchecked, it leads to substantial disability and pain due to the loss of joint functionality and even premature death. The aim of an RA therapy, therefore, is not to slow down the disease but to attain remission in order to stop the joint destruction. Besides the severity of the disease outcome, the high prevalence of RA (~0.8% of adults are affected worldwide) means a high socioeconomic impact (For reviews on RA, we refer to Smolen and Steiner (2003); Lee and Weinblatt (2001); Choy and Panayi (2001); O'Dell (2004) and Firestein (2003)).

Histological analysis of the joints of RA patients clearly evidences the mechanisms involved in the RA-associated degradative processes. The synovium is a cell layer, composed of a sublining and a lining region that separates the joint capsule from the synovial cavity. The inflamed synovium is central to the pathophysiology of RA. The synovial joint is shown as composed of two adjacent bony ends each covered with a layer of cartilage, separated by a joint space and surrounded by the synovial membrane and joint capsule. The synovial membrane is composed of the synovial lining (facing the cartilage and bone), which consists of a thin (1-3 cells) layer of synoviocytes and the sublining connective tissue layer that is highly vascularised. Histological differences in the synovium between normal and RA patients are indicated in FIG. 1.

Like many other forms of arthritis, rheumatoid arthritis (RA) is initially characterized by an inflammatory response of the synovial membrane ('synovitis') that is characterized by an important influx of various types of mononuclear cells as well as by the activation of the local or infiltrated mononuclear cells. The lining layer becomes hyperplastic (it can have a thickness of >20 cells) and the synovial membrane expands. However, in addition, the hallmark of RA is joint destruction: the joint spaces narrow or disappear as a sign of cartilage degradation and destructions of the adjacent bone, also termed 'erosions', have occurred. The destructive portion of the synovial membrane is termed 'pannus'. Various forms of bone degradation are apparent in RA. Besides a generalized osteoporosis, RA is also characterized by the erosion of the bone under and adjacent to the cartilage. These focal erosions result principally from the presence of an increased population of osteoclasts at the interface of bone and pannus (for a review on bone degradation in RA, we refer to Gravallese, 2002). Osteoclasts are multinucleated cells that attach to bone and secrete bone matrix degrading enzymes (e.g. Cathepsin K, MMP9) in an acidified space between the cell and the bone tissue (the resorption lacuna). In healthy individuals, the remodeling of bone is controlled by the activity of these osteoclasts, which resorb bone, and the activity of osteoblasts, which are involved in the production of the calcified bone matrix. Osteoblasts differentiate from mesenchymal stem cells, while osteoclasts differentiate from hematopoietic monocyte/macrophage precursors.

In RA, the concentration of the factors inducing osteoclast differentiation is increased at the interface between bone and the pannus (Pettit et al., 2006), leading to the dysregulation of the balance between bone formation and bone degradation. Key players in osteoclast differentiation are the receptor activator of NF-κB (RANK) and its ligand (RANKL) and osteoprotegerin (OPG).

RANKL is a membrane-anchored ligand of the TNF superfamily. In normal bone tissue, RANKL is expressed by osteoblasts, but in RA, synovial fibroblasts as well as activated T lymphocytes are important sources of RANKL. RANKL exerts its effect on osteoclasts or osteoclast precursor cells through RANK, a member of the TNF receptor superfamily. Another key player in osteoclast biology is OPG, a RANKL decoy receptor, which belongs to the TNF receptor superfamily and competes with RANK for the binding of RANKL. OPG, therefore, effectively inhibits osteoclast maturation and osteoclast activation. OPG-transgenic mice have a high bone mass (osteopetrosic phenotype), whereas the absence of OPG results in severe osteoporosis, as shown in OPG-knockout mice (Bucay et al., 1998). In summary, the balance between RANK/RANKL signaling and levels of OPG, the soluble decoy receptor for RANKL, regulates the development and activation of osteoclasts and therefore is strongly involved in bone metabolism. Thus, inhibition of RANKL function via OPG might prevent bone destruction in several diseases, e.g., RA. Of significance in this respect is the observation that RANKL knock-out mice are less prone to bone erosion when subjected to CIA (Pettit et al., 2001) and that recombinant OPG, alone or in combination with an anti-TNFα, prevents bone erosions in animal models for RA (Redlich et al., 2004). In addition, the capacity of drugs inducing OPG expression to protect bone in animal models of arthritis, in PTH induced bone resorption in rats and in metastasis of breast cancer cells to bone has been demonstrated (Onyia et al., 2004).

From the description of the biology of RANK, RANKL and OPG, it is clear that influencing the activity or differentiation of osteoclasts through modulation of these factors has potential not only in RA, but also for the treatment of osteoporosis. In addition, as bone metastasis associated with cancer also requires bone remodeling, inhibitors of osteoclast activity or differentiation could also be of use for this indication. For a review on bone metastasis, see Roodman, 2004.

Reported Developments

NSAIDS (Non-steroidal anti-inflammatory drugs) are used to reduce the pain associated with RA and improve life quality of the patients. These drugs will not, however, put a brake on the RA-associated joint destruction.

Corticosteroids are found to decrease the progression of RA as detected radiographically and are used at low doses to treat a subset of RA patients (30 to 60%). Serious side effects, however, are associated with long corticosteroid use (e.g. skin thinning, osteoporosis, cataracts, hypertension, hyperlipidemia).

Synthetic Disease-Modifying Anti-Rheumatic Drugs (DMARDs, e.g. methotrexate, leflunomide, sulfasalazine) mainly tackle the immuno-inflammatory component of RA. As a main disadvantage, these drugs only have a limited efficacy (joint destruction is only slowed down but not blocked by DMARDs such that disease progression in the long term continues). The lack of efficacy is indicated by the fact that, on average, only 30% of the patients achieve an ACR50 score after 24 months treatment with methotrexate, meaning that, according to the American College of Rheumatology, only 30% of the patients achieve a 50% improvement of their symptoms (O'Dell et al., 1996). In addition, the precise mechanism of action of DMARDs is often unclear.

Biological DMARDs (Infliximab, Etanercept, Adalimumab, Rituximab, CTLA4-Ig) are therapeutic proteins that inactivate cytokines (for example, TNF-α) or cells (for example, T-cells or B-cells) that have an important role in the RA pathophysiology (Kremer et al., 2003; Edwards et al., 2004). Although the TNF-α-blockers (Infliximab, Etanercept, Adalimumab) and methotrexate combination therapy is the most effective RA treatment currently available, it is striking that even this therapy only achieves a 50% improvement (ACR50) in disease symptoms in 50-60% of patients after 12 months therapy (St Clair et al., 2004). Increased risk of infections (tuberculosis), hematologic events and demyelinating disorders have been described for the TNF-α blockers (see also Gomez-Reino et al., 2003). TNF-α blockers, which are biological therapies, also require an unpleasant method of administration (frequent injections accompanied by infusion site reactions) and have high production cost. The fact that a variety of targeted therapies have similar but limited efficacies, suggests that there is a multiplicity of pathogenic factors for RA.

This calls for additional strategies to achieve remission. Remission is required since residual disease bears the risk of progressive joint damage and thus progressive disability. Inhibiting the immuno-inflammatory component of the RA disease, which represents the main target of drugs currently used for RA treatment, does not result in a blockade of joint degradation, the major hallmark of the disease.

Additionally, bisphosphonates are inhibitors of OC activity that are accepted as the most potent inhibitors of bone resorption clinically available and as a mainstay in the treatment of osteoporosis. Remarkably, however, bisphosphonate treatment does not prevent radiologic progression in RA patients (Valleala et al., 2004), potentially because of a poor bioavailability of bisphosphonates at the level of the OC in the pannus. A clear need exists, therefore, for innovative antiresorptive therapies in the field of RA.

The present invention is based on the discovery that agents which inhibit the expression and/or activity of the TARGETS disclosed herein are able to increase the expression of osteoprotegrin and thus have utility in decreasing bone resorption in joints. The present invention therefore provides TARGETS which are involved in the pathway leading to OPG expression and osteoclastogenesis, methods for screening for agents capable of inhibiting the expression and/or activity of TARGETS and uses of these agents in the prevention and/or treatment of joint degenerative conditions such as rheumatoid arthritis.

SUMMARY OF THE INVENTION

The present invention relates to a method for identifying compounds that inhibit osteoclastogenesis, comprising contacting a compound with a polypeptide comprising an amino acid sequence selected from the group consisting of SEQ ID NO: 41-69 and 80 (hereinafter "TARGETS") and fragments thereof, under conditions that allow said polypeptide to bind to said compound, and measuring a compound-polypeptide property related to osteoclastogenesis. In a specific embodiment the compound-polypeptide property measured is OPG expression levels.

Aspects of the present method include the in vitro assay of compounds using the polypeptide corresponding to a TARGET, or fragments thereof, such fragments being fragments of the amino acid sequences described by SEQ ID NO: 41-69 and 80, and cellular assays wherein TARGET inhibition is followed by observing indicators of efficacy including, for example, TARGET expression levels, TARGET enzymatic activity and/or OPG levels.

The present invention also relates to
(1) expression inhibitory agents comprising a polynucleotide selected from the group of an antisense polynucleotide, a ribozyme, and a small interfering RNA (siRNA), wherein said polynucleotide comprises a nucleic acid sequence complementary to, or engineered from, a naturally occurring polynucleotide sequence encoding a TARGET polypeptide said polynucleotide sequence comprising a sequence selected from the group consisting of SEQ ID NO: 1-29 and 40, and
(2) pharmaceutical compositions comprising said agent(s), useful in the treatment, or prevention, of chronic joint degenerative diseases such as rheumatoid arthritis.

Another aspect of the invention is a method of treatment, or prevention, of a condition related to bone and/or joint degeneration, in a subject suffering or susceptible thereto, by administering a pharmaceutical composition comprising an effective TARGET-expression inhibiting amount of a expression-inhibitory agent or an effective TARGET activity inhibiting amount of a activity-inhibitory agent.

A further aspect of the present invention is a method for diagnosis of a condition related to bone and/or joint degeneration comprising measurement of indicators of levels of TARGET expression in a subject.

Another aspect of this invention relates to the use of agents which inhibit a TARGET as disclosed herein in a therapeutic method, a pharmaceutical composition, and the manufacture of such composition, useful for the treatment of a disease involving bone and/or joint degeneration. In particular, the present method relates to the use of the agents which inhibit a TARGET in the treatment of a disease characterized by osteoclastogenesis, and in particular, a disease characterized by abnormal OPG expression. The agents are useful for amelioration or treatment of bone disease, particularly wherein it is desired to reduce or control osteoclast function and differentiation, including but not limited to osteoporosis, juvenile osteoporosis, osteogenesis imperfecta, hypercalcemia, hyperparathyroidism, osteomalacia, osteohalisteresis, osteolytic bone disease, osteonecrosis, Paget's disease of bone, bone loss due to rheumatoid arthritis, inflammatory arthritis, osteomyelitis, corticosteroid treatment, metastatic bone diseases, periodontal bone loss, bone loss due to cancer, age-related loss of bone mass, other forms of osteopenia, as well as in instances where facilitation of bone repair or replacement is desired such as bone fractures, bone defects, plastic surgery, dental and other implantations. In a particular embodiment the disease is rheumatoid arthritis.

Other objects and advantages will become apparent from a consideration of the ensuing description taken in conjunction with the following illustrative drawings.

BRIEF DESCRIPTION OF THE DRAWINGS

FIG. 4: Layout and performance of the control plate used in the screening of the SilenceSelect® collection in the OPG assay.

FIG. 6A Principle of the osteoclast—RASF coculture assay.

FIG. 6B Principle of the screening of Ad5-siRNA's in the osteoclast —RASF coculture assay.

FIG. 7C: Inhibition of osteoclast differentiation in a OC-RASF coculture by adenovirus induced overexpression of OPG.

FIG. 9A: Tabulated raw data from secondary assay and MOI rescreen (screen A) for particular targets.

FIG. 9B: Tabulated raw data from secondary assay and MOI rescreen (screen B) for particular targets.

FIG. 10: Layout of the "hit plates" used for the MMP1 assay. For selected OPG hits, the original OPG hit KD viruses as well as independent KD viruses targeting the same genes through the expression of different shRNAs are collected and grouped in wells C1 to F11.3 different negative control viruses (Ad5-Luc-KD_v13, Ad5-eGFP-KD_v5, Ad5-M6PR-KD_v1) and one positive control virus (Ad5-MMP1-KD) are grouped in rows B and G. The content of the "hit plates" is repropagated to generate a sufficient amount of virus crude lysate for the tests and to ensure homogeneity of the titers of the viruses. During the MMP1 experiments, the wells B2, B3 and B4 (shown in italics) of the plates containing the RASFs tranduced with the content of the "hit plates" are left untriggered, whereas all other wells are activated with "TNFalpha based trigger"

DETAILED DESCRIPTION

Figure 1:
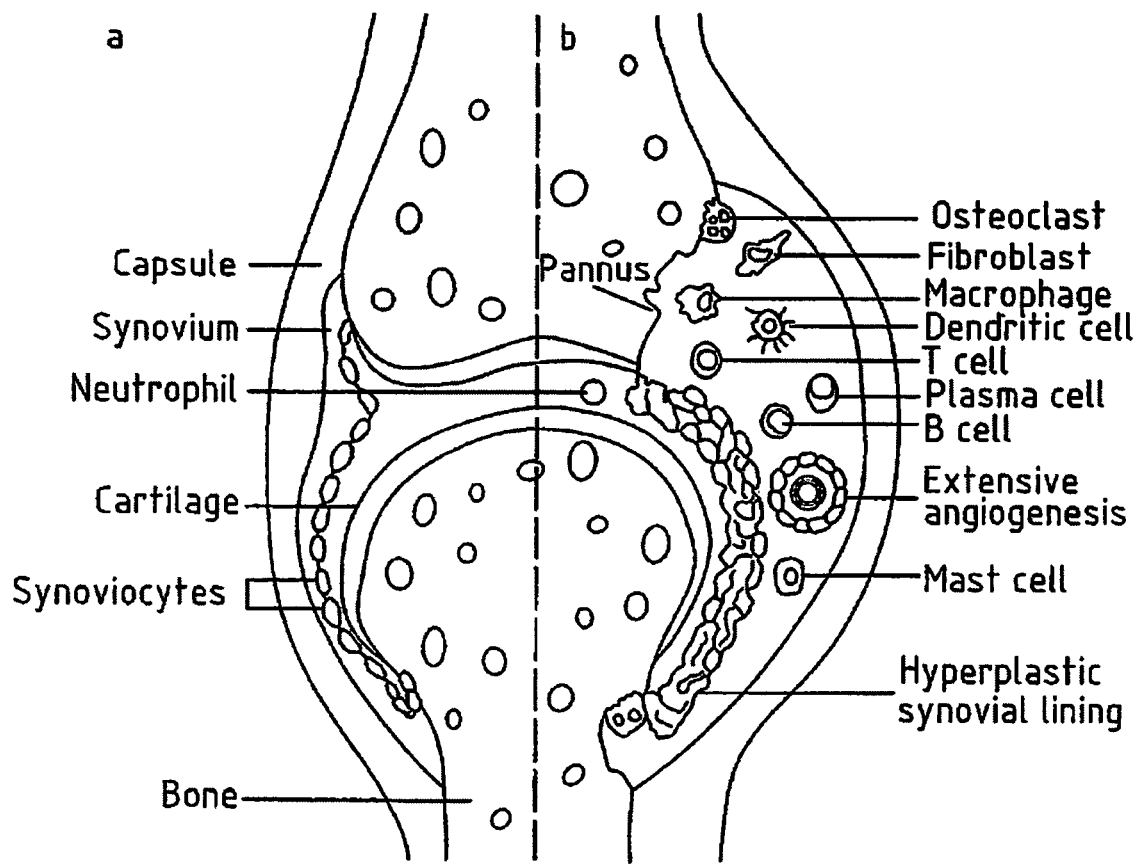
FIG. 1: Schematic view of a normal joint and its changes in rheumatoid arthritis (From Smolen and Steiner, 2003).

The following terms are intended to have the meanings presented therewith below and are useful in understanding the description and intended scope of the present invention.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense.

The term 'assay' means any process used to measure a specific property of a compound. A 'screening assay' means a process used to characterize or select compounds based upon their activity from a collection of compounds.

The term 'binding affinity' is a property that describes how strongly two or more compounds associate with each other in a non-covalent relationship. Binding affinities can be characterized qualitatively, (such as 'strong', 'weak', 'high', or 'low') or quantitatively (such as measuring the $K_D$).

The term 'carrier' means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

The term 'complex' means the entity created when two or more compounds bind to, contact, or associate with each other.

The term 'compound' is used herein in the context of a 'test compound' or a 'drug candidate compound' described in connection with the assays of the present invention. As such, these compounds comprise organic or inorganic compounds, derived synthetically or from natural sources. The compounds include inorganic or organic compounds such as polynucleotides, lipids or hormone analogs. Other biopolymeric organic test compounds include peptides comprising from about 2 to about 40 amino acids and larger polypeptides comprising from about 40 to about 500 amino acids, including polypeptide ligands, enzymes, receptors, channels, antibodies or antibody conjugates.

The term 'condition' or 'disease' means the overt presentation of symptoms (i.e., illness) or the manifestation of abnormal clinical indicators (for example, biochemical indicators or diagnostic indicators). Alternatively, the term 'disease' refers to a genetic or environmental risk of or propensity for developing such symptoms or abnormal clinical indicators.

The term 'contact' or 'contacting' means bringing at least two moieties together, whether in an in vitro system or an in vivo system.

The term 'derivatives of a polypeptide' relates to those peptides, oligopeptides, polypeptides, proteins and enzymes that comprise a stretch of contiguous amino acid residues of the polypeptide and that retain a biological activity of the protein, for example, polypeptides that have amino acid mutations compared to the amino acid sequence of a naturally-occurring form of the polypeptide. A derivative may further comprise additional naturally occurring, altered, glycosylated, acylated or non-naturally occurring amino acid residues compared to the amino acid sequence of a naturally occurring form of the polypeptide. It may also contain one or more non-amino acid substituents, or heterologous amino acid substituents, compared to the amino acid sequence of a naturally occurring form of the polypeptide, for example a reporter molecule or other ligand, covalently or non-covalently bound to the amino acid sequence.

The term 'derivatives of a polynucleotide' relates to DNA-molecules, RNA-molecules, and oligonucleotides that comprise a stretch of nucleic acid residues of the polynucleotide, for example, polynucleotides that may have nucleic acid mutations as compared to the nucleic acid sequence of a naturally occurring form of the polynucleotide. A derivative may further comprise nucleic acids with modified backbones such as PNA, polysiloxane, and 2'-O-(2-methoxy) ethylphosphorothioate, non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection.

The term 'osteoclast' refers to the large multinucleate cells found in growing bone that resorbs bony tissue, as in the formation of canals and cavities.

The term 'osteoclastogenesis' refers to the process by which osteoclasts are generated by fusion of cells of the monocyte-macrophage cell line.

The term 'effective amount' or 'therapeutically effective amount' means that amount of a compound or agent that will elicit the biological or medical response of a subject that is being sought by a medical doctor or other clinician.

The term 'endogenous' shall mean a material that a mammal naturally produces. Endogenous in reference to the term 'protease', 'kinase', or G-Protein Coupled Receptor ('GPCR') shall mean that which is naturally produced by a mammal (for example, and not limitation, a human). In contrast, the term non-endogenous in this context shall mean that which is not naturally produced by a mammal (for example, and not limitation, a human). Both terms can be utilized to describe both in vivo and in vitro systems. For example, and without limitation, in a screening approach, the endogenous or non-endogenous TARGET may be in reference to an in vitro screening system. As a further example and not limitation, where the genome of a mammal has been manipulated to include a non-endogenous TARGET, screening of a candidate compound by means of an in vivo system is viable.

The term 'expressible nucleic acid' means a nucleic acid coding for a proteinaceous molecule, an RNA molecule, or a DNA molecule.

The term 'expression' comprises both endogenous expression and overexpression by transduction.

The term 'expression inhibitory agent' means a polynucleotide designed to interfere selectively with the transcription, translation and/or expression of a specific polypeptide or protein normally expressed within a cell. More particularly, 'expression inhibitory agent' comprises a DNA or RNA molecule that contains a nucleotide sequence identical to or complementary to at least about 15-30, particularly at least 17, sequential nucleotides within the polyribonucleotide sequence coding for a specific polypeptide or protein. Exemplary expression inhibitory molecules include ribozymes, double stranded siRNA molecules, self-complementary single-stranded siRNA molecules, genetic antisense constructs, and synthetic RNA antisense molecules with modified stabilized backbones.

The term 'fragment of a polynucleotide' relates to oligonucleotides that comprise a stretch of contiguous nucleic acid residues that exhibit substantially a similar, but not necessarily identical, activity as the complete sequence. In a particular aspect, 'fragment' may refer to a oligonucleotide comprising a nucleic acid sequence of at least 5 nucleic acid residues (preferably, at least 10 nucleic acid residues, at least 15 nucleic acid residues, at least 20 nucleic acid residues, at least 25 nucleic acid residues, at least 40 nucleic acid residues, at least 50 nucleic acid residues, at least 60 nucleic residues, at least 70 nucleic acid residues, at least 80 nucleic acid residues, at least 90 nucleic acid residues, at least 100 nucleic acid residues, at least 125 nucleic acid residues, at least 150 nucleic acid residues, at least 175 nucleic acid residues, at least 200 nucleic acid residues, or at least 250 nucleic acid residues) of the nucleic acid sequence of said complete sequence.

The term 'fragment of a polypeptide' relates to peptides, oligopeptides, polypeptides, proteins, monomers, subunits and enzymes that comprise a stretch of contiguous amino acid residues, and exhibit substantially a similar, but not necessarily identical, functional or expression activity as the complete sequence. In a particular aspect, 'fragment' may refer to a peptide or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of said complete sequence.

The term 'hybridization' means any process by which a strand of nucleic acid binds with a complementary strand through base pairing. The term 'hybridization complex' refers to a complex formed between two nucleic acid sequences by virtue of the formation of hydrogen bonds between complementary bases. A hybridization complex may be formed in solution (for example, Cot or Rot analysis) or formed between one nucleic acid sequence present in solution and another nucleic acid sequence immobilized on a solid support (for example, paper, membranes, filters, chips, pins or glass slides, or any other appropriate substrate to which cells or their nucleic acids have been fixed). The term "stringent conditions" refers to conditions that permit hybridization between polynucleotides and the claimed polynucleotides. Stringent conditions can be defined by salt concentration, the concentration of organic solvent, for example, formamide, temperature, and other conditions well known in the art. In particular, reducing the concentration of salt, increasing the concentration of formamide, or raising the hybridization temperature can increase stringency. The term 'standard hybridization conditions' refers to salt and temperature conditions substantially equivalent to 5×SSC and 65° C. for both hybridization and wash. However, one skilled in the art will appreciate that such 'standard hybridization conditions' are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20$^N$C below the predicted or determined $T_m$ with washes of higher stringency, if desired.

The term 'inhibit' or 'inhibiting', in relationship to the term 'response' means that a response is decreased or prevented in the presence of a compound as opposed to in the absence of the compound.

The term 'inhibition' refers to the reduction, down regulation of a process or the elimination of a stimulus for a process, which results in the absence or minimization of the expression or activity of a protein or polypeptide.

The term 'induction' refers to the inducing, up-regulation, or stimulation of a process, which results in the expression or activity of a protein or polypeptide.

The term 'ligand' means an endogenous, naturally occurring molecule specific for an endogenous, naturally occurring receptor.

The term 'pharmaceutically acceptable salts' refers to the non-toxic, inorganic and organic acid addition salts, and base addition salts, of compounds which inhibit the expression or activity of TARGETS as disclosed herein. These salts can be prepared in situ during the final isolation and purification of compounds useful in the present invention.

The term 'polypeptide' relates to proteins (such as TARGETS), proteinaceous molecules, fragments of proteins, monomers, subunits or portions of polymeric proteins, peptides, oligopeptides and enzymes (such as kinases, proteases, GPCR's etc.).

The term 'polynucleotide' means a polynucleic acid, in single or double stranded form, and in the sense or antisense orientation, complementary polynucleic acids that hybridize to a particular polynucleic acid under stringent conditions, and polynucleotides that are homologous in at least about 60 percent of its base pairs, and more particularly 70 percent of its base pairs are in common, most particularly 90 percent, and in a particular embodiment, 100 percent of its base pairs. The polynucleotides include polyribonucleic acids, polydeoxyribonucleic acids, and synthetic analogues thereof. It also includes nucleic acids with modified backbones such as peptide nucleic acid (PNA), polysiloxane, and 2'-O-(2-methoxy)ethylphosphorothioate. The polynucleotides are described by sequences that vary in length, that range from about 10 to about 5000 bases, particularly about 100 to about 4000 bases, more particularly about 250 to about 2500 bases. One polynucleotide embodiment comprises from about 10 to about 30 bases in length. A particular embodiment of polynucleotide is the polyribonucleotide of from about 17 to about 22 nucleotides, more commonly described as small interfering RNAs (siRNAs). Another particular embodiment are nucleic acids with modified backbones such as peptide nucleic acid (PNA), polysiloxane, and 2'-O-(2-methoxy)ethylphosphorothioate, or including non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection. Polynucleotides herein are selected to be 'substantially' complementary to different strands of a particular target DNA sequence. This means that the polynucleotides must be sufficiently complementary to hybridize with their respective strands. Therefore, the polynucleotide sequence need not reflect the exact sequence of the target sequence. For example, a non-complementary nucleotide fragment may be attached to the 5' end of the polynucleotide, with the remainder of the polynucleotide sequence being complementary to the strand. Alternatively, non-complementary bases or longer sequences can be interspersed into the polynucleotide, provided that the polynucleotide sequence has sufficient complementarity with the sequence of the strand to hybridize therewith under stringent conditions or to form the template for the synthesis of an extension product.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term 'solvate' means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

The term 'subject' includes humans and other mammals.

The term 'TARGET' or 'TARGETS' means the protein(s) or polypeptide(s) identified in accordance with the assays described herein and determined to be involved in the modulation of OPG expression levels.

'Therapeutically effective amount' means that amount of a drug, compound, expression inhibitory agent, or pharmaceutical agent that will elicit the biological or medical response of a subject that is being sought by a medical doctor or other clinician. In particular, with regard to treating an disease condition characterized by the activation of osteoclastogenesis, the term 'effective bone resorption inhibiting amount' is intended to mean that effective amount of a compound that inhibits a TARGET as disclosed herein that will bring about a biologically meaningful increase in the expression of OPG in the subject's disease affected tissues such that osteoclastogenesis is inhibited and bone resorption is reduced.

A compound having OPG inducing properties or an 'OPG inducing compound' means a compound that when provided to a cell in effective amounts is able to cause a biologically meaningful increase in the expression or production of OPG in such cells.

The term 'treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, 'treating' or 'treatment' relates to slowing the progression of the disease.

Applicants' invention is relevant to the reduction of bone resorption and osteoclastogenesis, and is in part based on the TARGET's relationship to OPG expression and osteoclast differentiation. The TARGETs are relevant in bone and joint diseases which involve or invoke bone resorption or degradation. In particular, the TARGETs are relevant in rheumatoid arthritis.

OPG expression is relevant to bone resorption as it inversely correlates to the stimulation of osteoclastogenesis towards an activated phenotype that, in vivo, is responsible for bone resorption. This is supported by the observation that RANKL knock-out mice are less prone to bone erosion when subjected to CIA (Pettit et al., 2001) and recombinant OPG, alone or in combination with an anti-TNFα, prevents bone erosions in animal models for RA (Redlich et al., 2004).

Therefore, induction of OPG expression represents a valuable therapeutic approach towards the treatment of RA. Accordingly, if the reduction in expression of a candidate protein in synovial fibroblasts or another cell composing the joint leads to an increased in OPG expression and/or activity levels, then such protein is involved in the regulation of OPG expression and is a relevant target for the development of therapeutic strategies for the treatment of RA. The present inventors have identified such target proteins by screening recombinant adenoviruses mediating the expression of a library of shRNAs, referred to herein as 'Ad-siRNAs'. The collection used herein is further referred to as an 'adenoviral siRNA library' or the 'SilenceSelect®' collection. These libraries contain recombinant adenoviruses, further referred to as knock-down (KD) viruses or Ad-siRNAs, that mediate the expression in cells of shRNAs which reduce the expression levels of targeted genes by a RNA interference (RNAi)-based mechanism (WO03/020931). The screening work is described below in Example 1.

As noted above, the present invention is based on the present inventors' discovery that the TARGET polypeptides, identified as a result of a variety of screens described below in the Examples, are factors not only in the regulation of expression of OPG, but also in the modulation of osteoclastogenesis. A reduced activity of the OPG-inducing proteins is believed to be causative and to correlate with the progression of various diseases associated with an increased bone resorption, including diseases that involve the degradation of the joint, e.g. rheumatoid arthritis. OPG expression is involved in bone disease, including but not limited to osteoporosis, juvenile osteoporosis, osteogenesis imperfecta, hypercalcemia, hyperparathyroidism, osteomalacia, osteohalisteresis, osteolytic bone disease, osteonecrosis, Paget's disease of bone, bone loss due to rheumatoid arthritis, inflammatory arthritis, osteomyelitis, corticosteroid treatment, metastatic bone diseases, periodontal bone loss, bone loss due to cancer, age-related loss of bone mass, other forms of osteopenia. Modulation of OPG may also be useful in instances where facilitation of bone repair or replacement is desired such as bone fractures, bone defects, plastic surgery, dental and other implantations.

In one aspect, the present invention relates to a method for assaying for drug candidate compounds that inhibit bone resorption, comprising contacting the compound with a polypeptide comprising an amino acid sequence of SEQ ID NO: 41-69 and 80, or fragment thereof, under conditions that allow said polypeptide to bind to the compound, and detecting the formation of a complex between the polypeptide and the compound. One particular means of measuring the complex formation is to determine the binding affinity of said compound to said polypeptide.

More particularly, the invention relates to a method for identifying an agent that inhibits bone resorption, the method comprising:
  (a) contacting a population of mammalian cells with one or more compound that exhibits binding affinity for a TARGET polypeptide, or fragment thereof, and
  (b) measuring a compound-polypeptide property related to bone resorption.

In a further aspect, the present invention relates to a method for assaying for drug candidate compounds that inhibit bone resorption, comprising contacting the compound with a polypeptide comprising an amino acid sequence of SEQ ID NO: 41-69 and 80, or fragment thereof, under conditions that allow said compound to modulate the activity or expression of the polypeptide, and determining the activity or expression of the polypeptide. One particular means of measuring the activity or expression of the polypeptide is to determine the amount of said polypeptide using a polypeptide binding agent, such as an antibody, or to determine the activity of said polypeptide in a biological or biochemical measure, for instance the amount of phosphorylation of a target of a kinase polypeptide.

The compound-polypeptide property referred to above is related to the expression and/or activity of the TARGET, and is a measurable phenomenon chosen by the person of ordinary skill in the art. The measurable property may be, for example, the binding affinity of said compound for a peptide domain of the polypeptide TARGET or the level of any one of a number of biochemical marker levels of bone resorption. An event or activity related to bone resorption can be measured, for example, the measurement of the amount or activity of osteoclasts or the measurement of markers indicative for bone resorption, as e.g. CTX-I or osteocalcin. The compound may be incubated with osteoclasts, osteoclast precursors, or related cell lines and the differentiation, maturation activation and functional status of said cells determined. There are multiple osteoclast culture systems or methods and bone formation assays that can be used successfully to screen potential osteogenic compounds of this invention. See, e.g., U.S. Pat. No. 6,080,779. One osteoclast culture for use in screening is a neonatal mouse calvaria assay. In addition to this assay, the effect of compounds on murine calvarial bone growth can also be tested in vivo. In addition, osteoclast cultures, containing macrophages, osteoclast precursors and osteoclasts, can be generated from bone marrow precursors, particularly from bone marrow macrophages and utilized in assessment of compounds for osteoclast modulating activity. Bone marrow macrophages are cultured in 48- or 96-well cell culture dishes in the presence of M-CSF (10 ng/mL), RANKL (100 ng/mL), with or without addition of compound(s) or control(s), and medium changed (e.g. on day 3). Osteoclast-like cells are characterized by staining for tartrate-resistant acid phosphatase (TRAP) activity. In assessing bone resorption, for instance using a pit assay, osteoclasts are generated on whale dentin slices from bone marrow macrophages. After three days of culture to generate osteoclasts, compound(s) or control(s) are added to the culture for two days. At the end of the experiment, cells are TRAP stained and photographed to document cell number. Cells are then removed from the dentin slices with 0.5M ammonium hydroxide and mechanical agitation. Maximum resorption lacunae depth is measured using a confocal microscope (Microradiance, Bio-Rad Laboratories, Hercules, Calif.). For evaluation of pit number and resorbed area, dentin slices are stained with Coumassie brilliant blue and analyzed with light microscopy using Osteomeasure software (Osteometrics, Decatur, Ga.) for quantitation.

In an additional aspect, the present invention relates to a method for assaying for drug candidate compounds that inhibit bone resorption, comprising contacting the compound with a nucleic acid encoding a TARGET polypeptide, including comprising a nucleic acid sequence of SEQ ID NO: 1-29 and 40, or fragment/portion thereof, under conditions that allow said nucleic acid to bind to or otherwise associate with the compound, and detecting the formation of a complex between the nucleic acid and the compound. One particular means of measuring the complex formation is to determine the binding affinity of said compound to said nucleic acid or the presence of a complex by virtue of resistance to nucleases or by gel mobility assays. Alternatively, complex formation may be determined by inhibition of nucleic acid transcription or translation.

In a particular embodiment of the invention, the TARGET polypeptide comprises an amino acid sequence selected from the group consisting of SEQ ID No: 41-69 and 80 as listed in Table 1. In an embodiment of the invention, the nucleic acid capable of encoding the TARGET polypeptide comprises a nucleic acid sequence selected from the group consisting of SEQ ID NO: 1-29 and 40 as listed in Table 1.

TABLE 1

| Target Gene Symbol | GenBank Nucleic Acid Acc #: | SEQ ID NO: DNA | GenBank Protein Acc # | SEQ ID NO: Protein | NAME | Class |
|---|---|---|---|---|---|---|
| NTRK2 | NM_006180 | 1 | NP_006171 | 41 | neurotrophic tyrosine kinase, receptor, type 2, transcript variant a | Kinase |
|  | NM_001007097 | 2 | NP_001007098 | 42 | neurotrophic tyrosine kinase, receptor, type 2, transcript variant b |  |
|  | NM_001018064 | 3 | NP_001018074 | 43 | neurotrophic tyrosine kinase, receptor, type 2, transcript variant c |  |
|  | NM_001018065 | 4 | NP_001018075 | 44 | neurotrophic tyrosine kinase, receptor, type 2, transcript variant d |  |
|  | NM_001018066 | 5 | NP_001018076 | 45 | neurotrophic tyrosine kinase, receptor, type 2, transcript variant e |  |
| MAP4K4 | NM_004834 | 6 | NP_004825 | 46 | mitogen-activated protein kinase kinase kinase kinase 4, transcript variant 1 | Kinase |
|  | NM_145686 | 7 | NP_663719 | 47 | mitogen-activated protein kinase kinase kinase kinase 4, transcript variant 2 |  |
|  | NM_145687 | 8 | NP_663720 | 48 | mitogen-activated protein kinase kinase kinase kinase 4, transcript variant 3 |  |
|  | SK437 | 9 | n/a | 49 | kinase SK437 from Manning et al., Science. |  |
| MMP17 | NM_016155 | 10 | NP_057239 | 50 | matrix metalloproteinase 17 (membrane-inserted) | Protease |
| PLA2G12A | NM_030821 | 11 | NP_110448 | 51 | phospholipase A2, group XIIA | Enzyme |
| MGLL | NM_007283 | 12 | NP_009214 | 52 | monoglyceride lipase, transcript variant 1 | Enzyme |
|  | NM_001003794 | 13 | NP_001003794 | 53 | monoglyceride lipase, transcript variant 2 |  |
| GPR44 | NM_004778 | 14 | NP_004769 | 54 | G protein-coupled receptor 44 | GPCR |
| MIR16 | NM_016641 | 15 | NP_057725 | 55 | membrane interacting protein of RGS16 | PDE |

TABLE 1-continued

| Target Gene Symbol | GenBank Nucleic Acid Acc #: | SEQ ID NO: DNA | GenBank Protein Acc # | SEQ ID NO: Protein | NAME | Class |
|---|---|---|---|---|---|---|
| PTK6 | NM_005975 | 16 | NP_005966 | 56 | PTK6 protein tyrosine kinase 6 | Kinase |
| MRAS | NM_012219 | 17 | NP_036351 | 57 | muscle RAS oncogene homolog | Enzyme |
| SLC4A8 | NM_004858 | 18 | NP_004849 | 58 | solute carrier family 4, sodium bicarbonate cotransporter, member 8 | Ion Channel |
| ENPP2 | NM_006209 | 19 | NP_006200 | 59 | ectonucleotide pyrophosphatase/ phosphodiesterase 2 (autotaxin) | PDE |
| MAP3K3 | NM_002401 | 20 | NP_002392 | 60 | mitogen-activated protein kinase kinase kinase 3, transcript variant 2 | Kinase |
|  | NM_203351 | 21 | NP_976226 | 61 | mitogen-activated protein kinase kinase kinase 3, transcript variant 1 | Kinase |
| P2RY14 | NM_014879 | 22 | NP_055694 | 62 | purinergic receptor P2Y, G-protein coupled, 14 | GPCR |
| NEK3 | NM_002498 | 23 | NP_002489 | 63 | NIMA (never in mitosis gene a)- related kinase 3, transcript variant 1 | Kinase |
|  | NM_152720 | 24 | NP_689933 | 64 | NIMA (never in mitosis gene a)- related kinase 3, transcript variant 2 |  |
| KLKB1 | NM_000892 | 25 | NP_000883 | 65 | kallikrein B, plasma (Fletcher factor) 1 | Protease |
| FNTA | NM_002027 | 26 | NP_002018 | 66 | farnesyltransferase, CAAX box, alpha, transcript variant 1 | Enzyme |
|  | NM_001018676 | 27 | NP_001018196 | 67 | farnesyltransferase, CAAX box, alpha, transcript variant 2 |  |
|  | NM_001018677 | 28 | NP_001018197 | 68 | farnesyltransferase, CAAX box, alpha, transcript variant 3 |  |
| LOC283226 | XM_208554 | 29 | XP_208554 | 69 | similar to Protein farnesyltransferase/ geranylgeranyl- transferase type I alpha subunit (CAAX farnesyltransferase alpha subunit) (Ras proteins prenyltransferase alpha) (FTase-alpha) (Type I protein geranyl- geranyltransferase alpha subunit) (GGTase-I- . . . |  |
| USP9Y | NM_004654 | 30 | NP_004645 | 70 | ubiquitin specific peptidase 9, Y-linked (fat facets-like, *Drosophila*) | Protease |
| CDC7 | NM_003503 | 31 | NP_003494 | 71 | CDC7 cell division cycle 7 (*S. cerevisiae*) | Kinase |
| PPIA | NM_021130 | 32 | NP_066953 | 72 | peptidylprolyl isomerase A (cyclophilin A), transcript variant 1 | Enzyme |
| TOP2B | NM_001068 | 33 | NP_001059 | 73 | topoisomerase (DNA) II beta 180 kDa | Kinase |

TABLE 1-continued

| Target Gene Symbol | GenBank Nucleic Acid Acc #: | SEQ ID NO: DNA | GenBank Protein Acc # | SEQ ID NO: Protein | NAME | Class |
|---|---|---|---|---|---|---|
| PPP2CB | NM_004156 | 34 | NP_004147 | 74 | protein phosphatase 2 (formerly 2A), catalytic subunit, beta isoform, transcript variant 1 | Phosphatase |
| | NM_001009552 | 35 | NP_001009552 | 75 | protein phosphatase 2 (formerly 2A), catalytic subunit, beta isoform, transcript variant 2 | |
| COX10 | NM_001303 | 36 | NP_001294 | 76 | COX10 homolog, cytochrome c oxidase assembly protein, heme A: farnesyltransferase (yeast), nuclear gene encoding mitochondrial protein | Enzyme |
| CCR1 | NM_001295 | 37 | NP_001286 | 77 | chemokine (C—C motif) receptor 1 | GPCR |
| B3GALT1 | NM_020981 | 38 | NP_066191 | 78 | UDP-Gal:betaGlcNAc beta 1,3-galactosyltransferase, polypeptide 1 | Enzyme |
| SLC9A8 | NM_015266 | 39 | NP_056081 | 79 | solute carrier family 9 (sodium/hydrogen exchanger), isoform 8 | Ion Channel |
| CXCR6 | NM_006564 | 40 | NP_006555 | 80 | chemokine (C-X-C motif) receptor 6 | GPCR |

Another particular embodiment of the invention comprises the TARGETS identified as SEQ ID NOS. 56, 57, 59-61 and 80. Another particular embodiment of the invention comprises the ion channel TARGET identified as SEQ ID NO: 58. A further particular embodiment of the invention comprises the GPCR TARGETs identified as SEQ ID NOs: 54, 62 and 80. A further particular embodiment of the invention comprises the kinase TARGETs identified as SEQ ID NOs: 41-49, 56, 60-61 and 63-64. A further particular embodiment of the invention comprises the protease TARGETs identified as SEQ ID NOs: 50 and 65. A further particular embodiment of the invention comprises the enzyme TARGETs identified as SEQ ID NOs: 51-53, 57, 66-69. A further particular embodiment of the invention comprises the phosphodiesterase TARGETs identified as SEQ ID NOs: 55 and 59. It will be appreciated by a person of skill in the art that one protein may have a number of reported sequences and these sequences may interchangeably be used to explore the same TARGET. In particular, in one embodiment the TARGET is NTRK2 which may be described by any one of SEQ ID NOs: 41, 42, 43, 44 or 45. In a further embodiment the TARGET is MAP4K4 which may be described by any one of SEQ ID NOs: 46, 47, 48 or 49. In a further embodiment the TARGET is MGLL which may be described by SEQ ID NO: 52 or 53. In a further embodiment the TARGET is MAP3K3 which may be described by SEQ ID NO: 60 or 61. In a further embodiment the TARGET is NEK3 which may be described by SEQ ID NO: 63 or 64. In a further embodiment the TARGET is FNTA which may be described by any one of SEQ ID NOs: 66, 65, 68 or 69.

Depending on the choice of the skilled artisan, the present assay method may be designed to function as a series of measurements, each of which is designed to determine whether the drug candidate compound is indeed acting on the polypeptide to thereby inhibit bone resorption. For example, an assay designed to determine the binding affinity of a compound to the polypeptide, or fragment thereof, may be necessary, but not sufficient, to ascertain whether the test compound would be useful for inhibiting bone resorption when administered to a subject.

Such binding information would be useful in identifying a set of test compounds for use in an assay that would measure a different property, such as one further down the biochemical pathway, such as for example OPG expression. Such second assay may be designed to confirm that the test compound, having binding affinity for the polypeptide, actually inhibits bone resorption. Such assay may be designed to confirm that the test compound inhibits osteoclast differentiation, affects RANK or RANKL, has anti-inflammatory effects, such as effects on MMP1. Suitable and exemplary assays are known in the art and/or described further herein. Suitable controls should always be in place to insure against false positive or false negative readings. In a particular embodiment of the present invention the screening method comprises the additional step of comparing the compound to a suitable control. In one embodiment, the control may be a cell or a sample that has not been in contact with the test compound. In an alternative embodiment, the control may be a cell that does not express the TARGET; for example in one aspect of such an embodiment the test cell may naturally express the TARGET and the control cell may have been contacted with an agent, e.g. an siRNA, which inhibits or prevents expression of the TARGET. Alternatively, in another aspect of such an embodiment, the cell in its native state does not express the TARGET and the test cell has been engineered so as to express the TARGET, so that in this embodiment, the control could be the untransformed native cell.

Whilst exemplary controls are described herein, this should not be taken as limiting; it is within the scope of a person of skill in the art to select appropriate controls for the experimental conditions being used.

The order of taking these measurements or of performing said steps is not believed to be critical to the practice of the present invention, which may be practiced in any order. For example, one may first perform a screening assay of a set of compounds for which no information is known respecting the compounds' binding affinity for the polypeptide. Alternatively, one may screen a set of compounds identified as having binding affinity for a polypeptide domain, or a class of compounds identified as being an inhibitor of the polypeptide. However, for the present assay to be meaningful to the ultimate use of the drug candidate compounds, a measurement of bone resorption activity may be necessary. Validation studies including controls and measurements of binding affinity to the polypeptides of the invention are nonetheless useful in identifying a compound useful in any therapeutic or diagnostic application.

The present assay method may be practiced in vitro, using one or more of the TARGET proteins, or fragments thereof, including monomers, portions or subunits of polymeric proteins, peptides, oligopeptides and enzymatically active portions thereof.

The binding affinity of a compound with the polypeptide TARGET can be measured by methods known in the art, such as using surface plasmon resonance biosensors (Biacore®), by saturation binding analysis with a labeled compound (for example, Scatchard and Lindmo analysis), by differential UV spectrophotometer, fluorescence polarization assay, Fluorometric Imaging Plate Reader (FLIPR®) system, Fluorescence resonance energy transfer, and Bioluminescence resonance energy transfer. The binding affinity of compounds can also be expressed in dissociation constant (Kd) or as $IC_{50}$ or $EC_{50}$. The $IC_{50}$ represents the concentration of a compound that is required for 50% inhibition of binding of another ligand to the polypeptide. The $EC_{50}$ represents the concentration required for obtaining 50% of the maximum effect in any assay that measures TARGET function. The dissociation constant, Kd, is a measure of how well a ligand binds to the polypeptide, it is equivalent to the ligand concentration required to saturate exactly half of the binding-sites on the polypeptide. Compounds with a high affinity binding have low Kd, $IC_{50}$ and $EC_{50}$ values, for example, in the range of 100 nM to 1 pM; a moderate- to low-affinity binding relates to high Kd, $IC_{50}$ and $EC_{50}$ values, for example in the micromolar range.

The present assay method may also be practiced in a cellular assay. A host cell expressing the TARGET, or fragment(s) thereof, can be a cell with endogenous expression or a cell over-expressing the TARGET, for example, by transduction. When the endogenous expression of the polypeptide is not sufficient to determine a baseline that can easily be measured, one may use host cells that over-express TARGET. Over-expression has the advantage that the level of the TARGET substrate end-products is higher than the activity level by endogenous expression. Accordingly, measuring such levels using presently available techniques is easier. Alternatively, a non-endogenous form of TARGET may be expressed or overexpressed in a cell and utilized in screening.

One embodiment of the present method for identifying a compound that increases OPG expression and/or activity comprises culturing a population of mammalian cells expressing a TARGET polypeptide, or a functional fragment or derivative thereof, determining a first level of OPG expression and/or activity in said population of cells; eventually activating the population of cells; exposing said population of cells to a compound, or a mixture of compounds; determining a second level of OPG expression and/or activity in said population of cells during or after exposure of said population of cells to said compound, or the mixture of said compounds; and identifying the compound(s) that induce OPG expression and/or activity.

As noted above, inhibition of osteoclastogenesis and bone resorption may be determined by measuring the expression and/or activity of the TARGET polypeptide and/or a known osteoclastogenesis and/or bone resorption inhibiting protein. In a particular embodiment, said osteoclastogenesis and/or bone resorption inhibiting protein is able to prevent the formation of activated osteoclasts which act to remove bone tissue. In a specific embodiment of the present invention, said osteoclastogenesis and/or bone resorption inhibiting protein is osteoprotegerin (OPG).

The expression of an osteoclastogenesis and/or bone resorption inhibiting protein can be determined by methods known in the art such as Western blotting using specific antibodies, or an ELISA using antibodies specifically recognizing a particular osteoclastogenesis and/or bone resorption inhibiting protein.

The present inventors have developed a protocol allowing the detection, in a high throughput mode, of the level of OPG in complex media such as the supernatant of cultured cells.

The present inventors have developed a protocol allowing the detection, in a high throughput mode, of the level of osteoclast differentiation in complex media and in monoculture or coculture, based on a cell-based ELISA for $\alpha_v\beta_3$ integrin.

The present inventors identified TARGET genes involved in osteoclastogenesis and/or bone resorption by using a 'knock-down' library. This type of library is a screen in which siRNA molecules are transduced into cells by recombinant adenoviruses, which siRNA molecules inhibit or repress the expression of a specific gene as well as expression and activity of the corresponding gene product in a cell. Each siRNA in a viral vector corresponds to a specific natural gene. By identifying a siRNA that induces OPG expression, a direct correlation can be drawn between the specific gene expression and the pathway between OPG expression and activity and osteoclastogenesis leading to bone resorption. The TARGET genes identified using the knock-down library (the protein expression products thereof herein referred to as "TARGET" polypeptides) are then used in the present inventive method for identifying compounds that can be used to prevent bone resorption. Indeed, shRNA compounds comprising the sequences listed in Table 2 (particularly SEQ ID NOs: 81-97 and 107, particularly SEQ ID NOs: 88, 89, 91, 92 and 107) inhibit the expression and/or activity of these TARGET genes and increase the OPG expression in cells, confirming the role of the TARGETS in the pathway from OPG expression to inhibition of bone resorption.

TABLE 2

Exemplary KD target sequences useful in the practice of the present expression-inhibitory agent invention

| HIT ID | SYMBOL | TARGET KD Sequence | TARGET SEQ ID NO: |
|---|---|---|---|
| H51-082 | NTRK2 | ATGCAGTGCCTCTCGGATC | 81 |
| H51-054 | MAP4K4 | TGGCACCTATGGACAAGTC | 82 |
| H51-104 | MMP17 | CTGTTTGCAGTGGCTGTCC | 83 |

TABLE 2-continued

Exemplary KD target sequences useful in the practice of the present expression-inhibitory agent invention

| HIT ID | SYMBOL | TARGET KD Sequence | TARGET SEQ ID NO: |
|---|---|---|---|
| H51-172 | PLA2G12A | TGCAGTGACGGATCTAAGC | 84 |
| H51-181 | MGLL | CATGTTCTCCACAAGGAGC | 85 |
| H51-225 | GPR44 | CATGTTCGCCAGCGGCTTC | 86 |
| H51-236 | MIR16 | GTGGTCAGCTAAAGGAATC | 87 |
| H51-240 | PTK6 | GAAGCTGCGGCACAAACAC | 88 |
| H51-137 | MRAS | AGAAATGGCGACCAAACAC | 89 |
| H51-121 | SLC4A8 | AGCATGAGGGTTAAAGTGC | 90 |
| H51-122 | ENPP2 | CTGCAGTGCTTTATCGGAC | 91 |
| H51-014 | MAP3K3 | TTCCTTGTCTGGAAGCTGC | 92 |
| H51-018 | P2RY14 | GATCCTTGGTGACTCAGGC | 93 |
| H51-041 | P2RY14 | AGCTCAGAATGACCTAGAC | 94 |
| H51-040 | NEK3 | GCAGTGGCTCAAAGAGACC | 95 |
| H51-046 | KLKB1 | CATCTGCACCTATCACCCC | 96 |
| H51-142 | FNTA/ LOC283226 | TGGCTAAGAGATCCATCTC | 97 |
| H51-103 | USP9Y | ATGAACTCTGTGATCCAGC | 98 |
| H51-119 | CDC7 | TTCAGTGCCTAACAGTGGC | 99 |
| H51-145 | PPIA | GCATGAATATTGTGGAGGC | 100 |
| H51-153 | TOP2B | AGCATGATGATAGTTCCTC | 101 |
| H51-177 | PPP2CB | TGTGCAAGAGGTTCGTTGC | 102 |
| H51-183 | COX10 | TGCATGATGTCGGTCACCC | 103 |
| H51-206 | CCR1 | AGCCTACGAGAGTGGAAGC | 104 |
| H51-251 | B3GALT1 | AGTTTGTGTAGGTATCGCC | 105 |
| H51-270 | SLC9A8 | TGTTCTTTGGCTCTGCAGC | 106 |
| H51-261 | CXCR6 | CTTCTACACGTCCATGCTC | 107 |

Table 1 lists the TARGETS identified using applicants' knock-down library in the OPG assay described below, including the class of polypeptides identified. TARGETS have been identified in polypeptide classes including kinase, protease, enzyme, ion channel, GPCR, phosphodiesterase and phosphatase, for instance. Specific methods to determine the activity of a kinase by measuring the phosphorylation of a substrate by the kinase, which measurements are performed in the presence or absence of a compound, are well known in the art.

Ion channels are membrane protein complexes and their function is to facilitate the diffusion of ions across biological membranes. Membranes, or phospholipid bilayers, build a hydrophobic, low dielectric barrier to hydrophilic and charged molecules. Ion channels provide a high conducting, hydrophilic pathway across the hydrophobic interior of the membrane. The activity of an ion channel can be measured using classical patch clamping. High-throughput fluorescence-based or tracer-based assays are also widely available to measure ion channel activity. These fluorescent-based assays screen compounds on the basis of their ability to either open or close an ion channel thereby changing the concentration of specific fluorescent dyes across a membrane. In the case of the tracer-based assay, the changes in concentration of the tracer within and outside the cell are measured by radioactivity measurement or gas absorption spectrometry.

Specific methods to determine the inhibition by a compound by measuring the cleavage of the substrate by the polypeptide, which is a protease, are well known in the art. Classically, substrates are used in which a fluorescent group is linked to a quencher through a peptide sequence that is a substrate that can be cleaved by the target protease. Cleavage of the linker separates the fluorescent group and quencher, giving rise to an increase in fluorescence.

G-protein coupled receptors (GPCR) are capable of activating an effector protein, resulting in changes in second messenger levels in the cell. The activity of a GPCR can be measured by measuring the activity level of such second messengers. Two important and useful second messengers in the cell are cyclic AMP (cAMP) and $Ca^{2+}$. The activity levels can be measured by methods known to persons skilled in the art, either directly by ELISA or radioactive technologies or by using substrates that generate a fluorescent or luminescent signal when contacted with $Ca^{2+}$ or indirectly by reporter gene analysis. The activity level of the one or more secondary messengers may typically be determined with a reporter gene controlled by a promoter, wherein the promoter is responsive to the second messenger. Promoters known and used in the art for such purposes are the cyclic-AMP responsive promoter that is responsive for the cyclic-AMP levels in the cell, and the NF-AT responsive promoter that is sensitive to cytoplasmic $Ca^{2+}$-levels in the cell. The reporter gene typically has a gene product that is easily detectable. The reporter gene can either be stably infected or transiently transfected in the host cell. Useful reporter genes are alkaline phosphatase, enhanced green fluorescent protein, destabilized green fluorescent protein, luciferase and β-galactosidase.

It should be understood that the cells expressing the polypeptides, may be cells naturally expressing the polypeptides, or the cells may be transfected to express the polypeptides, as described above. Also, the cells may be transduced to overexpress the polypeptide, or may be transfected to express a non-endogenous form of the polypeptide, which can be differentially assayed or assessed.

In one particular embodiment the methods of the present invention further comprise the step of contacting the population of cells with an agonist of the polypeptide. This is useful in methods wherein the expression of the polypeptide in a certain chosen population of cells is too low for a proper detection of its activity. By using an agonist the polypeptide may be triggered, enabling a proper read-out if the compound inhibits the polypeptide. Similar considerations apply to the measurement of bone resorption. In a particular embodiment, the cells used in the present method are mammalian synovial fibroblasts The fibroblasts, in the assay contemplated, may be activated (e.g. by cytokines).

A method for identifying a compound that inhibits bone resorption, comprising:
 (a) contacting a compound with a polypeptide comprising an amino acid sequence selected from the group consisting of SEQ ID NO: 41-69 and 80, and fragments thereof; and
 (b) measuring a compound-polypeptide property related to bone resorption.

In one embodiment of the present invention the compound-polypeptide property related to bone resorption is binding affinity.

In one embodiment of the present invention the compound-polypeptide property related to bone resorption is upregulation of a biological pathway producing a biochemical marker indicative of the inhibition of bone resorption. In particular, in one embodiment the compound induces or upregulates OPG activity or expression.

In one embodiment of the present invention the compound-polypeptide property related to bone resorption is the activity of said polypeptide. In particular, in one embodiment the compound inhibits the activity of said polypeptide.

In one embodiment of the present invention the compound-polypeptide property related to bone resorption is the expression of said polypeptide. In particular, in one embodiment the compound inhibits the expression of said polypeptide.

The present invention further relates to a method for identifying a compound that inhibits bone resorption, comprising:
  a) contacting a compound with a polypeptide comprising an amino acid sequence selected from the group consisting of SEQ ID NO: 41-69 and 80;
  b) determining the binding affinity of the compound to the polypeptide;
  c) contacting a population of mammalian cells expressing said polypeptide with the compound that exhibits a binding affinity of at least 10 micromolar; and
  d) identifying the compound that inhibits bone resorption.

The present invention further relates to a method for identifying a compound that inhibits bone resorption, comprising:
  a) contacting a compound with a polypeptide comprising an amino acid sequence selected from the group consisting of SEQ ID NO: 41-69 and 80;
  b) determining the ability of the compound inhibit the expression or activity of the polypeptide;
  c) contacting a population of mammalian cells expressing said polypeptide with the compound that significantly inhibits the expression or activity of the polypeptide; and
  d) identifying the compound that inhibits bone resorption.

In a particular aspect of the present invention the methods described above include the additional step of comparing the compound to be tested to a control, where the control is a population of cells that have not been contacted with the test compound.

In a particular aspect of the present invention the methods described above include the additional step of comparing the compound to be tested to a control, where the control is a population of cells that do not express said polypeptide.

The methods of the present invention may be performed in the presence of, or in combination with, a Disease-Modifying Anti-Rheumatic Drug (DMARD), or an anti-inflammatory compound. The population of cells may be exposed to the compound or the mixture of compounds through different means, for instance by direct incubation in the medium, or by nucleic acid transfer into the cells. Such transfer may be achieved by a wide variety of means, for instance by direct transfection of naked isolated DNA, or RNA, or by means of delivery systems, such as recombinant vectors. Other delivery means such as liposomes, or other lipid-based vectors may also be used. Particularly, the nucleic acid compound is delivered by means of a (recombinant) vector such as a recombinant virus.

For high-throughput purposes, libraries of compounds may be used such as antibody fragment libraries, peptide phage display libraries, peptide libraries (for example, LOPAP™, Sigma Aldrich), lipid libraries (BioMol), synthetic compound libraries (for example, LOPAC™, Sigma Aldrich; BioFocus DPI) or natural compound libraries (Specs, TimTec).

Particular drug candidate compounds are low molecular weight compounds. Low molecular weight compounds, for example with a molecular weight of 500 Dalton or less, are likely to have good absorption and permeation in biological systems and are consequently more likely to be successful drug candidates than compounds with a molecular weight above 500 Dalton (Lipinski et al., (1997)). Peptides comprise another particular class of drug candidate compounds. Peptides may be excellent drug candidates and there are multiple examples of commercially valuable peptides such as fertility hormones and platelet aggregation inhibitors. Natural compounds are another particular class of drug candidate compound. Such compounds are found in and extracted from natural sources, and which may thereafter be synthesized. The lipids are another particular class of drug candidate compound.

Another particular class of drug candidate compounds is an antibody. The present invention also provides antibodies directed against a TARGET. These antibodies may be endogenously produced to bind to the TARGET within the cell, or added to the tissue to bind to TARGET polypeptide present outside the cell. These antibodies may be monoclonal antibodies or polyclonal antibodies. The present invention includes chimeric, single chain, and humanized antibodies, as well as Fab fragments and the products of a Fab expression library, and Fv fragments and the products of an Fv expression library. In another embodiment, the compound may be a nanobody, the smallest functional fragment of naturally occurring single-domain antibodies (Cortez-Retamozo et al. 2004).

In certain embodiments, polyclonal antibodies may be used in the practice of the invention. The skilled artisan knows methods of preparing polyclonal antibodies. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. Antibodies may also be generated against the intact TARGET protein or polypeptide, or against a fragment, derivatives including conjugates, or other epitope of the TARGET protein or polypeptide, such as the TARGET embedded in a cellular membrane, or a library of antibody variable regions, such as a phage display library.

It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). One skilled in the art without undue experimentation may select the immunization protocol.

In some embodiments, the antibodies may be monoclonal antibodies. Monoclonal antibodies may be prepared using methods known in the art. The monoclonal antibodies of the present invention may be "humanized" to prevent the host from mounting an immune response to the antibodies. A "humanized antibody" is one in which the complementarity determining regions (CDRs) and/or other portions of the light and/or heavy variable domain framework are derived from a non-human immunoglobulin, but the remaining portions of the molecule are derived from one or more human immunoglobulins. Humanized antibodies also include antibodies characterized by a humanized heavy chain associated with a donor or acceptor unmodified light chain or a chimeric light chain, or vice versa. The humanization of antibodies may be accomplished by methods known in the art (see, for example, Mark and Padlan, (1994) "Chapter 4. Humanization of Monoclonal Antibodies", The Handbook of Experimental Pharmacology Vol. 113, Springer-Verlag, New York). Transgenic animals may be used to express humanized antibodies.

Human antibodies can also be produced using various techniques known in the art, including phage display libraries (Hoogenboom and Winter, (1991) J. Mol. Biol. 227:381-8; Marks et al. (1991). J. Mol. Biol. 222:581-97). The techniques of Cole, et al. and Boerner, et al. are also available for the preparation of human monoclonal antibodies (Cole, et al. (1985) Monoclonal Antibodies and Cancer Therapy, Alan R. Liss, p. 77; Boerner, et al (1991). J. Immunol., 147(1):86-95).

Techniques known in the art for the production of single chain antibodies can be adapted to produce single chain antibodies to the TARGET polypeptides and proteins of the present invention. The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

Bispecific antibodies are monoclonal, particularly human or humanized, antibodies that have binding specificities for at least two different antigens and particularly for a cell-surface protein or receptor or receptor subunit. In the present case, one of the binding specificities is for one domain of the TARGET, while the other one is for another domain of the same or different TARGET.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, (1983) Nature 305:537-9). Because of the random assortment of immunoglobulin heavy and light chains, these hybridomas (quadromas) produce a potential mixture of ten different antibody molecules, of which only one has the correct bispecific structure. Affinity chromatography steps usually accomplish the purification of the correct molecule. Similar procedures are disclosed in Trauneeker, et al. (1991) EMBO J. 10:3655-9.

According to another particular embodiment, the assay method uses a drug candidate compound identified as having a binding affinity for a TARGET, and/or has already been identified as having down-regulating activity such as antagonist activity vis-à-vis one or more TARGET.

The present invention further relates to a method for inhibiting bone resorption comprising contacting mammalian cells with an expression inhibitory agent comprising a polyribonucleotide sequence that complements at least about 15 to about 30, particularly at least 17 to about 30, most particularly at least 17 to about 25 contiguous nucleotides of a nucleotide sequence encoding a polypeptide TARGET or portion thereof, including the nucleotide sequence selected from the group consisting of SEQ ID NO: 1-29 and 40, particularly selected from the group consisting of SEQ ID NO: 16, 17, 19-21 and 40.

Another aspect of the present invention relates to a method for inhibiting bone resorption, comprising by contacting mammalian cells with an expression-inhibiting agent that inhibits the translation in the cell of a polyribonucleotide encoding a TARGET polypeptide. A particular embodiment relates to a composition comprising a polynucleotide including at least one antisense strand that functions to pair the agent with the TARGET mRNA, and thereby down-regulate or block the expression of TARGET polypeptide. The inhibitory agent particularly comprises antisense polynucleotide, a ribozyme, and a small interfering RNA (siRNA), wherein said agent comprises a nucleic acid sequence complementary to, or engineered from, a naturally-occurring polynucleotide sequence selected from the group consisting of SEQ ID NO: 1-29 and 40, particularly selected from the group consisting of SEQ ID NO: 16, 17, 19-21 and 40.

A particular embodiment of the present invention relates to a method wherein the expression-inhibiting agent is selected from the group consisting of antisense RNA, antisense oligodeoxynucleotide (ODN), a ribozyme that cleaves the polyribonucleotide coding for SEQ ID NO: 41-69 and 80, a small interfering RNA (siRNA, particularly shRNA,) that is sufficiently homologous to a portion of the polyribonucleotide corresponding to SEQ ID NO: 1-29 and 40, particularly selected from the group consisting of SEQ ID NO: 16, 17, 19-21 and 40, such that the siRNA, particularly shRNA, interferes with the translation of the TARGET polyribonucleotide to the TARGET polypeptide.

Another embodiment of the present invention relates to a method wherein the expression-inhibiting agent is a nucleic acid expressing the antisense RNA, antisense oligodeoxynucleotide (ODN), a ribozyme that cleaves the polyribonucleotide corresponding to SEQ ID NO: 1-29 and 40, particularly selected from the group consisting of SEQ ID NO: 16, 17, 19-21 and 40, a small interfering RNA (siRNA, particularly shRNA,) that is sufficiently complementary to a portion of the polyribonucleotide corresponding to SEQ ID NO: 1-29 and 40, particularly selected from the group consisting of SEQ ID NO: 16, 17, 19-21 and 40, such that the siRNA, particularly shRNA, interferes with the translation of the TARGET polyribonucleotide to the TARGET polypeptide. Particularly the expression-inhibiting agent is an antisense RNA, ribozyme, antisense oligodeoxynucleotide, or siRNA, particularly shRNA, comprising a polyribonucleotide sequence that complements at least about 17 to about 30 contiguous nucleotides of a nucleotide sequence selected from the group consisting of SEQ ID NO: 1-29 and 40, particularly selected from the group consisting of SEQ ID NO: 16, 17, 19-21 and 40. More particularly, the expression-inhibiting agent is an antisense RNA, ribozyme, antisense oligodeoxynucleotide, or siRNA, particularly shRNA, comprising a polyribonucleotide sequence that complements at least 15 to about 30, particularly at least 17 to about 30, most particularly at least 17 to about 25 contiguous nucleotides of a nucleotide sequence selected from the group consisting of SEQ ID NO: 1-29 and 40, particularly selected from the group consisting of SEQ ID NO: 16, 17, 19-21 and 40. A particular embodiment comprises a polyribonucleotide sequence that complements a polynucleotide sequence selected from the group consisting of SEQ ID NO: 81-97 and 107. A particular embodiment comprises a polyribonucleotide sequence that complements a polynucleotide sequence selected from the group consisting of 88, 89, 91, 92 and 107.

The down regulation of gene expression using antisense nucleic acids can be achieved at the translational or transcriptional level. Antisense nucleic acids of the invention are particularly nucleic acid fragments capable of specifically hybridizing with all or part of a nucleic acid encoding a TARGET polypeptide or the corresponding messenger RNA. In addition, antisense nucleic acids may be designed which decrease expression of the nucleic acid sequence capable of encoding a TARGET polypeptide by inhibiting splicing of its primary transcript. Any length of antisense sequence is suitable for practice of the invention so long as it is capable of down-regulating or blocking expression of a nucleic acid coding for a TARGET. Particularly, the antisense sequence is at least about 15-30, and particularly at least 17 nucleotides in length. The preparation and use of antisense nucleic acids, DNA encoding antisense RNAs and the use of oligo and genetic antisense is known in the art.

One embodiment of expression-inhibitory agent is a nucleic acid that is antisense to a nucleic acid comprising SEQ ID NO: 1-29 and 40, particularly SEQ ID NO: 16, 17, 19-21 and 40, for example, an antisense nucleic acid (for example, DNA) may be introduced into cells in vitro, or administered to a subject in vivo, as gene therapy to inhibit cellular expression of nucleic acids comprising SEQ ID NO: 1-29 and 40, particularly SEQ ID NO: 16, 17, 19-21 and 40. Antisense oligonucleotides may comprise a sequence containing from about 15 to about 100 nucleotides, more particularly from about 15 to about 30 nucleotides, and most particularly, from about 17 to about 25 nucleotides. Antisense nucleic acids may be prepared from about 15 to about 30 contiguous nucleotides selected from the sequences of SEQ ID NO: 1-29 and 40, particularly SEQ ID NO: 16, 17, 19-21 and 40, expressed in the opposite orientation.

The skilled artisan can readily utilize any of several strategies to facilitate and simplify the selection process for antisense nucleic acids and oligonucleotides effective in inhibition of TARGET and/or OPG expression. Predictions of the binding energy or calculation of thermodynamic indices between an oligonucleotide and a complementary sequence in an mRNA molecule may be utilized (Chiang et al. (1991) J. Biol. Chem. 266:18162-18171; Stull et al. (1992) Nucl. Acids Res. 20:3501-3508). Antisense oligonucleotides may be selected on the basis of secondary structure (Wickstrom et al (1991) in Prospects for Antisense Nucleic Acid Therapy of Cancer and AIDS, Wickstrom, ed., Wiley-Liss, Inc., New York, pp. 7-24; Lima et al. (1992) Biochem. 31:12055-12061). Schmidt and Thompson (U.S. Pat. No. 6,416,951) describe a method for identifying a functional antisense agent comprising hybridizing an RNA with an oligonucleotide and measuring in real time the kinetics of hybridization by hybridizing in the presence of an intercalation dye or incorporating a label and measuring the spectroscopic properties of the dye or the label's signal in the presence of unlabelled oligonucleotide. In addition, any of a variety of computer programs may be utilized which predict suitable antisense oligonucleotide sequences or antisense targets utilizing various criteria recognized by the skilled artisan, including for example the absence of self-complementarity, the absence hairpin loops, the absence of stable homodimer and duplex formation (stability being assessed by predicted energy in kcal/mol). Examples of such computer programs are readily available and known to the skilled artisan and include the OLIGO 4 or OLIGO 6 program (Molecular Biology Insights, Inc., Cascade, Colo.) and the Oligo Tech program (Oligo Therapeutics Inc., Wilsonville, Oreg.). In addition, antisense oligonucleotides suitable in the present invention may be identified by screening an oligonucleotide library, or a library of nucleic acid molecules, under hybridization conditions and selecting for those which hybridize to the target RNA or nucleic acid (see for example U.S. Pat. No. 6,500,615). Mishra and Toulme have also developed a selection procedure based on selective amplification of oligonucleotides that bind target (Mishra et al (1994) Life Sciences 317:977-982). Oligonucleotides may also be selected by their ability to mediate cleavage of target RNA by RNAse H, by selection and characterization of the cleavage fragments (Ho et al (1996) Nucl Acids Res 24:1901-1907; Ho et al (1998) Nature Biotechnology 16:59-630). Generation and targeting of oligonucleotides to GGGA motifs of RNA molecules has also been described (U.S. Pat. No. 6,277,981).

The antisense nucleic acids are particularly oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Specific examples of some particular oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its TARGET site, the RNA-DNA duplex activates the endogenous enzyme ribonuclease (RNase) H, which cleaves the mRNA component of the hybrid molecule. Oligonucleotides may also contain one or more substituted sugar moieties. Particular oligonucleotides comprise one of the following at the 2' position: OH, SH, $SCH_3$, F, OCN, heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. Similar modifications may also be made at other positions on the oligonucleotide, particularly the 3' position of the sugar on the 3' terminal nucleotide and the 5' position of 5' terminal nucleotide.

In addition, antisense oligonucleotides with phosphoramidite and polyamide (peptide) linkages can be synthesized. These molecules should be very resistant to nuclease degradation. Furthermore, chemical groups can be added to the 2' carbon of the sugar moiety and the 5 carbon (C-5) of pyrimidines to enhance stability and facilitate the binding of the antisense oligonucleotide to its TARGET site. Modifications may include 2'-deoxy, O-pentoxy, O-propoxy, O-methoxy, fluoro, methoxyethoxy phosphorothioates, modified bases, as well as other modifications known to those of skill in the art.

Another type of expression-inhibitory agent that reduces the levels of TARGETS is the ribozyme. Ribozymes are catalytic RNA molecules (RNA enzymes) that have separate catalytic and substrate binding domains. The substrate binding sequence combines by nucleotide complementarity and, possibly, non-hydrogen bond interactions with its TARGET sequence. The catalytic portion cleaves the TARGET RNA at a specific site. The substrate domain of a ribozyme can be engineered to direct it to a specified mRNA sequence. The ribozyme recognizes and then binds a TARGET mRNA through complementary base pairing. Once it is bound to the correct TARGET site, the ribozyme acts enzymatically to cut the TARGET mRNA. Cleavage of the mRNA by a ribozyme destroys its ability to direct synthesis of the corresponding polypeptide. Once the ribozyme has cleaved its TARGET sequence, it is released and can repeatedly bind and cleave at other mRNAs.

Ribozyme forms include a hammerhead motif, a hairpin motif, a hepatitis delta virus, group I intron or RNaseP RNA (in association with an RNA guide sequence) motif or *Neurospora* VS RNA motif. Ribozymes possessing a hammerhead or hairpin structure are readily prepared since these catalytic RNA molecules can be expressed within cells from eukaryotic promoters (Chen, et al. (1992) Nucleic Acids Res. 20:4581-9). A ribozyme of the present invention can be expressed in eukaryotic cells from the appropriate DNA vector. If desired, the activity of the ribozyme may be augmented by its release from the primary transcript by a second ribozyme (Ventura, et al. (1993) Nucleic Acids Res. 21:3249-55).

Ribozymes may be chemically synthesized by combining an oligodeoxyribonucleotide with a ribozyme catalytic domain (20 nucleotides) flanked by sequences that hybridize to the TARGET mRNA after transcription. The oligodeoxyribonucleotide is amplified by using the substrate binding sequences as primers. The amplification product is cloned into a eukaryotic expression vector.

Ribozymes are expressed from transcription units inserted into DNA, RNA, or viral vectors. Transcription of the ribozyme sequences are driven from a promoter for eukaryotic RNA polymerase I (pol (I), RNA polymerase II (pol II), or RNA polymerase III (pol III). Transcripts from pol II or pol III promoters will be expressed at high levels in all cells; the levels of a given pol II promoter in a given cell type will depend on nearby gene regulatory sequences. Prokaryotic RNA polymerase promoters are also used, providing that the prokaryotic RNA polymerase enzyme is expressed in the appropriate cells (Gao and Huang, (1993) Nucleic Acids Res. 21:2867-72). It has been demonstrated that ribozymes expressed from these promoters can function in mammalian cells (Kashani-Sabet, et al. (1992) Antisense Res. Dev. 2:3-15).

A particular inhibitory agent is a small interfering RNA (siRNA, particularly small hairpin RNA, "shRNA"). siRNA, particularly shRNA, mediate the post-transcriptional process of gene silencing by double stranded RNA (dsRNA) that is homologous in sequence to the silenced RNA. siRNA according to the present invention comprises a sense strand of 15-30, particularly 17-30, most particularly 17-25 nucleotides complementary or homologous to a contiguous 17-25 nucleotide sequence selected from the group of sequences described in SEQ ID NO: 1-29 and 40, particularly SEQ ID NO: 16, 17, 19-21 and 40, particularly from the group of sequences described in SEQ ID No: 81-97 and 107, most particularly those described in SEQ ID NO: 88, 89, 91, 92 and 107, and an antisense strand of 15-30, particularly 17-30, most particularly 17-25 nucleotides complementary to the sense strand. The most particular siRNA comprises sense and anti-sense strands that are 100 percent complementary to each other and the TARGET polynucleotide sequence. Particularly the siRNA further comprises a loop region linking the sense and the antisense strand.

A self-complementing single stranded shRNA molecule polynucleotide according to the present invention comprises a sense portion and an antisense portion connected by a loop region linker. Particularly, the loop region sequence is 4-30 nucleotides long, more particularly 5-15 nucleotides long and most particularly 8 or 12 nucleotides long. In a most particular embodiment the linker sequence is UUGCUAUA or GUUUGCUAUAAC (SEQ ID NO: 108). Self-complementary single stranded siRNAs form hairpin loops and are more stable than ordinary dsRNA. In addition, they are more easily produced from vectors.

Analogous to antisense RNA, the siRNA can be modified to confer resistance to nucleolytic degradation, or to enhance activity, or to enhance cellular distribution, or to enhance cellular uptake, such modifications may consist of modified internucleoside linkages, modified nucleic acid bases, modified sugars and/or chemical linkage the siRNA to one or more moieties or conjugates. The nucleotide sequences may be selected according to siRNA designing rules that give an improved reduction of the TARGET sequences compared to nucleotide sequences that do not comply with these siRNA designing rules (For a discussion of these rules and examples of the preparation of siRNA, WO 2004/094636 and US 2003/0198627, are hereby incorporated by reference).

The present invention also relates to compositions, and methods using said compositions, comprising a DNA expression vector capable of expressing a polynucleotide capable of inhibiting bone resorption and described hereinabove as an expression inhibition agent.

A particular aspect of these compositions and methods relates to the down-regulation or blocking of the expression of a TARGET polypeptide by the induced expression of a polynucleotide encoding an intracellular binding protein that is capable of selectively interacting with the TARGET polypeptide. An intracellular binding protein includes any protein capable of selectively interacting, or binding, with the polypeptide in the cell in which it is expressed and neutralizing or otherwise inhibiting or blocking the function of the polypeptide. Particularly, the intracellular binding protein is a neutralizing antibody or a fragment of a neutralizing antibody having binding affinity to an epitope of the TARGET polypeptide of SEQ ID NO: 41-69 and 80, particularly to an epitope of the TARGET polypeptide of SEQ ID NO: 56, 57, 59-61 and 80. More particularly, the intracellular binding protein is a single chain antibody.

A particular embodiment of this composition comprises the expression-inhibiting agent selected from the group consisting of antisense RNA, antisense oligodeoxynucleotide (ODN), a ribozyme that cleaves the polyribonucleotide coding for SEQ ID NO: 41-69 or 80, particularly SEQ ID NO: 56, 57, 59-61 or 80, and a small interfering RNA (siRNA) that is sufficiently homologous to a portion of the polyribonucleotide corresponding to SEQ ID NO: 1-29 and 40, particularly SEQ ID NO: 16, 17, 19-21 and 40, such that the siRNA interferes with the translation of the TARGET polyribonucleotide to the TARGET polypeptide.

The polynucleotide expressing the expression-inhibiting agent, or a polynucleotide expressing the TARGET polypeptide in cells, is particularly included within a vector. The polynucleic acid is operably linked to signals enabling expression of the nucleic acid sequence and is introduced into a cell utilizing, particularly, recombinant vector constructs, which will express the nucleic acid or antisense nucleic acid once the vector is introduced into the cell. A variety of viral-based systems are available, including adenoviral, retroviral, adeno-associated viral, lentiviral, herpes simplex viral or a sendaviral vector systems. All may be used to introduce and express polynucleotide sequence for the expression-inhibiting agents in TARGET cells.

Particularly, the viral vectors used in the methods of the present invention are replication defective. Such replication defective vectors will usually pack at least one region that is necessary for the replication of the virus in the infected cell. These regions can either be eliminated (in whole or in part), or be rendered non-functional by any technique known to a person skilled in the art. These techniques include the total removal, substitution, partial deletion or addition of one or more bases to an essential (for replication) region. Such techniques may be performed in vitro (on the isolated DNA) or in situ, using the techniques of genetic manipulation or by treatment with mutagenic agents. Particularly, the replication defective virus retains the sequences of its genome, which are necessary for encapsidating, the viral particles.

In a particular embodiment, the viral element is derived from an adenovirus. Particularly, the vehicle includes an adenoviral vector packaged into an adenoviral capsid, or a functional part, derivative, and/or analogue thereof. Adenovirus biology is also comparatively well known on the molecular level. Many tools for adenoviral vectors have been and continue to be developed, thus making an adenoviral capsid a particular vehicle for incorporating in a library of the invention. An adenovirus is capable of infecting a wide variety of cells. However, different adenoviral serotypes have different preferences for cells. To combine and widen the TARGET cell population that an adenoviral capsid of the invention can enter in a particular embodiment, the vehicle includes adenoviral fiber proteins from at least two adenoviruses. Particular adenoviral fiber protein sequences are serotype 17, 45 and 51. Techniques or construction and expression of these chimeric vectors are disclosed in US 2003/0180258 and US 2004/0071660, hereby incorporated by reference.

In a particular embodiment, the nucleic acid derived from an adenovirus includes the nucleic acid encoding an adenoviral late protein or a functional part, derivative, and/or analogue thereof. An adenoviral late protein, for instance an adenoviral fiber protein, may be favorably used to TARGET the vehicle to a certain cell or to induce enhanced delivery of the vehicle to the cell. Particularly, the nucleic acid derived from an adenovirus encodes for essentially all adenoviral late proteins, enabling the formation of entire adenoviral capsids or functional parts, analogues, and/or derivatives thereof. Particularly, the nucleic acid derived from an adenovirus includes the nucleic acid encoding adenovirus E2A or a functional part, derivative, and/or analogue thereof. Particularly, the nucleic acid derived from an adenovirus includes the nucleic acid encoding at least one E4-region protein or a functional part, derivative, and/or analogue thereof, which facilitates, at least in part, replication of an adenoviral derived nucleic acid in a cell. The adenoviral vectors used in the examples of this application are exemplary of the vectors useful in the present method of treatment invention.

Certain embodiments of the present invention use retroviral vector systems. Retroviruses are integrating viruses that infect dividing cells, and their construction is known in the art. Retroviral vectors can be constructed from different types of retrovirus, such as, MoMuLV ("Moloney murine leukemia virus" MSV ("Moloney murine sarcoma virus"), HaSV ("Harvey sarcoma virus"); SNV ("spleen necrosis virus"); RSV ("Rous sarcoma virus") and Friend virus. Lentiviral vector systems may also be used in the practice of the present invention. Retroviral systems and herpes virus system may be particular vehicles for transfection of neuronal cells.

In other embodiments of the present invention, adeno-associated viruses ("AAV") are utilized. The AAV viruses are DNA viruses of relatively small size that integrate, in a stable and site-specific manner, into the genome of the infected cells. They are able to infect a wide spectrum of cells without inducing any effects on cellular growth, morphology or differentiation, and they do not appear to be involved in human pathologies.

In the vector construction, the polynucleotide agents of the present invention may be linked to one or more regulatory regions. Selection of the appropriate regulatory region or regions is a routine matter, within the level of ordinary skill in the art. Regulatory regions include promoters, and may include enhancers, suppressors, etc.

Promoters that may be used in the expression vectors of the present invention include both constitutive promoters and regulated (inducible) promoters. The promoters may be prokaryotic or eukaryotic depending on the host. Among the prokaryotic (including bacteriophage) promoters useful for practice of this invention are lac, lacZ, T3, T7, lambda $P_r$, $P_l$, and trp promoters. Among the eukaryotic (including viral) promoters useful for practice of this invention are ubiquitous promoters (for example, HPRT, vimentin, actin, tubulin), intermediate filament promoters (for example, desmin, neurofilaments, keratin, GFAP), therapeutic gene promoters (for example, MDR type, CFTR, factor VIII), tissue-specific promoters (for example, actin promoter in smooth muscle cells, or Flt and Flk promoters active in endothelial cells), including animal transcriptional control regions, which exhibit tissue specificity and have been utilized in transgenic animals: elastase I gene control region which is active in pancreatic acinar cells (Swift, et al. (1984) Cell 38:639-46; Ornitz, et al. (1986) Cold Spring Harbor Symp. Quant. Biol. 50:399-409; MacDonald, (1987) Hepatology 7:425-515); insulin gene control region which is active in pancreatic beta cells (Hanahan, (1985) Nature 315:115-22), immunoglobulin gene control region which is active in lymphoid cells (Grosschedl, et al. (1984) Cell 38:647-58; Adames, et al. (1985) Nature 318: 533-8; Alexander, et al. (1987) Mol. Cell. Biol. 7:1436-44), mouse mammary tumor virus control region which is active in testicular, breast, lymphoid and mast cells (Leder, et al. (1986) Cell 45:485-95), albumin gene control region which is active in liver (Pinkert, et al. (1987) Genes and Devel. 1:268-76), alpha-fetoprotein gene control region which is active in liver (Krumlauf, et al. (1985) Mol. Cell. Biol., 5:1639-48; Hammer, et al. (1987) Science 235:53-8), alpha 1-antitrypsin gene control region which is active in the liver (Kelsey, et al. (1987) Genes and Devel., 1: 161-71), beta-globin gene control region which is active in myeloid cells (Mogram, et al. (1985) Nature 315:338-40; Kollias, et al. (1986) Cell 46:89-94), myelin basic protein gene control region which is active in oligodendrocyte cells in the brain (Readhead, et al. (1987) Cell 48:703-12), myosin light chain-2 gene control region which is active in skeletal muscle (Sani, (1985) Nature 314.283-6), and gonadotropic releasing hormone gene control region which is active in the hypothalamus (Mason, et al. (1986) Science 234:1372-8).

Other promoters which may be used in the practice of the invention include promoters which are preferentially activated in dividing cells, promoters which respond to a stimulus (for example, steroid hormone receptor, retinoic acid receptor), tetracycline-regulated transcriptional modulators, cytomegalovirus immediate-early, retroviral LTR, metallothionein, SV-40, E1a, and MLP promoters.

Additional vector systems include the non-viral systems that facilitate introduction of polynucleotide agents into a patient, for example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker (Felgner, et al. (1987) Proc. Natl. Acad. Sci. USA 84:7413-7); see Mackey, et al. (1988) Proc. Natl. Acad. Sci. USA 85:8027-31; Ulmer, et al. (1993) Science 259:1745-8). The use of cationic lipids may promote encapsulation of negatively charged nucleic acids, and also promote fusion with negatively charged cell membranes (Felgner and Ringold, (1989) Nature 337:387-8). Particularly useful lipid compounds and compositions for transfer of nucleic acids are described in International Patent Publications WO 95/18863 and WO 96/17823, and in U.S. Pat. No. 5,459,127. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, for example, hormones or neurotransmitters, and proteins, for example, antibodies, or nonpeptide molecules could be coupled to liposomes chemically. Other molecules are also useful for facilitating transfection of a nucleic acid in vivo, for example, a cationic oligopeptide (for example, International Patent Publication WO 95/21931), peptides derived from DNA binding proteins (for example, International Patent Publication WO 96/25508), or a cationic polymer (for example, International Patent Publication WO 95/21931).

It is also possible to introduce a DNA vector in vivo as a naked DNA plasmid (see U.S. Pat. Nos. 5,693,622; 5,589,466; and 5,580,859). Naked DNA vectors for therapeutic purposes can be introduced into the desired host cells by methods known in the art, for example, transfection, electroporation, microinjection, transduction, cell fusion, DEAE dextran, calcium phosphate precipitation, use of a gene gun, or use of a DNA vector transporter (see, for example, Wilson, et al. (1992) J. Biol. Chem. 267:963-7; Wu and Wu, (1988) J. Biol. Chem. 263:14621-4; Hartmut, et al. Canadian Patent Application No. 2,012,311, filed Mar. 15, 1990; Williams, et al (1991). Proc. Natl. Acad. Sci. USA 88:2726-30). Receptor-mediated DNA delivery approaches can also be used (Curiel, et al. (1992) Hum. Gene Ther. 3:147-54; Wu and Wu, (1987) J. Biol. Chem. 262:4429-32).

The present invention also provides biologically compatible, bone resorption inhibiting compositions comprising an effective amount of one or more compounds identified as TARGET inhibitors, and/or the expression-inhibiting agents as described hereinabove.

A biologically compatible composition is a composition, that may be solid, liquid, gel, or other form, in which the compound, polynucleotide, vector, or antibody of the invention is maintained in an active form, for example, in a form able to affect a biological activity. For example, a compound of the invention would have inverse agonist or antagonist activity on the TARGET; a nucleic acid would be able to replicate, translate a message, or hybridize to a complementary mRNA of a TARGET; a vector would be able to transfect a TARGET cell and express the antisense, antibody, ribozyme or siRNA as described hereinabove; an antibody would bind a TARGET polypeptide domain.

A particular biologically compatible composition is an aqueous solution that is buffered using, for example, Tris, phosphate, or HEPES buffer, containing salt ions. Usually the concentration of salt ions will be similar to physiological levels. Biologically compatible solutions may include stabilizing agents and preservatives. In a more particular embodiment, the biocompatible composition is a pharmaceutically acceptable composition. Such compositions can be formulated for administration by topical, oral, parenteral, intranasal, subcutaneous, and intraocular, routes. Parenteral administration is meant to include intravenous injection, intramuscular injection, intraarterial injection or infusion techniques. The composition may be administered parenterally in dosage unit formulations containing standard, well-known non-toxic physiologically acceptable carriers, adjuvants and vehicles as desired.

A particular embodiment of the present composition invention is a bone resorption inhibiting pharmaceutical composition comprising a therapeutically effective amount of an expression-inhibiting agent as described hereinabove, in admixture with a pharmaceutically acceptable carrier. Another particular embodiment is a pharmaceutical composition for the treatment or prevention of a condition involving bone resorption, or a susceptibility to the condition, comprising an effective bone resorption inhibiting amount of a TARGET antagonist or inverse agonist, its pharmaceutically acceptable salts, hydrates, solvates, or prodrugs thereof in admixture with a pharmaceutically acceptable carrier.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical compositions for oral use can be prepared by combining active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum arabic, talc, polyvinyl-pyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Particular sterile injectable preparations can be a solution or suspension in a non-toxic parenterally acceptable solvent or diluent. Examples of pharmaceutically acceptable carriers are saline, buffered saline, isotonic saline (for example, monosodium or disodium phosphate, sodium, potassium; calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The compounds or compositions of the invention may be combined for administration with or embedded in polymeric carrier(s), biodegradable or biomimetic matrices or in a scaffold. The carrier, matrix or scaffold may be of any material that will allow composition to be incorporated and expressed and will be compatible with the addition of cells or in the presence of cells. Particularly, the carrier matrix or scaffold is predominantly non-immunogenic and is biodegradable. Examples of biodegradable materials include, but are not limited to, polyglycolic acid (PGA), polylactic acid (PLA), hyaluronic acid, catgut suture material, gelatin, cellulose, nitrocellulose, collagen, albumin, fibrin, alginate, cotton, or other naturally-occurring biodegradable materials. It may be preferable to sterilize the matrix or scaffold material prior to administration or implantation, e.g., by treatment with ethylene oxide or by gamma irradiation or irradiation with an electron beam. In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), polymers of hydroxy acids such as polylactic acid (PLA), polyglycolic acid (PGA), and polylactic acid-glycolic acid (PLGA), polyorthoesters, polyanhydrides, polyphosphazenes, and a variety of polyhydroxyalkanoates, and combinations thereof. Matrices suitable include a polymeric mesh or sponge and a polymeric hydrogel. In the particular embodiment, the matrix is biodegradable over a time period of less than a year, more particularly less than six months, most particularly over two to ten weeks. The polymer composition, as well as method of manufacture, can be used to determine the rate of degradation. For example, mixing increasing amounts of polylactic acid with polyglycolic acid decreases the degradation time. Meshes of polyglycolic acid that can be used can be obtained commercially, for instance, from surgical supply companies (e.g., Ethicon, N.J.). In general, these polymers are at least partially soluble in aqueous solutions, such as water, buffered salt solutions, or aqueous alcohol solutions, that have charged side groups, or a monovalent ionic salt thereof.

The composition medium can also be a hydrogel, which is prepared from any biocompatible or non-cytotoxic homo- or hetero-polymer, such as a hydrophilic polyacrylic acid polymer that can act as a drug absorbing sponge. Certain of them, such as, in particular, those obtained from ethylene and/or propylene oxide are commercially available. A hydrogel can be deposited directly onto the surface of the tissue to be treated, for example during surgical intervention.

Embodiments of pharmaceutical compositions of the present invention comprise a replication defective recombinant viral vector encoding the agent of the present invention and a transfection enhancer, such as poloxamer. An example of a poloxamer is Poloxamer 407, which is commercially available (BASF, Parsippany, N.J.) and is a non-toxic, biocompatible polyol. A poloxamer impregnated with recombinant viruses may be deposited directly on the surface of the tissue to be treated, for example during a surgical intervention. Poloxamer possesses essentially the same advantages as hydrogel while having a lower viscosity.

The active agents may also be entrapped in microcapsules prepared, for example, by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1980) 16th edition, Osol, A. Ed.

Sustained-release preparations may be prepared. Suitable examples of sustained-release preparations include semi-permeable matrices of solid hydrophobic polymers containing the antibody, which matrices are in the form of shaped articles, for example, films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™. (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

As defined above, therapeutically effective dose means that amount of compound, agent, protein, polynucleotide, peptide, or its antibodies, agonists or antagonists, which ameliorate a condition or one or more symptoms thereof. Therapeutic efficacy and toxicity of such compounds can be determined by standard pharmaceutical procedures in cell cultures or experimental animals, for example, $ED_{50}$ (the dose therapeutically effective in 50% of the population) and $LD_{50}$ (the dose lethal to 50% of the population). The dose ratio of toxic to therapeutic effects is the therapeutic index, and it can be expressed as the ratio, $LD_{50}/ED_{50}$. Pharmaceutical compositions that exhibit large therapeutic indices are particular. The data obtained from cell culture assays and animal studies are used in formulating a range of dosage for human use. The dosage of such compounds lies particularly within a range of circulating concentrations that include the $ED_{50}$ with little or no toxicity. The dosage varies within this range depending upon the dosage form employed, sensitivity of the patient, and the route of administration.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions according to this invention may be administered to a subject by a variety of methods. They may be added directly to targeted tissues, complexed with cationic lipids, packaged within liposomes, or delivered to targeted cells by other methods known in the art. Localized administration to the desired tissues may be done by direct injection, transdermal absorption, catheter, infusion pump or stent. The DNA, DNA/vehicle complexes, or the recombinant virus particles are locally administered to the site of treatment. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery. Examples of ribozyme delivery and administration are provided in Sullivan et al. WO 94/02595.

Antibodies according to the invention may be delivered as a bolus only, infused over time or both administered as a bolus and infused over time. Those skilled in the art may employ different formulations for polynucleotides than for proteins. Similarly, delivery of polynucleotides or polypeptides will be specific to particular cells, conditions, locations, etc.

As discussed hereinabove, recombinant viruses may be used to introduce DNA encoding polynucleotide agents useful in the present invention. Recombinant viruses according to the invention are generally formulated and administered in the form of doses of between about $10^4$ and about $10^{14}$ pfu. In the case of AAVs and adenoviruses, doses of from about $10^6$ to about $10^{11}$ pfu are particularly used. The term pfu ("plaque-forming unit") corresponds to the infective power of a suspension of virions and is determined by infecting an appropriate cell culture and measuring the number of plaques formed. The techniques for determining the pfu titre of a viral solution are well documented in the prior art.

The present invention also provides methods of inhibiting bone or joint degradation, comprising administering, to a subject suffering from a disease condition involving bone or joint degradation, a bone or joint degradation inhibiting pharmaceutical composition as described herein, particularly a therapeutically effective amount of an expression-inhibiting agent of the present invention. The present invention further provides methods of reducing the number or prevalence of bone fractures, comprising administering, to a subject suffering from a disease condition involving bone or joint degradation, a bone or joint degradation inhibiting pharmaceutical composition as described herein, particularly a therapeutically effective amount of an expression-inhibiting agent of the present invention. The diseases involving bone resorption, include osteoporosis, juvenile osteoporosis, osteogenesis imperfecta, hypercalcemia, hyperparathyroidism, osteomalacia, osteohalisteresis, osteolytic bone disease, osteonecrosis, Paget's disease of bone, bone loss due to rheumatoid arthritis, inflammatory arthritis, osteomyelitis, corticosteroid treatment, metastatic bone diseases, periodontal bone loss, bone loss due to cancer, age-related loss of bone mass, other forms of osteopenia. More particular diseases for treatment in accordance with the present invention are the degenerative joint diseases such as rheumatoid arthritis, psoriatic arthritis, juvenile arthritis, early arthritis, reactive arthritis, osteoarthritis, ankylosing spondylitis. The most particular degenerative joint disease for treatment in accordance with the present method is rheumatoid arthritis.

The present invention also provides methods of inhibiting bone or joint degradation, comprising administering, to a subject suffering from a disease condition involving bone or joint degradation, a bone resorption inhibiting pharmaceutical composition as described herein, particularly a therapeutically effective amount of an agent which inhibits the expression or activity of a TARGET as identified herein. The diseases involving bone or joint degradation, include osteoporosis, juvenile osteoporosis, osteogenesis imperfecta, hypercalcemia, hyperparathyroidism, osteomalacia, osteo- halisteresis, osteolytic bone disease, osteonecrosis, Paget's disease of bone, bone loss due to rheumatoid arthritis, inflammatory arthritis, osteomyelitis, corticosteroid treatment, metastatic bone diseases, periodontal bone loss, bone loss due to cancer, age-related loss of bone mass, other forms of osteopenia. More particular diseases for treatment in accordance with the present invention are the degenerative joint diseases such as rheumatoid arthritis, psoriatic arthritis, juvenile arthritis, early arthritis, reactive arthritis, osteoarthritis, ankylosing spondylitis. The most particular degenerative joint disease for treatment in accordance with the present method is rheumatoid arthritis.

In a further aspect the present invention provides methods of inhibiting bone or joint degradation, comprising administering, to a subject suffering from a disease condition involving bone or joint degradation, a bone resorption inhibiting pharmaceutical composition as described herein, particularly a therapeutically effective amount of an agent which inhibits the expression or activity of a TARGET as identified herein in combination with a disease-modifying anti-rheumatic drug (DMARD) or an anti-inflammatory compound. The diseases involving bone or joint degradation, include osteoporosis, juvenile osteoporosis, osteogenesis imperfecta, hypercalcemia, hyperparathyroidism, osteomalacia, osteohalisteresis, osteolytic bone disease, osteonecrosis, Paget's disease of bone, bone loss due to rheumatoid arthritis, inflammatory arthritis, osteomyelitis, corticosteroid treatment, metastatic bone diseases, periodontal bone loss, bone loss due to cancer, age-related loss of bone mass, other forms of osteopenia. Particular anti-inflammatory compounds include corticosteroids or non-steroidal anti-inflammatory agents. Particular DMARDs include biological DMARDs such as Infliximab, Etanercept, Adalimumab, Rituximab or CTLA4-Ig or synthetic DMARDs such as methotrexate, leflunomide or sulfasalazine. More particular diseases for treatment in accordance with the present invention are the degenerative joint diseases such as rheumatoid arthritis, psoriatic arthritis, juvenile arthritis, early arthritis, reactive arthritis, osteoarthritis, ankylosing spondylitis. The most particular degenerative joint disease for treatment in accordance with the present method is rheumatoid arthritis.

Administration of the expression-inhibiting agent of the present invention to the subject patient includes both self-administration and administration by another person. The patient may be in need of treatment for an existing disease or medical condition, or may desire prophylactic treatment to prevent or reduce the risk for diseases and medical conditions affected by a disturbance in bone metabolism. The expression-inhibiting agent of the present invention may be delivered to the subject patient orally, transdermally, via inhalation, injection, nasally, rectally or via a sustained release formulation.

A particular regimen of the present method comprises the administration to a subject suffering from a disease condition characterized by a disturbance in bone metabolism, an effective bone resorption inhibiting amount of an expression-inhibiting agent of the present invention for a period of time sufficient to reduce the abnormal levels of bone resorption in the patient, and particularly terminate, the self-perpetuating processes responsible for said resorption. A particular embodiment of the method comprises administering of an effective OPG inducing amount of a expression-inhibiting agent of the present invention to a subject patient suffering from or susceptible to the development of rheumatoid arthritis, for a period of time sufficient to reduce or prevent, respectively, bone resorption in the joints of said patient, and particularly terminate, the self-perpetuating processes responsible for said resorption.

The invention also relates to the use of an agent as described above for the preparation of a medicament for treating or preventing a disease involving bone resorption. Particularly the pathological condition is arthritis. More particularly, the pathological condition is rheumatoid arthritis.

The polypeptides and polynucleotides useful in the practice of the present invention described herein may be free in solution, affixed to a solid support, borne on a cell surface, or located intracellularly. To perform the methods it is feasible to immobilize either the TARGET polypeptide or the compound to facilitate separation of complexes from uncomplexed forms of the polypeptide, as well as to accommodate automation of the assay. Interaction (for example, binding of) of the TARGET polypeptide with a compound can be accomplished in any vessel suitable for containing the reactants. Examples of such vessels include microtitre plates, test tubes, and microcentrifuge tubes. In one embodiment, a fusion protein can be provided which adds a domain that allows the polypeptide to be bound to a matrix. For example, the TARGET polypeptide can be "His" tagged, and subsequently adsorbed onto Ni-NTA microtitre plates, or ProtA fusions with the TARGET polypeptides can be adsorbed to IgG, which are then combined with the cell lysates (for example, $^{35}$S-labelled) and the candidate compound, and the mixture incubated under conditions favorable for complex formation (for example, at physiological conditions for salt and pH). Following incubation, the plates are washed to remove any unbound label, and the matrix is immobilized. The amount of radioactivity can be determined directly, or in the supernatant after dissociation of the complexes. Alternatively, the complexes can be dissociated from the matrix, separated by SDS-PAGE, and the level of the protein binding to the TARGET protein quantified from the gel using standard electrophoretic techniques.

Other techniques for immobilizing protein on matrices can also be used in the method of identifying compounds. For example, either the TARGET or the compound can be immobilized utilizing conjugation of biotin and streptavidin. Biotinylated TARGET protein molecules can be prepared from biotin-NHS (N-hydroxy-succinimide) using techniques well known in the art (for example, biotinylation kit, Pierce Chemicals, Rockford, Ill.), and immobilized in the wells of streptavidin-coated 96 well plates (Pierce Chemical). Alternatively, antibodies reactive with the TARGETS but which do not interfere with binding of the TARGET to the compound can be derivatized to the wells of the plate, and the TARGET can be trapped in the wells by antibody conjugation. As described above, preparations of a labeled candidate compound are incubated in the wells of the plate presenting the TARGETS, and the amount of complex trapped in the well can be quantitated.

The polynucleotides encoding the TARGET polypeptides are identified as SEQ ID NO: 1-29 and 40. The present inventors show herein that transfection of mammalian cells with Ad-siRNAs targeting these genes decreases the release of factors that promote osteoclast differentiation and bone resorption.

The present invention also relates to a method for diagnosis of a pathological condition involving bone resorption, comprising determining the nucleic acid sequence of at least one of the genes of SEQ ID NO: 1-29 and 40, particularly SEQ ID NO: 16, 17, 19-21 and 40 within the genomic DNA of a subject; comparing the sequence with the nucleic acid sequence obtained from a database and/or a healthy subject; and identifying any difference(s) related to the onset of the pathological condition.

Still another aspect of the invention relates to a method for diagnosing a pathological condition involving bone resorption or a susceptibility to the condition in a subject, comprising determining the amount of polypeptide comprising an amino acid sequence selected from the group consisting of SEQ ID NO: 41-69 and 80, particularly SEQ ID NO: 56, 57, 59-61 and 80 in a biological sample, and comparing the amount with the amount of the polypeptide in a healthy subject, wherein an increase of the amount of polypeptide compared to the healthy subject is indicative of the presence of the pathological condition.

The invention is further illustrated in the following figures and examples.

EXAMPLES

As described in the introduction, OPG has been identified in the arthritis and osteoporosis literature as one of the key players involved in the regulation of the differentiation and activity of osteoclasts and therefore of the maintenance of bone. Current bone protective therapies display a lack of efficacy in rheumatoid arthritis. Increased concentration of RANKL, originating from synovial fibroblasts and T-cells, has been observed in the joints of RA patients. This is believed to lead to an increased differentiation and activity of osteoclasts (OCs). It was decided, based on these observations, to initiate a functional genomics effort in order to identify factors that modulate the expression of OPG in primary human synovial fibroblasts derived from RA patients (RASF). The following assays, when used in combination with arrayed adenoviral shRNA (small hairpin RNA) expression libraries (the production and use of which are described in WO99/64582), are useful for the discovery of factors that modulate the capacity of synovial fibroblasts (SFs) to produce OPG. Candidate factors are filtered first through a primary assay (further referred to as the "OPG assay") followed by a secondary assay. These factors can be used as the basis for the development of novel therapies for the protection, maintenance, or stabilization of bone in rheumatoid arthritis, osteoporosis and also to reduce metastasis of cancer cells to bone.

Example 1 describes the development and setup of the primary assay screen of an adenoviral siRNA library using an ELISA for detection of protein levels of osteoprotegerin (OPG), and is referred to herein as the "OPG assay".

Example 2 describes the screening and its results.

Example 3 describes the 3MOI rescreen procedure.

Example 4 describes the setup of the secondary assay, referred to as the OC-RASF-coculture assay.

Example 5. describes the validation of the OPG hits in the OC-RASF-coculture assay.

Example 6 describes the determination of the endogenous expression levels of the target genes in RASFs.

Example 7 describes the confirmation of the OPG upregulation with independent Ad5-siRNAs.

Example 8 describes the determination of the anti-inflammatory effects of TARGETS.

Example 9 describes the OPG dependency of Ad-siRNA-mediated inhibition of osteoclast differentiation.

Example 1

Design and Setup of a High-Throughput Screening Method for the Identification of Regulators of OPG Expression by RASFs The OPG assay that has been developed for the screening of the SilenceSelect® collection has following distinctive features:
1) The assay is run with primary human synovial fibroblasts, but with minimal adaptations, could be used for any other source of primary cells or even cell lines susceptible to express OPG.
2) The assay has been optimized for the use with arrayed adenoviral collections for functional genomics purposes.
3) With minimal adaptations, the assay can also be used to screen compounds or compound collections.
4) The assay can be run in high throughput mode.

The protocol of the OPG ELISA is described below. This protocol is the result of the testing of various antibodies and various protocols:

The supernatant of cultures of primary human synovial fibroblasts derived from RA patients (RASF cultures) to be analysed is diluted 8 times in dilution buffer (1×PBS+0.1% BSA), and 35 µL is transferred to a pre-coated ELISA plate. The coating of this plate is performed as follows: a capture antibody (anti-hosteoprotegerin Purified Mouse Monoclonal IgG2A (Clone 69127.1), R&D systems, Cat. No. MAB8051, 500 µg/mL) is diluted to 1 µg/mL in PBS. 40 µL of this dilution is added per well and an overnight incubation is performed at 4° C. The next day (day 2), the plates are washed once with PBST (1×PBS with 0.5% Tween) and once with 1×PBS (GIBCO). After the washes, the plates are blocked with 100 µL blocking buffer (1% BSA, 5% sucrose, 0.05% NaN$_3$) for 4 hours. Another wash step is performed with PBST, and a detection antibody mixture (50 ng/mL) is then added to the plates. This detection mixture contains following detection antibody: biotinylated hOPG affinity purified Goat IgG (R&D systems Cat. No. BAF805) diluted in PBS+1% BSA. The plate is then stored in the dark for 2 hours and After this incubation time, 2 wash steps are performed, the first with PBST and the second with PBS. In every well, 35 µL of a streptavidine-HRP conjugate (BioSource Cat. No. SN2004) is added. This conjugate is diluted 1/3000 in 1×PBS supplemented with 1% BSA before addition. After a 45 min incubation step, 2 wash steps are performed, the first with PBST and the second with PBS. The PBS is then removed and 50 µL POD chemiluminescence substrate (Luminol (POD Roche, 1582950) is added to the plates. After a 5 min incubation in the dark, readout is performed on a LumiAscent luminometer (Labsystems), PMT default voltage, 100 msec read time.

Figure 2:
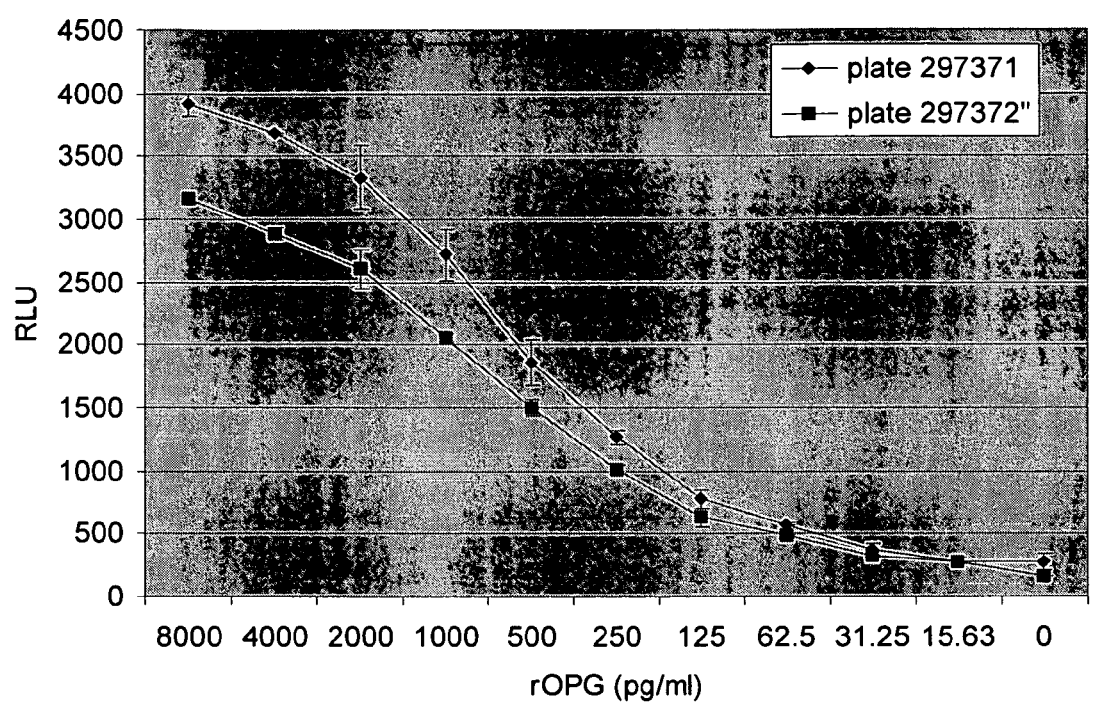
FIG. 2: Example of the performance of the OPG ELISA.

An example of the performance of the control plate is shown in FIG. 2. Recombinant OPG (R&D cat185-05-025) is diluted from 25 µg/mL to 8 ng/mL in dilution buffer (PBS+ 0.1% BSA). After that, a 2-fold dilution is made, also in the dilution buffer to become the standard curve. The samples are then tested in the OPG ELISA according to the protocol described above. A dose-dependent increase in the signal detected indicates the quality of the assay developed.

Example 2

Screening of 11330 "Ad-siRNA's" in the OPG Assay

Figure 3:
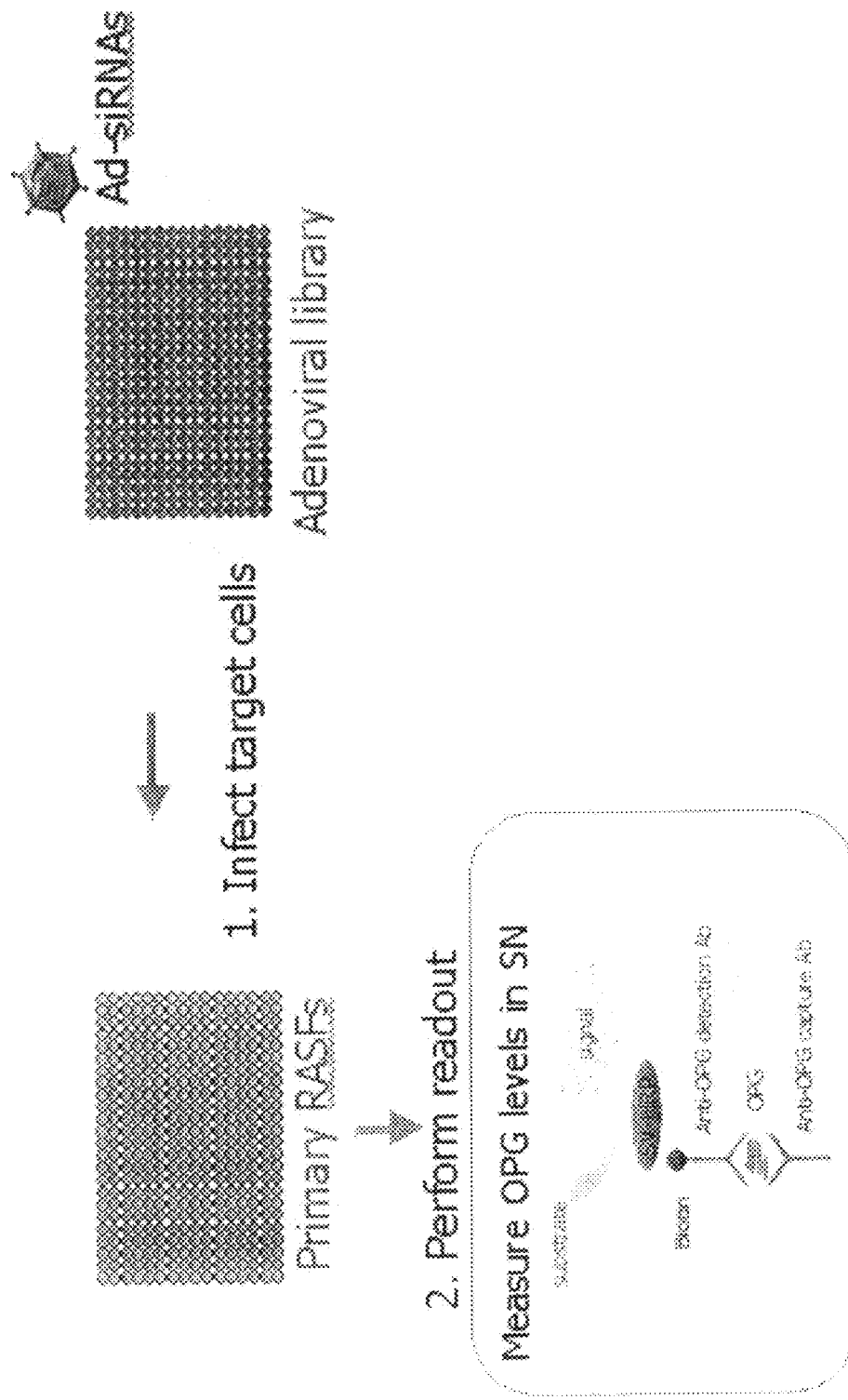
FIG. 3: Schematic representation of the primary screening: Principle of the screening of the SilenceSelect® collection in the OPG assay.

The OPG assay, the development of which is described in Example 1, has been screened against an arrayed collection of 11330 different recombinant adenoviruses mediating the expression of shRNAs in primary human synovial fibroblasts derived from RA patients (RASFs). These shRNAs cause a reduction in expression levels of genes that contain homologous sequences by a mechanism known as RNA interference (RNAi). The 11330Ad-siRNAs contained in the arrayed collection target 5046 different transcripts. On average, every transcript is targeted by 2 to 3 independent Ad-siRNAs. The principle of the screening is illustrated in FIG. 3. In brief, synovial fibroblasts (SFs) are seeded in 384 well plates and they are infected the day after seeding with the arrayed shRNA library, whereby each well is infected with one individual Ad-siRNA. Five days after infection, the medium on the cells is refreshed and cells are subject to a further incubation of 2 days. Two days later, supernatant is collected and subjected to the OPG ELISA.

RASFs, passage 1, were acquired from Cell Applications, Inc. and cultured in DMEM medium (Invitrogen), supplemented with 10% fetal bovine serum (HyClone), 100 units/ml penicillin (Invitrogen) and 100 µg/mL streptomycin (Invitrogen), and incubated at 37° C. and 10% CO$_2$ until passage 6. The cells are typically passaged once a week by a ⅓ split. At passage 6, a "master cell stock" is generated that is stored in liquid nitrogen. Cells from this master stock are used for the complete screening. When a cell stock is thawed, cells are subcultured and used for experiments between passages 10 and 12.

For screening, RASFs are seeded in transparent 384 well plates (Greiner) coated with 0.1% gelatin (Merck) at a density of 1000 cells/well in 50 µL Synovial Cell growth medium (Cell Applications, Inc.). One day post seeding, 2.5 µL Ad-siRNA virus from each well of the SilenceSelect® collection (WO 03/020931), stored in 384 well plates (estimated titer of 2.5×10$^9$ viral particles per mL) is transferred with the aid of a 96/384 channel dispenser (Tecan Freedom 200 equipped with TeMO96, TeMO384 and RoMa, Tecan AG, Switzerland) to individual wells of the 384 well plates containing SFs. Five days after infection, the medium is removed with a VacuSafe device (Integra) and 80 µL of aMEM (Invitrogen)+10% FBS (HI)+Pen/Strep medium is added to the wells by means of a Multidrop. After two days incubation, the supernatant was collected in 384 well plates (Greiner) and stored at −80° C. till further processing in the OPG ELISA (described in Example 1). For analysis, 35 µL of an 8-fold dilution—made by transfer of 8.57 µL supernatant into 384-wells filled with 60 µL dilution buffer (PBS 1×+1% (w/v) BSA)—is subjected to the OPG ELISA. Dilution and transfer to the ELISA plate is performed with the TECAN Freedom workstation.

A 384 well control plate is generated to assess the quality of each assay. The control plate is run in parallel with and under the same conditions as the aliquot plates from the SilenceSelect® collection during the different screening runs. The composition of this plate is shown in FIG. 4, upper panel. The control plate contains control viruses that are produced under the same conditions as the SilenceSelect® adenoviral collection. The viruses include three sets of negative control viruses ($N_1$(Ad5-eGFP_v1_KI), $N_2$ (Ad5-Luc_v13_KD), $N_3$ (Ad5-eGFP_v5_KD)), arranged in diagonal, interspaced with positive control viruses ($P_1$=$P_3$=$P_3$ (Ad5-OPG_v1_KI), B1: blanco, uninfected). Every well of a control plate contains 50 µL of virus crude lysate. Multiple aliquots of this control plate are produced and stored at −80° C. A representative example of the layout and performance of the control plate tested with the screening protocol described above is shown in FIG. 4, lower panel. In this figure, the layout of the control plate is indicated (upper panel) and the raw OPG signal detected upon performing the assay for every recombinant adenovirus on the plate is shown in the lower panel. When the value for the OPG level exceeds the cutoff value (defined as 2.6 fold the standard deviation over the negative controls), the format of the field in the table is black background, white characters.

The complete SilenceSelect® collection (11330 Ad-siR-NAs targeting 5046 transcripts, contained in 30 384 well plates) is screened in the OPG assay according to the protocol described above in two phases. In the first screening round (screen A), 7 virus library plates are screened and rescreened in single, resulting in 2 datapoints for every Ad-siRNA. In a second screening round (screen B) the remaining 23 virus library plates are screened in duplicate on independent assay plates in both a primary and an independent rescreen. As such, 4 datapoints are thus obtained for every Ad-siRNA in screen B. Ad-siRNA viruses are nominated as primary hits if half of the data points scored above threshold. Threshold settings for screen A and screen B are set at average of all data points per plate plus 2.6 times standard deviation over all data points per plate. A total of 271 hits (80 out of screen A and 193 out of screen B) were isolated that scored above the threshold.

Figure 5:
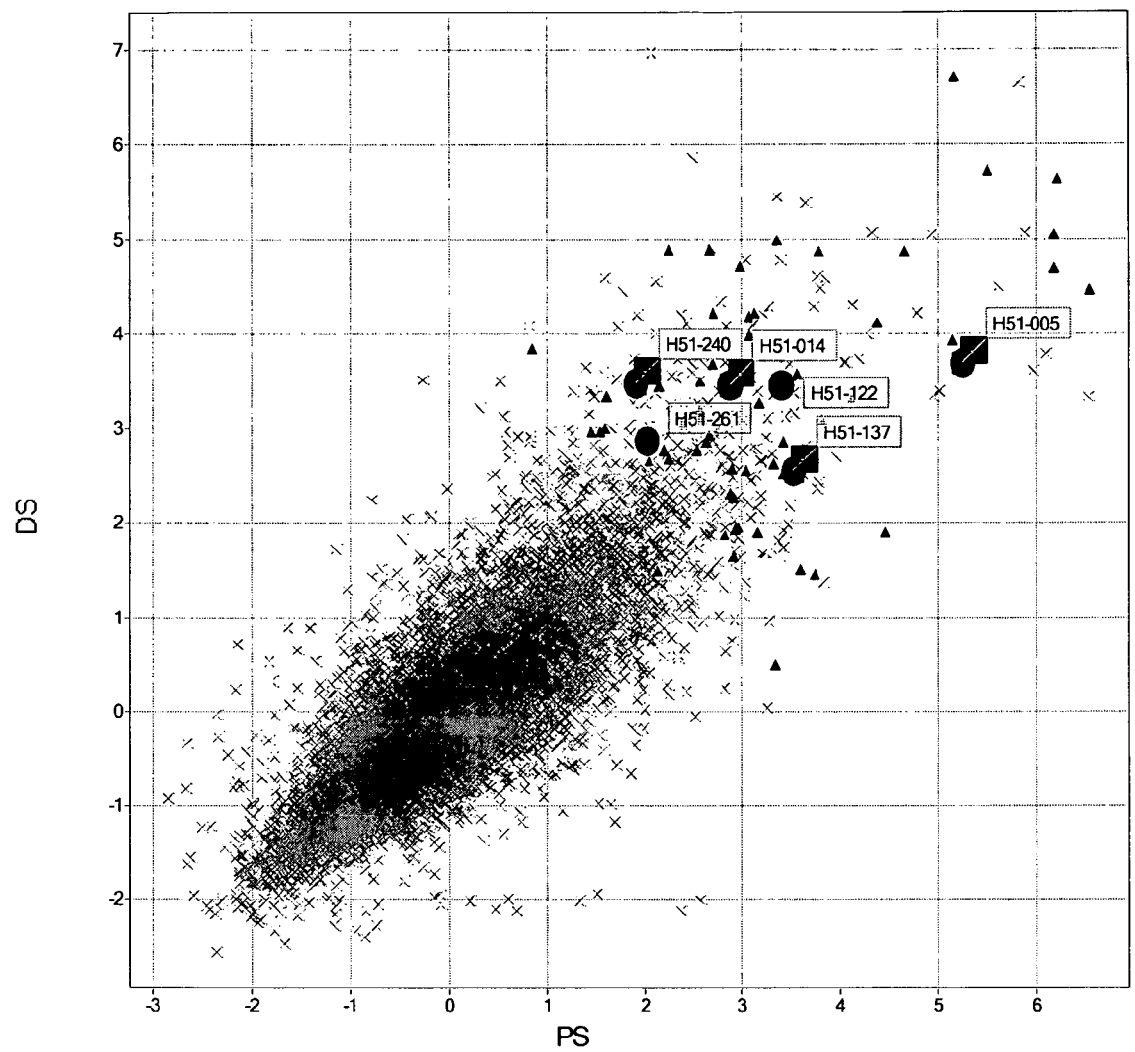
FIG. 5: Scatterplot representing the datapoints obtained in the primary screen of the OPG assay against the SilenceSelect® collection.

In FIG. 5, all datapoints obtained in the screening of the SilenceSelect® collection in the OPG assay are shown. The averaged relative luminescence data obtained from the duplicate samples in the primary screen (PS) is plotted against the averaged relative luminescence data for the corresponding Ad-siRNA obtained in the rescreen (DS). The threshold (2.6 times standard deviation) is indicated by dotted lines. The data for the most particular targets are shown as filled circles, the data for Ad-siRNA's nominated as hits are indicated as filled triangles, the data for the non-hit Ad-siRNA's are indicated as crosses. The strong symmetry observed between the data of the primary screen and that of the rescreen (the datapoints are concentrated around a straight line) demonstrates the quality and reproducibility of the screening. The relative OPG expression levels obtained in the primary screens for all targets, expressed in terms of "fold standard deviation above plate average", are listed in Table 3 below.

TABLE 3

The relative OPG expression levels obtained in the primary screens for all targets, expressed in terms of "fold standard deviation above plate average"

| Hit # | Primary screen | | Double screen | |
|---|---|---|---|---|
| | 1 | 2 | 1 | 2 |
| H51-082 | 2.751 | 2.666 | 4.204 | 4.216 |
| H51-054 | 2.245 | n/a | 2.679 | n/a |
| H51-104 | 3.385 | 3.266 | 2.719 | 2.53 |
| H51-172 | 3.175 | 4.384 | 3.916 | 5.817 |
| H51-181 | 6.299 | 6.04 | 4.736 | 4.661 |
| H51-225 | 1.635 | 1.563 | 3.322 | 3.365 |
| H51-236 | 1.742 | 1.435 | 2.755 | 3.245 |
| H51-240 | 1.507 | 2.316 | 3.818 | 3.12 |
| H51-137 | 4.012 | 3.055 | 2.765 | 2.33 |
| H51-121 | 5.804 | 5.205 | 5.981 | 5.477 |
| H51-122 | 3.611 | 3.201 | 3.274 | 3.653 |
| H51-014 | 2.88 | n/a | 3.453 | n/a |
| H51-018 | 3.598 | n/a | 1.503 | n/a |
| H51-040 | 2.985 | n/a | 4.703 | n/a |
| H51-046 | 5.154 | n/a | 6.711 | n/a |
| H51-142 | 3.058 | 2.758 | 1.605 | 1.711 |
| H51-103 | 3.183 | 3.134 | 1.729 | 2.077 |
| H51-119 | 2.645 | 2.616 | 3.456 | 2.28 |
| H51-145 | 3.318 | 4.329 | 2.654 | 3.524 |
| H51-153 | 3.332 | 3.519 | 3.57 | 2.16 |
| H51-177 | 2.61 | 2.559 | 3.26 | 3.02 |
| H51-183 | 4.587 | 3.653 | 3.665 | 2.972 |
| H51-206 | 2.576 | 2.753 | 2.511 | 3.351 |
| H51-251 | 2.016 | 2.266 | 3.387 | 3.512 |

TABLE 3-continued

The relative OPG expression levels obtained in the primary screens for all targets, expressed in terms of "fold standard deviation above plate average"

| Hit # | Primary screen | | Double screen | |
|---|---|---|---|---|
| | 1 | 2 | 1 | 2 |
| H51-270 | 1.516 | 1.376 | 2.76 | 3.182 |
| H51-261 | 2.067 | 1.979 | 2.664 | 3.086 |

In this primary screen certain targets are obtained, which have been identified previously in rheumatoid arthritis (RA) and/or osteoporosis (OP) independently designed and unrelated screens. This serves to validate these polypeptides as RA/OP targets and demonstrates the accuracy and relevance of the screen utilized herein. These targets relate to hits H51-103, H51-119, H51-145, H51-153, H51-177, H51-183, H51-206, H51-251 and H51-270. Their nucleic acid sequences are given in SEQ ID NO: 30-39 and their amino acid sequences are SEQ ID NO: 70-79, and their appropriate particulars are provided in Tables 1-5 herein. These are described in WO 2005/063976, WO 2005/121778 and WO 2005/124342 each and all of which are incorporated herein by reference.

Example 3

Three MOI Rescreen of the Primary Hits Using Independent Repropagation Material

To confirm the results of the identified Ad-siRNA in the OPG ELISA the following approach may be taken: the Ad-siRNA hits are repropagated using PerC6 cells (Crucell, Leiden, The Netherlands) at a 96-well plate level, followed by retesting in the OPG assay at three MOIs (multiplicity of infection). First, tubes containing the crude lysates of the identified hit Ad-siRNA's samples are picked from the SilenceSelect® collection and rearranged in 96 well plates together with negative/positive controls. The primary hits from screen A and screen B are each rearranged over four 96-well plates. As the tubes are labeled with a barcode (Screenmates™, Matrix technologies), quality checks are performed on the rearranged plates. To propagate the rearranged hit viruses, 40.000 PerC6.E2A cells are seeded in 200 µL of DMEM containing 10% non-heat inactivated FBS into each well of a 96 well plate and incubated overnight at 39° C. in a humidified incubator at 10% $CO_2$. Subsequently, 2 µL of crude lysate from the hit Ad-siRNA's rearranged in the 96 well plates as indicated above is added to the PerC6.E2A cells using a 96 well dispenser. The plates may then be incubated at 34° C. in a humidified incubator at 10% $CO_2$ for 7 to 10 days. After this period, the repropagation plates are frozen at −20° C., provided that complete CPE could be seen. The propagated Ad-siRNAs are rescreened in the OPG assay at 3 MOI's (4 µL, 2 µL and 1 µL). Infection at 3 MOIs is carried out as follows: using the 96/384 TeMo pipettor, a 1/2 and 1/4 dilution is made of each 96-well plate that contains the crude lysate of repropagated hits. Subsequently, an aliquot of each of the four 96-well plates containing the undiluted crude lysate of the repropagated hits of screen A or screen B are transferred to one 384-well plate. Similarly, aliquots of the 1/2 or 1/4 (respectively) dilutions are combined into one 384-well plate resulting in three 384 well plates containing undiluted, 1/2 or 1/4 diluted crude lysates of repropagated hits of screen A (or of screen B). Finally, 4 µL of each of these three 384-well plates is transferred to the assay plates, resulting in the 4 µL, 2 µL and 1 µL infections. Within one 3 MOI rescreen, infections at each MOI is performed in duplicate, with each singular on a different assay plate.

For most of the primary hits (screen B) the identified Ad-siRNAs are retested in two independent three MOI rescreens. Data analysis for each of the three MOI screen is performed as follows. For every plate the average and standard deviation is calculated for the negative controls and may be used to convert each data point into a "cutoff value" that indicates the difference between the sample and the average of all negatives in terms of standard deviation of all negatives. For each MOI, a threshold setting is defined as the minimal "cutoff value" at which none of the negatives would score positive. Threshold settings for the first three MOI rescreen are 2.3-2.0-2.0 (for each MOI 4 µL/2 µL/1 µL respectively). Threshold settings for the second 3 MOI rescreen are 2.2-2.4-2.3 for each MOI respectively. Within one of the three MOI rescreens the Ad-siRNA must to score in duplicate in at least one MOI to be positive. Hits that are found to be positive in both 3 MOI experiments are defined as "confirmed OPG hits". 159 of the 193 primary hits (screen B) are confirmed in this way.

For a minority of the primary hits (screen A) the identified Ad-siRNAs are retested in only one 3 MOI rescreen. Cutoff settings here are as follow 5-3.6-3.2 (for each MOI 4 µL/2 µL/1 µL respectively) and are based on 2 negative controls (N2 and N3). 63 out of the 80 primary hits from screen A are found to score in duplicate in at least one MOI within this 3 MOI rescreen and are confirmed.

In summary, 222 out of the 273 primary hits (or 81.3%) are confirmed using repropagated Ad-siRNA material. The 3MOI screening data are summarized in Table 4: overview of performance of primary OPG hits identified in screen A (A) or screen B (B) in further validation experiments: OPG 3MOI retesting (this example) and testing in coculture OC assay (see next example). Each of these validation experiments is done at 3 MOIs (duplicates within one MOI) (*). The table indicates the number of MOIs at which a hit scored in duplicate above the cutoff setting (for OPG) or below the cutoff setting (for the osteoclast assay, OC) for each repeat that is performed (RUN A, B, C). The table also indicates if a hit is confirmed (1) or not (0) within each of the validation experiments according to hit calling criteria outlined discussed above.

Figure 9A:
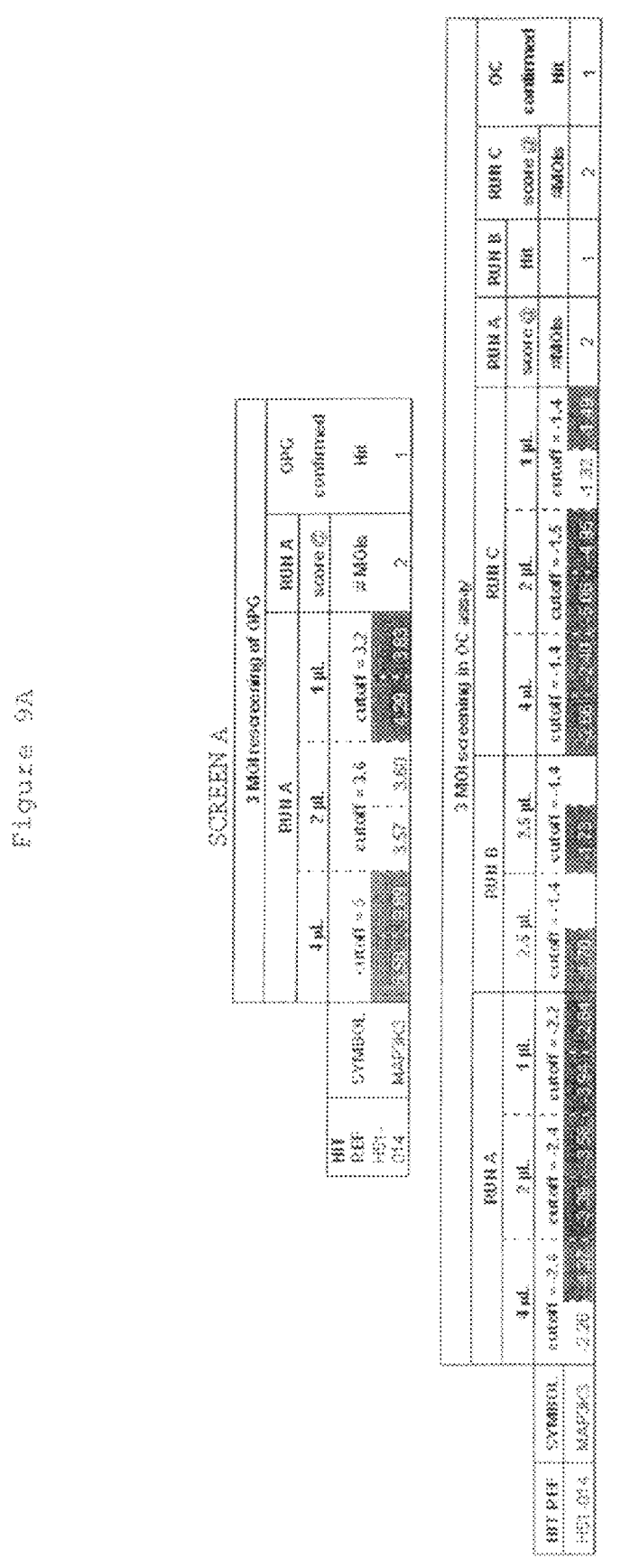

All data for the most particular targets obtained in the OPG three MOI retesting (this example) and testing in coculture OC assay (see next example) are shown in FIG. 9B. This figure summarizes the cutoff settings and performance of some primary OPG hits identified in screen A (A) or screen B (B) in further validation experiments: OPG 3MOI retesting and testing in coculture OC assay. Values having cutoff setting above cutoff value (for OPG assay) or below cutoff value (for OC assay) are indicated by gray shading.

A quality control of target Ad-siRNAs is performed as follows: Target Ad-siRNAs are propagated using derivatives of PER.C6© cells (Crucell, Leiden, The Netherlands) in 96-well plates, followed by sequencing the siRNAs encoded by the target Ad-siRNA viruses. PERC6.E2A cells are seeded in 96 well plates at a density of 40,000 cells/well in 180 µL PER.E2A medium. Cells are then incubated overnight at 39° C. in a 10% $CO_2$ humidified incubator. One day later, cells are infected with 1 µL of crude cell lysate from SilenceSelect® stocks containing target Ad-siRNAs. Cells are incubated further at 34° C., 10% $CO_2$ until appearance of cytopathic effect (as revealed by the swelling and rounding up of the cells, typically 7 days post infection). The supernatant is collected, and the virus crude lysate is treated with proteinase K by adding to 4 µL Lysis buffer (1× Expand High Fidelity buffer with $MgCl_2$ (Roche Molecular Biochemicals, Cat. No. 1332465) supplemented with 1 mg/mL proteinase K (Roche Molecular Biochemicals, Cat No. 745 723) and 0.45% Tween-20 (Roche Molecular Biochemicals, Cat No. 1335465) to 12 µL crude lysate in sterile PCR tubes. These tubes are incubated at 55° C. for 2 hours followed by a 15 minutes inactivation step at 95° C. For the PCR reaction, 1 µL lysate is added to a PCR master mix composed of 5 µL 10× Expand High Fidelity buffer with $MgCl_2$, 0.5 µL of dNTP mix (10 mM for each dNTP), 1 µL of "Forward primer" (10 mM stock, sequence: 5' CCG TTT ACG TGG AGA CTC GCC 3') (SEQ. ID NO: 110), 1 µL of "Reverse Primer" (10 mM stock, sequence: 5' CCC CCA CCT TAT ATA TAT TCT TTC C) (SEQ. ID NO: 111), 0.2 µL of Expand High Fidelity DNA polymerase (3.5 U/µL, Roche Molecular Biochemicals) and 41.3 µL of $H_2O$. PCR is performed in a PE Biosystems Gene-Amp PCR system 9700 as follows: the PCR mixture (50 µL in total) is incubated at 95° C. for 5 minutes; each cycle runs at 95° C. for 15 sec., 55° C. for 30 sec., 68° C. for 4 minutes, and is repeated for 35 cycles. A final incubation at 68° C. is performed for 7 minutes, 5 µL of the PCR mixture is mixed with 2 mL of 6× gel loading buffer, loaded on a 0.8% agarose gel containing 0.5 µg/µL ethidium bromide to resolve the amplification products. The size of the amplified fragments is estimated from a standard DNA ladder loaded on the same gel. The expected size is approximately 500 bp. For sequencing analysis, the siRNA constructs expressed by the target adenoviruses are amplified by PCR using primers complementary to vector sequences flanking the SapI site of the pIPspAdapt6-U6 plasmid. The sequence of the PCR fragments is determined and compared with the expected sequence. All sequences are found to be identical to the expected sequence.

Example 4

Design and Setup of a Screening Method for the Identification of Regulators of Osteoclast Differentiation in Coculture Background and Principle of the Osteoclast Coculture Assay.

FIG. 6A represents the principle of the osteoclast coculture assay. In this assay, RASFs are seeded in a multi-well plate. These cells are capable of expressing factors that modulate the differentiation of osteoclast precursor cells either in a negative way (e.g. OPG) or in a positive way (e.g. TNF or RANKL). Osteoclast precursor cells are then seeded on top of the RASFs and M-CSF as well as RANKL are added to the coculture. In this setting, the osteoclast precursor cells will differentiate unless an inhibiting factor is expressed by the cocultured RASFs. As such, this assay allows one to functionally monitor the expression of factors modulating osteoclast differentiation by RASFs. The readout applied to quantify the differentiation of the osteoclasts in coculture is a cell-based ELISA that measures the expression of a marker specific for differentiated osteoclasts (vitronectin receptor, also called alphav-beta3 integrin). The principle of the screening of arrayed adenoviral collections in the osteoclast coculture assay is illustrated in FIG. 6B. In brief, RASFs are seeded in multi-well plates and infected with the Ad-siRNA's in an arrayed fashion on day 1. On day 7, the osteoclast precursor cells and M-CSF are added on top of the RASFs. Day 8, sRANKL is added and day 19 (after 10 days incubation), the vitronectin cELISA is performed.

4.1 Selection of a Readout for the Osteoclast-RASF Coculture.

Antibody-based detection methods are amenable to HTS development. Therefore, we aimed at evaluating a cELISA detection method for $\alpha_v\beta_3$ integrin (vitronectin receptor) and calcitonin receptor, two markers that are frequently used to assay OC differentiation and for which antibodies are commercially available.

Figure 7A:
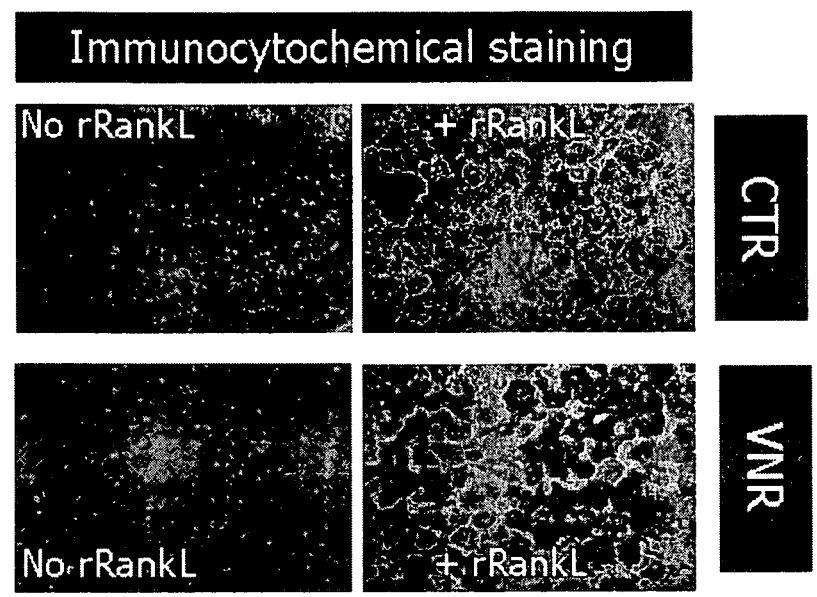
FIG. 7A: $\alpha_v\beta_3$ and calcitonin receptor cELISA of an osteoclast monoculture.

Readouts for these markers are evaluated using the commercially available Poetics™ Osteoclast Precursor Cell System (Cambrex). This cell system contains cryopreserved human OC precursors for which, upon thawing and culturing in the provided optimized differentiation medium, differentiate towards mature functional multinucleated OCs. These specific precursor cells will be further referred to as OCPs. A cELISA-based readout with commercially available antibodies for $\alpha_v\beta_3$ integrin and calcitonin receptor is tested (See FIG. 7A). For the experiment depicted, primary human OCPs cells are seeded at a density of 10,000 cells/well in a 96-well plate format and cultured for 10 days in medium (proprietary Cambrex medium) containing both rRANKL (66 ng/mL) and M-CSF (33 ng/mL) or in medium containing only M-CSF (undifferentiated control). Immunostaining is performed using primary antibodies for $\alpha_v\beta_3$ (Monosan) or calcitonin receptor (Serotec) in combination with the Alkaline Phosphatase-Fast Red staining kit (Dako) to visualise the bound primary antibody. The expression of $\alpha_v\beta_3$ integrin and calcitonin receptor is barely detected on undifferentiated control cultures but is clearly increased if culture conditions allow OC differentiation, validating the approach for the detection of osteoclasts.

Figure 7B:
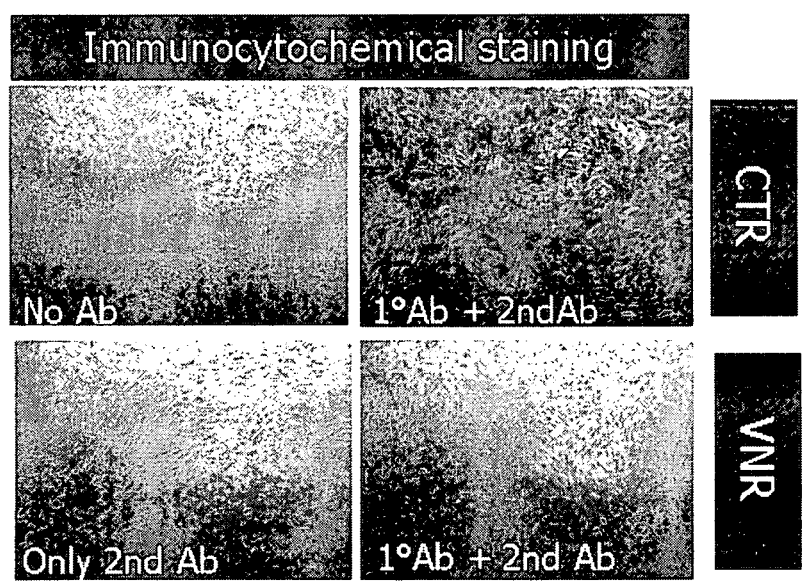
FIG. 7B: $\alpha_v\beta_3$ and calcitonin receptor staining of a RASF-osteoclast coculture.

While these results prove the feasibility of a cELISA-based measurement of $\alpha_v\beta_3$ integrin and calcitonin receptor expression to assay OC differentiation in monocultures of OCPs, we aim at developing a co-culture assay in which differentiation takes place on top of RASFs. Therefore, we need to show the absence of background signal when RASF cultures, run under conditions suited to OC differentiation, are subjected to the cELISA procedure for $\alpha_v\beta_3$ and calcitonin receptor detection. While no background staining is detected for $\alpha_v\beta_3$, a clear signal is detected when the cells are assayed for calcitonin receptor expression (See FIG. 7B). The experiment depicted is performed as follows. RASF are seeded at 3000 cells/well in a 96-well plate. After 3 days of culture, cell layers are fixed and stained using antibodies for $\alpha_v\beta_3$ and calcitonin receptor, as described below. A clear staining is observed with the calcitonin receptor mAb, while no signal higher than background (only $2^{nd}$ Ab or no Ab) when cells are incubated with the $\alpha_v\beta_3$ mAb. Only the $\alpha_v\beta_3$ integrin cELISA readout, therefore, is considered for further assay development.

In next experiments, proof of principle is delivered for the inhibition of RANKL induced OC differentiation by RASFs. RASFs (100 cells/well) are seeded in 384 well plates and infected with either Ad5-eGFP or Ad5-OPG (FIG. 7C, panel A) or left uninfected (FIG. 7C, panel B). 24 hrs after seeding, OC precursor cells (OCP, Cambrex, 1500 cells/well) and M-CSF (40 ng/mL, R&D systems) are added to all wells, as well as the recombinant OPG (rOPG, 22 ng/mL or 66 ng/mL, R&D systems) and IL4 (10 ng/mL, R&D systems) (panel B). After one day rRANKL (0 to 60 ng/mL, Cambrex) is added and incubation is performed for 11 days before the $\alpha_v\beta_3$ integrin cELISA luminescent readout. Luminescence data are expressed as percentage of the signal obtained for the negative controls at 15 ng/mL rRANKL concentration (=100%). Results are shown in FIG. 7C. A clear rRANKL dose-dependent induction of OC differentiation is obtained in this experiment (as seen in the uninfected and Ad5-eGFP infected samples). The differentiation is inhibited by OPG (either recombinant or expressed by SFs). The rOPG dose added (22 ng/mL) is sufficient to inhibit the effect of up to 7.5 ng/mL rRANKL. As expected, a higher dose of rOPG is able to inhibit even higher concentrations of rRANKL: up to 15 ng/mL of rRANKL is efficiently inhibited by 66 ng/mL rOPG. Also rIL4 addition could potently block the rRANKL-driven OC differentiation through the inhibition of the RANKL signalisation in pre-OCs. Taken together, this experiment demonstrates that the rRANKL-driven OC differentiation process can be blocked by various secreted factors and represents a proof of principle experiment for the 'inhibition of RANKL induced OC differentiation assay'.

The protocol of the vitronectin receptor cELISA used for the detection of osteoclasts in screening setting is as follows:

The medium on top of an osteoclast monoculture or of a osteoclast-RASF coculture or is removed and 50 μL ice cold MeOH (Riedel-de-Haen, cat No. 32213) is added for fixation of the cells. The MeOH is refreshed with 80 μL MeOH. After incubation for 20 min at −20° C., the MeOH is removed and the plates were dried in air for 20 minutes. The plates are then washed twice with 80 μL PBS 1× (GIBCO) and 75 μL of 0.1% casein buffer are immediately added to block the plates. The casein buffer is prepared as follows: 2 g casein in 80 mL Milli Q, adjust to PH 12, stir 15 min at RT, adding 200 mL 10×PBS, adjust to 2 L Milli Q and adjust to PH7.4. The plates are blocked for at least 2 hours at RT and the casein buffer is then removed. 25 μL of EC buffer is then added to the plates. The EC buffer is prepared as follows: 8 g casein, 4.26 g $Na_2HPO_4$, 4 g albumine bovine, 1.38 g $NaH_2PO_4.H_2O$, 1 g CHAPS, 46.6 g NaCl in 150 mL MilliQ, 8 mL EDTA pH8, adjusting to pH12, stirring 15 min at low heat, adding 10 mL $NaN_3$ 10%, adjusting to 2 L with MilliQ, adjusting to pH7.0. The EC buffer is then removed and 35 μL of the primary antibody (Monosan, Mon2033) is added to the plates. The plates are incubated overnight at 4° C. and then washed twice, once with PBST (1×PBS with 0.05% Tween20) and once with 1×PBS. The secondary antibody (2000-fold dilution of goat anti-mouse immunoglobulins from DAKO) is then added to the plate in buffer C. Buffer C is prepared as follows: 0.82 g $NaH_2PO_4.H_2O$, 4.82 g $Na_2HPO_4$, 46.6 g NaCl, 20 g Albumin bovine, adjust to 2 L with MilliQ, add 8 mL 0.5M EDTA pH8.0, adjusting to pH7.0 and sterilize. An incubation of maximally 1 hour is performed. After the incubation, the plates are washed twice with PBST (1×PBS with 0.05% Tween20) and once with 1×PBS. The read out is performed with Luminol (POD Roche, 1582950), a chemiluminescence substrate.

The vitronectin receptor cELISA is adapted for the screening of an arrayed adenoviral collection on a coculture as follows. Day 1, the RASF cells (1000 cells/well) are seeded on a 0.1% gelatin coated plate (Greiner, cat. No. 781080) in 50 μL medium (Synovial Growth medium, Cell Application). One day later (day 2) the cells are infected with 4 μL of Ad-siRNA material from library (at 3 dilutions). On day 7, the medium was refreshed with 30 μL co-culture medium (aMEM, (GIBCO, cat. No. 22571-020) supplemented with 10% FBS and a mixture of penicillin and streptomycin), containing 60 ng/mL rhMCSF (Cambrex; PT-9010). 1250 osteoclast precursor cells (Cambrex; Cat. No. 2T-110, contained in 30 μl medium) are then added on top of the RASFs. Day 8, sRANKL (Cambrex, osteoclast culture bullet kit) is added to a concentration of 30 ng/mL. On day 19 (after 10 days incubation at 37° C.; 5% $CO_2$), the vitronectin receptor cELISA is performed.

Example 5

Validation of the OPG Hits in the Osteoclast-RASF Coculture Assay

Confirmed OPG hits are further analyzed in the osteoclast RASF co-culture assay that is developed and performed described above (Example 4). The desired effect is the following: knock-down of the Ad-siRNA target gene expression in the RASFs monolayer should inhibit osteoclast differentiation driven by RANKL and MCSF. For the majority of the confirmed OPG hits (hits originating from screen B) testing in the osteoclast differentiation assay is as follows. Ad-siRNA are tested in two independent experiments, each carried out at 3 MOIs. The virus material for the Ad-siRNA and positive and negative controls is the same as that prepared for retesting of the primary hits in 3 MOI OPG. The results obtained after read out of the osteoclast differentiation assay are converted into "cutoff values" based on the average and standard deviation of the negative controls on each plate as described for the 3 MOI OPG ELISA, except that results for even and odd rows are first separated in order to correct for an observed difference in signal strength of controls on even/odd rows. For each MOI, a threshold for hitcalling is set. The threshold is the lowest "cutoff" value at which none of the negatives score positive (i.e. have a cutoff values lower than the threshold). Settings in the two independent three MOI OC testings are −1.8/−1.8/−1.8 (for the 3 MOIs 4 μL/2 μL/1 μL respectively).

The Ad-siRNA is required to score in duplicate in at least one of the MOIs to be positive within a three MOI experiment. 53 of the 159 confirmed OPG hits (screen B) are positive in both three MOI experiments and passed this control test. 33 others, were positive in only one of the two three MOI experiments. These 33 Ad-siRNAs are cherry picked out of the virus plates together with the controls and tested for a $3^{rd}$ time in the OC assay at 3 MOIs. 7 of the 33 are found to have a positive score after analysis and passed the OC differentiation control test. Therefore, 60 out of the 159 OPG confirmed hits originating from screen B (i.e 37.7%) are thus found to pass the OC co-culture assay.

For a minority of the confirmed OPG hits (originating out of screen A), Ad-siRNAs are tested in 3 independent OC co-culture experiments. One of these is performed at only one MOI (2.5 μL infection out of SilenceSelect® collection tubes) and 2 are performed at 3 MOIs using repropagated virus material obtained after primary screening. Threshold settings for hitcalling are based on the results of the appropriate negative controls as described above. To pass the OC differentiation criterium, Ad-siRNAs are required to have a positive score in 2 out of the 3 experiments. Of the 63 confirmed OPG hits, 23 (i.e. 36.5%) passed this criterium.

In summary, 83 of the 222 confirmed OPG hits (or 37.4%) are also found to inhibit OC differentiation in the co-culture assay. The results obtained in the secondary assay for the TARGETS are summarized in Table 4 (screen A and screen B) and the raw data obtained for the particular targets are shown in FIG. 9 (screen A and screen B).

TABLE 4

Summary of the data obtained for the MOI rescreen and secondary assay (osteoclast differentiation assay) for all hits Screen A. Data for the hits from 7 SilenceSelect ® plates:

| | | 3 MOI OPG | | 3 MOI OC | | | |
| --- | --- | --- | --- | --- | --- | --- | --- |
| HIT REF | SYMBOL | RUN A score @ # MOIs | OPG confirmed Hit | RUN A score @ #MOIs | RUN B Hit | RUN C score @ #MOIs | OC confirmed Hit |
| H51-014 | MAP3K3 | 2 | 1 | 2 | 1 | 2 | 1 |
| H51-018 | P2RY14 | 1 | 1 | 1 | 1 | 0 | 1 |
| H51-040 | NEK3 | 3 | 1 | 0 | 1 | 1 | 1 |
| H51-046 | KLKB1 | 2 | 1 | 2 | 1 | 0 | 1 |
| H51-054 | MAP4K4 | 3 | 1 | 3 | 1 | 2 | 1 |

Screen B. Data for the hits from the screening 23 SilenceSelect ® plates:

| | | 3 MOI OPG | | | 3 MOI OC | | | |
| --- | --- | --- | --- | --- | --- | --- | --- | --- |
| HIT REF | SYMBOL | RUN A score @ # MOIs | RUN B score @ # MOIs | OPG confirmed Hit | RUN A score @ # MOIs | RUN B score @ # MOIs | RUN C score @ # MOIs | OC confirmed Hit |
| H51-082 | NTRK2 | 3 | 3 | 1 | 3 | 3 | NA | 1 |
| H51-104 | MMP17 | 3 | 3 | 1 | 3 | 1 | NA | 1 |
| H51-121 | SLC4A8 | 3 | 3 | 1 | 3 | 3 | NA | 1 |
| H51-122 | ENPP2 | 3 | 3 | 1 | 3 | 2 | NA | 1 |
| H51-137 | MRAS | 3 | 3 | 1 | 3 | 1 | NA | 1 |
| H51-142 | FNTA | 1 | 2 | 1 | 3 | 1 | NA | 1 |
| H51-172 | PLA2G12A | 3 | 2 | 1 | 3 | 3 | NA | 1 |
| H51-181 | MGLL | 3 | 3 | 1 | 1 | 2 | NA | 1 |
| H51-225 | GPR44 | 3 | 2 | 1 | 3 | 3 | NA | 1 |
| H51-236 | MIR16 | 3 | 3 | 1 | 1 | 2 | NA | 1 |
| H51-240 | PTK6 | 3 | 2 | 1 | 2 | 3 | NA | 1 |
| H51-103 | USP9Y | 3 | 3 | 1 | 3 | 2 | NA | 1 |
| H51-119 | CDC7 | 3 | 2 | 1 | 1 | 1 | NA | 1 |
| H51-145 | PPIA | 3 | 3 | 1 | 3 | 3 | NA | 1 |
| H51-153 | TOP2B | 3 | 3 | 1 | 2 | 3 | NA | 1 |
| H51-177 | PPP2CB | 3 | 3 | 1 | 3 | 1 | NA | 1 |
| H51-183 | COX10 | 3 | 3 | 1 | 2 | 2 | NA | 1 |

TABLE 4-continued

Summary of the data obtained for the MOI rescreen and secondary assay
(osteoclast differentiation assay) for all hits

| H51-206 | CCR1 | 3 | 1 | 1 | 1 | 1 | NA | 1 |
|---|---|---|---|---|---|---|---|---|
| H51-251 | B3GALT1 | 3 | 3 | 1 | 2 | 2 | NA | 1 |
| H51-261 | CXCR6 | 3 | 3 | 1 | 3 | 3 | NA | 1 |
| H51-270 | SLC9A8 | 2 | 3 | 1 | 2 | 1 | NA | 1 |

NA = not applicable (a third run of the OC assay was not done because it scored in previous two).
(*) = OC run B for hits identified out of screen A was done at only 1 MOI in two independent experiments. To be a hit in this run, the Ad-siRNA had to score in one of the two experiments.

Example 6

Analysis of the Expression Levels for Certain Targets Identified in Human Primary Synovial Fibroblasts Derived from Synovium of RA Patients Expression levels for certain identified targets are determined in different isolates of primary human synovial fibroblasts as follows.

The RASFs isolates are obtained as cryo-preserved passage 2 cells from Cell Applications Inc. (Cat. No. 404-05). These cells are cultured and propagated in DMEM (Invitrogen) supplemented with 10% (v/v) heat-inactivated FBS (ICN) and 1× Pen/Strep (Invitrogen). For expression analysis, cells are cultured to passage 11.

For RNA preparation, the primary human synovial fibroblasts are seeded in 10-cm Petri dishes (500,000 cells/dish) in 6-well plates. After overnight incubation, medium is refreshed with 6 mL of M199 medium supplemented with 1% (v/v) heat-inactivated FBS containing 1× Pen/Strep. 24 hours later, total RNA is extracted using the "SV Total RNA Isolation kit" (Promega).

The concentration of RNA in each sample is fluorimetrically quantified using the "Ribogreen RNA quantitation kit" (Molecular Probes). A similar amount of RNA from each preparation is reverse transcribed into first strand cDNA with the "Taqman reverse transcription kit" from Applied Biosystems. Briefly, 40 ng RNA is included per 20 µL reaction mix containing 50 µmol of random hexamers, 10 U Rnase inhibitor, 25 U Multiscribe reverse transcriptase, 5 mM $MgCl_2$ and 0.5 mM of each dNTP. The reaction mixture is incubated at 25° C. for 10 minutes, followed by 30 minutes incubation at 48° C. and heat inactivation (5 minutes 95° C.) of the reverse transcriptase in a thermocycler (Dyad, MJ Research). Reactions are immediately chilled to 4° C. at the end of the program. To avoid multiple freeze/thaw cycles of the obtained cDNA, the different samples are pooled in 96-well plates, aliquoted and stored at −20° C.

Real-time PCR reactions are performed and monitored using the "ABI PRISM 7000 Sequence Detection System Instrument" (Applied Biosystems). Pre-designed, gene-specific Taqman probe and primer sets for quantitative gene expression are purchased from Applied Biosystems as part of the "Assays on Demand" Gene expression products. These commercially available kits are quality checked by the supplier and allow quantitative determination of the amount of target cDNA in the sample. The "Assays on Demand" gene expression products are used according to the protocol delivered by the supplier. The PCR mixture consisted of 1× "Taqman Universal PCR Mastermix no AmpErase UNG" and 1× "Taqman Gene Expression Assay on Demand mix" and 5 µL of the retro-transcription reaction product (1-100 ng of RNA converted into cDNA) in a total volume of 25 µL. After an initial denaturation step at 95° C. for 10 minutes, the cDNA products are amplified with 40 cycles consisting of 95° C. for 15 sec, and 60° C. for 1 minute. To normalize for variability in the initial quantities of cDNA between different samples, amplification reactions with the same cDNA are performed for the housekeeping gene β-actin using the predeveloped β-actin "Assays on demand" primer set and Taqman probe mix and "Taqman Universal PCR Mastermix" (all Applied Biosystems) according to the manufacturer's instructions. To identify any contamination resulting from residual genomic DNA, real-time PCR reactions with product from a control (-RT) reverse transcription reaction that is performed under the same conditions but without the addition of the reverse transcriptase are included for each sample. Threshold cycle values (Ct), for example, the cycle number at which the amount of amplified gene of interest reached a fixed threshold are determined for each sample. For each sample, the ΔCt value is determined by subtracting the Ct value of the endogenous control (β-actin) from the Ct value obtained for the target gene. A gene is considered as expressed in primary human SFs if the ΔCt value obtained for this hit is lower than 13.3 in at least one of the available 2 synovial isolates, activated or not. Genes with a ΔCt value below 9.9 are considered highly expressed in RASFs. The results of the expression profiling experiments are summarized in Table 5. The ΔCt value relative to β-actin obtained for various targets in 2 isolates of untriggered SFs are given in this Table 5.

TABLE 5

Determination of the Relative Expression Levels of the TARGETS in
Primary Synovial Fibroblasts by Real-Time PCR

| Target ID | SEQ ID # | Accession No. | Assay on demand | RASF cells - Untriggered | | RASF cells - THP1 Triggered | | expressed in RASFs |
|---|---|---|---|---|---|---|---|---|
| | | | | Ct | DCt(*) | Ct | DCt(*) | |
| KLKB1 | 25 | NM_000892 | Hs00168478_m1 | 35.09 | 13.68 | 35.15 | 13.64 | yes |
| ENPP2 | 19 | NM_006209 | Hs00196470_m1 | 23.78 | 2.37 | 23.95 | 2.44 | yes |
| FNTA | 26 | NM_002027 | Hs00357739_m1 | 24.69 | 3.28 | 24.86 | 3.35 | yes |
| MAP3K3 | 20 | NM_002401 | Hs00176747_m1 | 26.39 | 4.81 | 26.29 | 4.58 | yes |
| MAP4K4 | 6 | NM_004834 | Hs00377415_m1 | 24.47 | 2.89 | 24.53 | 2.82 | yes |

TABLE 5-continued

Determination of the Relative Expression Levels of the TARGETS in Primary Synovial Fibroblasts by Real-Time PCR

| Target ID | SEQ ID # | Accession No. | Assay on demand | RASF cells - Untriggered | | RASF cells - THP1 Triggered | | expressed in RASFs |
|---|---|---|---|---|---|---|---|---|
| | | | | Ct | DCt(*) | Ct | DCt(*) | |
| MMP17 | 10 | NM_016155 | Hs00211754_m1 | 28.79 | 7.21 | 28.32 | 6.61 | yes |
| GPR44 | 14 | NM_004778 | Hs00173717_m1 | # | | 38.15 | 16.64 | |
| MGLL | 13 | NM_007283 | Hs00200752_m1 | 24.11 | 2.7 | 23.55 | 2.04 | yes |
| MRAS | 17 | NM_012219 | Hs00171926_m1 | 25.96 | 4.38 | 26.78 | 5.07 | yes |
| PLA2G12A | 11 | NM_030821 | Hs00830106_s1 | 27.34 | 5.76 | 27.57 | 5.86 | yes |
| MIR16 | 15 | NM_016641 | Hs00213347_m1 | 26.45 | 4.87 | 26.85 | 5.14 | Yes |
| NTRK2 | 1 | NM_006180 | Hs00178811_m1 | 25.23 | 3.82 | 25.49 | 3.98 | Yes |
| NEK3 | 23 | NM_002498 | Hs00300928_m1 | 31.11 | 9.53 | 31.66 | 9.95 | Yes |
| PTK6 | 16 | NM_005975 | Hs00178742_m1 | 35.36 | 15.94 | 35.26 | 15.97 | Yes |
| SLC4A8 | 18 | NM_004858 | Hs00191516_m1 | 30.08 | 8.5 | 30.8 | 9.09 | Yes |
| CXCR6 | 40 | NM_006564 | Sybr Green Primers | 28.45 | 6.87 | 29.76 | 8.05 | Yes |
| CCR1 | 37 | NM_001295 | Hs00174298_m1 | 36.96 | 15.55 | 38.07 | 16.56 | Yes |

Example 7

"On Target Analysis" Using KD Viruses

Figure 8:
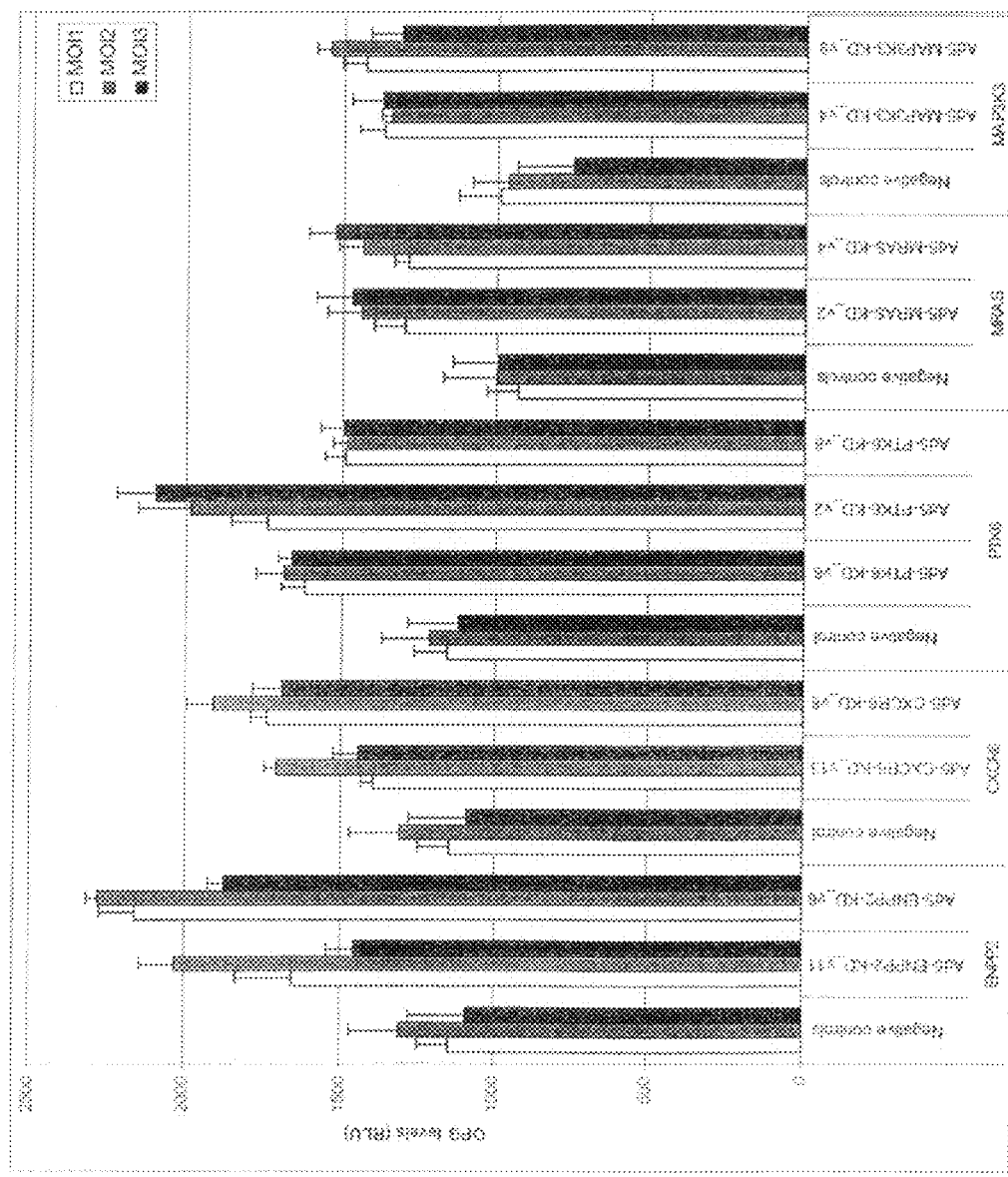
FIG. 8: Target analysis: data obtained for 6 targets

To strengthen the validation of a hit, it is helpful to recapitulate its effect using a completely independent siRNA targeting the same target gene through a different sequence. This analysis is called the "on target analysis". In practice, this is done by designing multiple new shRNA oligonucleotides against the target using a specialised algorithm described, and incorporating these into adenoviruses according to WO 03/020931. After virus production, these viruses are arrayed in 96 well plates, together with positive and negative control viruses. On average, 6 new independent Ad-siRNAs are produced for a set of targets. Two independent repropagations of these virus plates are then performed as described above for the 3 MOI rescreen. The plates produced in these 2 independent repropagations are tested in the OPG assay at 3 MOIS and in duplicate in 2 independent experiments according to the protocol described for the 3 MOI rescreen (Example 3). Ad-siRNAs mediating an increase in OPG levels above the set cutoff value in at least 1 MOI in the 2 independent experiments are nominated as hits scoring in the "on target analysis". The cutoff value in these experiments is defined as the average over the negative controls+2 times the standard deviation over the negative controls. Through this exercise, the following most particular targets are identified: ENPP2, CXCR6, MAP3K3, PTK6, MRAS. The data obtained for these targets in one of the "on target analysis" tests are shown in FIG. 8. In this Figure, the raw data obtained in the determination of the OPG levels are shown. For every target, the average of the raw OPG data obtained for the negative controls tested on the same plate are shown and allow to appreciate the increase in OPG expression for the hit Ad-siRNAs.

Example 8

Determination of the Anti-Inflammatory Effects of OPG Targets

In addition to the bone erosion aspect described above, rheumatoid arthritis has also a strong inflammatory component, as indicated by the efficacy of TNFα blocking agents. To further strengthen the profile of a selection of OPG hits an additional investigation may be performed. The aim of this exercise is to demonstrate, besides the OPG-inducing and thus bone-protective properties, the additional anti-inflammatory character of these OPG hits. Basically, the additional testing performed is aimed at demonstrating which OPG hits are able to reduce cytokine activation of RASFs as monitored by the expression of a cytokine-induced marker, MMP1. This additional testing allows the identification of more preferred hits. This additional testing may be performed as follows:

8.1 Virus Collection and Handling:

For a selection of OPG hits targeting expression of a certain gene, a set of independent KD viruses are collected, that mediate the reduction of the expression of the same target gene through different sequences on the target mRNA. These viruses, together with the original OPG hit viruses, are arrayed in 96 well plates ("hit plates"), together with positive and negative control viruses. The general layout of the plate is depicted in FIG. 10h. As the outer wells are left empty to avoid edge effects, every control plate can accommodate 60 samples in total: 40 hit viruses and 20 control viruses. A KD virus that targets MMP1 is selected as positive control (4 wells per plate), whereas 3 different types of negative control viruses were used that target either luciferase gene transcripts (8 wells per plate), M6PR gene transcripts (4 wells per plate) or eGFP gene transcripts (4 wells per plate). The reconstituted plates are repropagated to ensure homogeneity of the titers of the viruses tested.

8.2 Cell Handling and Transduction of RASFs

At day 0, RASFs (with passage number below 11) are seeded in 96 well plates at a density of 3000 cells/well in 50 µL of medium. One day later (day 1), 8, 16 or 24 µL of the virus crude lysate contained in the virus plates is transferred to the plates containing the cells. As every virus load is tested in duplicate, 6×60 datapoints are generated for every "hit plate" tested.

8.3 Cell Triggering and Supernatant Collection

Five days after transduction of the cells, the reduction in the expression of the target gene mediated by the KD viruses is fully effective. Day 6, medium is removed and replaced by M199 medium+1% FBS containing an eight-fold dilution of a "TNFα based trigger". This trigger is prepared as follows. The production of the "TNFα based trigger" is initiated by seeding THP-1 monocytic cells in M199 medium supplemented with 1% serum at a density of 1×10E6 cells/mL. One day after seeding, recombinant human TNFalpha (Sigma) is added to the culture flasks to a final concentration of 25 ng/mL. 48 hours after addition of the cytokine, the supernatant is collected and stored at −80° C. in aliquots until further use. Every new batch of "TNFα based trigger" is characterized for its efficacy at inducing MMP1 expression by RASFs. This trigger contains a variety of inflammatory mediators that activate diverse signal transduction pathways in RASFs. Day 8, supernatant on top of the triggered cells is collected and subjected to a MMP1 ELISA.

8.4 MMP1 ELISA

The MMP1 ELISA is performed in 384 well format as described in WO 2006/040357. The following protocol is applied: white Lumitrac 600 384 well plates (Greiner) are coated with 2 µg/ml anti-MMP1 antibody MAB1346 (Chemicon). The antibody is diluted in buffer 40 (1.21 g Tris base (Sigma), 0.58 g NaCl (Calbiochem) and 5 mL 10% $NaN_3$ (Sigma) in 1 L milliQ water and adjusted to pH 8.5). After overnight incubation at 4° C., plates are washed with PBS (80 g NaCl, 2 g KCl (Sigma), 11.5 g $Na_2HPO_4.7H_2O$ and 2 g $KH_2PO_4$ in 10 L milliQ; pH 7.4) and blocked with 100 µL/well Casein buffer (2% Casein (VWR International) in PBS). Next day, casein buffer is removed from ELISA plates and replaced by 50 µL/well EC buffer (4 g casein, 2.13 g $Na_2HPO_4$ (Sigma), 2 g bovine albumin (Sigma), 0.69 g $NaH_2PO_4.H_2O$ (Sigma), 0.5 g CHAPS (Roche), 23.3 g NaCl, 4 ml 0.5 M EDTA pH 8 (Invitrogen), 5 mL 10% $NaN_3$ in 1 L milliQ and adjusted to pH 7.0). 0.25 mM DTT (Sigma) is added to the thawed samples plates. After removal of the EC buffer, 20 µL of sample is transferred to the ELISA plates. After overnight incubation at 4° C., the plates are washed twice with PBS, once with PBST (PBS with 0.05% Tween-20 (Sigma)), and incubated with 35 µL/well biotinylated anti-MMP1 antibody solution (R&D). This secondary antibody is diluted in buffer C (0.82 g $NaH_2PO_4.H_2O$, 4.82 g $Na_2HPO_4$, 46.6 g NaCl, 20 g bovine albumin and 4 mL 0.5M EDTA pH 8 in 2 L milliQ and adjusted to pH 7.0) at a concentration of 5 µg/mL. After 2 hours of incubation at RT, the plates are washed as described above and incubated with 50 µL/well streptavidin-HRP conjugate (Biosource). Streptavidin-HRP conjugate is diluted in buffer C at a concentration of 0.25 µg/mL. After 45 minutes, the plates are washed as described above and incubated for 5 minutes with 50 µL/well BM Chem ELISA Substrate (Roche). Readout is performed on the Luminoscan Ascent Luminometer (Labsystems) with an integration time of 200 msec or with an Envision reader (Perkin Elmer).

8.5 Hit Analysis

The ability of the collected viruses to reduce the expression of MMP1 by RASFs activated with a "TNFα-based trigger" may be determined as follows. For every plate, 3 control wells are left untriggered, allowing to determine if the MMP1 expression is induced as expected. 17 control wells (containing 13 negative controls and 4 positive controls) are triggered. The average and standard deviation is calculated for the MMP1 signal over the 13 triggered negative control wells. For every datapoint, the normalized reduction in MMP1 expression is calculated as follows:

Normalized reduction of MMP1 signal for KD virus X=[(Average signal for 13 negative controls—signal for KD virus X)/(standard deviation of the MMP1 signal over the 13 negative controls)].

Figure 11:
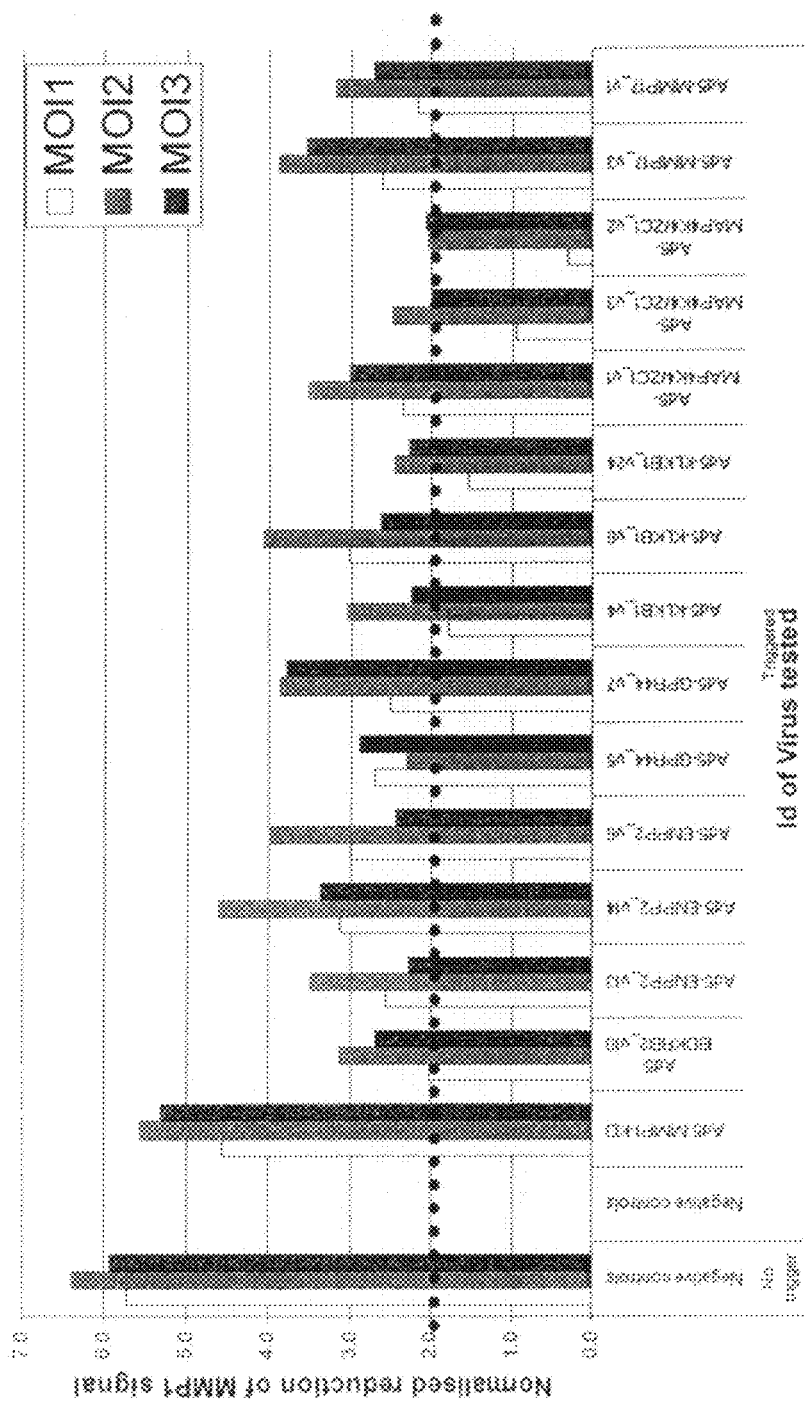
FIG. 11: Representative example of the outcome of a MMP1 assay experiment. The normalized reduction in MMP1 expression is shown for 14 KD viruses tested at 3 multiplicity of infections (MOIs) and compared to the performance of the positive control (Ad5-MMP1-KD) and of the untriggered or triggered negative controls. The negative control data represent the average of the data obtained for the 3 (untriggered condition) or 13 (triggered condition) negative controls present on the "hit plates". The cutoff for hit calling is represented with a dotted line. All 14 KD viruses tested significantly reduced the cytokine-induced MMP1 expression in RASFs.

Every datapoint for which the normalized reduction of MMP1 expression exceeding 2 is considered "positive", i.e. the "TNFα-based trigger"—induced MMP1 expression is considered to be reduced in a significant way in these samples. For these viruses, the difference between MMP1 signal for the virus X and of the negative controls exceeds 2 times the standard deviation over the negative controls. As such, 6 independent normalized MMP1 datapoints are generated for every tested KD virus. Viruses for which at least 3 out of the 6 datapoints are "positive" are considered a hit in the MMP1 assay. A summary of the data obtained for 7 OPG hits is shown in Table 6. For 6 out of the 7 targets tested, at least one KD virus is identified that significantly reduces "TNFα-based trigger" induced MMP1 expression. As such, the inhibition of the activity of these genes is expected to increase the OPG expression by RASFs and to reduce the response of RASFs to inflammatory cytokines. An example of the data obtained in the MMP1 assay is given in FIG. 11.

TABLE 6

Outcome of the additional testing of OPG hits in the "MMP1 assay"

| Target Name | SEQ ID NOs | Nr of independent KD viruses tested | Nr of constructs inhibiting "TNFα-based trigger"-induced MMP1 expression |
|---|---|---|---|
| ENPP2 | 19 | 7 | 3 |
| GPR44 | 14 | 3 | 2 |
| KLKB1 | 25 | 10 | 3 |
| MAP4K4 | 6, 7, 8, 9 | 8 | 3 |
| MMP17 | 10 | 3 | 2 |
| NTRK2 | 1, 2, 3, 4, 5 | 4 | 0 |

For 7 selected OPG hits, up to 9 additional KD virus constructs ("independent KD viruses") targeting the expression of the same gene are collected. The number of constructs per OPG hit that mediated a significant reduction of the "TNFα-based trigger"-induced MMP1 expression is indicated in the table.

Example 9

OPG Dependency of Ad-siRNA-Mediated Inhibition of Osteoclast Differentiation in RASF-Osteoclast Cocultures In example 5, Ad-siRNA OPG hits are selected based their ability to reduce RANKL-induced osteoclast differentiation in cocultures with transduced RASFs. The aim of the assay described in this example (further referred to as the "OPG dependency assay") is to demonstrate that the observed inhibition of osteoclast differentiation in the co-culture assay is due to the increased OPG release by RASFs, that were transduced with selected Ad-siRNAs. The principle of this assay is depicted in FIG. 6A. In brief, Ad-siRNAs are tested in the osteoclast co-culture assay with or without inclusion of an anti-OPG antibody that can neutralize OPG bioactivity. The desired profile for the Ad-siRNAs is the following: inhibition RANKL-driven osteoclast differentiation when the co-culture assay is performed in absence of the anti-OPG antibody and absence of effects when the assay is performed in presence of the anti-OPG antibody. The anti-OPG antibody (Cat. No. AF805, R&D Systems) selected for the experiments is a goat polyclonal IgG antibody and as shown in FIG. 7C, is able to neutralize soluble OPG and prevent OPG-mediated inhibition of sRANKL-driven osteoclast formation in the co-culture assay. The additional testing is performed as follows:

9.1 Virus Collection and Handing

Confirmed OPG hits that are also found to inhibit OC differentiation in the co-culture assay (Example 5) may be selected for testing in the "OPG dependency assay". The virus material used for this experiment is the same as that prepared for retesting of the primary hits in the 3 MOI OPG (Example 3). Selected Ad-siRNAs are cherry picked out of these virus plates and re-arrayed in 96-well plates ("hit plates"), together with the respective positive and negative control viruses (i.e. control viruses that were repropagated simultaneously with the Ad-siRNAs upon preparing the material for the 3MOI retesting). The general layout of a plate is depicted in FIG. 4. Every plate contains 4 wells for 3 different types of negative control viruses (N1=Ad5-eGFP_v1_KI, N2=Ad5-Luc_v13_KD), N3=Ad5-eGFP_v5_KD), and one well containing a positive control (P=Ad5-OPG_v1_KI). In the assay, transduction is performed as follows: 3 µL out of the virus hit plates are transferred 4 times to a 384-well assay plate such that all four quadrants are infected with the same virus.

9.2 Assay Description

Day 1, RASFs cells (1000 cells/well) are seeded on a 0.1% gelatin coated 384-well plate (Greiner, cat No. 781080) in 50 µL medium. The following day (Day 2) the cells are infected with 3 µL of Ad-siRNA material. Transfection is done in quadruplo (all 4 quadrants relative to one 96-well, are infected with the same Ad-siRNA). On day 7, the medium is refreshed with 30 µL coculture medium and osteoclast precursor cells (1600 cells contained in 30 µL co-culture medium with 105 ng/ml rhMCSF) are then added on top of the RASFs, followed by addition of 10 µL of co-culture medium that does not (uneven columns only) or does (even columns only) contain the neutralizing anti-OPG antibody at a concentration of 24 µg/mL. In this way, four datapoints are generated for every "hit plate" tested, two in presence and two in absence of the anti-OPG antibody. After overnight incubation (Day 8), 10 µL of co-culture medium containing 40 ng/mL rhMCSF and 120 ng/mL sRANKL is added to all wells to induce osteoclast differentiation. Final concentrations of reagents at this time are 15 ng/mL sRANKL, 40 ng/mL rhMCSF and 3 µg/mL anti-OPG antibody (if added). On day 20 (after 11 days of incubation at 37° C.; 5% $CO_2$), osteoclast differentiation is read out by quantifying vitronectin receptor expression by cELISA.

9.3 Hit Analysis

Figure 12:
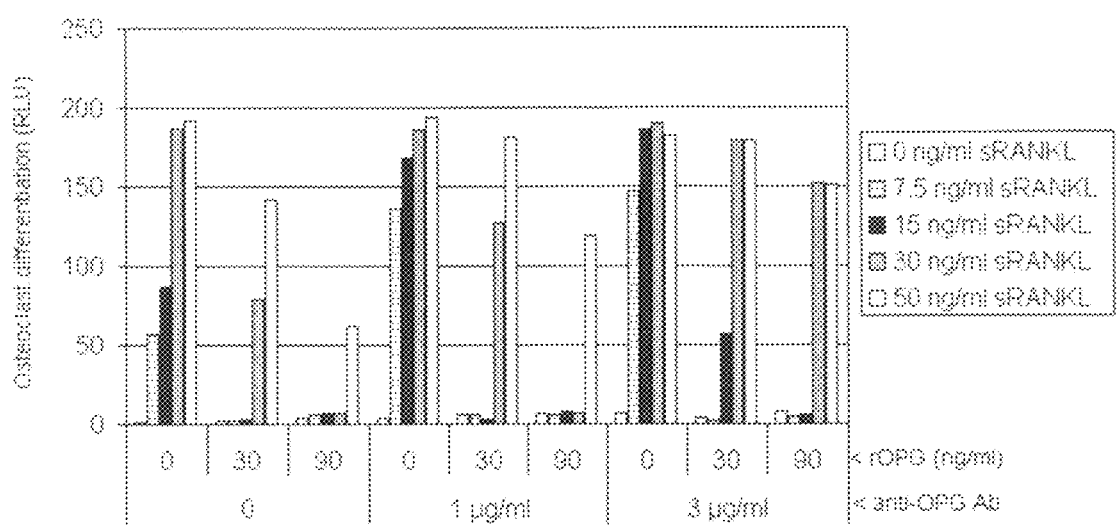
FIG. 12: Neutralization of OPG by a selected anti-OPG antibody. Pre-osteoclasts are seeded on top of RASFs in presence of indicated amounts of recombinant OPG and anti-OPG antibody and after overnight incubation osteoclast differentiation is triggered by addition of indicated amounts sRANKL. The number of osteoclasts formed after another 11 days incubation is quantified using a vitronectin cELISA readout. Without the addition of the anti-OPG (Cat. No. A805; R&D Systems), osteoclast formation is dependent on the dose of sRANKL and is blocked by the addition of OPG; the ability of OPG to prevent osteoclast formation is dependent upon the dose of sRANKL used to trigger osteoclast differentiation: the higher the dose of sRANKL, the more OPG that is needed to prevent osteoclast differentiation. Addition of the anti-OPG antibody is able to rescue osteoclast differentiation in the presence of OPG. The ability to rescue osteoclast differentiation is dependent upon the dose of the antibody, upon the concentration of OPG added and upon the dose of sRANKL: the more antibody, the more OPG can be neutralized and the lower the dose of RANKL at which rescue of OPG inhibition can be observed. As can be seen, dose-response of sRANKL when no OPG is added is already shifted to lower sRANKL concentrations when anti-OPG antibody is added due to neutralization of endogenous secreted OPG by RASFs. For the experiments, the anti-OPG Ab is used at a concentration of 3 μg/mL and 15 ng/mL sRANKL is used to trigger osteoclast differentiation.

For each hit virus, duplicate values in presence or absence of anti-OPG antibody are averaged and a threshold value was set. Hit viruses that generate values that are under the threshold value are considered to inhibit osteoclast differentiation driven by RANKL. The threshold signal for hit calling is defined such that none of the values generated by individual negative controls (in presence or absence of anti-OPG Ab) would score positive. The observed osteoclast inhibition for a hit virus is said to be OPG-dependent, when the averaged value in absence of the anti-OPG Ab is below the threshold and the value in presence of the anti-OPG Ab is above the threshold. An example of the data obtained in a representative experiment is given in FIG. 12.

REFERENCES

Roodman G D (2004) Mechanisms of Bone Metastasis. N Engl J Med 350:1655

Pettit A R, Ji H, von Stechow D, Goldring S R, Choi Y, Benoist C, Gravallese E M (2001) TRANCE/RANKL knockout mice are protected from bone erosion in a serum transfer model of arthritis. *Am J Pathol* 159: 1689.

Pettit A R, Walsh N C, Manning C, Goldring S R, Gravallese E M. (2006) RANKL protein is expressed at the pannus-bone interface at sites of articular bone erosion in rheumatoid arthritis. *Rheumatology* 45:1068-76.

Bucay N, Sarosi I, Dunstan C R, Morony S, Tarpley J, Capparelli C, Scully S, Tan H L, Xu W, Lacey D L, Boyle W J, Simonet W S. (1998) osteoprotegerin-deficient mice develop early onset osteoporosis and arterial calcification. *Genes Dev.* 12:1260-8.

Kim N, Odgren P R, Kim D K, Marks S C Jr, Choi Y. (2000) Diverse roles of the tumor necrosis factor family member TRANCE in skeletal physiology revealed by TRANCE deficiency and partial rescue by a lymphocyte-expressed TRANCE transgene. Proc Natl Acad Sci USA. 97:10905-10.

Gravallese E M. (2002) Bone destruction in arthritis. Ann Rheum Dis. 61 Suppl 2:ii84-6.

Onyia J E, Galvin R J, Ma Y L, Halladay D L, Miles R R, Yang X, Fuson T, Cain R L, Zeng Q Q, Chandrasekhar S, Emkey R, Xu Y, Thirunavukkarasu K, Bryant H U, Martin T J. (2004) Novel and selective small molecule stimulators of osteoprotegerin expression inhibit bone resorption. *J Pharmacol Exp Ther.* 309:369-79

Valleala H, Laasonen L, Koivula M K, Mandelin J, Friman C, Risteli J, Konttinen Y T. (2003) Two year randomized controlled trial of etidronate in rheumatoid arthritis: changes in serum aminoterminal telopeptides correlate with radiographic progression of disease. J. Rheumatol. 30: 468-73.

Redlich K, Gortz B, Hayer S, Zwerina J, Doerr N, Kostenuik P, Bergmeister H, Kollias G, Steiner G, Smolen J S, Schett G. (2004) Repair of local bone erosions and reversal of systemic bone loss upon therapy with anti-tumor necrosis factor in combination with osteoprotegerin or parathyroid hormone in tumor necrosis factor-mediated arthritis. *Am J Pathol.* 164: 543-55.

Smolen and Steiner (2003); Lee and Weinblatt (2001); Choy and Panayi (2001); O'Dell (2004) and Firestein (2003)

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

We claim:

1. A method for identifying a compound that inhibits bone resorption, comprising:
   (a) contacting a compound with a polypeptide comprising the amino acid sequence of SEQ ID NO: 59 or a nucleic acid encoding a polypeptide comprising the amino acid sequence of SEQ ID NO: 59; and
   (b) measuring a compound polypeptide property, wherein said property is the expression or enzymatic activity of said polypeptide; and
   (c) contacting a population of isolated mammalian cells in culture expressing said polypeptide with one or more compound(s) from step (b) that significantly inhibits the expression or enzymatic activity of the polypeptide; and
   (d) identifying one or more compound(s) that increases osteoprotegerin (OPG) levels in said culture;
   wherein a compound that inhibits bone resorption is identified.

2. The method according to claim 1, wherein said polypeptide in step (a) and (b) is in an in vitro cell-free preparation.

3. The method according to claim 1, wherein said polypeptide in step (a) and (b) is present in an isolated mammalian cell.

4. The method according to claim 1, wherein said property is the expression of said polypeptide.

5. The method according to claim 1, which additionally comprises the step of comparing the compound to be tested to a control.

6. The method according to claim 5, wherein said control is where the polypeptide or nucleic acid has not been contacted with said compound.

7. The method according to claim 1, which additionally comprises the step of comparing the compound(s) to a control, wherein said control is a population of isolated mammalian cells that does not express said polypeptide.

8. The method according to claim 1, wherein said compound is selected from compounds of a library of compounds and a knock-down library of siRNA molecules.

9. The method of claim 8 wherein said compound is selected from compounds having binding affinity for a polypeptide comprising the an amino acid sequence of SEQ ID NO: 59 or a nucleic acid encoding a polypeptide comprising the an amino acid sequence of SEQ ID NO: 59.

10. The method according to claim 1, wherein said compound is a peptide in a phage display library or an antibody fragment library.

11. The method of claim 1 wherein said property is the enzymatic activity of said polypeptide.

12. The method of claim 11 wherein the enzymatic activity is phosphodiesterase or phosphatase activity.

13. The method of claim 1 wherein the expression or enzymatic activity of said polypeptide is determined by measuring the cleavage of a substrate of the polypeptide.

14. A method for identifying a compound that inhibits bone resorption, comprising:
  (a) contacting a compound with a polypeptide comprising the amino acid sequence of SEQ ID NO: 59 or a nucleic acid encoding a polypeptide comprising the amino acid sequence of SEQ ID NO: 59, wherein said polypeptide is present in an isolated mammalian cell; and
  (b) measuring the expression or enzymatic activity of said polypeptide wherein reduction of the expression or enzymatic activity of said polypeptide results in upregulation of a biological pathway producing a biochemical marker indicative of the inhibition of bone resorption, and wherein said marker is osteprotegerein (OPG);
  wherein a compound that inhibits bone resorption is identified.

* * * * *